US012479859B2

(12) United States Patent
Sugiura et al.

(10) Patent No.: US 12,479,859 B2
(45) Date of Patent: Nov. 25, 2025

(54) PHOTOELECTRIC CONVERSION ELEMENT, IMAGING ELEMENT, OPTICAL SENSOR, AND COMPOUND

(71) Applicant: FUJIFILM Corporation, Tokyo (JP)

(72) Inventors: Hiroki Sugiura, Kanagawa (JP); Yukio Tani, Kanagawa (JP); Ryo Fujiwara, Kanagawa (JP); Yasunori Yonekuta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 381 days.

(21) Appl. No.: 18/334,368

(22) Filed: Jun. 13, 2023

(65) Prior Publication Data

US 2023/0345826 A1 Oct. 26, 2023

Related U.S. Application Data

(63) Continuation of application No. PCT/JP2021/047905, filed on Dec. 23, 2021.

(30) Foreign Application Priority Data

Dec. 24, 2020 (JP) ................................ 2020-215244

(51) Int. Cl.
*C07D 513/04* (2006.01)
*C07D 519/00* (2006.01)
(Continued)

(52) U.S. Cl.
CPC ......... *C07D 513/04* (2013.01); *C07D 519/00* (2013.01); *H10K 30/00* (2023.02);
(Continued)

(58) Field of Classification Search
CPC ........ H10K 30/20; H10K 30/30; H10K 39/32; H10K 85/6572; H10K 85/6574
See application file for complete search history.

(56) References Cited

U.S. PATENT DOCUMENTS

| | | | | |
|---|---|---|---|---|
| 8,860,016 | B2 | 10/2014 | Suzuki | |
| 2007/0044829 | A1* | 3/2007 | Osaka | H10K 30/88<br>136/249 |
| 2011/0303293 | A1* | 12/2011 | Yoshimura | C09B 67/0033<br>257/E51.026 |

FOREIGN PATENT DOCUMENTS

| | | |
|---|---|---|
| CN | 104177380 | 12/2014 |
| JP | H10340786 | 12/1998 |

(Continued)

OTHER PUBLICATIONS

"Office Action of Korea Counterpart Application", issued on Dec. 13, 2024, with English translation thereof, p. 1-p. 16.

(Continued)

*Primary Examiner* — Jesse Y Miyoshi
(74) *Attorney, Agent, or Firm* — JCIPRNET

(57) ABSTRACT

The present invention is to provide a photoelectric conversion element with the electric field strength dependence of a photoelectric conversion efficiency suppressed. In addition, an imaging element, an optical sensor, and a compound are provided. The photoelectric conversion element includes a conductive film, a photoelectric conversion film, and a transparent conductive film in this order, in which the photoelectric conversion film contains a compound represented by Formula (1)

(1)

(Continued)

-continued

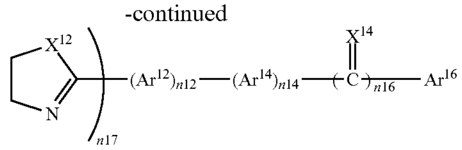

32 Claims, 1 Drawing Sheet

(51) Int. Cl.

| | |
|---|---|
| ***H10K 30/00*** | (2023.01) |
| ***H10K 30/30*** | (2023.01) |
| ***H10K 30/50*** | (2023.01) |
| ***H10K 39/32*** | (2023.01) |
| ***H10K 85/60*** | (2023.01) |

(52) U.S. Cl.

CPC ........... *H10K 39/32* (2023.02); *H10K 85/626* (2023.02); *H10K 85/654* (2023.02); *H10K 85/655* (2023.02); *H10K 85/656* (2023.02); *H10K 85/657* (2023.02); *H10K 85/6574* (2023.02); *H10K 85/6576* (2023.02); *H10K 30/30* (2023.02); *H10K 30/50* (2023.02)

(56) References Cited

FOREIGN PATENT DOCUMENTS

| | | |
|---|---|---|
| JP | 2006165015 | 6/2006 |
| JP | 2006216814 | 8/2006 |
| JP | 2014170929 | 9/2014 |
| KR | 1020130018730 | 2/2013 |
| KR | 20200022963 | 3/2020 |
| WO | 2014123215 | 8/2014 |

OTHER PUBLICATIONS

"International Search Report (Form PCT/ISA/210) of PCT/JP2021/047905," mailed on Feb. 15, 2022, with English translation thereof, pp. 1-5.
"Written Opinion of the International Searching Authority (Form PCT/ISA/237) of PCT/JP2021/047905," mailed on Feb. 15, 2022, with English translation thereof, pp. 1-6.
"Search Report of Europe Counterpart Application", issued on May 6, 2024, pp. 1-6.
"Office Action of Korea Counterpart Application", issued on Jul. 9, 2025, with English translation thereof, pp. 1-9.

* cited by examiner

PHOTOELECTRIC CONVERSION ELEMENT, IMAGING ELEMENT, OPTICAL SENSOR, AND COMPOUND

CROSS-REFERENCE TO RELATED APPLICATIONS

This application is a Continuation of PCT International Application No. PCT/JP2021/047905 filed on Dec. 23, 2021, which claims priority under 35 U.S.C. § 119(a) to Japanese Patent Application No. 2020-215244 filed on Dec. 24, 2020. The above applications are hereby expressly incorporated by reference, in their entirety, into the present application.

BACKGROUND OF THE INVENTION

1. Field of the Invention

The present invention relates to a photoelectric conversion element, an imaging element, an optical sensor, and a compound.

2. Description of the Related Art

In recent years, the development of an element (for example, an imaging element) having a photoelectric conversion film has been progressing.

For example, organic semiconductor materials described below are disclosed in CN104177380A as materials related to the photoelectric field. In the following structural formula, R is a predetermined alkyl group.

In view of the above circumstances, an object of the present invention is to provide a photoelectric conversion element with the electric field strength dependence of the photoelectric conversion efficiency suppressed.

Another object of the present invention is to provide an imaging element, an optical sensor, and a compound related to the above-described photoelectric conversion element.

The present inventors have conducted extensive studies on the above-described problems, and as a result, the inventors have found that it is possible to solve the above-described problems by configurations described below and have completed the present invention.

[1]

A photoelectric conversion element comprising, in the following order:

a conductive film;

a photoelectric conversion film; and a transparent conductive film, in which the photoelectric conversion film contains a compound represented by Formula (1) described later.

[2]

The photoelectric conversion element according to [1], in which $Ar^{11}$ to $Ar^{14}$ are each independently a group represented by any of Formula (2) to Formula (7) described later.

[3]

The photoelectric conversion element according to [1] or [2], in which $Ar^{15}$ and $Ar^{16}$ are each independently a group represented by any of Formula (8) to Formula (15) and Formula (47) to Formula (53) described later.

[4]

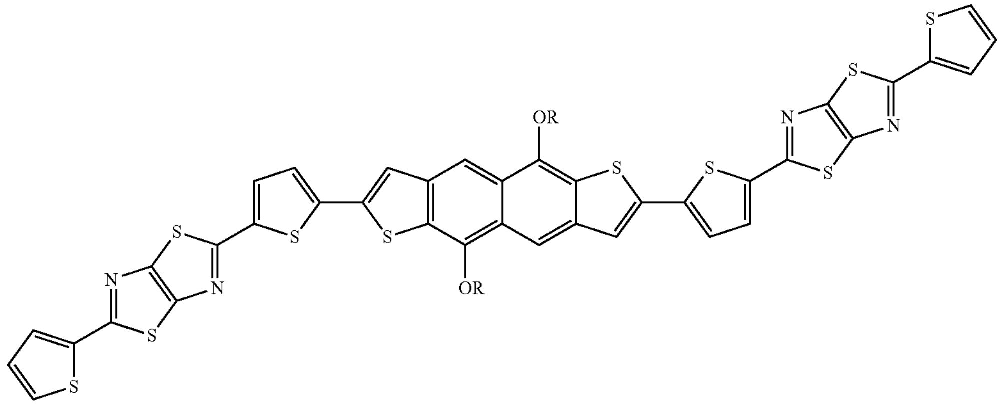

SUMMARY OF THE INVENTION

In recent years, along with the demand for improving the performance of imaging elements, optical sensors, and the like, further improvements are demanded with respect to various characteristics required for photoelectric conversion elements used therein.

For example, it is demanded that stable photoelectric conversion efficiency can be achieved even though a voltage applied to the photoelectric conversion element fluctuates.

The present inventors have studied a photoelectric conversion element formed of the material disclosed in CN104177380A, and have found that in such photoelectric conversion elements are difficult to suppress the dependence of the photoelectric conversion efficiency on the applied voltage.

The photoelectric conversion element according to any one of [1] to [3], in which n11 to n12 each represent 1, n13 to n16 each represent 0, n17 represents 1, and n18 represents 1 or 2.

[5]

The photoelectric conversion element according to any one of [1] to [3], in which n11 to n14 represent 1, n15 and n16 represent 0, n17 represents 1, and n18 represents 1 or 2.

[6]

The photoelectric conversion element according to any one of [1] to [3], in which n11 to n16 each represent 0, n17 represents 1, and n18 represents 1 or 2.

[7]

The photoelectric conversion element according to any one of [1] to [3], in which n11 and n12 each represent 1, n13 and n14 each represent 0, n15 and n16 each represent 1, n17 represents 1, and n18 represents 1 or 2.

[8]

The photoelectric conversion element according to any one of [1] to [3], in which n11 to n14 each represent 0, n15 and n16 each independently represent 0 or 1, n17 represents 2, and n18 represents 1.

[9]

The photoelectric conversion element according to any one of [1] to [3], in which the compound represented by Formula (1) is a compound represented by any of Formula (16) to Formula (46) and Formula (54) to Formula (60) described later.

[10]

The photoelectric conversion element according to [9], in which the compound represented by Formula (1) is the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y^{111}$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (29) in which $Y^{41}$ and $Y^{42}$ and $Y^{81}$ to $Y^{85}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom.

[11]

The photoelectric conversion element according to [9], in which the compound represented by Formula (1) is the compound represented by any one of Formula (16), Formula (31), Formula (32), Formula (35), Formula (37), Formula (39), or Formula (42).

[12]

The photoelectric conversion element according to any one of [1] to [11], in which Xu and $X^{12}$ each represent a sulfur atom.

[13]

The photoelectric conversion element according to any one of [1] to [12], in which the photoelectric conversion film further contains a n-type semiconductor material.

[14]

The photoelectric conversion element according to [13], in which the n-type semiconductor material includes fullerenes selected from the group consisting of a fullerene and a derivative thereof.

[15]

The photoelectric conversion element according to any one of [1] to [14], in which the photoelectric conversion film further contains a p-type semiconductor material.

[16]

The photoelectric conversion element according to any one of [1] to [15], in which the photoelectric conversion film contains two compounds represented by Formula (1).

[17]

The photoelectric conversion element according to any one of [1] to [16], in which the photoelectric conversion film further contains a coloring agent.

[18]

The photoelectric conversion element according to any one of [1] to [17], further comprising one or more interlayers between the conductive film and the transparent conductive film, in addition to the photoelectric conversion film.

[19]

An imaging element comprising the photoelectric conversion element according to any one of [1] to [18].

[20]

An optical sensor comprising the photoelectric conversion element according to any one of [1] to [18].

[21]

A compound represented by Formula (1) described later.

[22]

The compound according to [21], in which $Ar^{11}$ to $Ar^{14}$ are each independently a group represented by any of Formula (2) to Formula (7) described later.

[23]

The compound according to [21] or [22], in which $Ar^{15}$ and $Ar^{16}$ are each independently a group represented by any of Formula (8) to Formula (15) and Formula (47) to Formula (53) described later.

[24]

The compound according to any one of [21] to [23], in which n11 and n12 each represent 1, n13 to n16 each represent 0, n17 represents 1, and n18 represents 1 or 2.

[25]

The compound according to any one of [21] to [23], in which n11 to n14 each represent 1, n15 and n16 each represent 0, n17 represents 1, and n18 represents 1 or 2.

[26]

The compound according to any one of [21] to [23], in which n11 to n16 each represent 0, n17 represents 1, and n18 represents 1 or 2.

[27]

The compound according to any one of [21] to [23], in which n11 and n12 each represent 1, n13 and n14 each represent 0, n15 and n16 each represent 1, n17 represents 1, and n18 represents 1 or 2.

[28]

The compound according to any one of [21] to [23], in which n11 to n14 each represent 0, n15 and n16 each independently represent 0 or 1, n17 represents 2, and n18 represents 1.

[29]

The compound according to any one of [21] to [23], in which the compound represented by Formula (1) is a compound represented by any of Formula (16) to Formula (46) and Formula (54) to Formula (60) described later.

[30]

The compound according to [29], in which the compound represented by Formula (1) is the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y^{111}$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (29) in which $Y^{41}$ and $Y^{42}$ and $Y^{81}$ to $Y^{85}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom.

[31]

The compound according to [29], in which the compound represented by Formula (1) is the compound represented by any one of Formula (16), Formula (31), Formula (32), Formula (35), Formula (37), Formula (39), or Formula (42).

[32]

The compound according to any one of [21] to [31], in which $X^{11}$ and $X^{12}$ each represent a sulfur atom.

According to the present invention, it is possible to provide the photoelectric conversion element with an excellent photoelectric conversion efficiency.

In addition, according to the present invention, it is possible to provide the imaging element, the optical sensor, and the compound related to the photoelectric conversion element.

DESCRIPTION OF THE PREFERRED EMBODIMENTS

Figure 1:
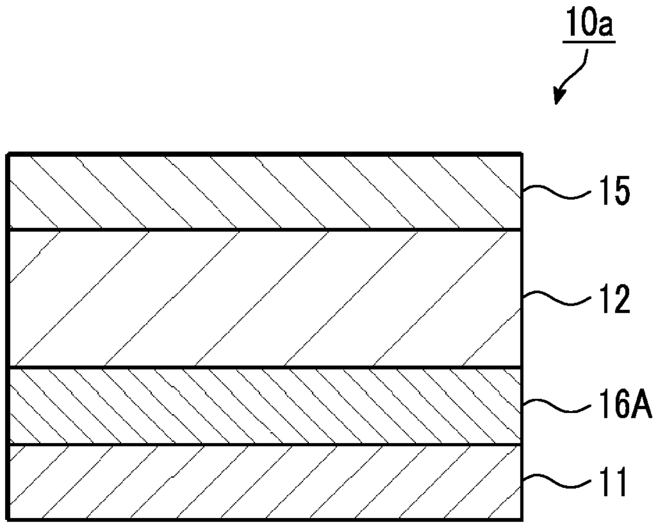
FIG. 1 is a schematic cross-sectional view illustrating a configuration example of a photoelectric conversion element.

Hereinafter, suitable embodiments of a photoelectric conversion element of the present invention will be described.

In the present invention, examples of the halogen atom include a fluorine atom, a chlorine atom, a bromine atom, and an iodine atom, a fluorine atom or a chlorine atom is preferable, and a fluorine atom is more preferable.

In the present specification, unless otherwise specified, an aromatic ring group may be monocyclic or polycyclic (for example, with 2 to 6 rings). The monocyclic aromatic ring group is an aromatic ring group having only one aromatic ring structure as a ring structure. The polycyclic (for example, 2 to 6 rings) aromatic ring group is an aromatic ring group formed of a plurality of (for example, 2 to 6) aromatic ring structures fused as a ring structure.

The number of ring member atoms of the aromatic ring group is preferably an integer of 5 to 15.

The aromatic ring group may be an aromatic hydrocarbon ring group or an aromatic heterocyclic group.

In a case where the aromatic ring group is an aromatic heterocyclic group, the number of heteroatoms included as ring member atoms is, for example, 1 to 10. Examples of the heteroatoms include a nitrogen atom, a sulfur atom, an oxygen atom, a selenium atom, a tellurium atom, a phosphorus atom, a silicon atom, and a boron atom.

Examples of the aromatic hydrocarbon ring group include a benzene ring group, a naphthalene ring group, an anthracene ring group, and a phenanthrene ring group.

Examples of the aromatic heterocyclic ring group include a pyridine ring group, a pyrimidine ring group, a pyridazine ring group, a pyrazine ring group, a triazine ring group (1,2,3-triazine ring group, 1,2,4-triazine ring group, 1,3,5-triazine ring group, or the like), and a tetrazine ring group (1,2,4,5-tetrazine ring group or the like), a quinoxaline ring group, a pyrrole ring group, a furan ring group, a thiophene ring group, an imidazole ring group, an oxazole ring group, a thiazole ring group, a benzopyrrole ring group, a benzofuran ring group, a benzothiophene ring group, a benzoimidazole ring group, a benzoxazole ring group, a benzothiazole ring group, a naphthopyrrole ring group, a naphthofuran ring group, a naphthothiophene ring group, a naphthimidazole ring group, a naphthoxazole ring group, a 3H-pyrrolidine ring group, a pyrroloimidazole ring group (a 5H-pyrrolo[1,2-a]imidazole ring and the like), an imidazooxazole ring group (an imidazo[2,1-b]oxazole ring group and the like), a thienothiazole ring group (a thieno[2,3-d]thiazole ring group and the like), a benzothiadiazole ring group, a benzodithiophene ring group (benzo[1,2-b:4,5-b']dithiophene ring group or the like), a thienothiophene ring group (thieno[3,2-b]thiophene ring group or the like), a thiazolothiazole ring group (thiazolo[5,4-d]thiazole ring group or the like), a naphthodithiophene ring group (naphtho[2,3-b:6,7-b']dithiophene ring group, a naphtho[2,1-b:6,5-b']dithiophene ring group, a naphtho[1,2-b:5,6-b']dithiophene ring group, a 1,8-dithiadicyclopenta[b,g]naphthalene ring group, or the like), a benzothienobenzothiophene ring group, a dithieno[3,2-b:2',3'-d]thiophene ring group, and a 3,4,7,8-tetrathiadicyclopenta[a,e]pentalene ring group.

In the present specification, in a case where the aromatic ring is simply referred to as an aromatic ring, an example thereof includes an aromatic ring constituting the aromatic ring group.

In a case where the aromatic ring group is monovalent, examples of such an aromatic ring group include a group formed with an aromatic ring in the above-described aromatic ring group, from which one hydrogen atom is removed. In this case, the aromatic ring group is a so-called aryl group or a heteroaryl group.

In a case where the aromatic ring group is divalent, examples of such an aromatic ring group include a group formed with an aromatic ring in the above-described aromatic ring group, from which two hydrogen atoms are removed. In this case, the aromatic ring group is a so-called aryl group or a heteroaryl group. In this case, the aromatic ring group is a so-called arylene group or heteroarylene group.

In the present specification, in a case where a plurality of identical symbols indicating a kind or the number of groups are present in Formula (General Formula), which indicates a chemical structure, contents of these plurality of identical symbols indicating a kind or the number of groups are independent of each other, and the contents of the identical symbols may be the same or different from each other unless otherwise specified.

In the present specification, in a case where a plurality of identical groups (such as aromatic ring groups) are present in one Formula (General Formula), which indicates a chemical structure, specific contents between these plurality of identical groups are independent of each other, and the specific contents between the plurality of identical groups may be the same or different from each other, unless otherwise specified.

In addition, in the present specification, the numerical range represented by "to" means a range including numerical values denoted before and after "to" as a lower limit value and an upper limit value.

In the present specification, a hydrogen atom may be a light hydrogen atom (an ordinary hydrogen atom) or a deuterium atom (a double hydrogen atom and the like).

[Photoelectric Conversion Element]

The photoelectric conversion element according to an embodiment of the present invention includes a conductive film, a photoelectric conversion film, and a transparent conductive film in this order, in which the photoelectric conversion film contains a compound represented by Formula (1) (hereinafter, referred to as a "specific compound").

The mechanism capable of solving the above problems by adopting such a configuration of the photoelectric conversion element according to the embodiment of the present invention is not always clear, but the present inventors have presumed as follows.

That is, the specific compound has a mother nucleus with a nitrogen-containing five-membered ring that has an aromatic property and that is present at both ends of the mother nucleus, and the mother nucleus further has predetermined substituents at both ends thereof. The mother nucleus has good crystallinity, and the types and arrangements of substituents that the mother nucleus may have are also limited to a range in which the crystallinity of the specific compound is not impaired. Thus, the charge transportability between the specific compounds is favorable in the photoelectric conversion film, and favorable charge transportability can be maintained even under a low voltage. As a result, in the photoelectric conversion element according to the embodiment of the present invention in which the photoelectric conversion film contains the specific compound, it is considered that the electric field strength dependence of the photoelectric conversion efficiency is suppressed.

In addition, the photoelectric conversion element according to the embodiment of the present invention has the favorable photoelectric conversion efficiency (particularly, the photoelectric conversion efficiency for light having a wavelength of 400 to 700 nm), and a dark current is also suppressed.

Hereinafter, the fact that the electric field strength dependence of the photoelectric conversion efficiency is further suppressed, the photoelectric conversion efficiency is more excellent and/or the dark current is further suppressed in the photoelectric conversion element is also referred to as "the effect of the present invention is more excellent".

FIG. 1 is a schematic cross-sectional view of one embodiment of a photoelectric conversion element according to the embodiment of the present invention.

A photoelectric conversion element 10*a* illustrated in FIG. 1 has a configuration in which a conductive film (hereinafter, also referred to as a lower electrode) 11 functioning as a lower electrode, an electron blocking film 16A, a photoelectric conversion film 12 containing the specific compound described later, and a transparent conductive film (hereinafter, also referred to as an upper electrode) 15 functioning as an upper electrode are laminated in this order.

Figure 2:
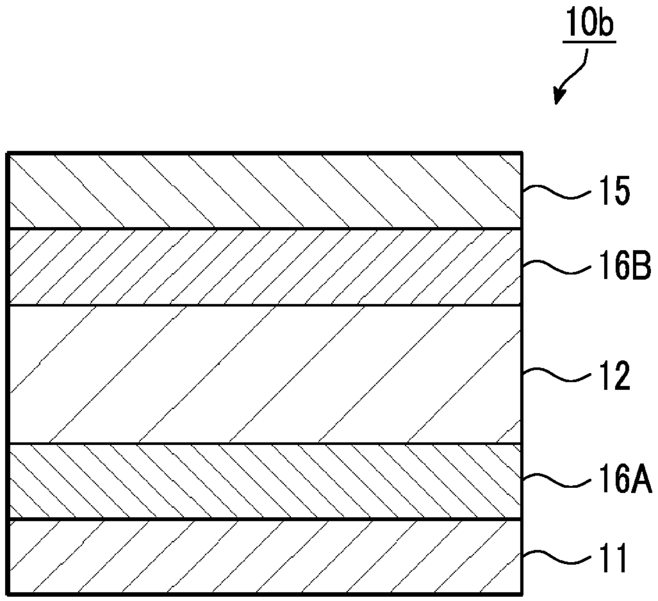
FIG. 2 is a schematic cross-sectional view illustrating a configuration example of the photoelectric conversion element.

FIG. 2 illustrates a configuration example of another photoelectric conversion element. A photoelectric conversion element 10*b* illustrated in FIG. 2 has a configuration in which the electron blocking film 16A, the photoelectric conversion film 12, a hole blocking film 16B, and the upper electrode 15 are laminated on the lower electrode 11 in this order. The lamination order of the electron blocking film 16A, the photoelectric conversion film 12, and the hole blocking film 16B in FIGS. 1 and 2 may be appropriately changed according to the application and the characteristics.

In the photoelectric conversion element 10*a* (or 10*b*), it is preferable that light is incident on the photoelectric conversion film 12 through the upper electrode 15.

In a case where the photoelectric conversion element 10*a* (or 10*b*) is used, a voltage can be applied. In this case, it is preferable that the lower electrode 11 and the upper electrode 15 form a pair of electrodes, and a voltage of $1\times10^{-5}$ to $1\times10^{7}$ V/cm is applied between the pair of electrodes. From the viewpoint of the performance and power consumption, the applied voltage is more preferably $1\times10^{-4}$ to $1\times10^{7}$ V/cm, and still more preferably $1\times10^{-3}$ to $5\times10^{6}$ V/cm.

Regarding a voltage application method, in FIGS. 1 and 2, it is preferable that the voltage is applied such that the electron blocking film 16A side is a cathode and the photoelectric conversion film 12 side is an anode. In a case where the photoelectric conversion element 10*a* (or 10*b*) is used as an optical sensor, or also in a case where the photoelectric conversion element 10*a* (or 10*b*) is incorporated in an imaging element, the voltage can be applied by the same method.

As described in detail below, the photoelectric conversion element 10*a* (or 10*b*) can be suitably applied to applications of the imaging element.

Hereinafter, the form of each layer constituting the photoelectric conversion element according to the embodiment of the present invention will be described in detail.

[Photoelectric Conversion Film]

The photoelectric conversion film is a film containing a specific compound.

Hereinafter, the specific compound will be described in detail.

<Compound (Specific Compound) Represented by Formula (1)>

The specific compound is a compound represented by Formula (1) described below.

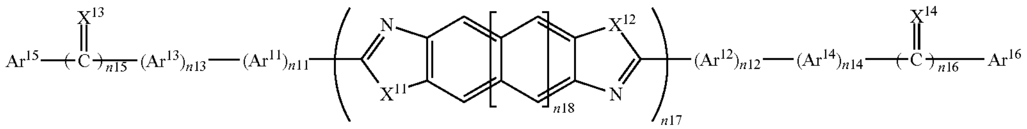

(1)

In Formula (1), $X^{11}$ and $X^{12}$ each independently represent a sulfur atom or an oxygen atom.

Among these, $X^{11}$ and $X^{12}$ are preferably sulfur atoms.

$Ar^{11}$ to $Ar^{16}$ each independently represent a monocyclic, bicyclic, or tricyclic aromatic ring group.

In addition, the aromatic ring group may have one or more groups selected from the group consisting of a halogen atom (preferably a fluorine atom), a cyano group, and a trifluoromethyl group as a substituent.

In other words, the aromatic ring group may not have a substituent other than one or more groups selected from the group consisting of a halogen atom (preferably a fluorine atom), a cyano group, and a trifluoromethyl group.

The total number of the one or more groups that the aromatic ring group represented by $Ar^{11}$ to $Ar^{16}$ has as a substituent is, for example, 0 to 5 independently.

$Ar^{11}$ to $Ar^{14}$ are divalent aromatic ring groups.

$Ar^{15}$ to $Ar^{16}$ are monovalent aromatic ring groups.

The aromatic ring groups represented by $Ar^{11}$ to $Ar^{16}$ are each independently preferably a nitrogen-containing aromatic ring group having one or more (for example, 1 to 3) nitrogen atoms as ring member atoms.

$Ar^{11}$ and $Ar^{12}$ are also preferably the same aromatic ring group as each other, $Ar^{13}$ and $Ar^{14}$ are also preferably the same aromatic ring group as each other, and $Ar^{15}$ and $Ar^{16}$ are also preferably the same aromatic ring group as each other. The case where the aromatic ring groups are the same as each other means that aromatic ring groups to be compared are the same group as each other, and it also means that the positional relationships of the individual structures constituting those aromatic ring groups (a hetero atom and a substituent which the aromatic ring group may have) are the same with reference to the mother nucleus of the specific compound (partial structure enclosed in parentheses with n17 in Formula (1)).

From the viewpoint that the effects of the present invention are more excellent, $Ar^{11}$ to $Ar^{14}$ are each independently preferably a group represented by any of Formula (2) to Formula (7).

(2)

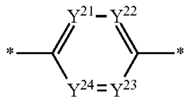

(3)

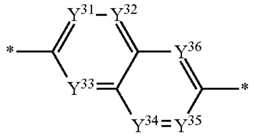

(4)

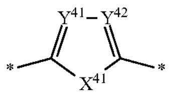

-continued (5)

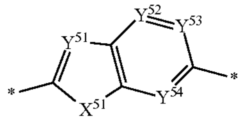

(6)

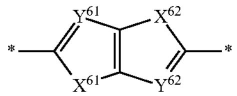

(7)

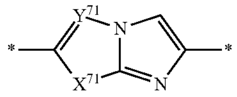

In Formula (2) to Formula (7), * represents a bonding position.

Regarding the two bonding positions present in each of Formula (2) to Formula (7), a bonding position (*) on the left side may be bonded to the mother nucleus side, and a bonding position (*) on the right side may be bonded to the mother nucleus side.

In Formula (2) to Formula (7), a group represented by $Y^N$ represents —CR═ or a nitrogen atom. "N" in $Y^N$ is an integer.

That is, in Formula (2) to Formula (7), $Y^{21}$ to $Y^{24}$, $Y^{31}$ to $Y^{36}$, $Y^{41}$ and $Y^{42}$, $Y^{51}$ to $Y^{54}$, $Y^{61}$ and $Y^{62}$, and $Y^{71}$ each independently represent —CR═ or a nitrogen atom (—N═).

R in —CR═ represents a hydrogen atom, a halogen atom (preferably a fluorine atom), a cyano group, or a trifluoromethyl group.

In Formula (2) to Formula (7), a group represented by $X^N$ represents a sulfur atom (—S—), an oxygen atom (—O—), or a selenium atom (—Se—). "N" in $X^N$ is an integer.

That is, in Formula (2) to Formula (7), $X^{41}$, $X^{51}$, $X^{61}$ and $X^{62}$, and $X^{71}$ each independently represent a sulfur atom (—S—), an oxygen atom (—O—), or a selenium atom (—Se—), and a sulfur atom or an oxygen atom is preferable.

From the viewpoint that the effect of the present invention is more excellent, $Ar^{15}$ and $Ar^{16}$ are each independently preferably a group represented by any of Formula (8) to Formula (15) and Formula (47) to Formula (53).

(8)

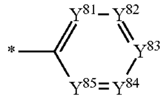

(9)

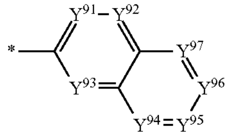

-continued (10)

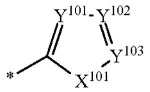

(11)

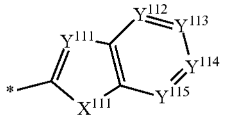

(12)

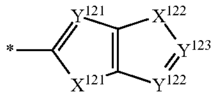

(13)

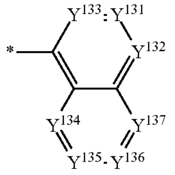

(14)

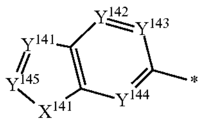

(15)

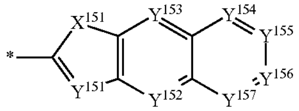

(47)

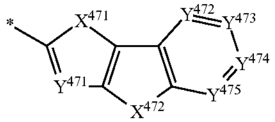

(48)

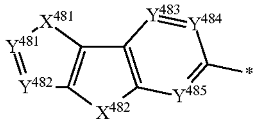

(49)

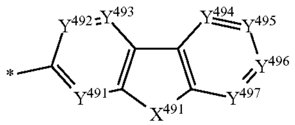

(50)

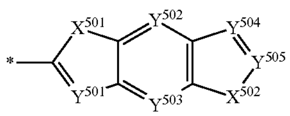

(51)

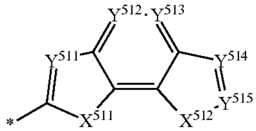

(52)

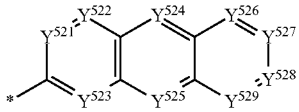

-continued (53)

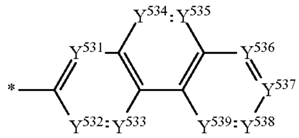

In Formula (8) to Formula (15) and Formula (47) to Formula (53), * represents a bonding position.

In Formula (8) to Formula (15) and Formula (47) to Formula (53), a group represented by $Y^N$ represents —CR═ or a nitrogen atom. "N" in $Y^N$ is an integer.

That is, in Formula (8) to Formula (15) and Formula (47) to Formula (53), $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$, and $Y^{531}$ to $Y^{539}$ each independently represent —CR═ or a nitrogen atom (—N═).

R in —CR═ represents a hydrogen atom, a halogen atom (preferably a fluorine atom), a cyano group, or a trifluoromethyl group.

Among these, as $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$, and $Y^{531}$ to $Y^{539}$, —CR═ is preferable, and —CR═ of which R is a hydrogen atom is more preferable. In other words, as $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$, and $Y^{531}$ to $Y^{539}$, —CH═ is preferable.

In Formula (8) to Formula (15) and Formula (47) to Formula (53), a group represented by $X^N$ represents a sulfur atom (—S—), an oxygen atom (—O—), or a selenium atom (—Se—). "N" in $X^N$ is an integer.

That is, in Formula (8) to Formula (15) and Formula (47) to Formula (53), $X^{101}$, $X^{111}$, $X^{121}$ and $X^{122}$, $X^{141}$, $X^{151}$, $X^{471}$ to $X^{472}$, $X^{481}$ and $X^{482}$, $X^{491}$, $X^{501}$ and $X^{502}$, and $X^{511}$ and $X^{512}$ are each independently a sulfur atom (—S—), an oxygen atom (—O—), or a selenium atom (—Se—), and a sulfur atom or an oxygen atom is preferable.

In Formula (1), $X^{13}$ and $X^{14}$ each independently represent an oxygen atom (═O) or a sulfur atom (═S), and an oxygen atom is preferable.

$X^{13}$ and $X^{14}$ are preferably the same atom as each other.

In Formula (1), n11 to n16 each independently represent 0 or 1.

n11 and n12 are preferably the same value as each other, n13 and n14 are preferably the same value as each other, and n15 and n16 are preferably the same value as each other.

In a case where n11 to n16 are each 0, a group enclosed in parentheses with n11 to n16 attached does not exist. For example, in a case where n11 is 1 and n13 and n15 are each 0, $Ar^{11}$ and $Ar^{15}$ are bonded by a single bond in Formula (1).

Here, in a case where all of n11 to n16 are 0 and n17 is 1, the aromatic ring groups represented by $Ar^{15}$ and $Ar^{16}$ are the tricyclic aromatic ring groups.

In addition, in a case where the specific compound is applied to Formula (1), and a specific compound that enables both interpretations of the interpretation that n11 is 1 and n13 is 0 and the interpretation that n11 is 0 and n13 is 1 exists, it is preferable to interpret that the specific compound is a compound in Formula (1) in which n11 is 1 and n13 is 0.

Similarly, in a case where the specific compound is applied to Formula (1), and a compound that enables both interpretations of the interpretation that n12 is 1 and n14 is 0 and the interpretation that n12 is 0 and n14 is 1 exists, it is preferable to interpret that the specific compound is a compound in Formula (1) in which n12 is 1 and n14 is 0.

In Formula (1), n17 represents 1 or 2.

In a case where n17 is 2, the mother nucleus of the specific compound has a structure in which two four- or five-membered aromatic ring groups are bonded by a single bond.

In a case where n17 is 2, $X^{11}$ and $X^{12}$ presenting outside the mother nucleus are also preferably the same atom as each other.

In a case where n17 is 2, $X^{11}$ and $X^{12}$ presenting inside the mother nucleus are also preferably the same atom as each other.

In Formula (1), n18 represents 1 or 2.

Among these, the following examples are exemplified as preferable combinations of n11 to n18 in Formula (1).

Example A: A combination in which n11 and n12 represent 1, n13 to n16 represent 0, n17 represents 1, and n18 represents 1 or 2.

Example B: A combination in which n11 to n14 represent 1, n15 and n16 represent 0, n17 represents 1, and n18 represents 1 or 2.

Example C: A combination in which n11 to n16 represent 0, n17 represents 1, and n18 represents 1 or 2.

Example D: a combination in which n11 and n12 represent 1, n13 and n14 represent 0, n15 and n16 represent 1, n17 represents 1, and n18 represents 1 or 2.

Example E: A combination in which n11 to n14 represent 0, n15 and n16 each independently represent 0 or 1, n17 represents 2, and n18 represents 1.

Among these, from the viewpoint that the effect of the present invention is more excellent, the specific compound is preferably a compound represented by any of Formula (16) to Formula (46) and Formula (54) to Formula (60) represented below.

(16)

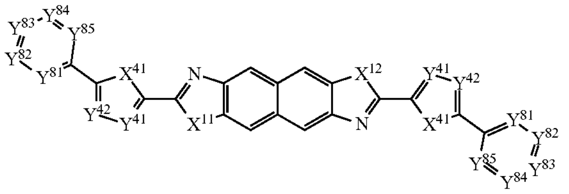

(17)

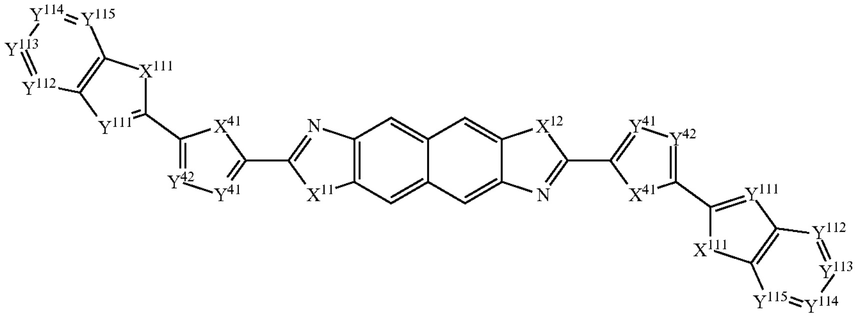

(18)

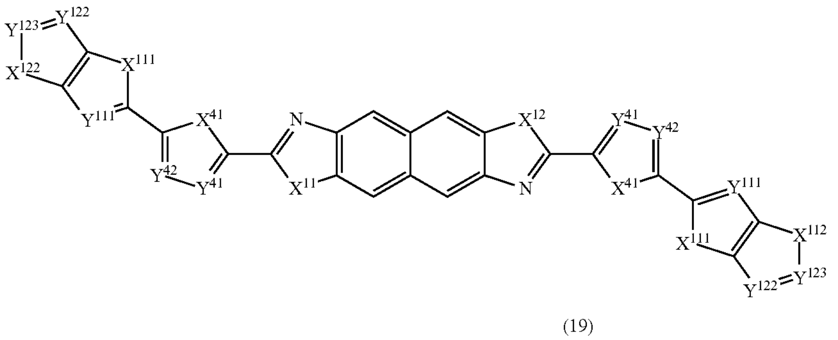

(19)

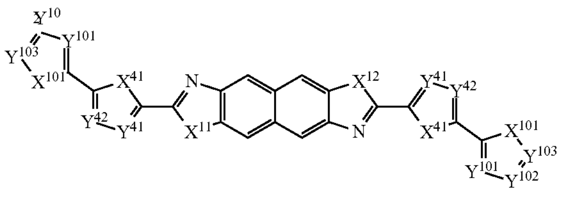

-continued
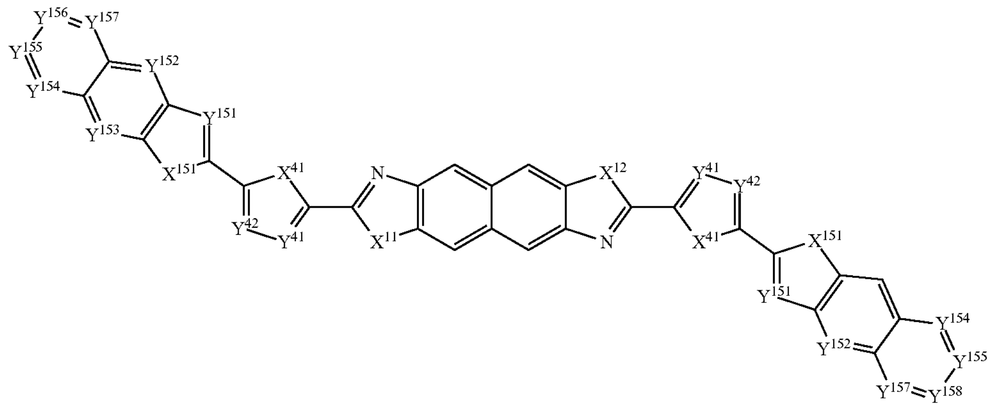
(20)
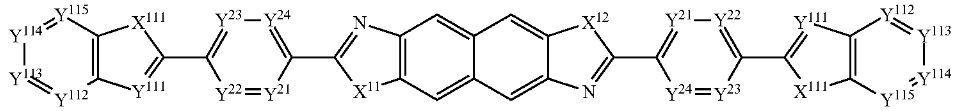
(21)
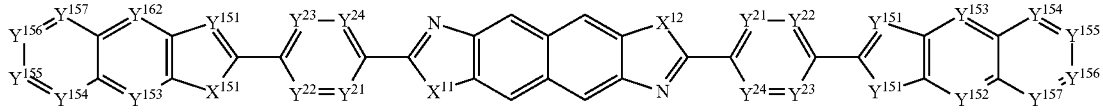
(22)
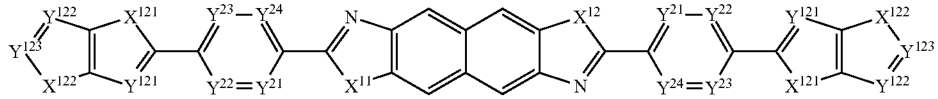
(23)
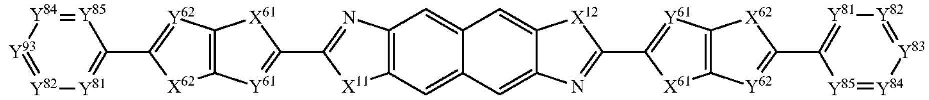
(24)
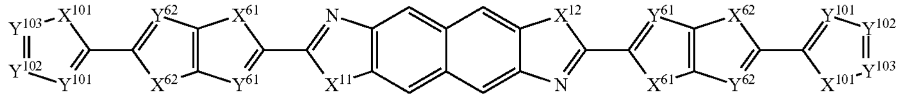
(25)
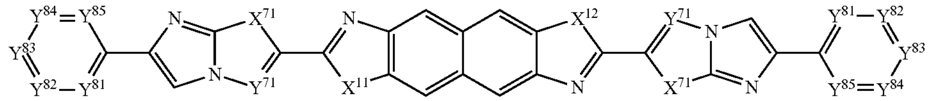
(26)
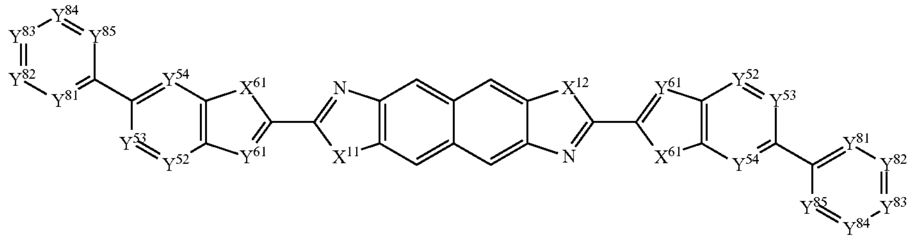
(27)
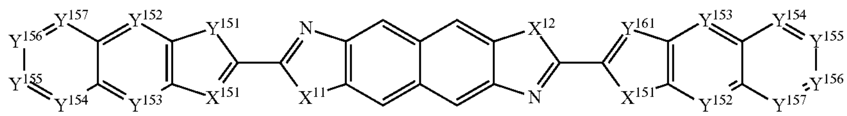
(28)

-continued
(29)
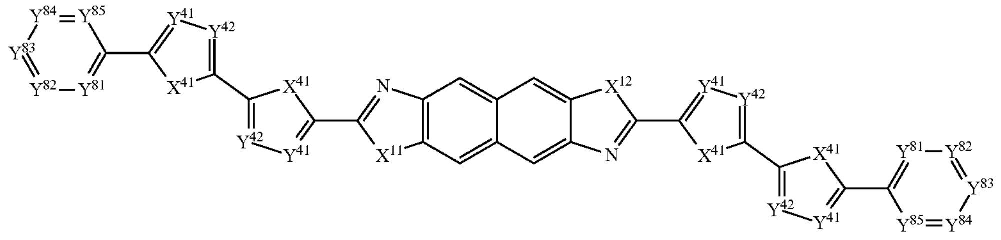
(30)
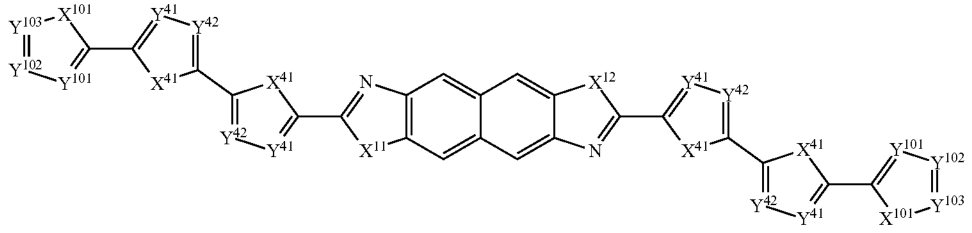
(31)
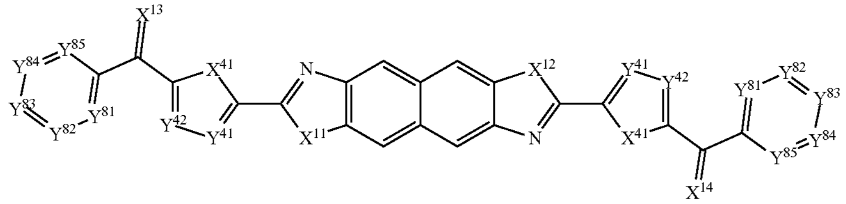
(32)
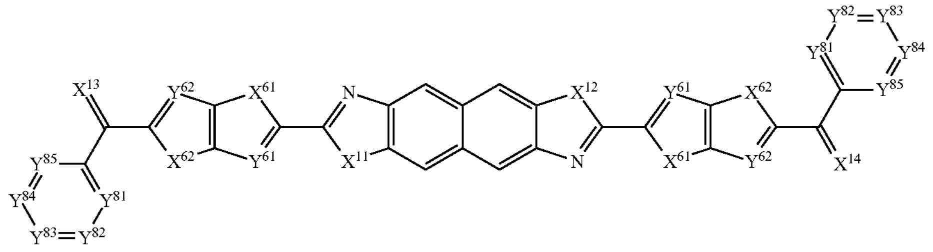
(33)
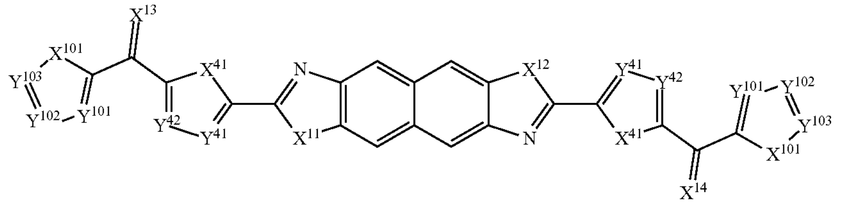
(34)
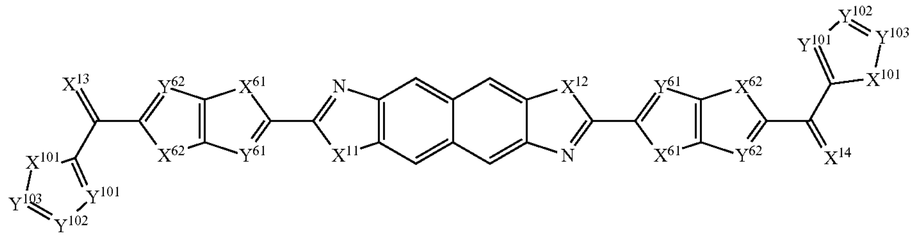

(35)
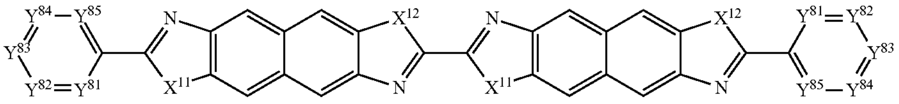
(36)
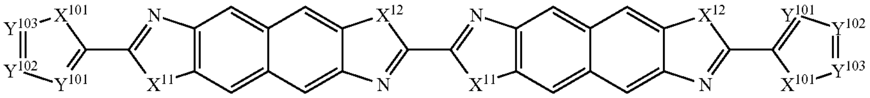
(37)
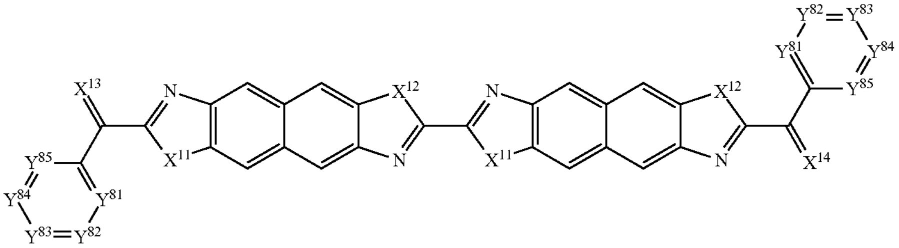
(38)
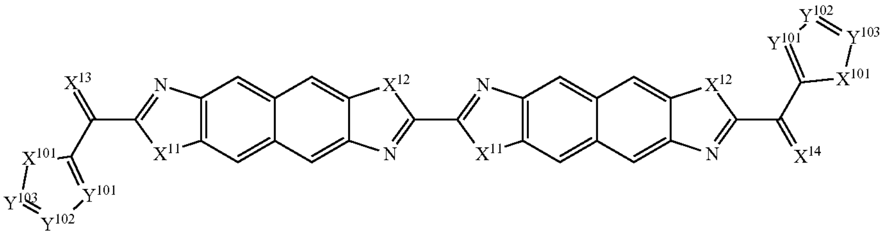
(39)
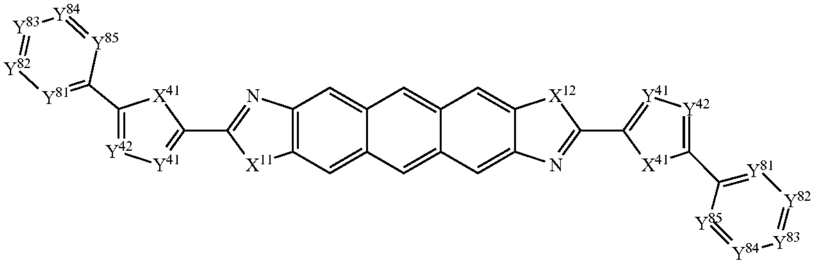
(40)
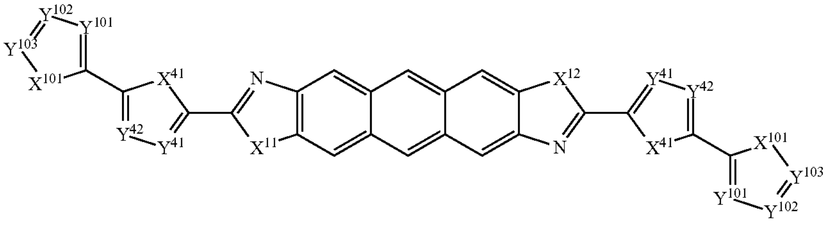
(41)
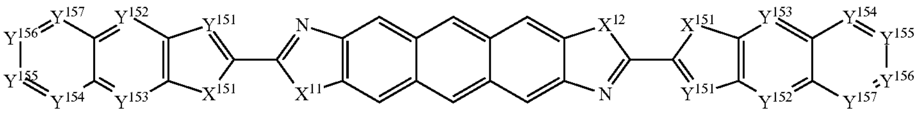
(42)
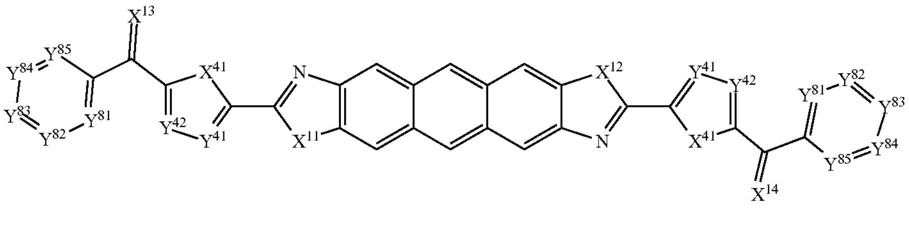

-continued
(43)
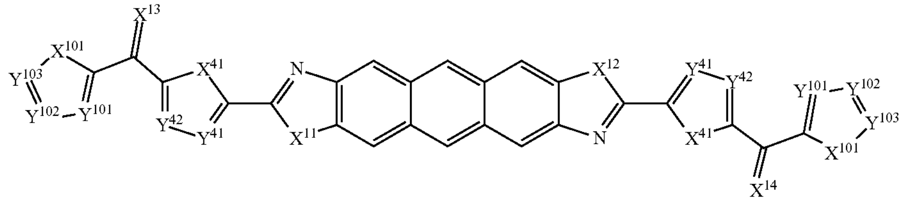
(44)
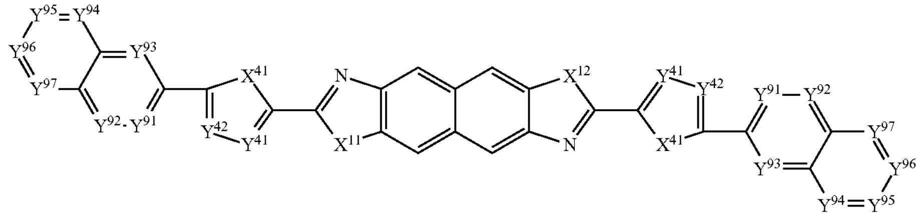
(45)
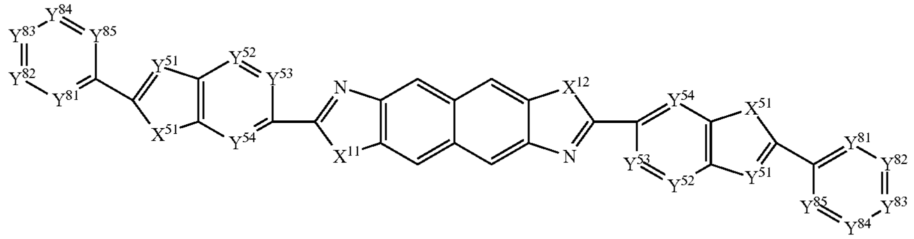
(46)
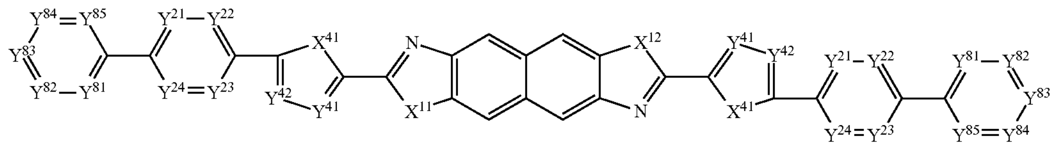
(54)
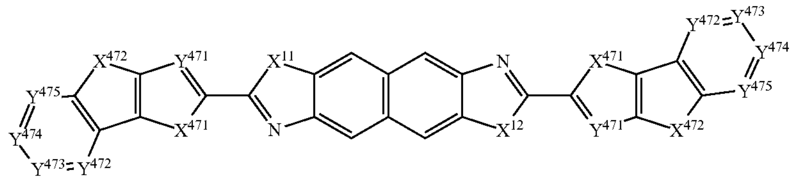
(55)
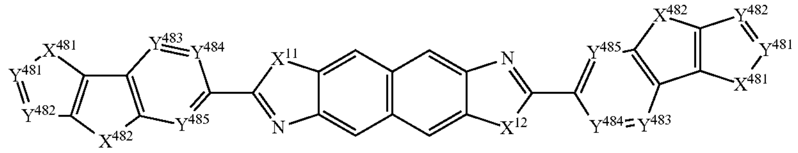
(56)
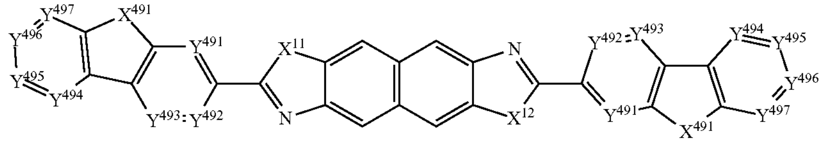
(57)
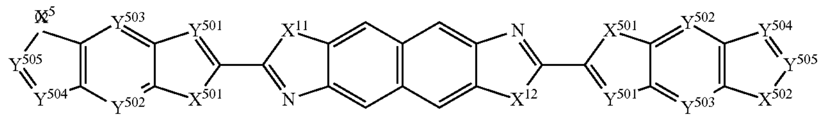

-continued (58)

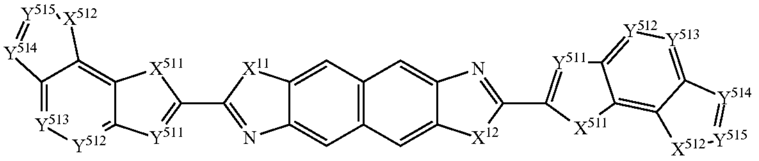

(59)

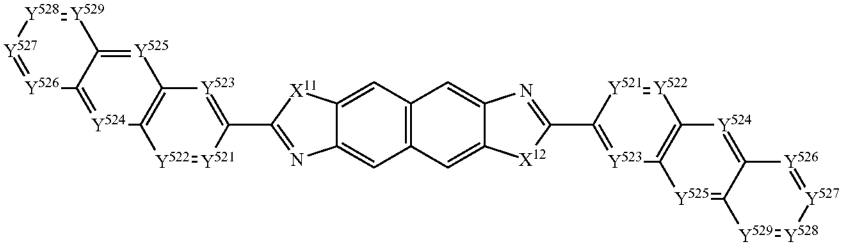

(60)

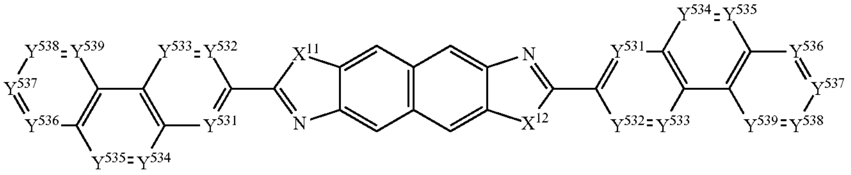

In Formula (16) to Formula (46) and Formula (54) to Formula (60), a group represented by $Y^N$ represents —CR═ or a nitrogen atom. "N" in $Y^N$ is an integer.

That is, in Formula (16) to Formula (46), $Y^{21}$ to $Y^{24}$, $Y^{41}$ and $Y^{42}$, $Y^{51}$ to $Y^{54}$, $Y^{61}$ and $Y^{62}$, $Y^{71}$, $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{528}$, and $Y^{531}$ to $Y^{539}$ each independently represent —CR═ or a nitrogen atom (—N═).

R in —CR═ represents a hydrogen atom, a halogen atom (preferably a fluorine atom), a cyano group, or a trifluoromethyl group.

Among these, as $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$, and $Y^{531}$ to $Y^{539}$, —CR═ is preferable, and —CR═ of which R is a hydrogen atom is more preferable. In other words, as $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$, and $Y^{531}$ to $Y^{539}$, —CH═ is preferable.

In Formula (16) to Formula (46) and Formula (54) to Formula (60), $X^{11}$ and $X^{12}$ each independently represent a sulfur atom (—S—) or an oxygen atom (—O—).

In Formula (16) to Formula (46), $X^{13}$ and $X^{14}$ each independently represent a sulfur atom (═S) or an oxygen atom (═O).

In Formula (16) to Formula (46), a group represented by $X^N$ except $X^{11}$ to $X^{14}$ is represented by a sulfur atom (—S—), an oxygen atom (—O—), or a selenium atom (—Se). "N" in $X^N$ is an integer.

In Formula (16) to Formula (46) and Formula (54) to Formula (60), $X^{41}$, $X^{51}$, $X^{61}$ and $X^{62}$, $X^{71}$, $X^{101}$, $X^{111}$, $X^{121}$ and $X^{122}$, $X^{151}$, $X^{471}$, $X^{481}$ and $X^{482}$, $X^{491}$, $X^{501}$ and $X^{502}$, and $X^{511}$ and $X^{512}$ are each independently a sulfur atom (—S—), an oxygen atom (—O—), or a selenium atom (—Se—), and a sulfur atom or an oxygen atom is preferable.

The specific compound (in particular, in a case where the specific compound is used as a n-type material described later) preferably satisfies at least one of a requirement of containing an aromatic ring group including a —N═ group in a ring structure as $Ar^{11}$ and $Ar^{12}$, or a requirement in which n15 and n16 are 1, and $Ar^{15}$ and $Ar^{16}$ are each preferably a group represented by Formula (8) in which $Y^{81}$ to $Y^{85}$ are each —CF═, —C(CN)═, or —N═.

The specific compound (in particular, in a case where the compound is used as a p-type material described later) is preferably the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y^{111}$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (29) in which $Y^{41}$ and $Y^{42}$ and $Y^{81}$ to $Y^{85}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom.

In addition, the notation of the above-described compound indicates an aspect in which a group represented by $Y^N$ (N is a numerical value) in each formula is —CR═(R represents a hydrogen atom). More specifically, for example, the "compound represented by Formula (16) in which $Y^{41}$ and $Y^{42}$ and $Y^{81}$ to $Y^{85}$ are each —CR═, and R is a hydrogen atom" means a compound in which $Y^{41}$ and $Y^{42}$ and $Y^{81}$ to $Y^{85}$ are each —CR═ in Formula (16) (R is a hydrogen atom).

The specific compound (in particular, in a case where the specific compound is used as a n-type material described later) is preferably the compound represented by any of Formula (16), Formula (31), Formula (32), Formula (35), Formula (37), Formula (39), and Formula (42).

Specific examples of the specific compound will be described below.

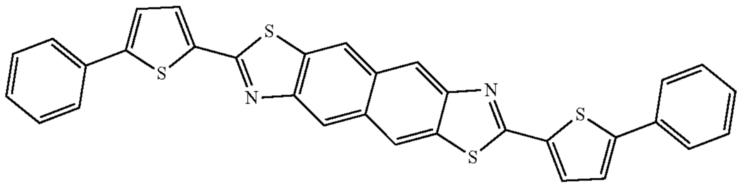

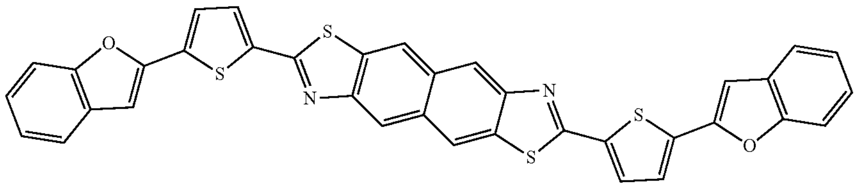

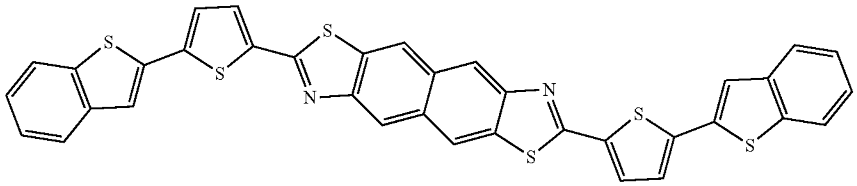

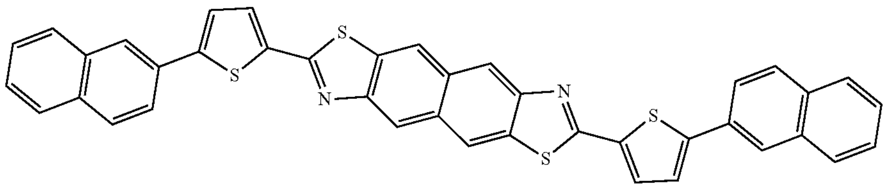

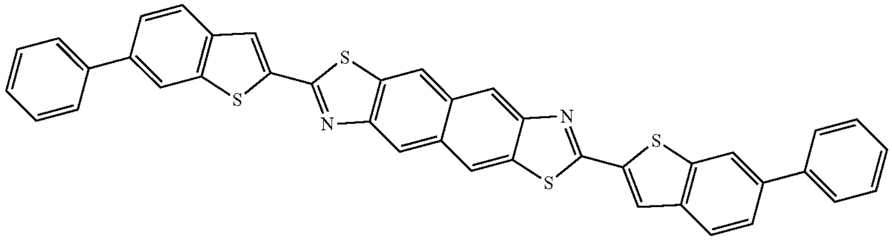

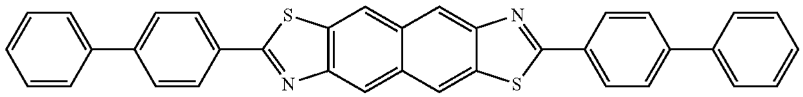

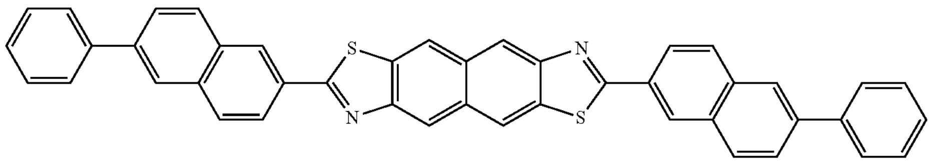

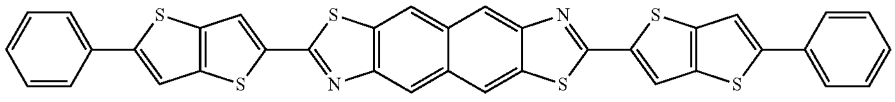

-continued
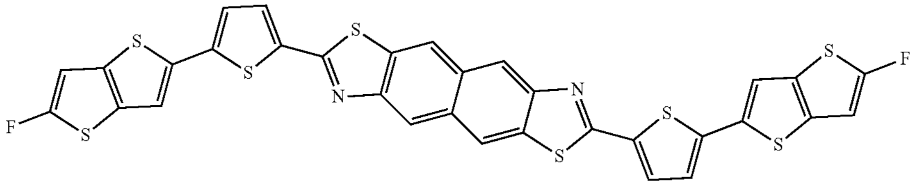
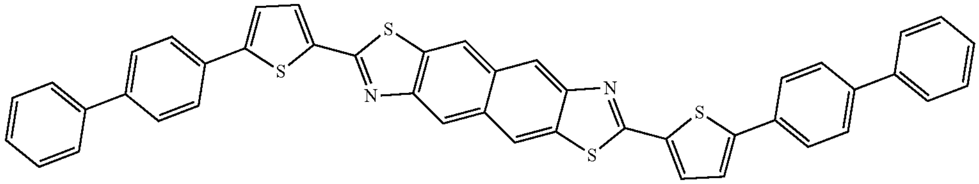
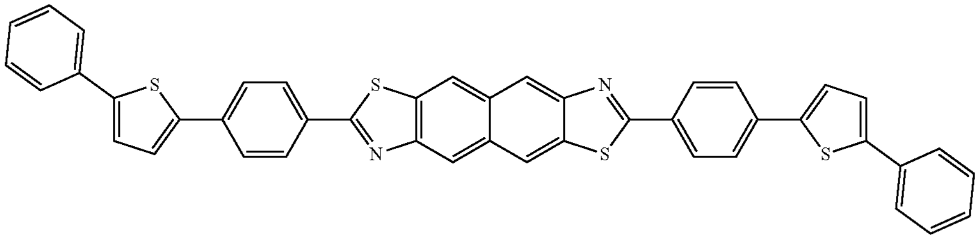
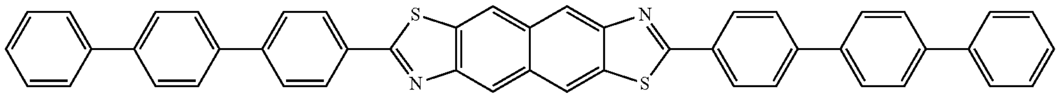
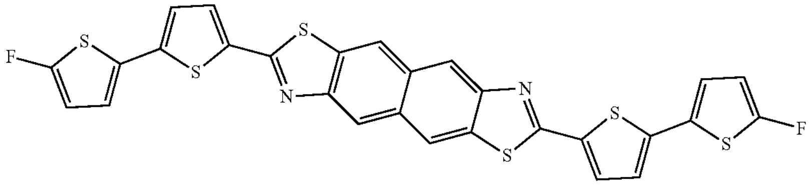
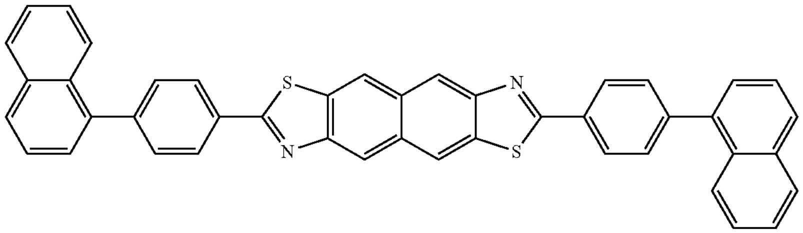
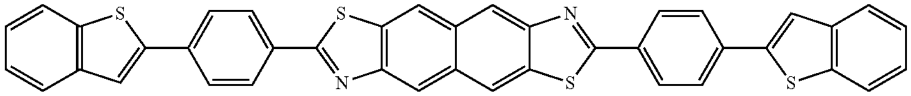
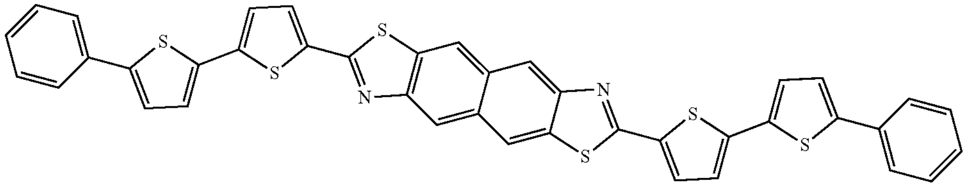
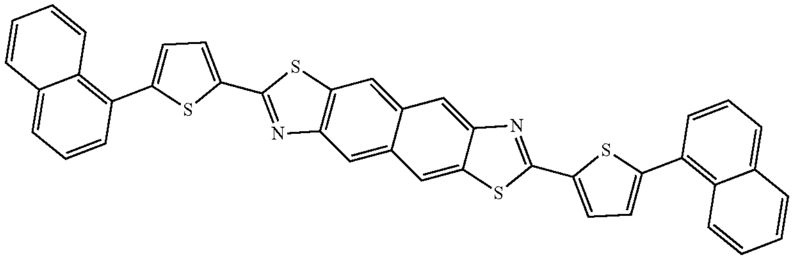

-continued
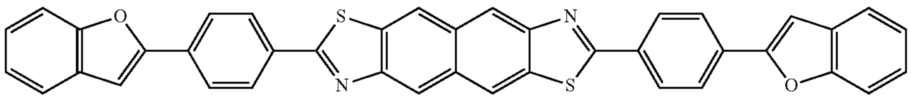
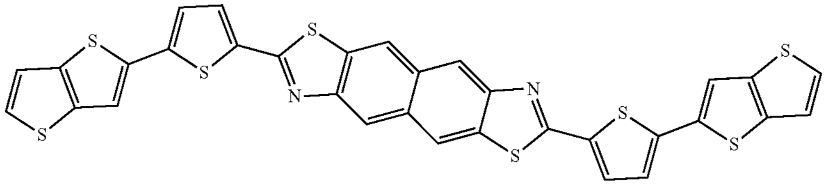
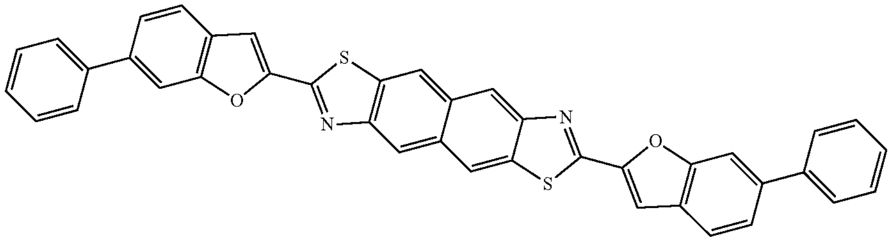
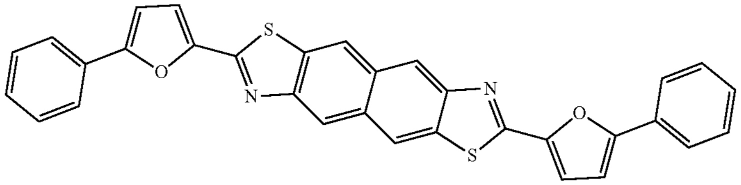
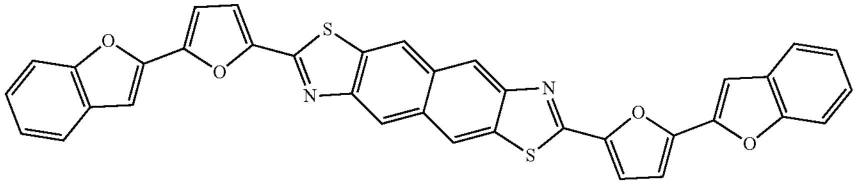
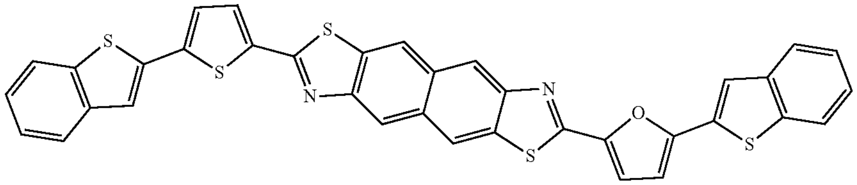
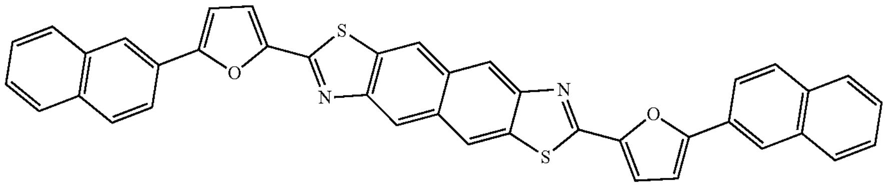
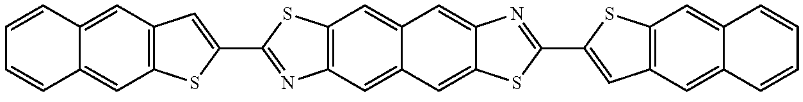
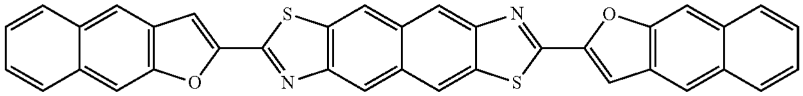
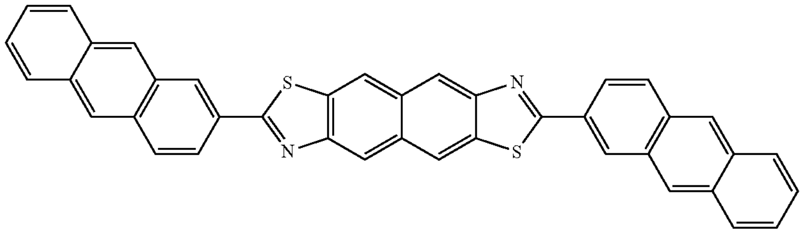

-continued
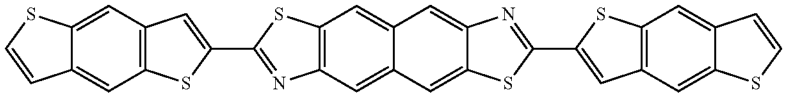
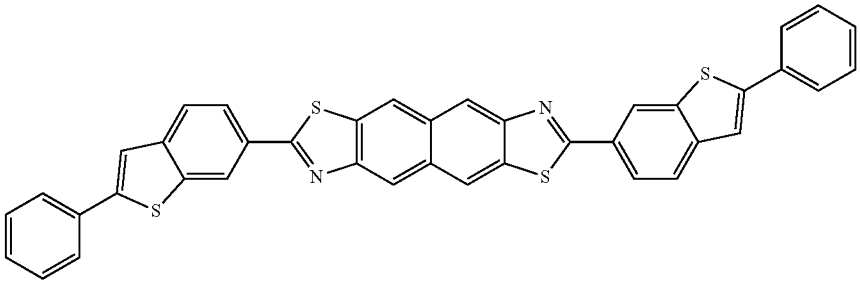
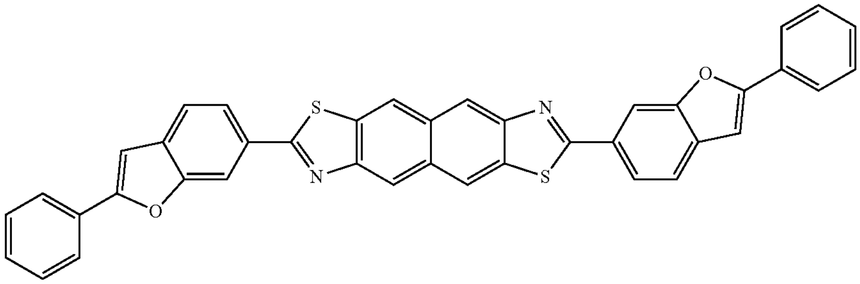
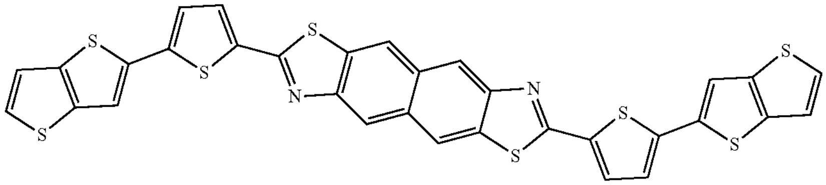
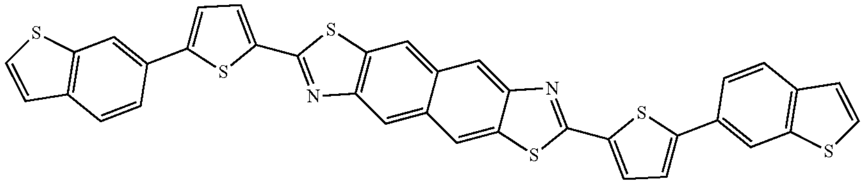
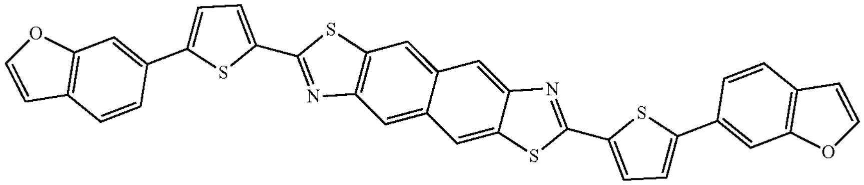
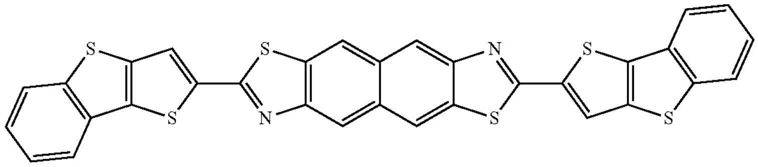
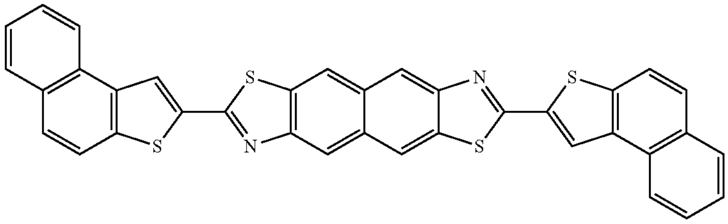

-continued
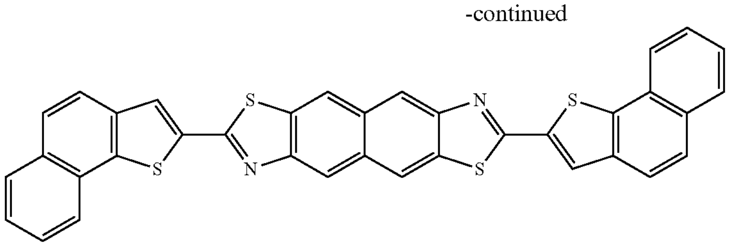
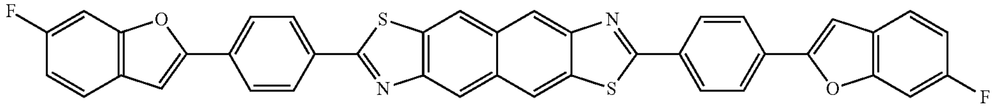
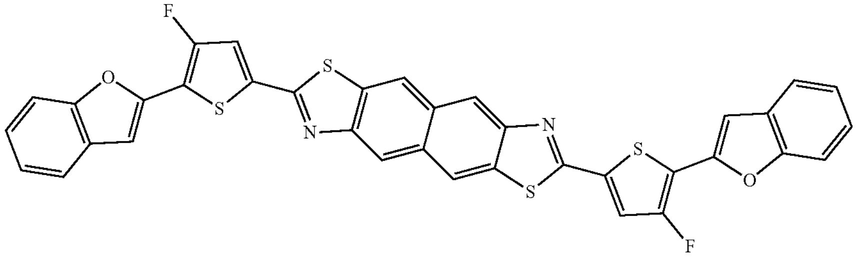
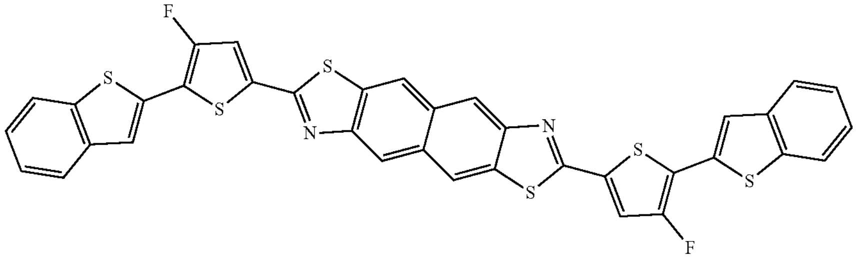
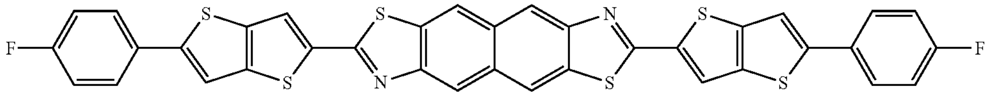
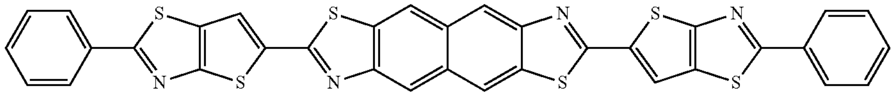
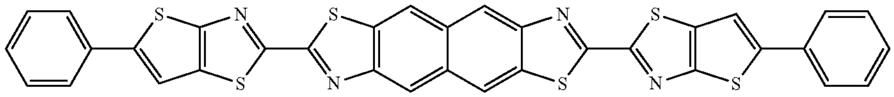
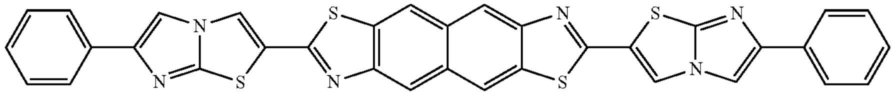
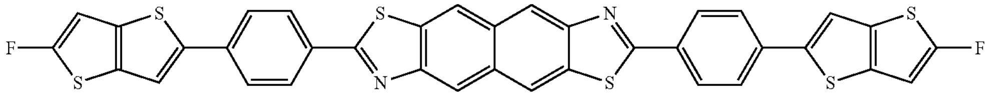
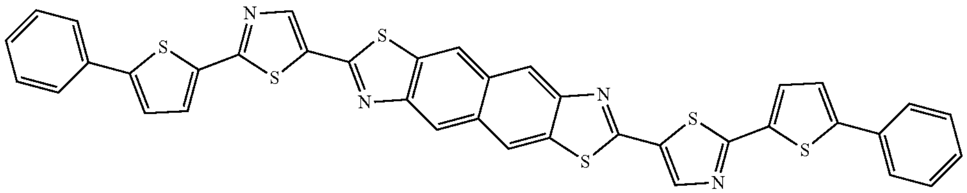
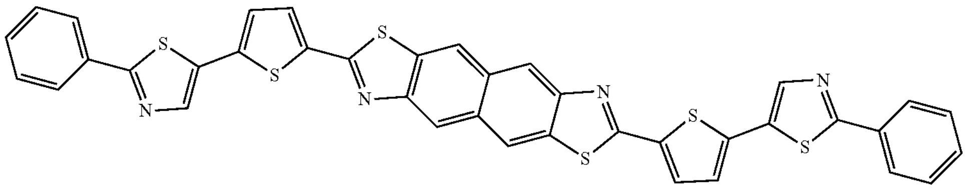

-continued
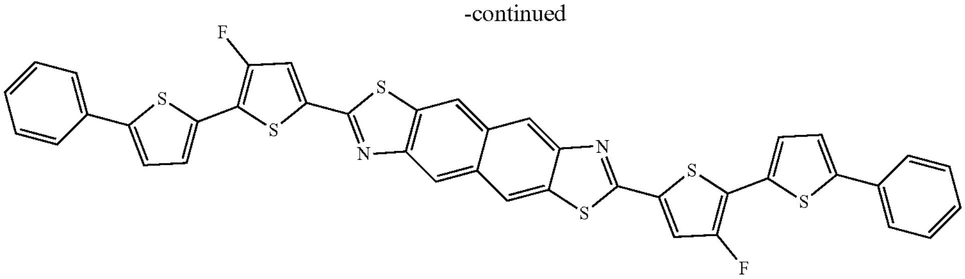
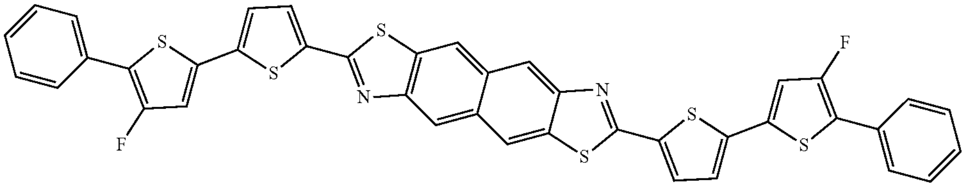
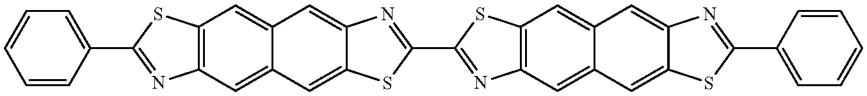
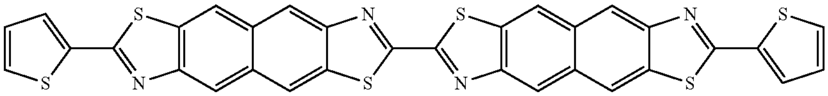
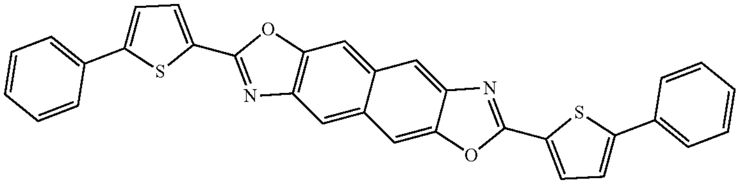
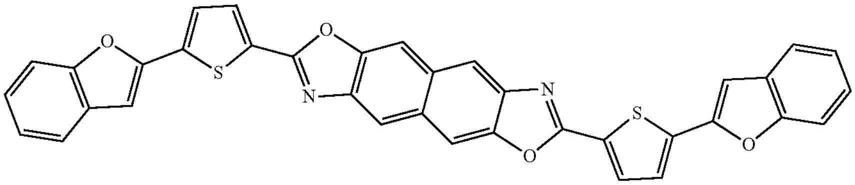
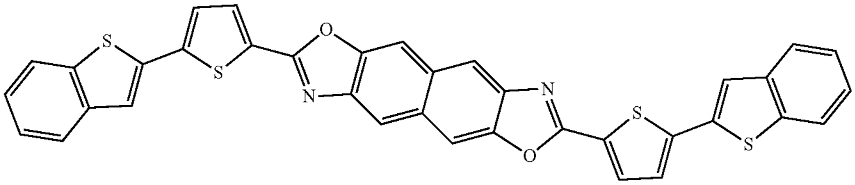
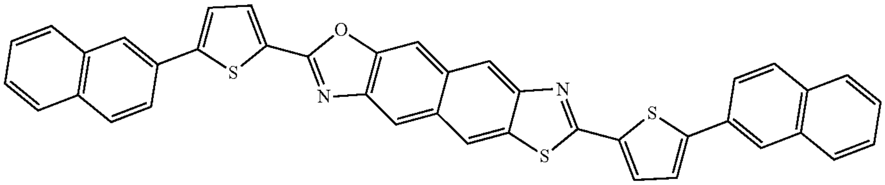
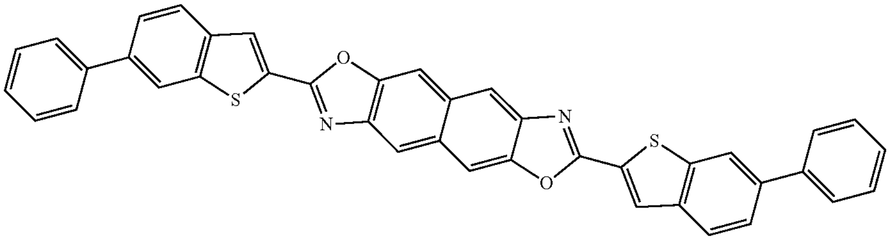
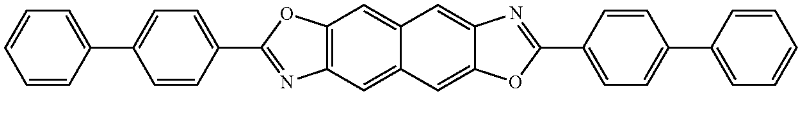

-continued
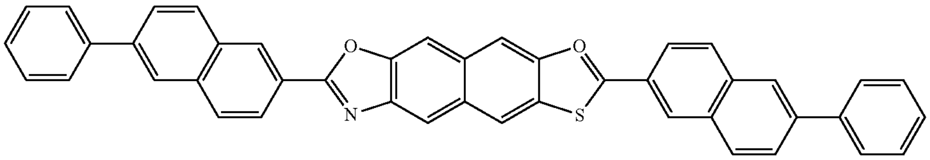
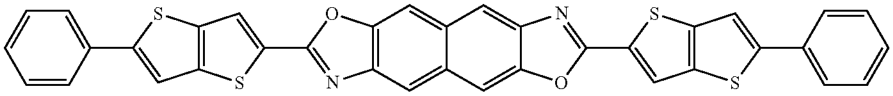
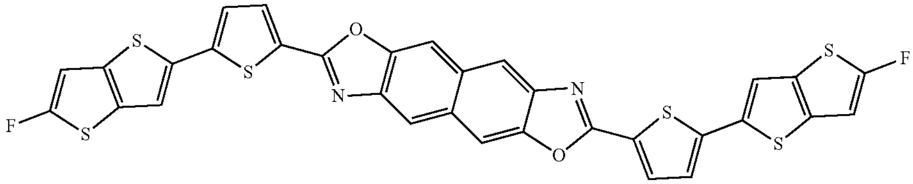
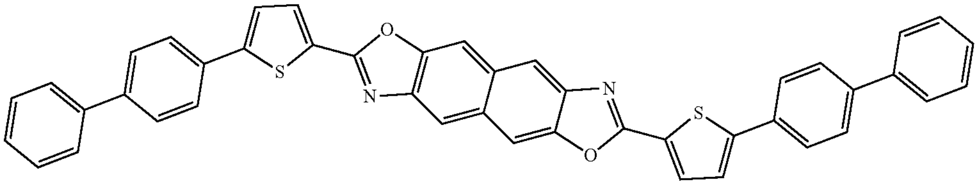
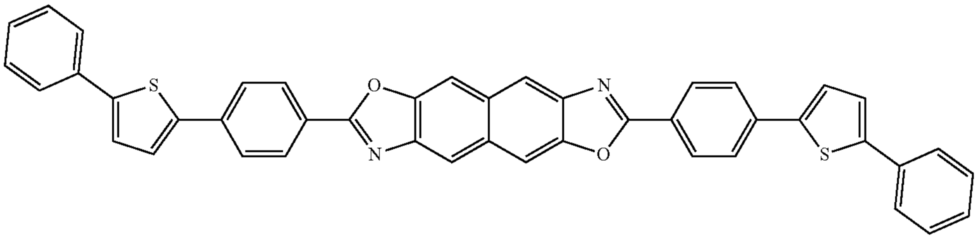
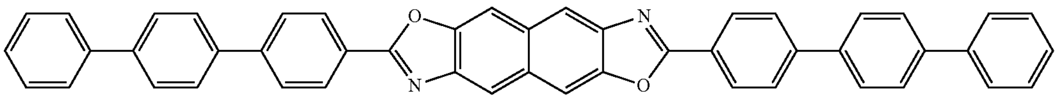
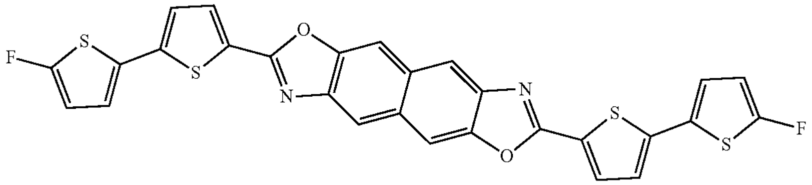
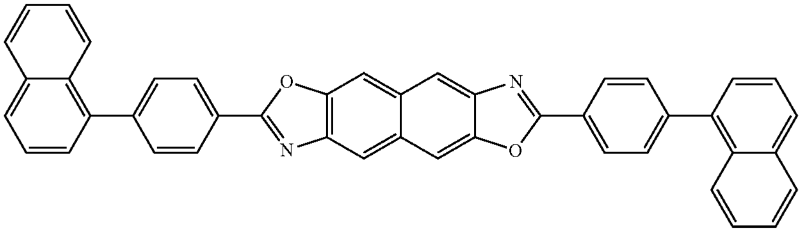
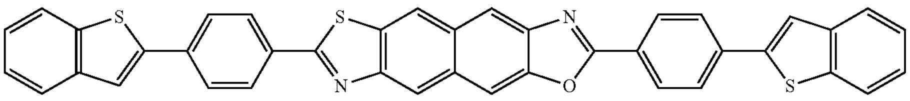
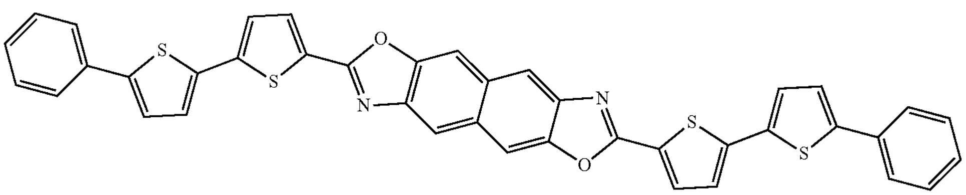

-continued
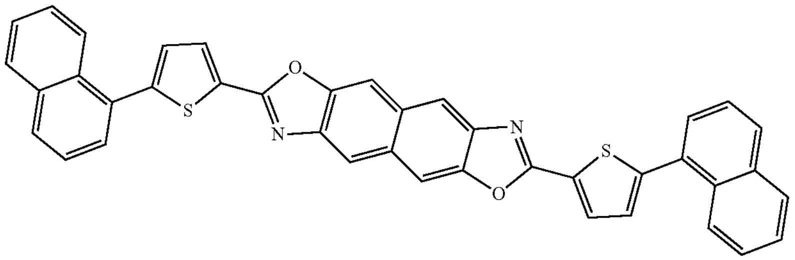
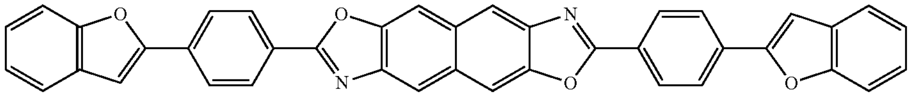
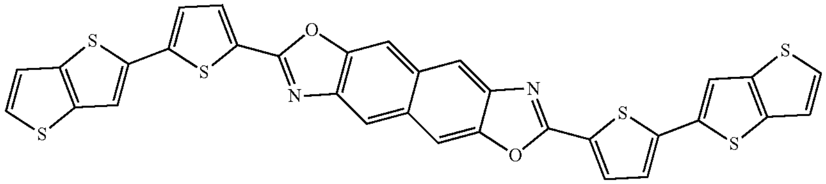
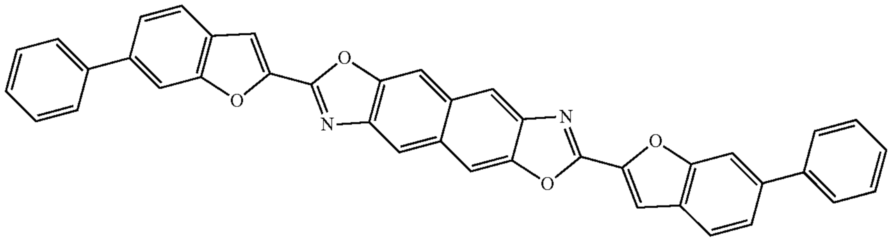
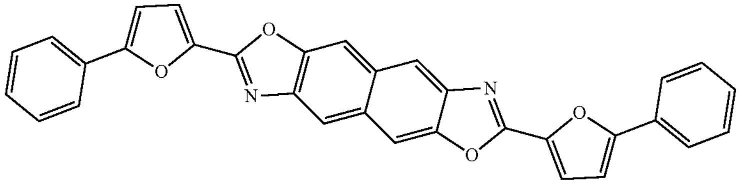
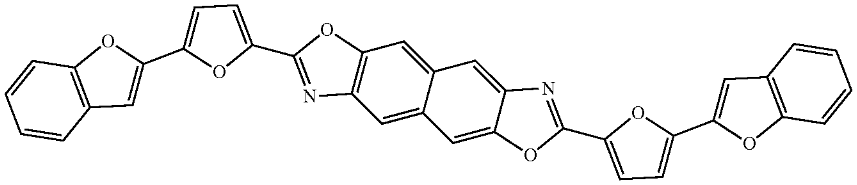
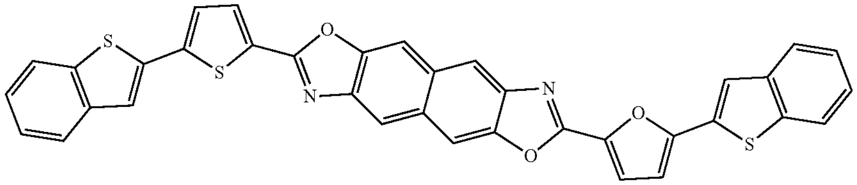
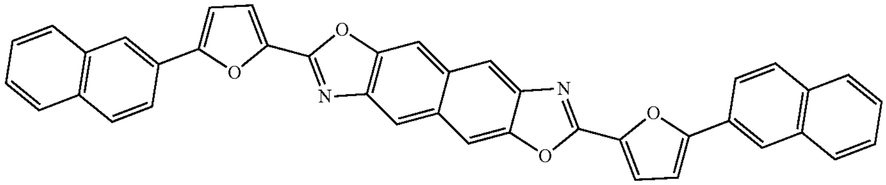
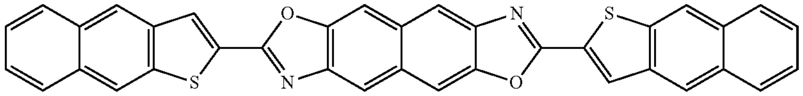
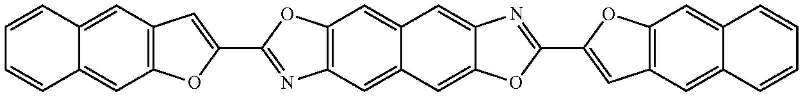

-continued
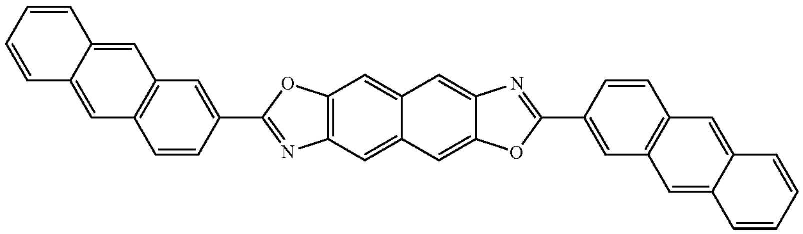
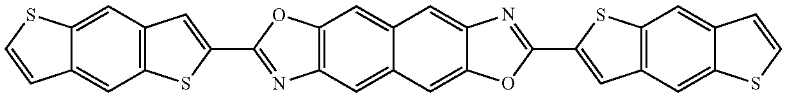
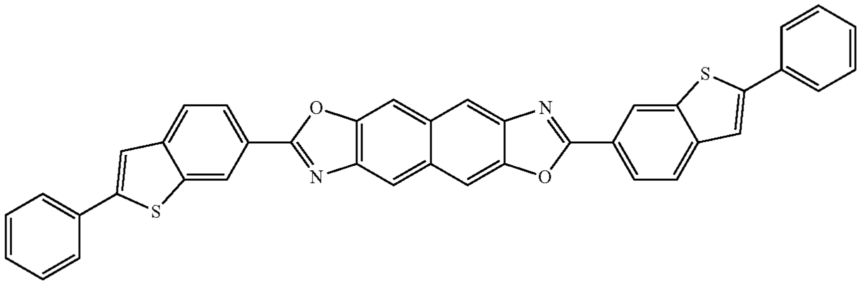
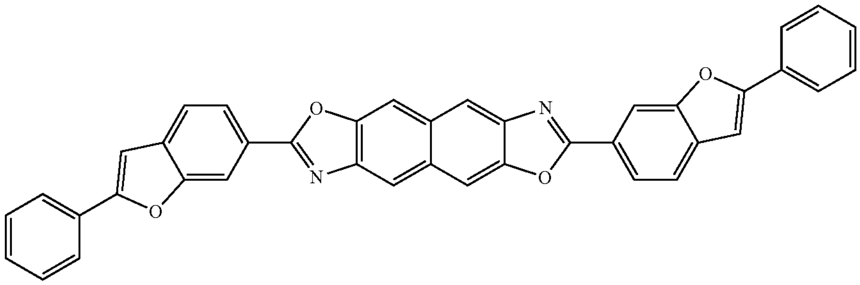
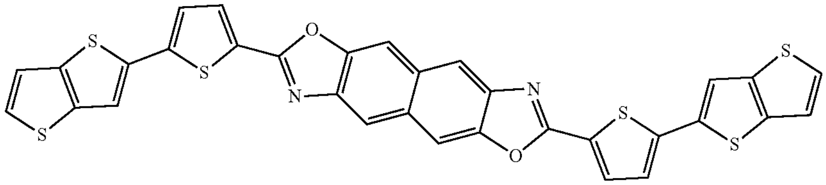
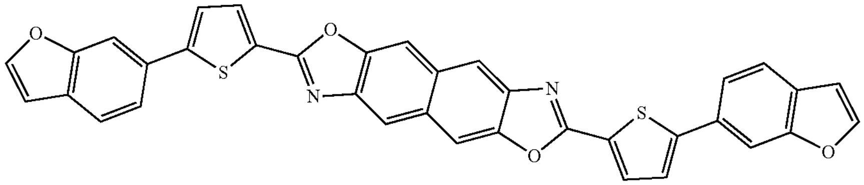
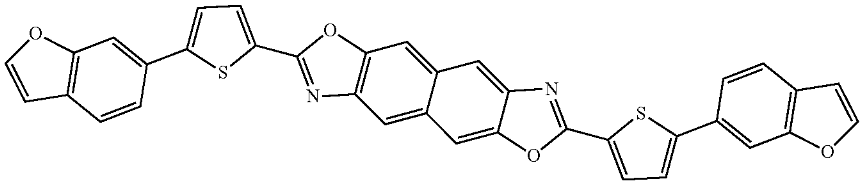
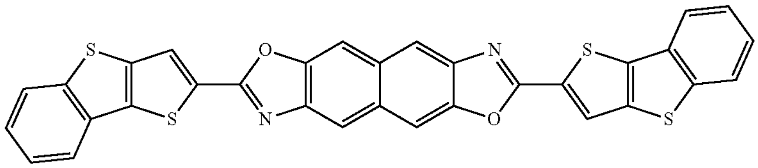

-continued
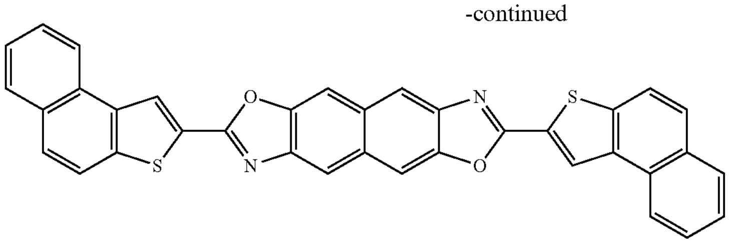
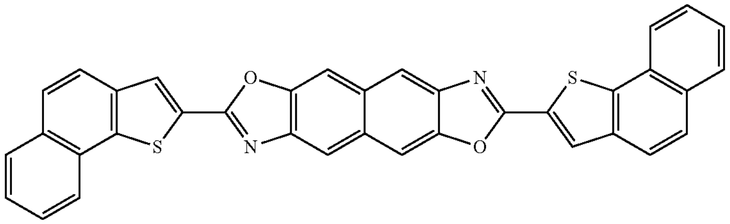
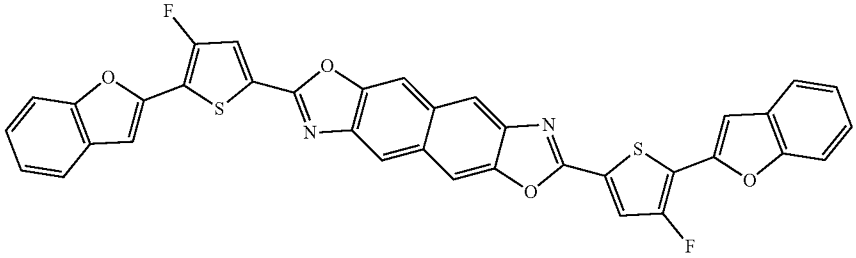
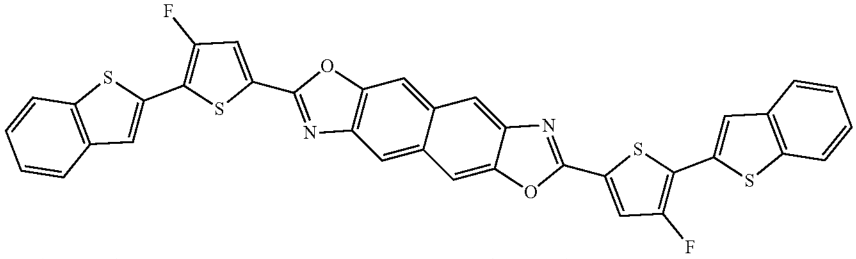
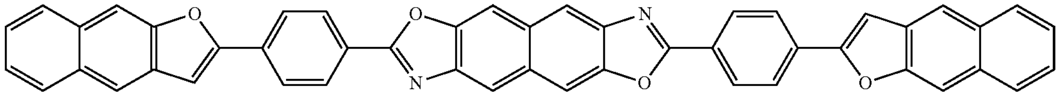
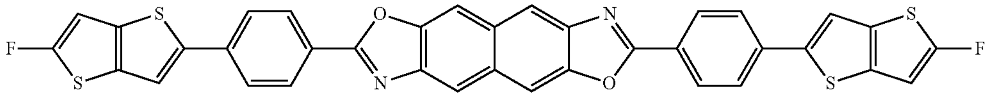
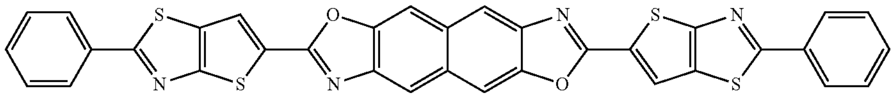
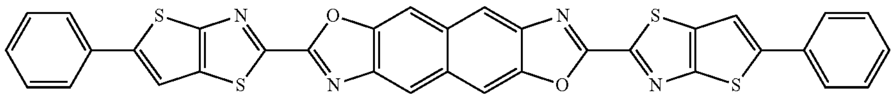
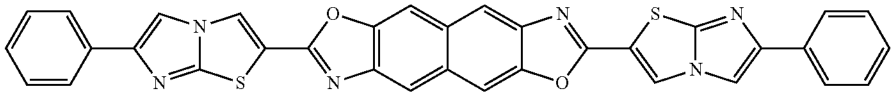
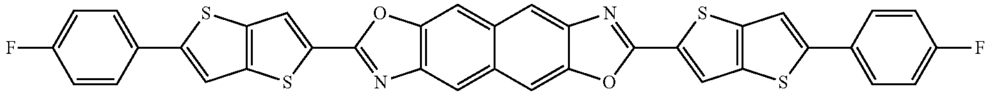
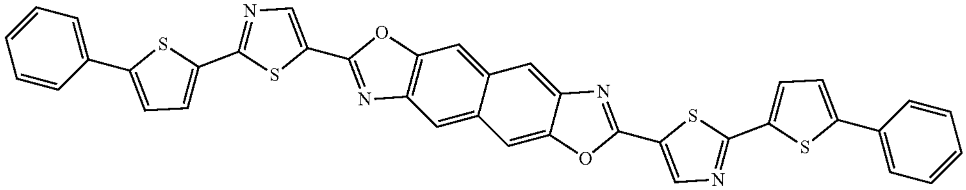

-continued
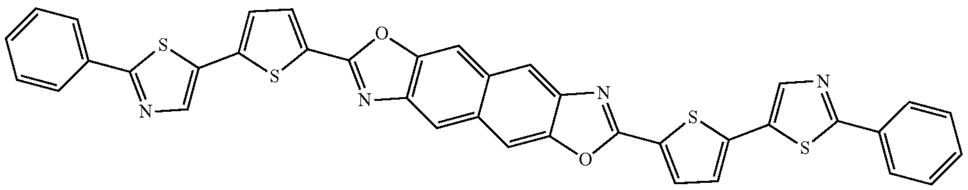
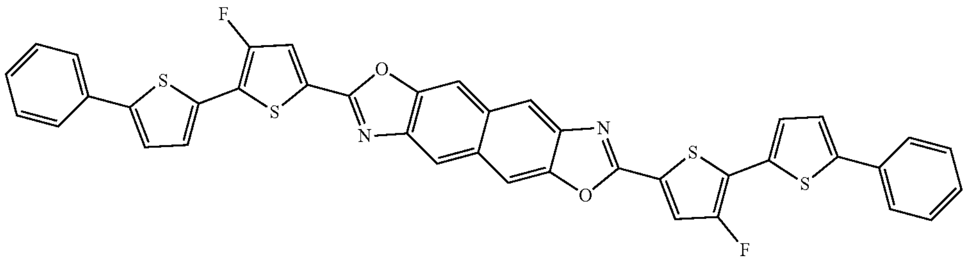
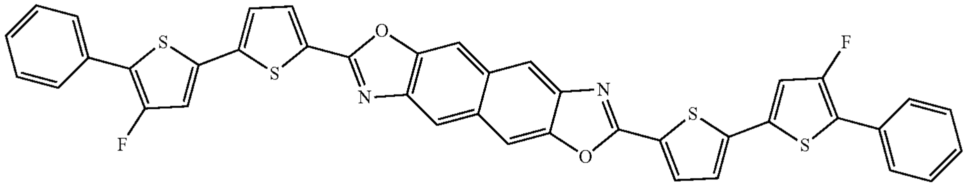
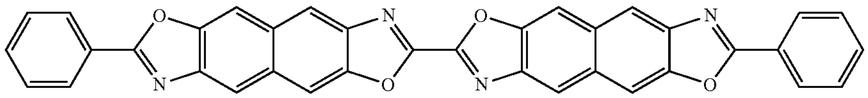
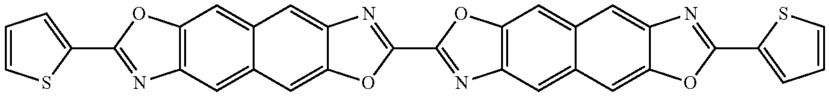
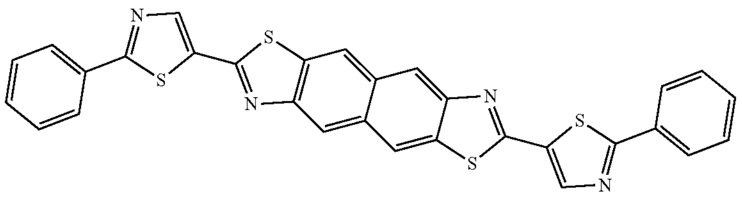
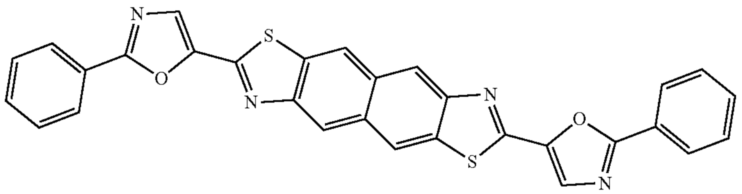
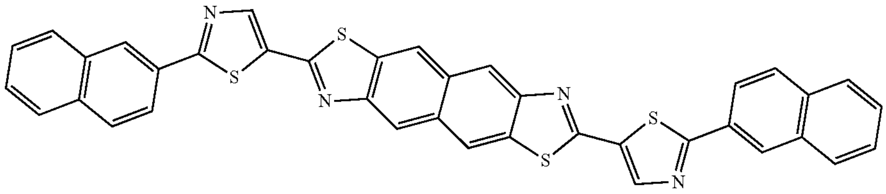
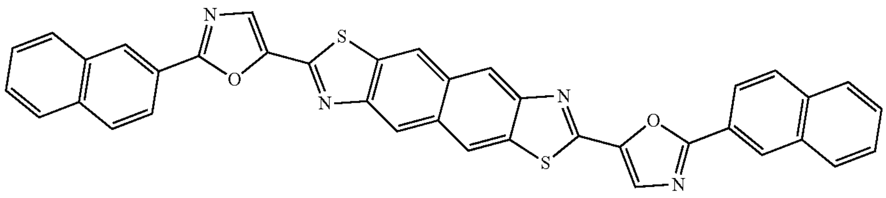

-continued
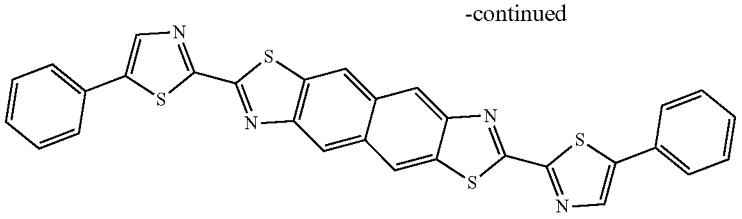
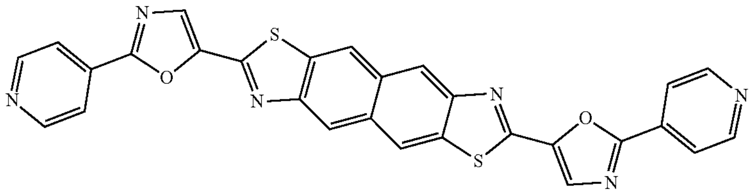
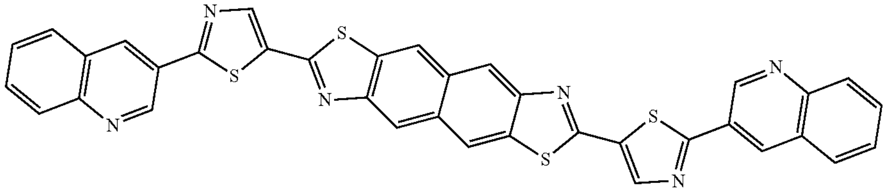
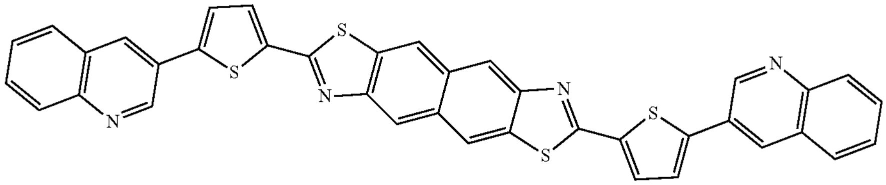
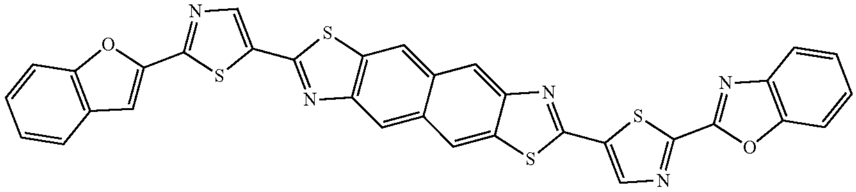
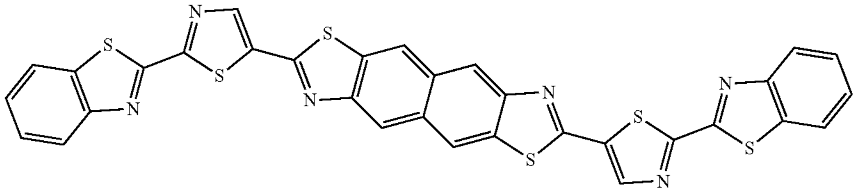
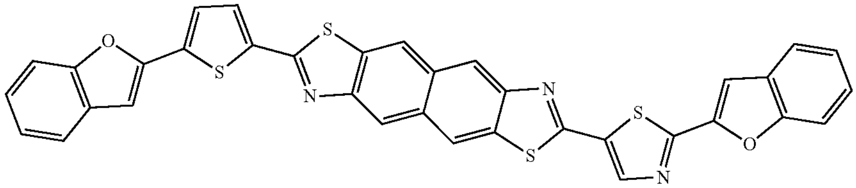
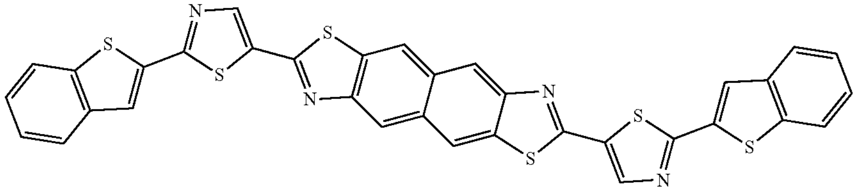
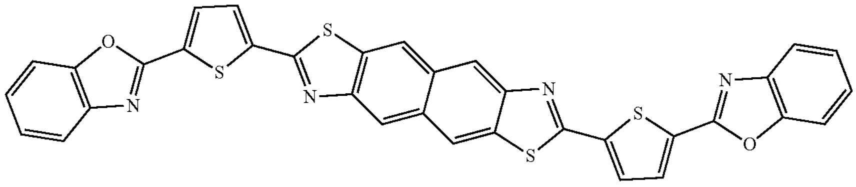

-continued
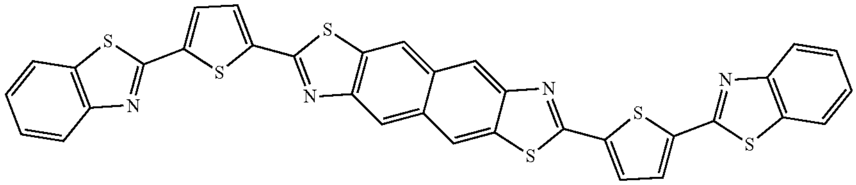
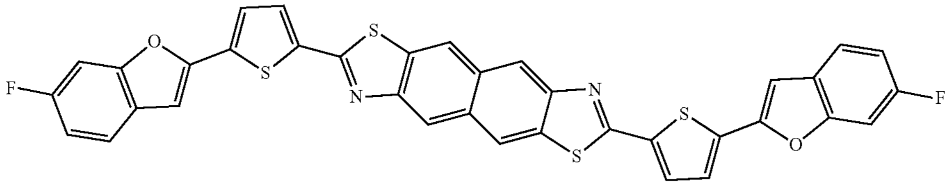
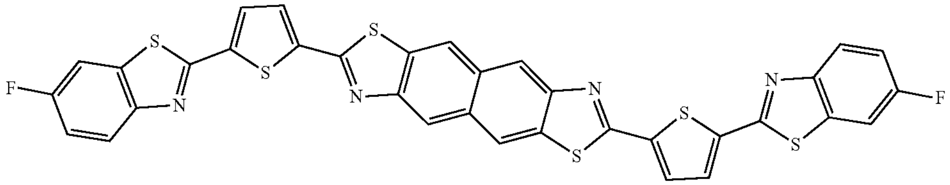
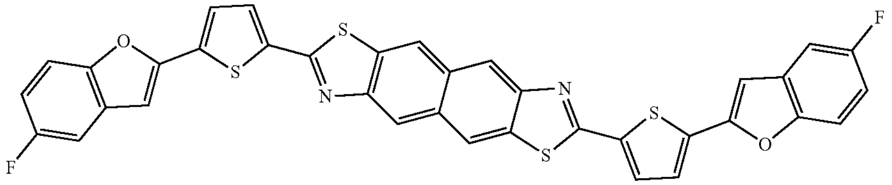
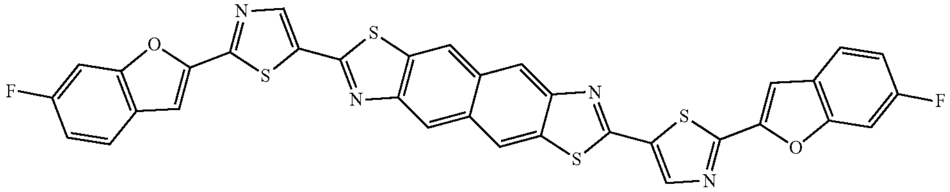
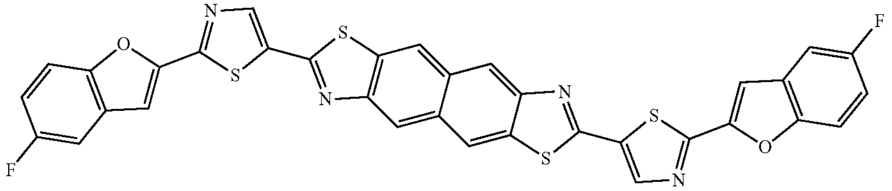
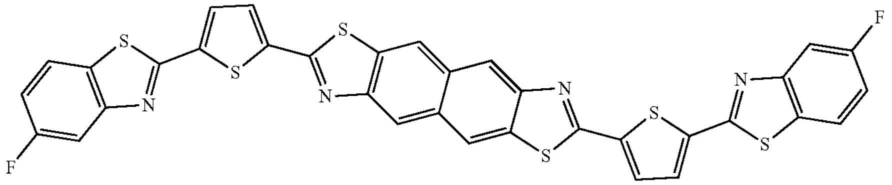
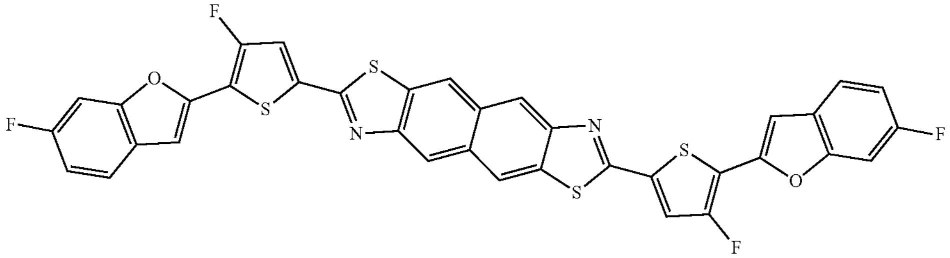

-continued
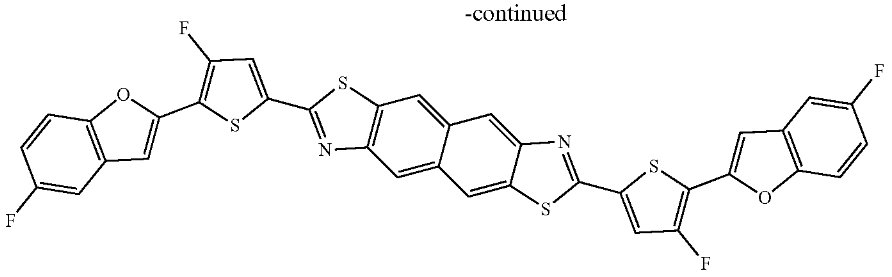
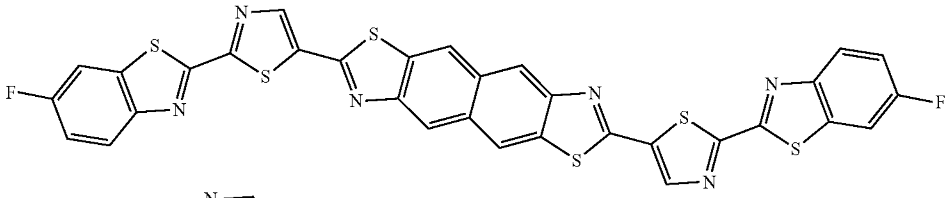
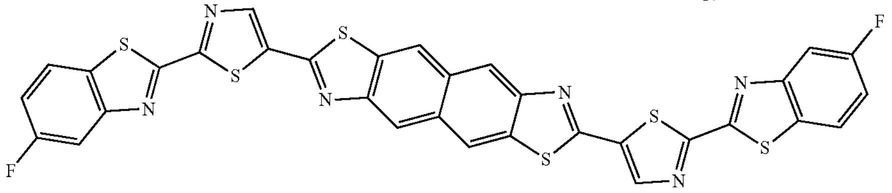
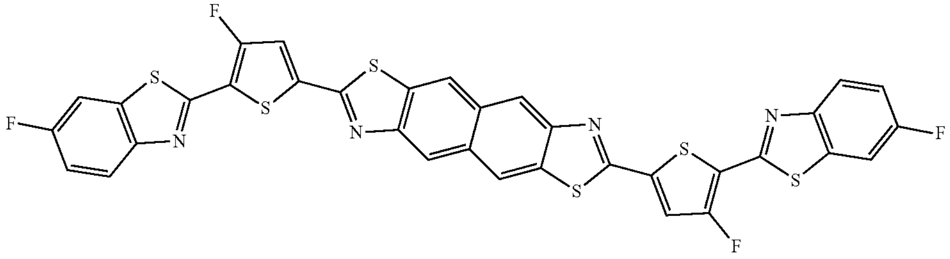
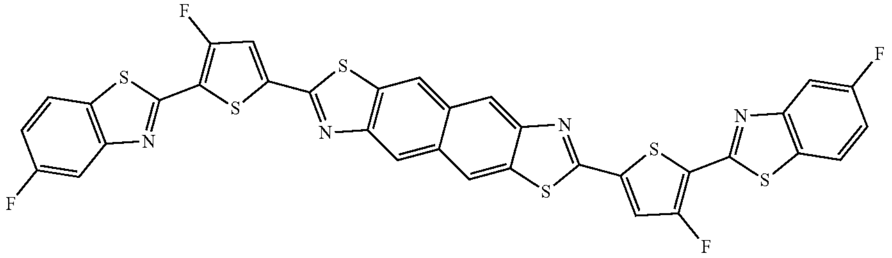
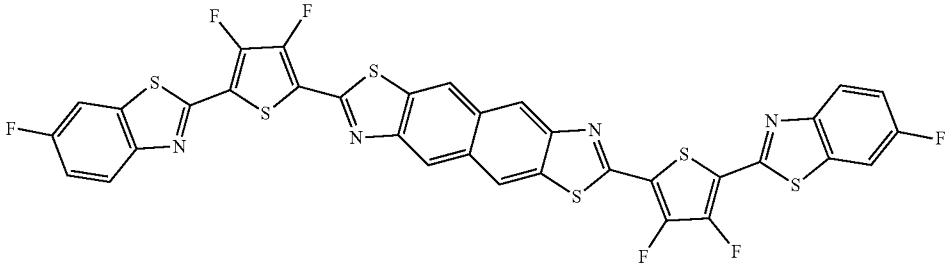

-continued
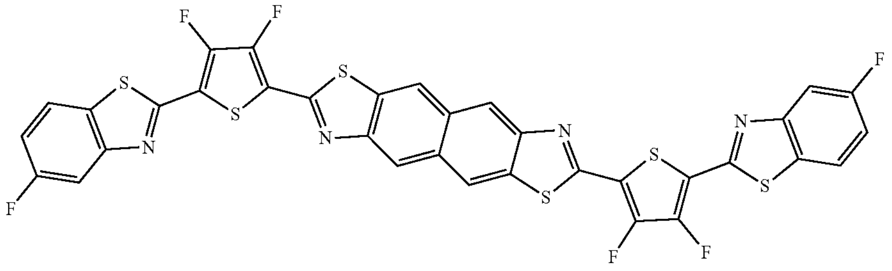
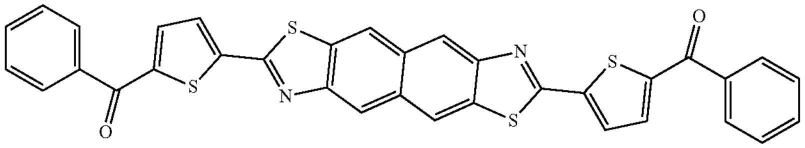
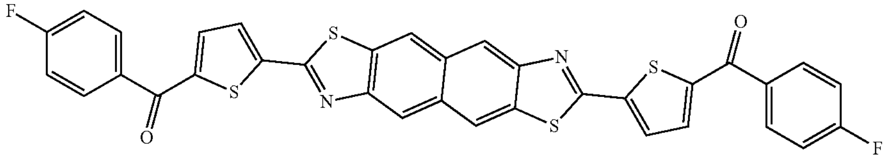
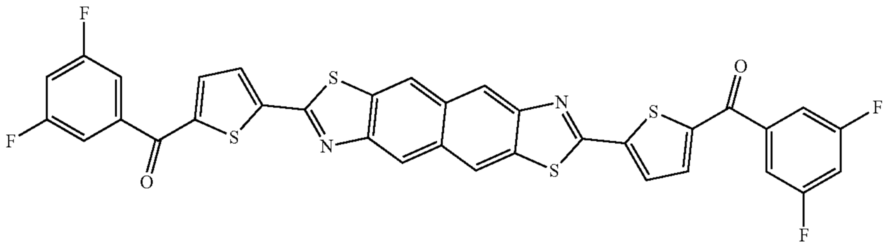
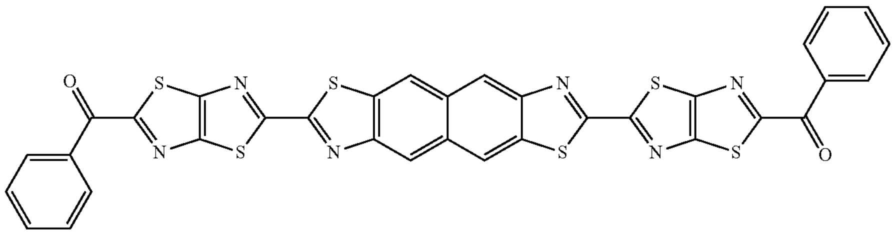
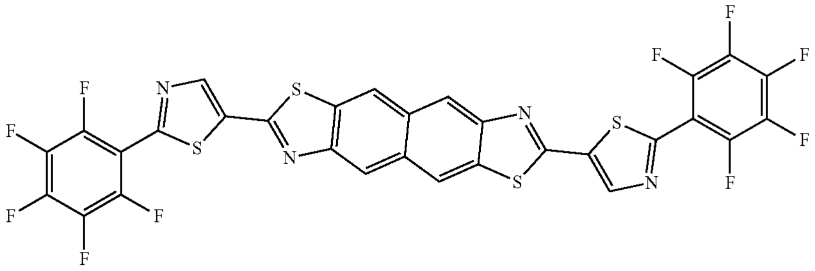
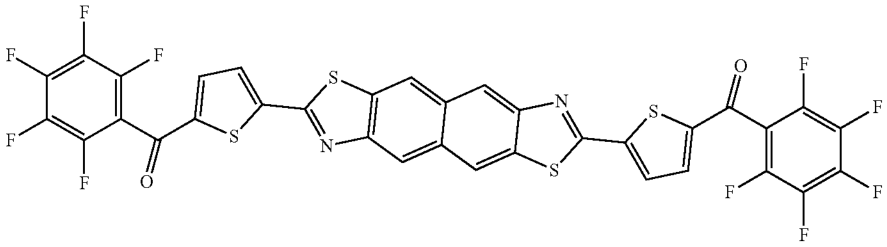

-continued
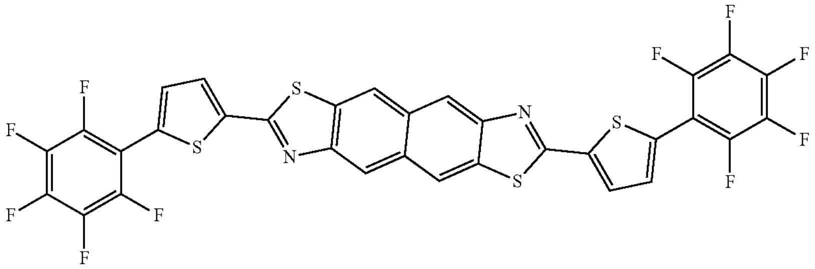
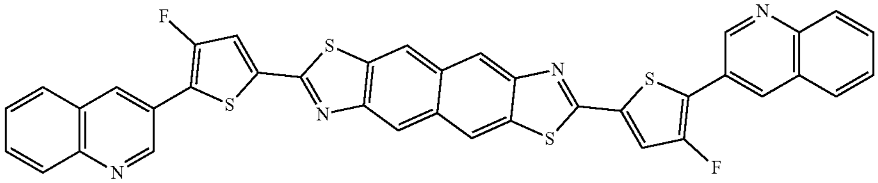
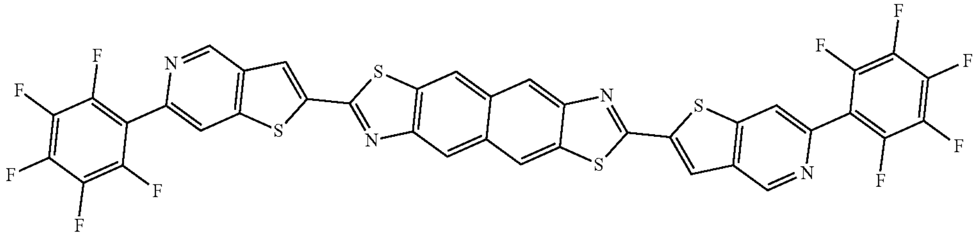
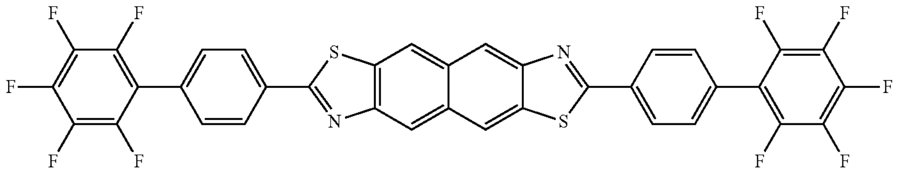
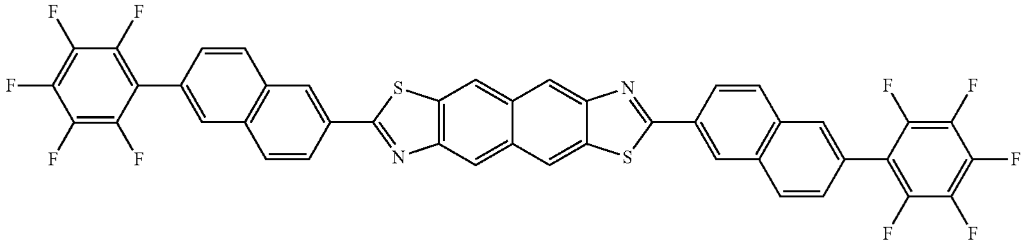
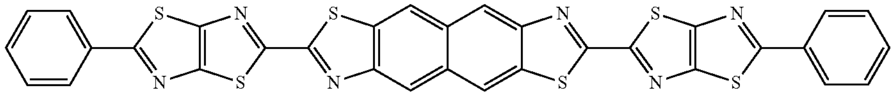
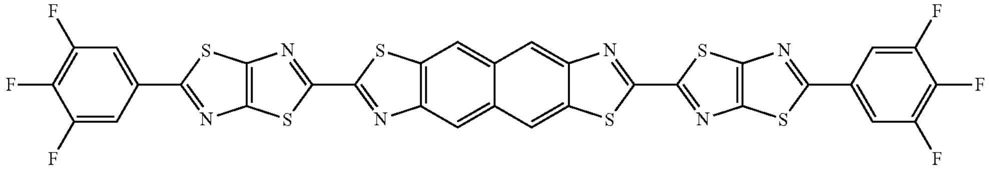
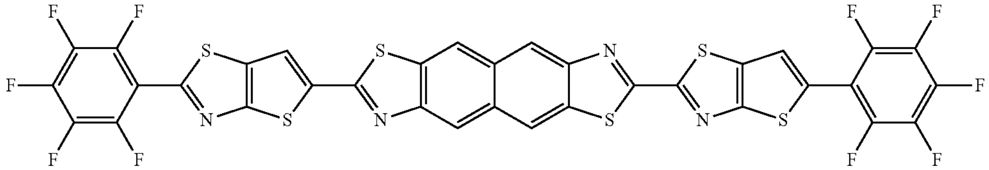
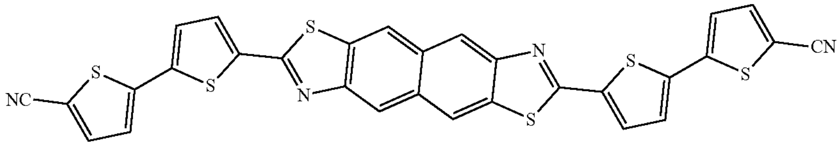

-continued
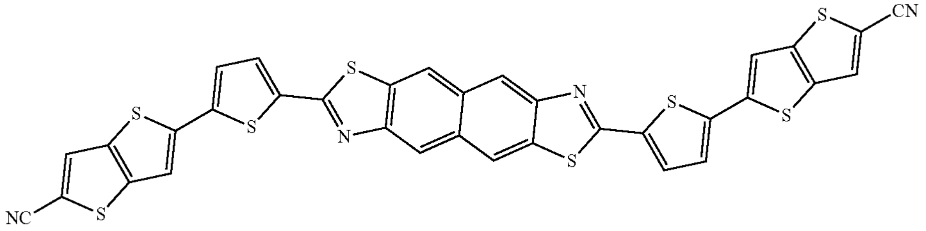
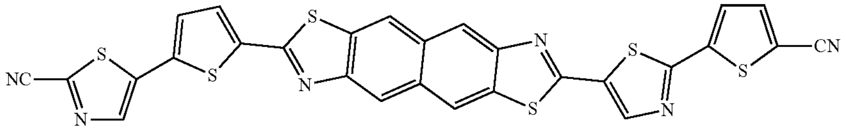
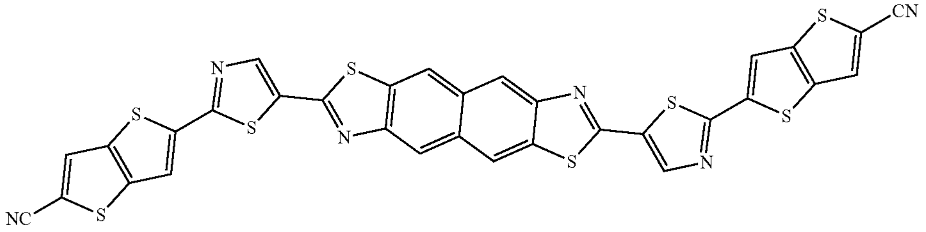
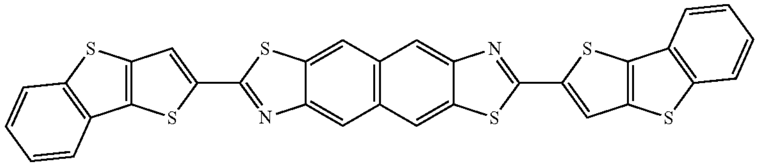
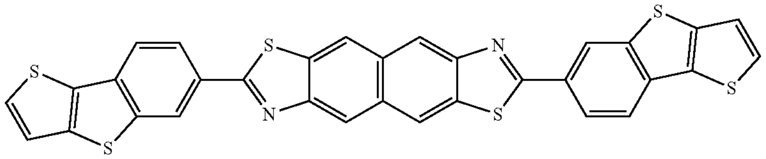
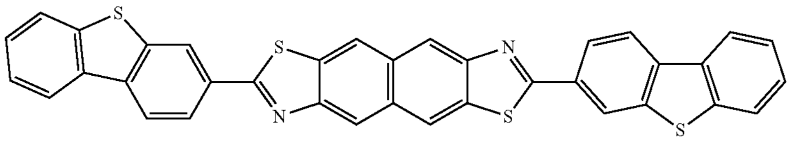
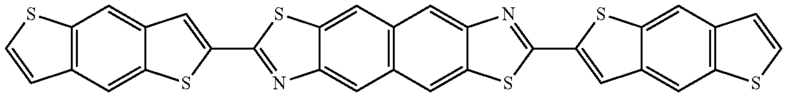
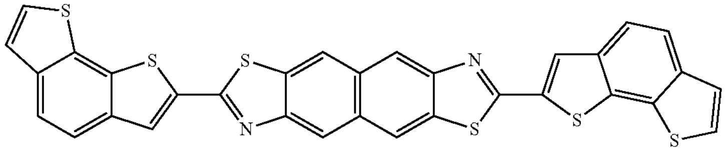
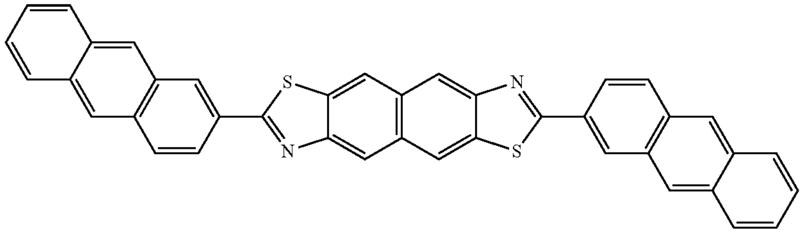
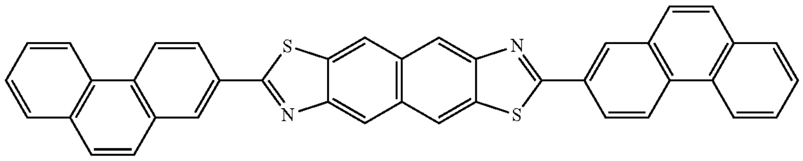

-continued
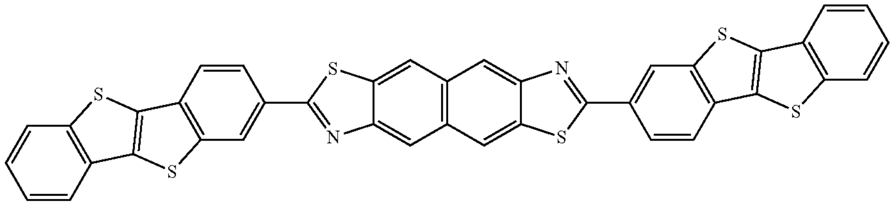
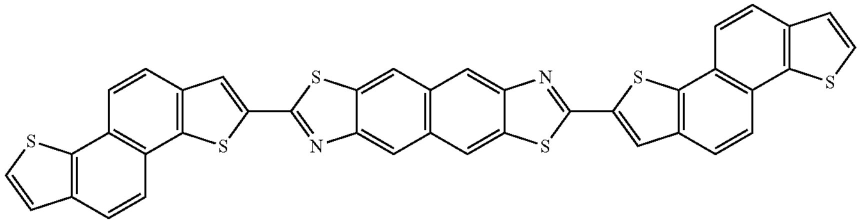
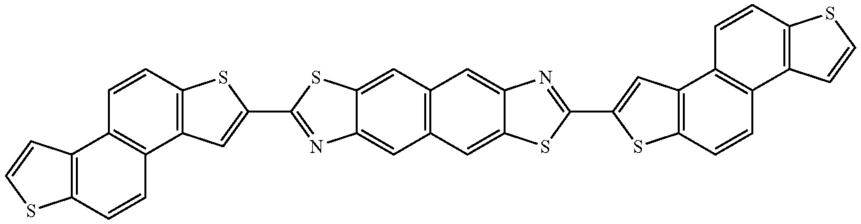
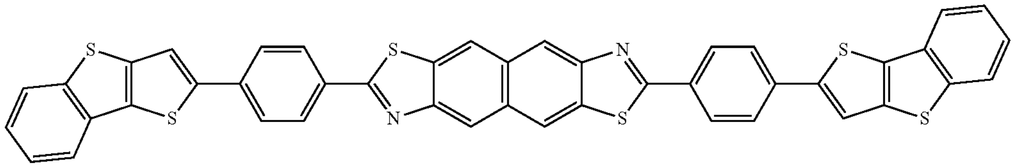
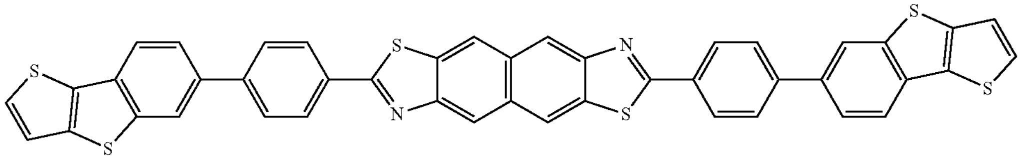
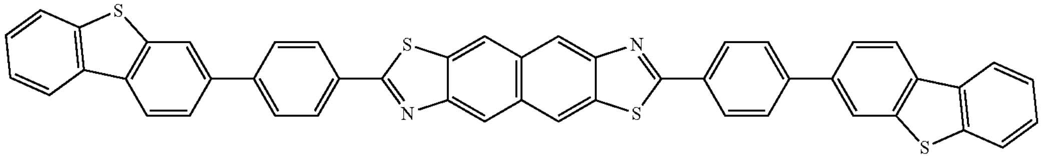
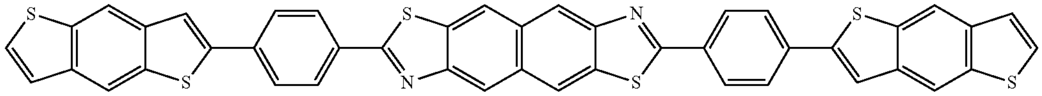
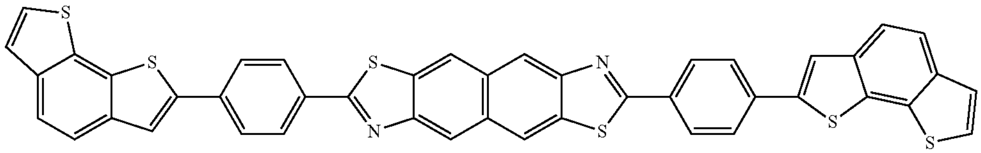
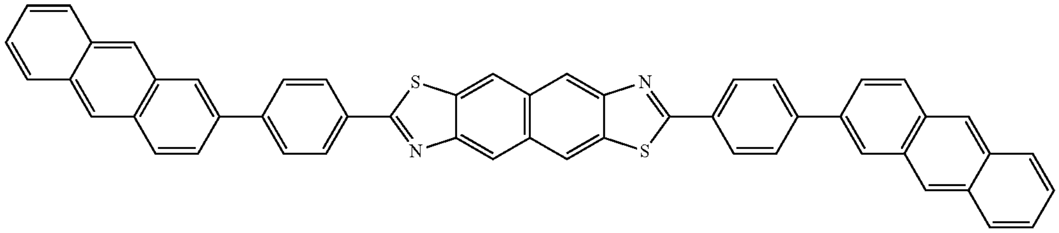

-continued
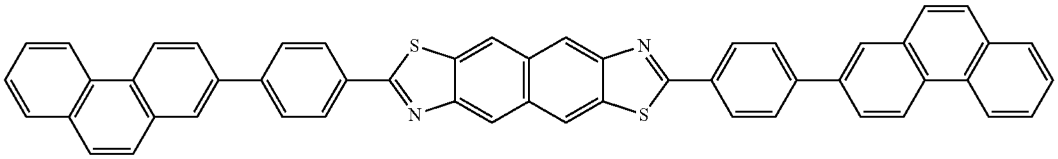
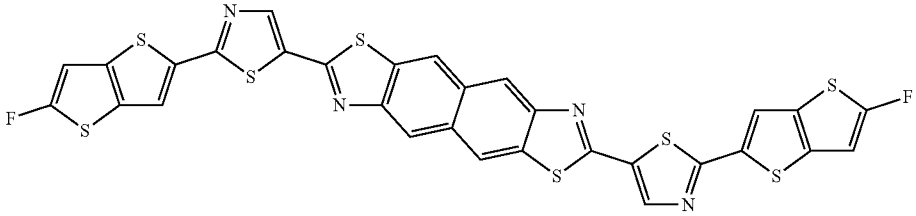
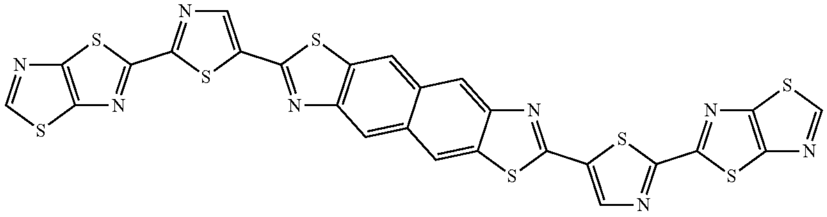
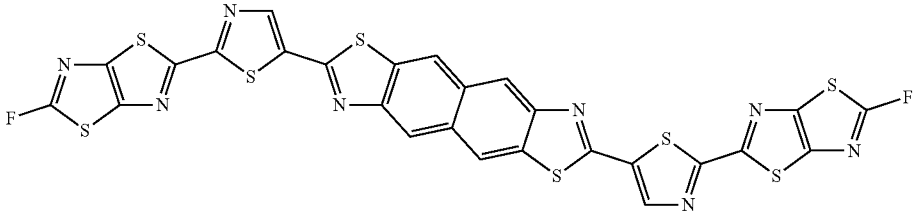
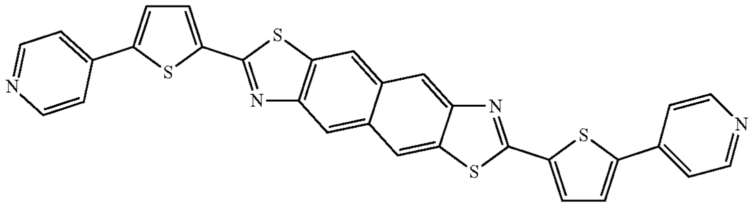
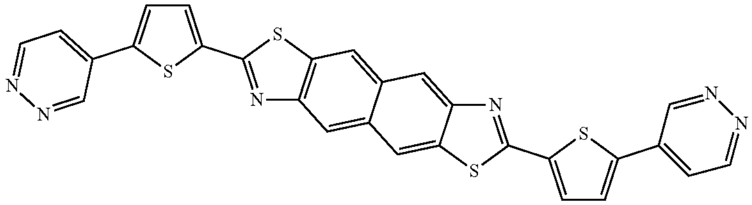
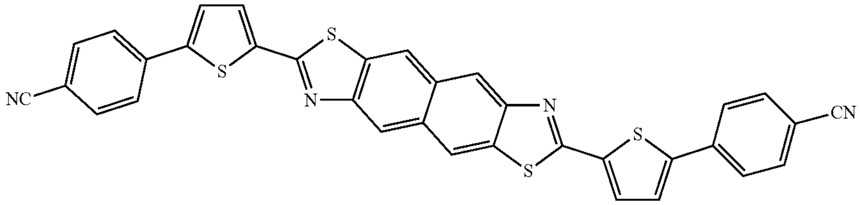
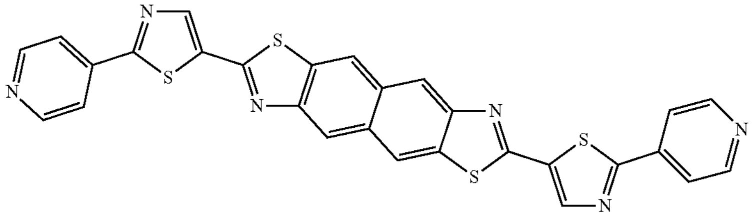

-continued
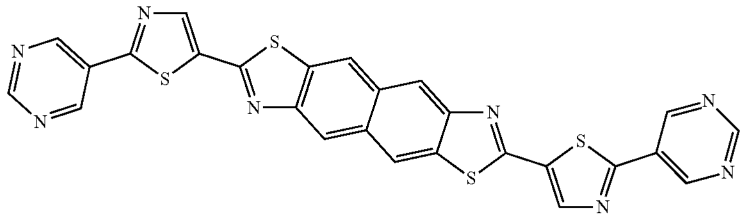
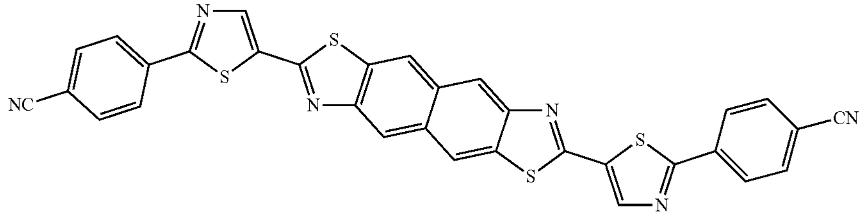
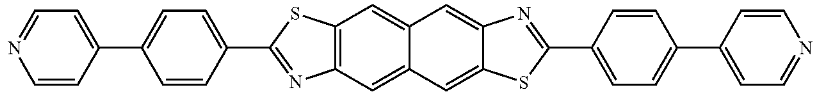
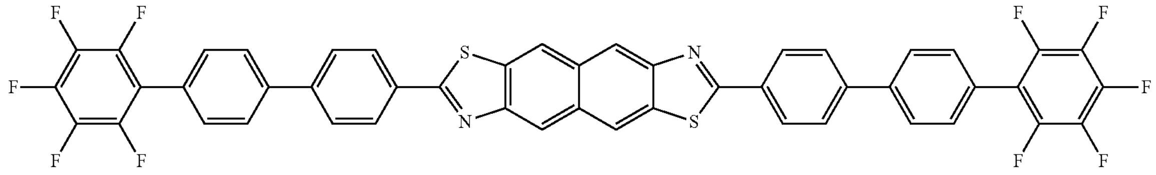
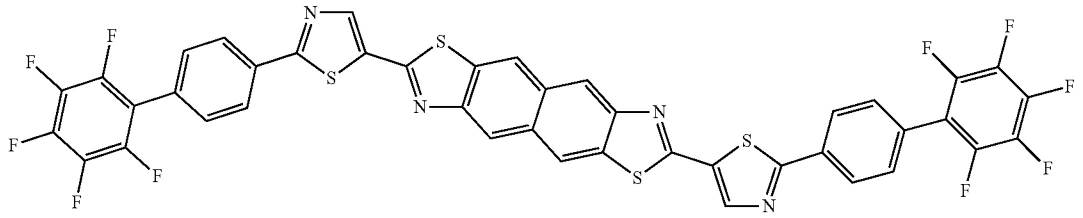
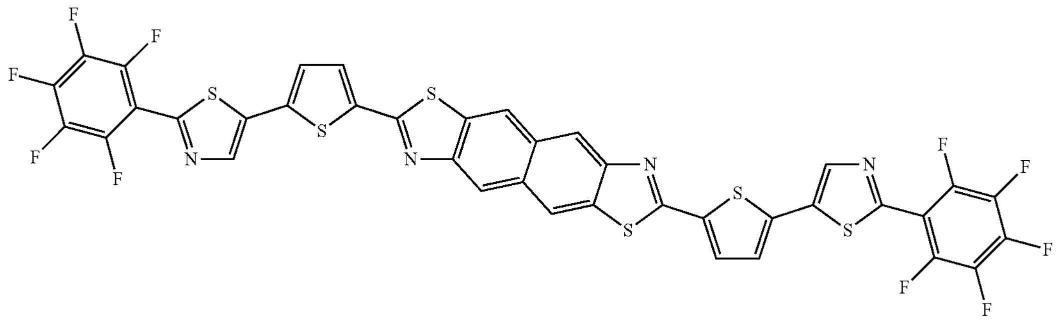
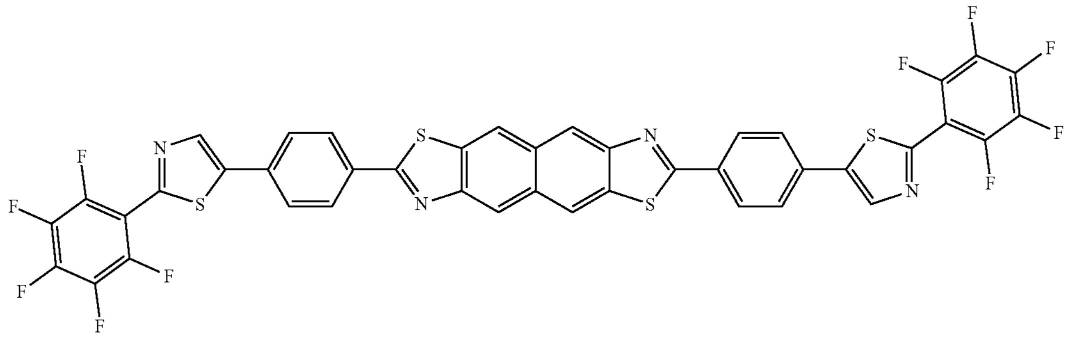

-continued
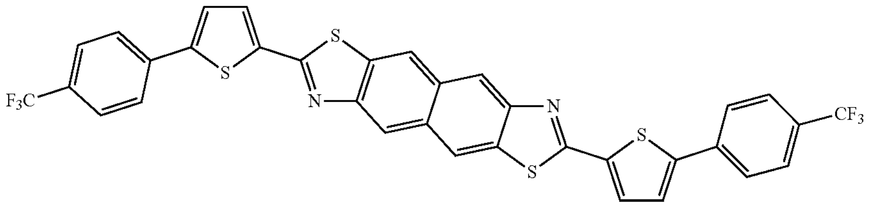
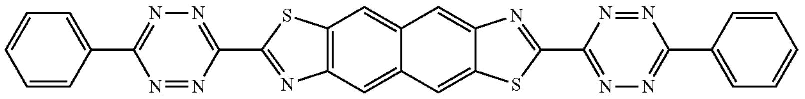
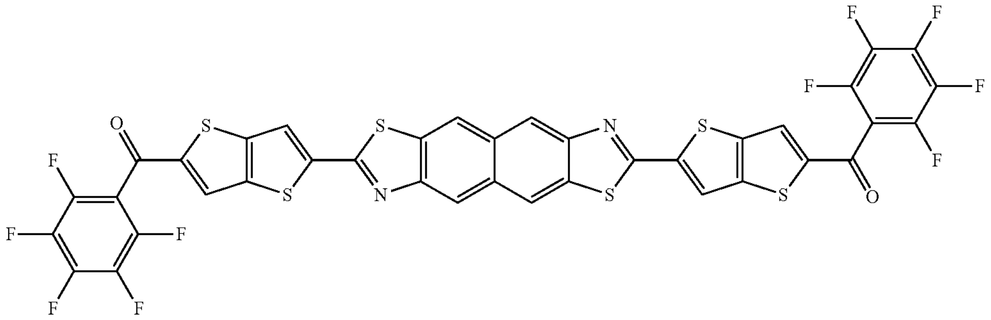
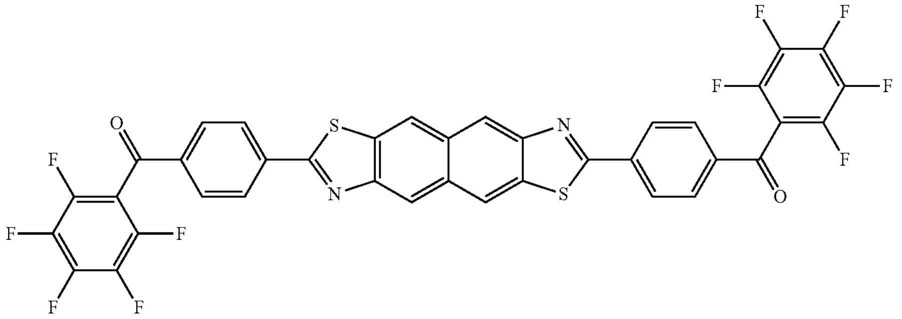
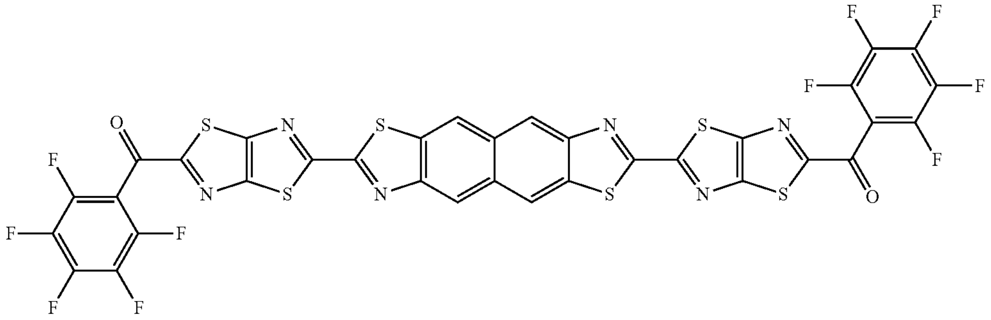
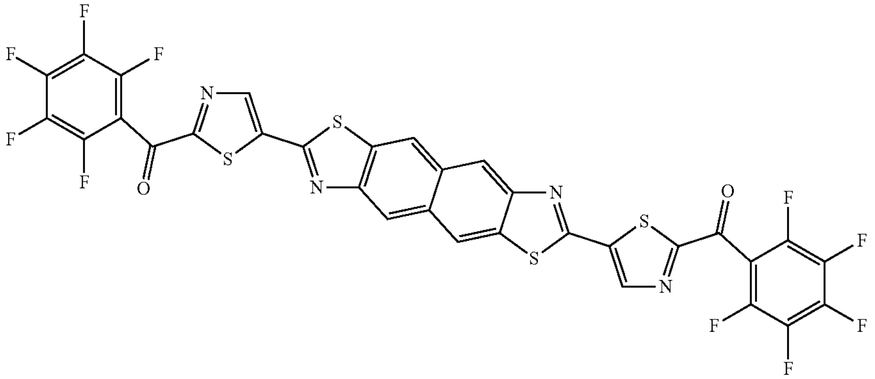

-continued
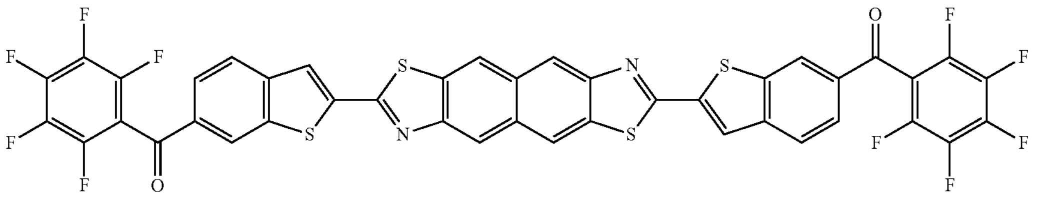
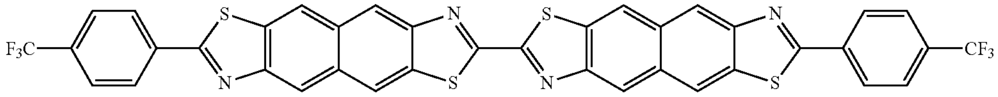
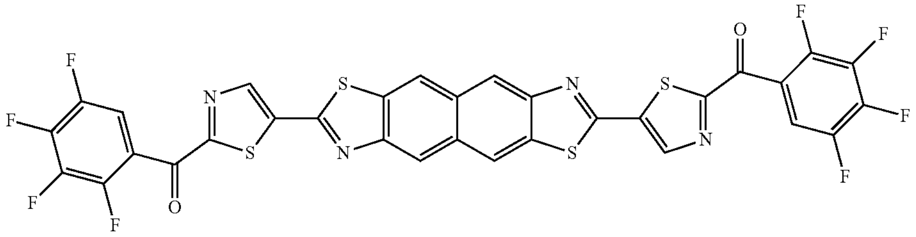
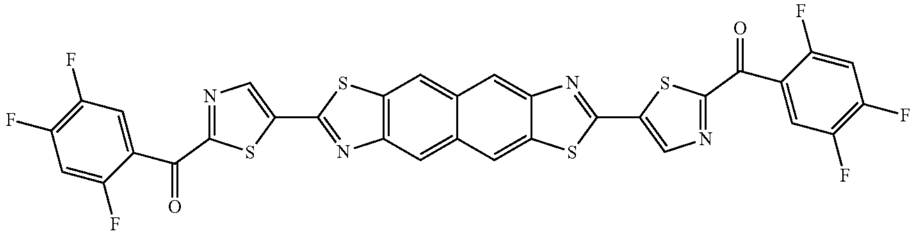
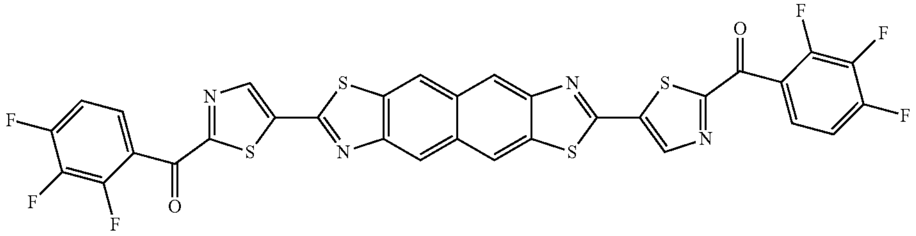
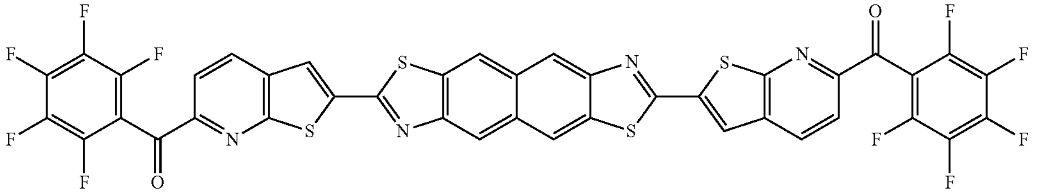
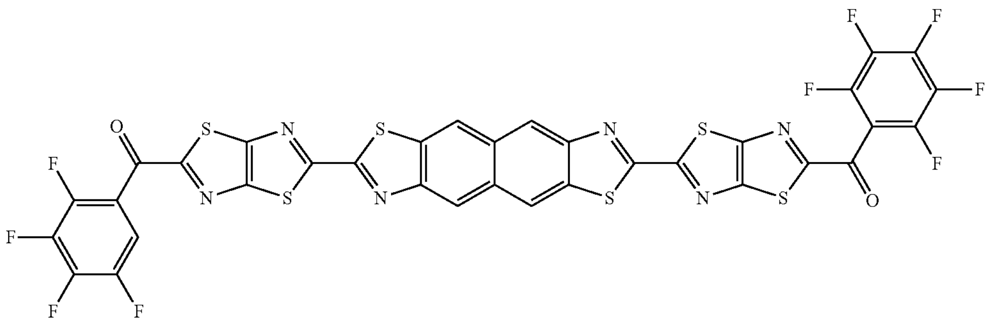

-continued
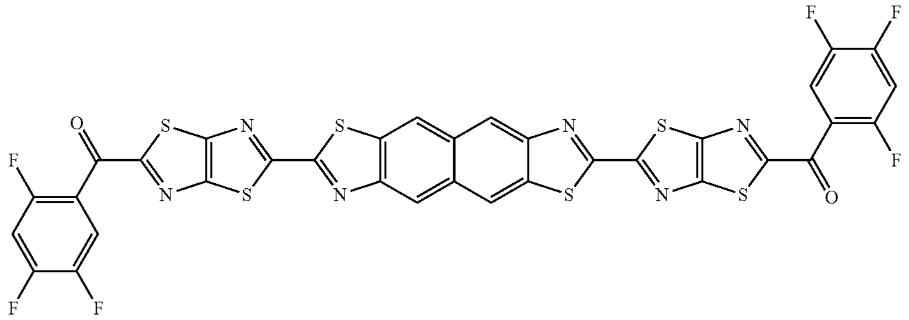
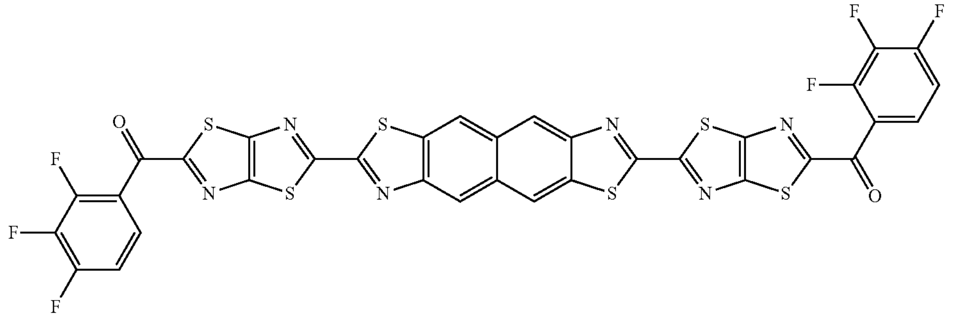
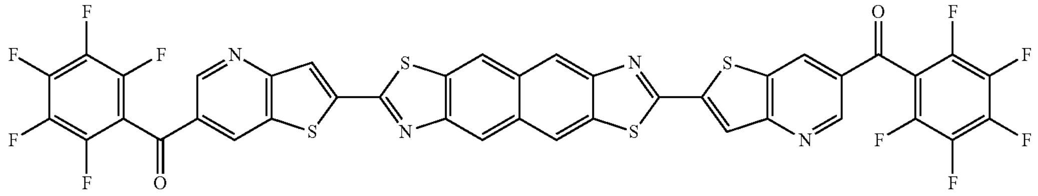
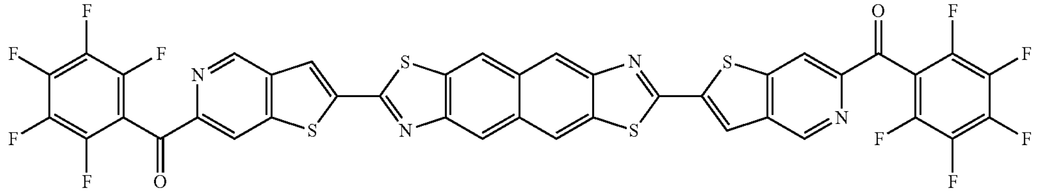
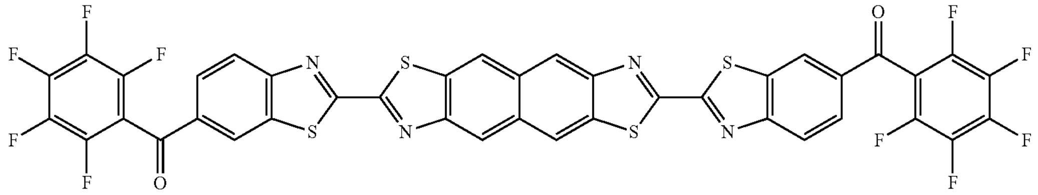
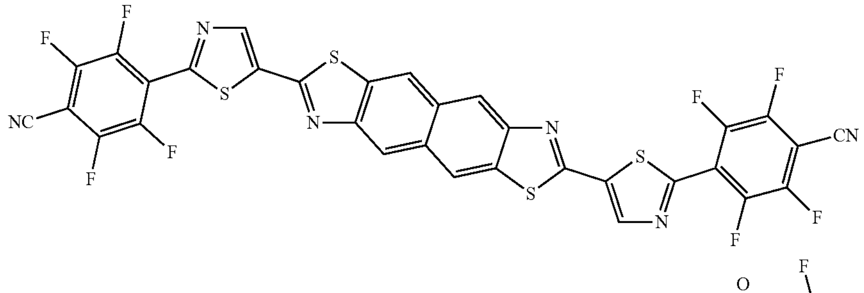
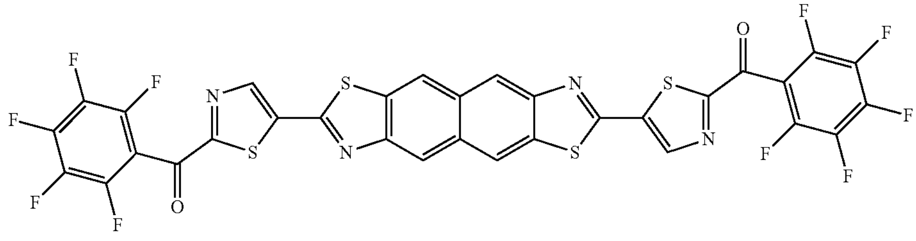

-continued
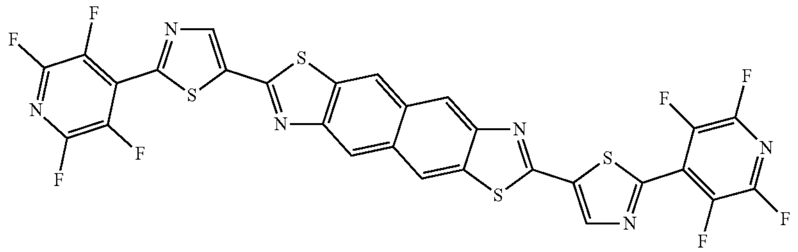
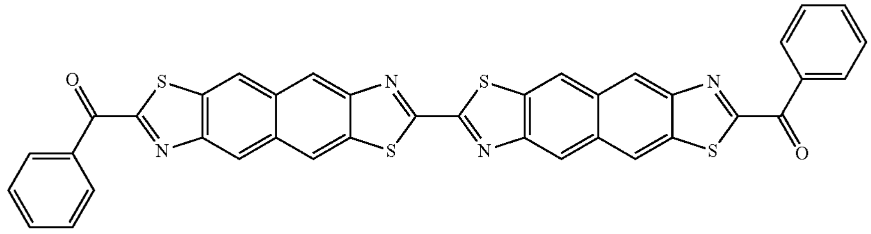
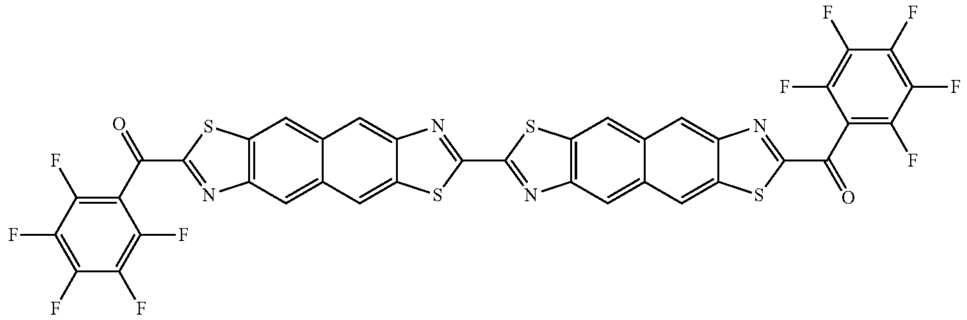
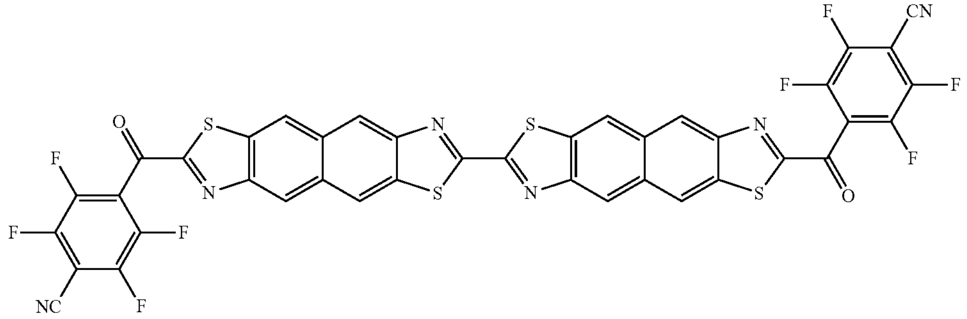
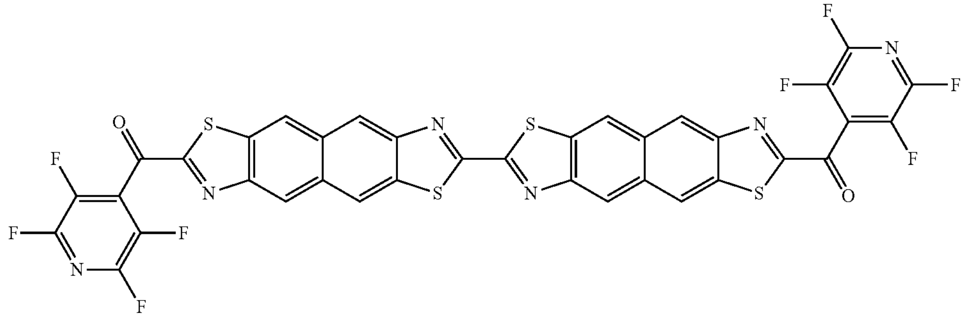
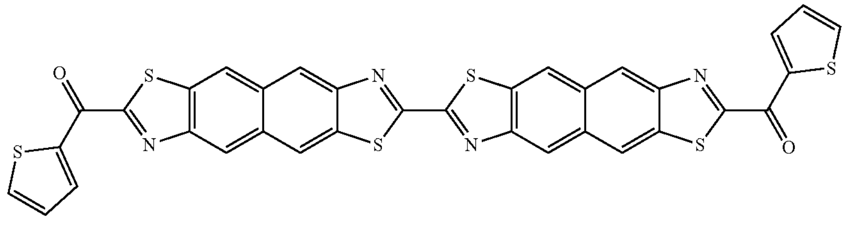

-continued
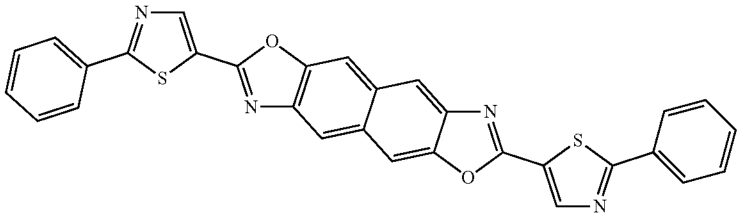
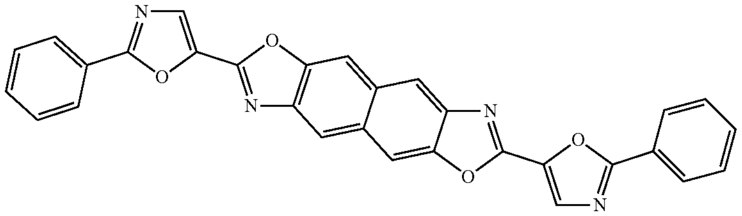
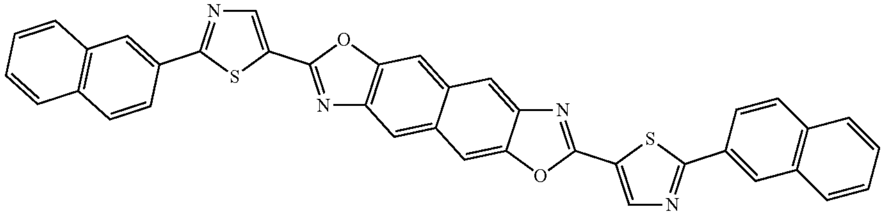
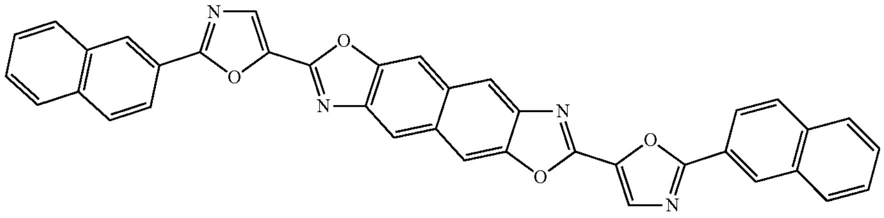
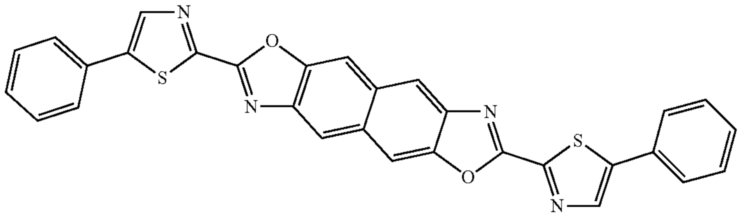
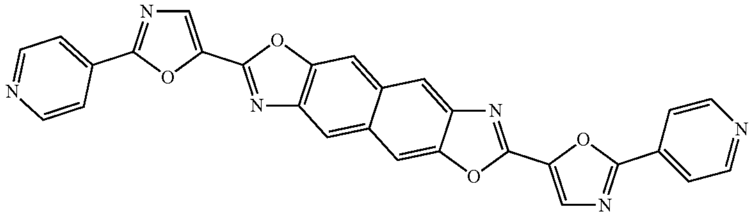
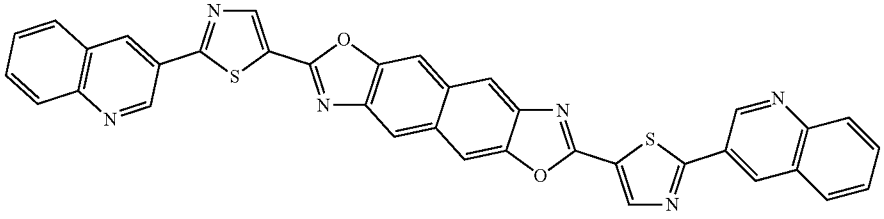
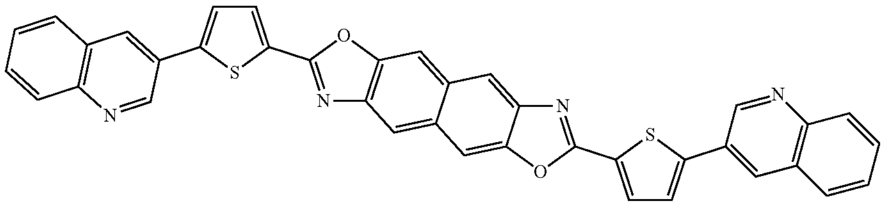

-continued
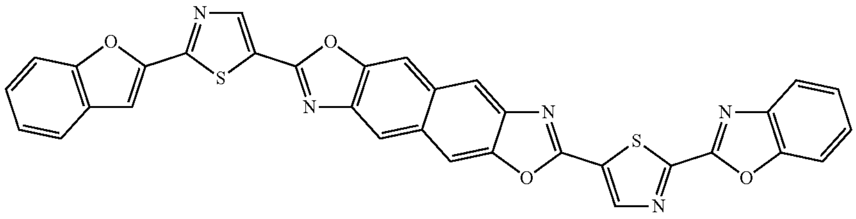
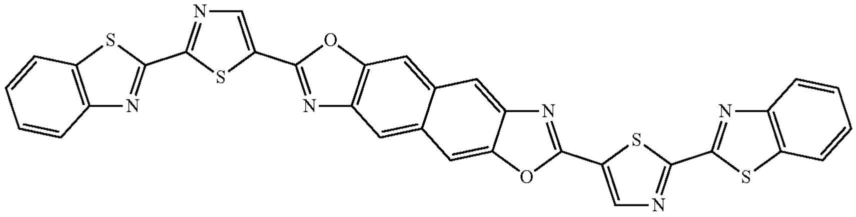
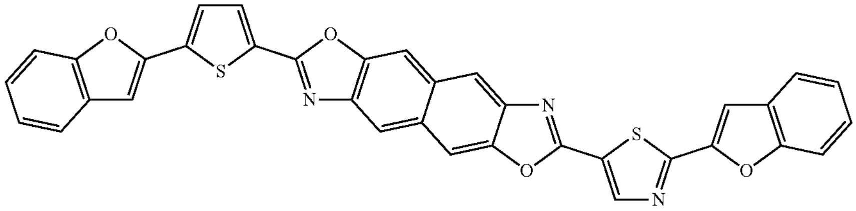
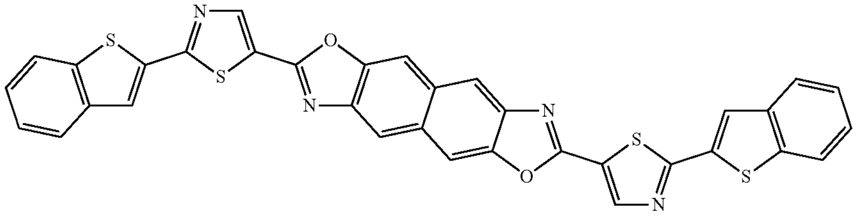
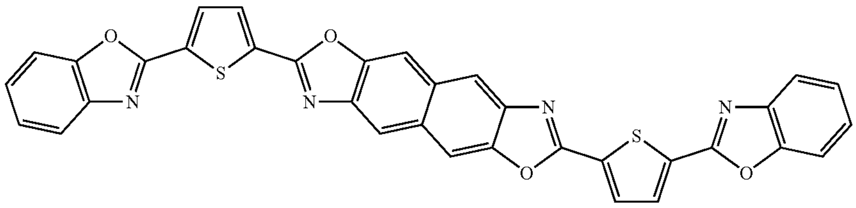
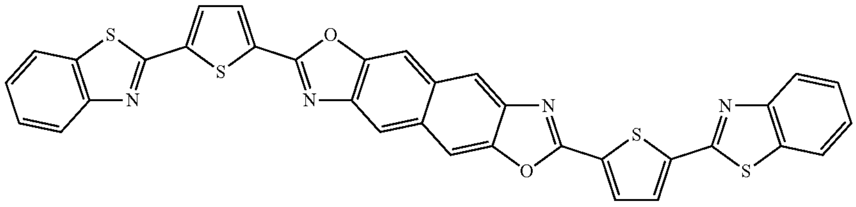
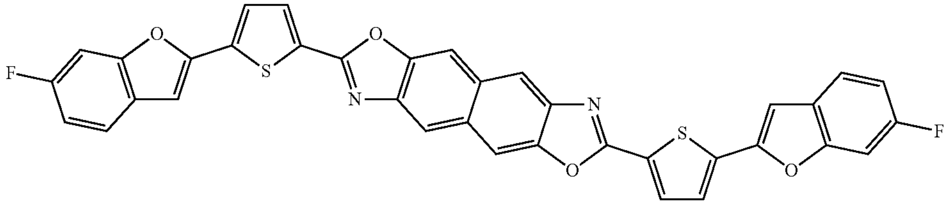
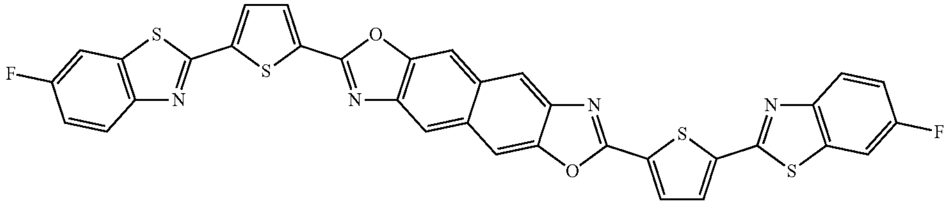

-continued
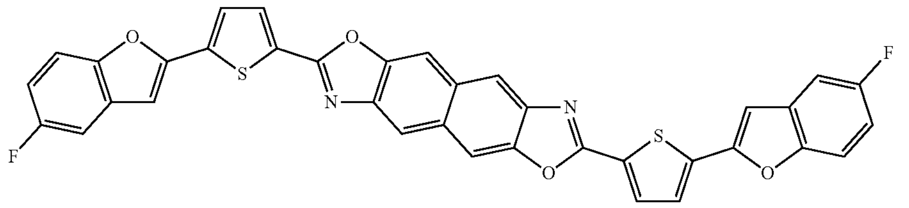
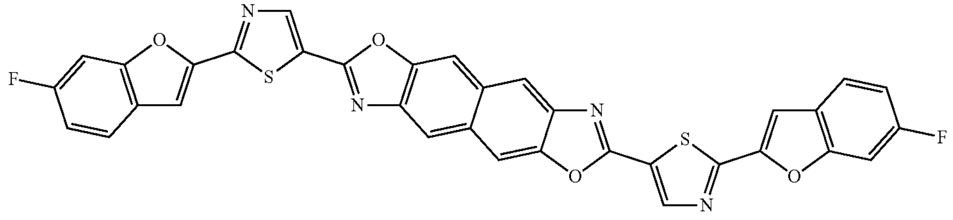
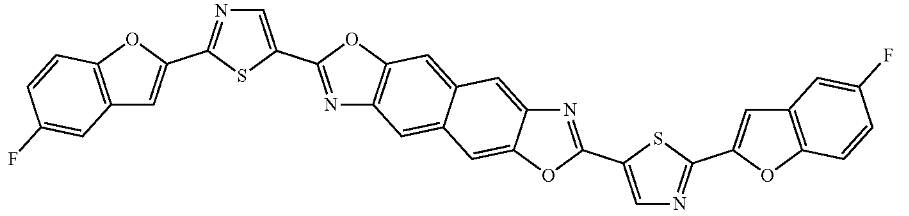
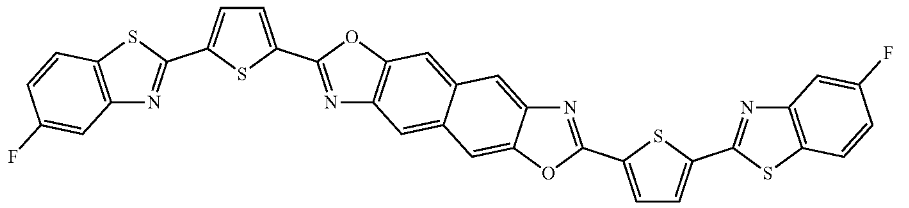
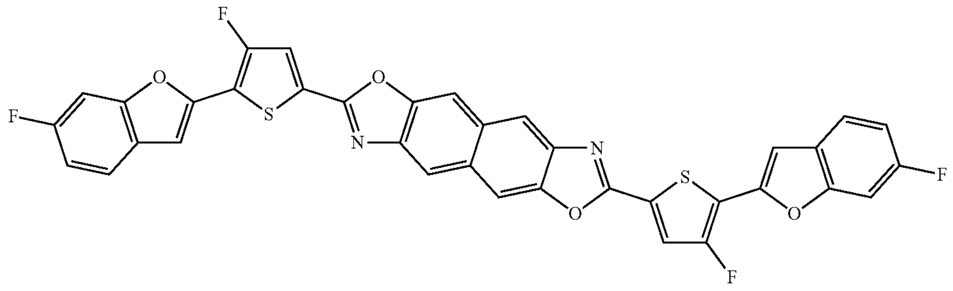
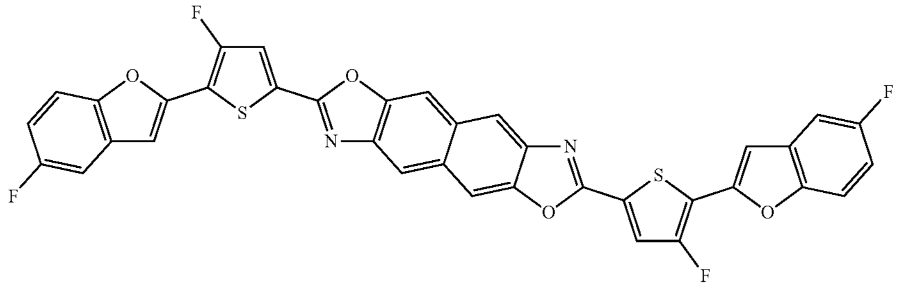
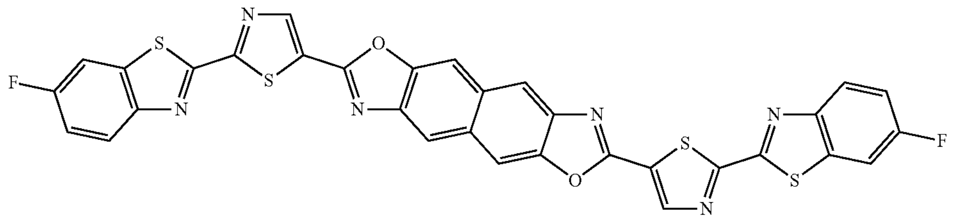

-continued
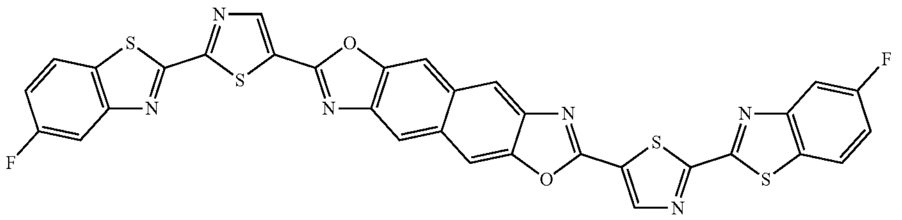
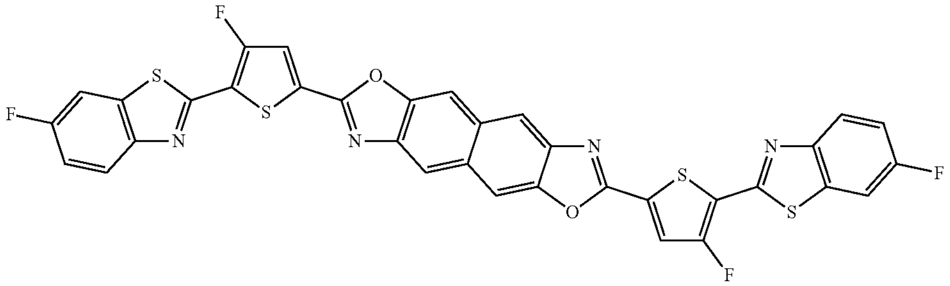
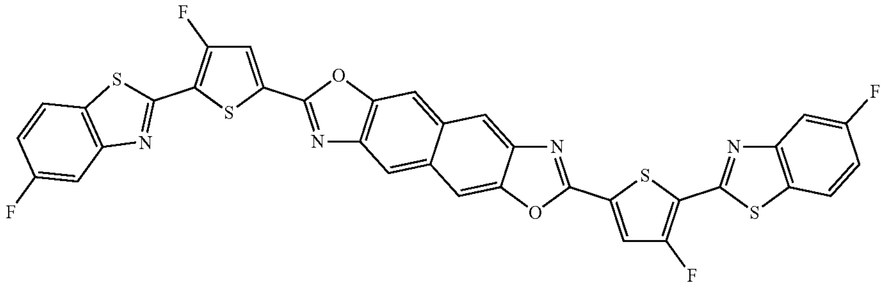
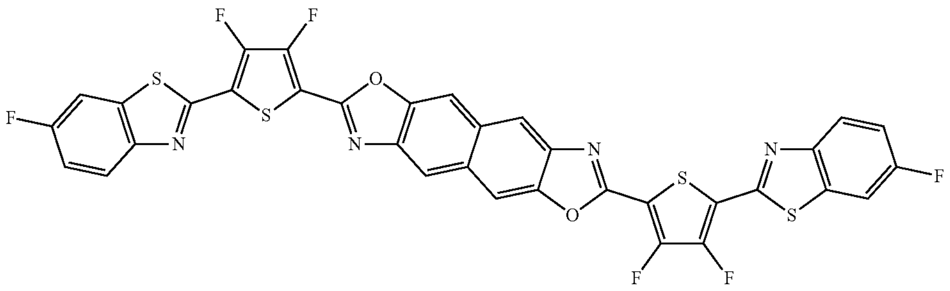
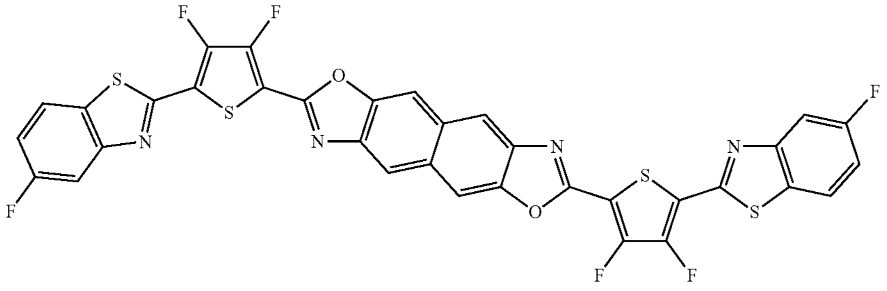
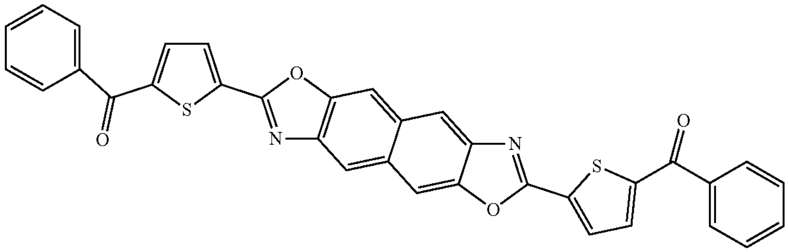

-continued
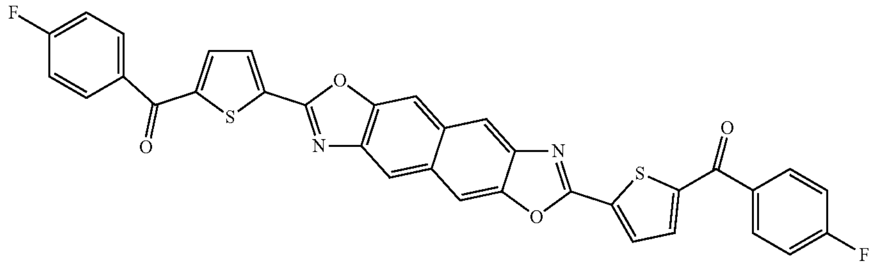
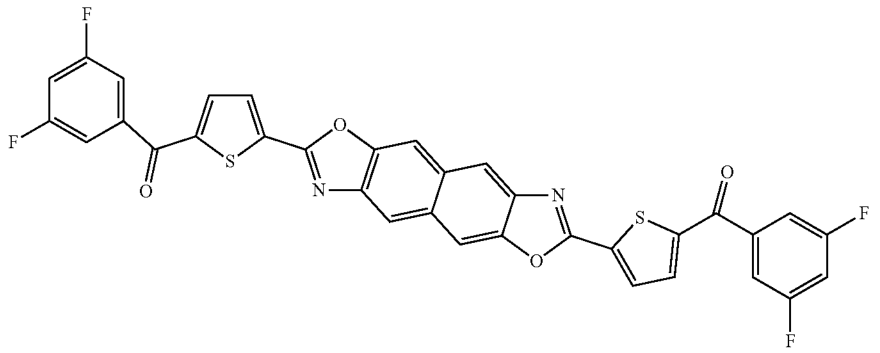
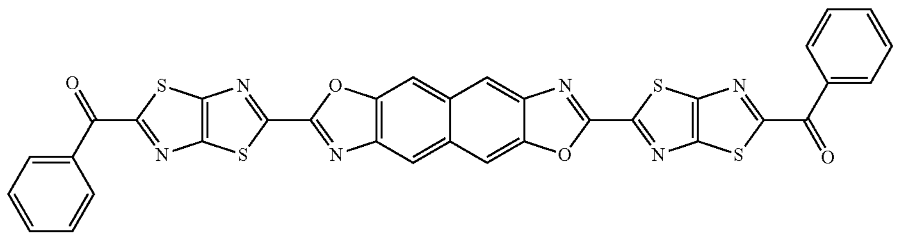
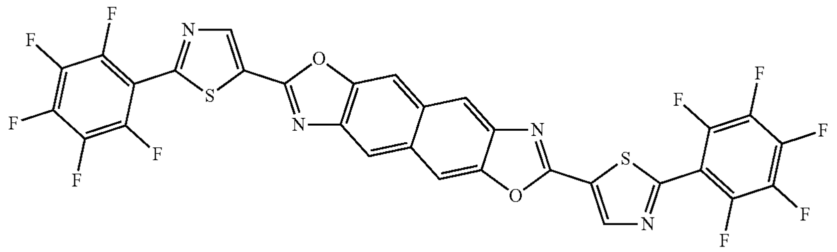
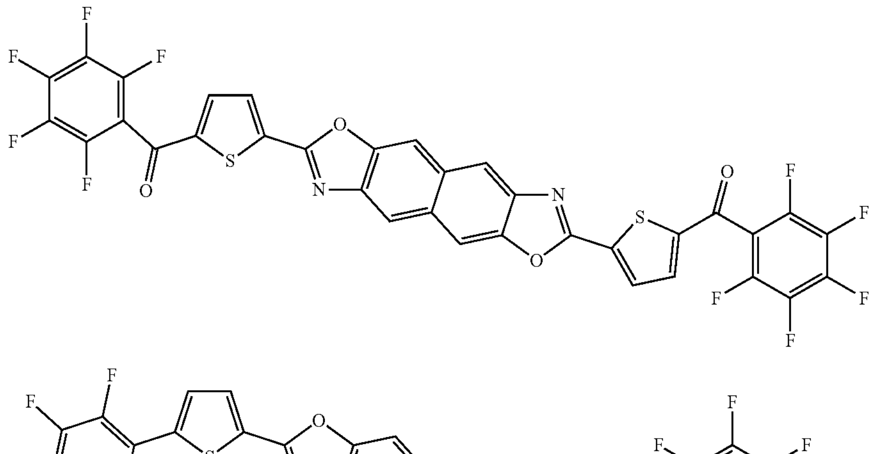
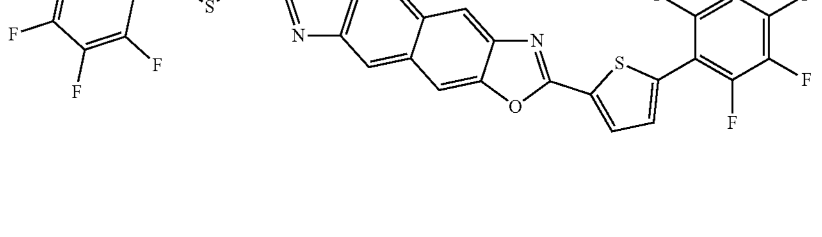

-continued
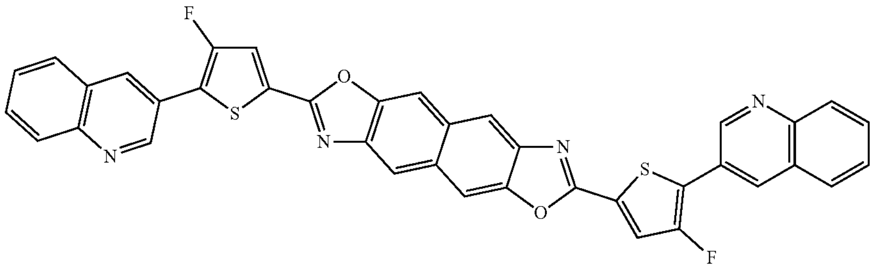
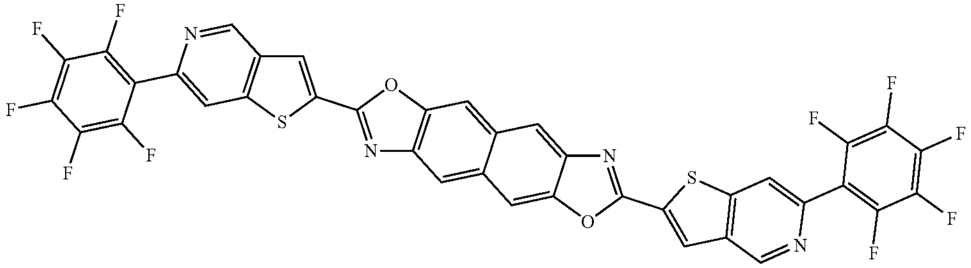
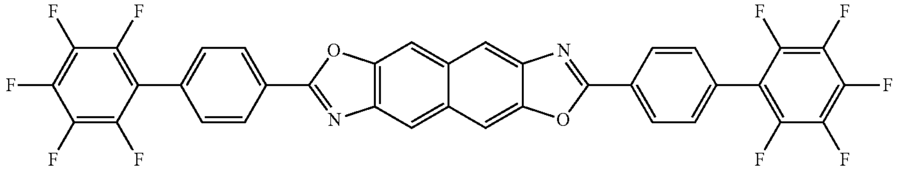
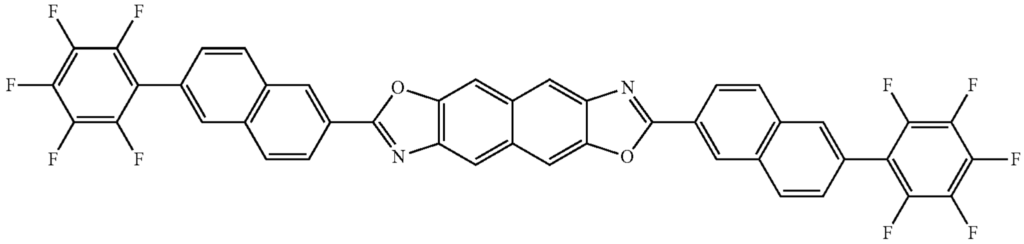
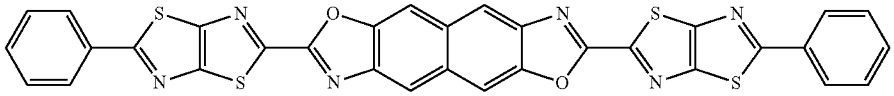
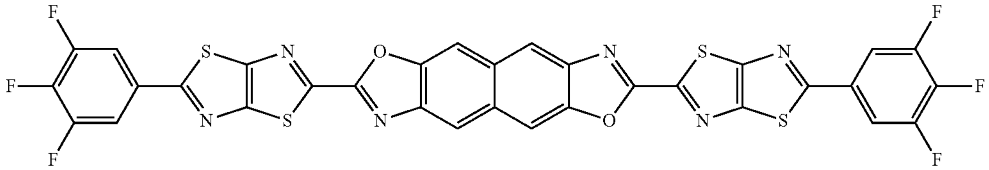
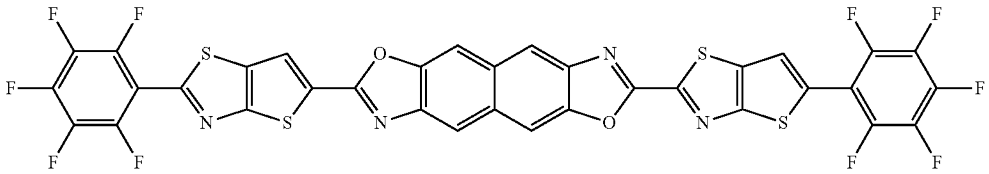
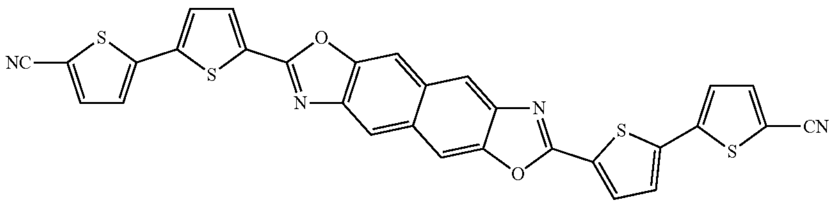

-continued
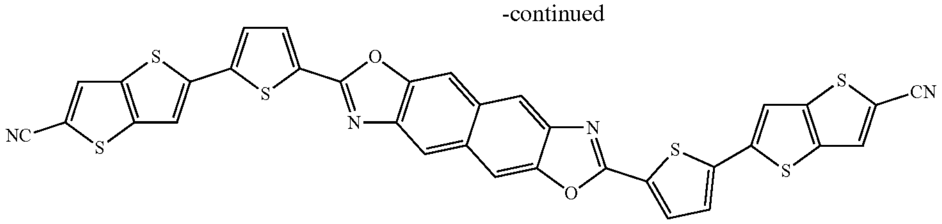
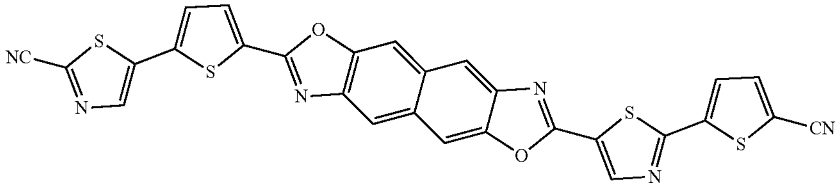
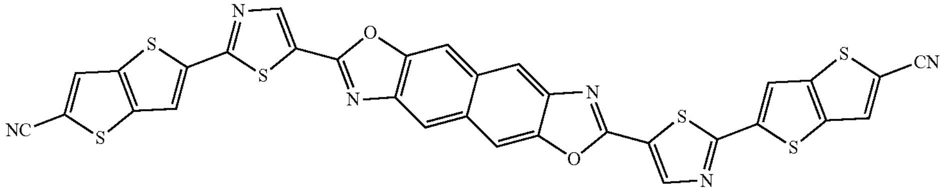
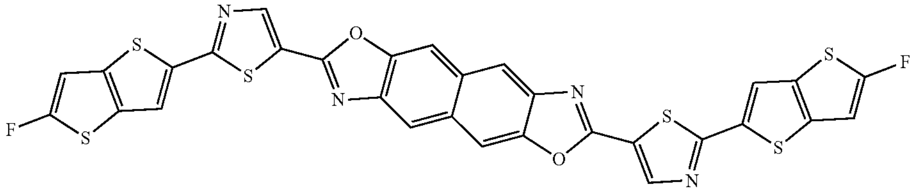
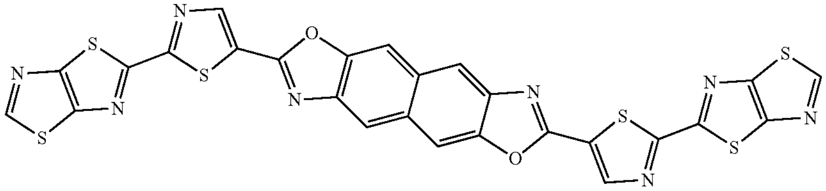
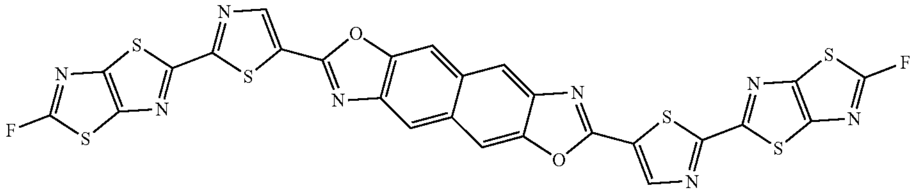
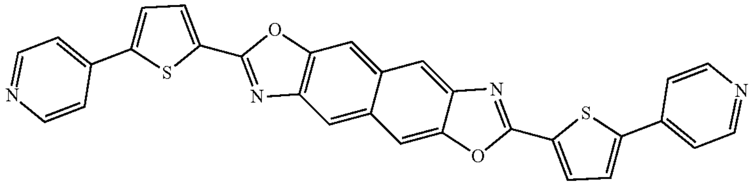
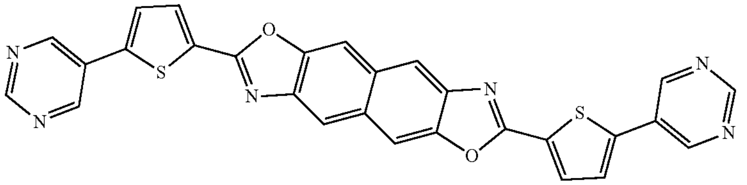

-continued
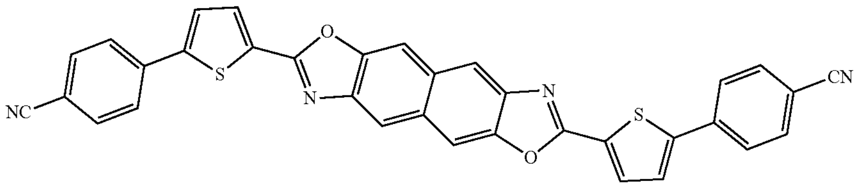
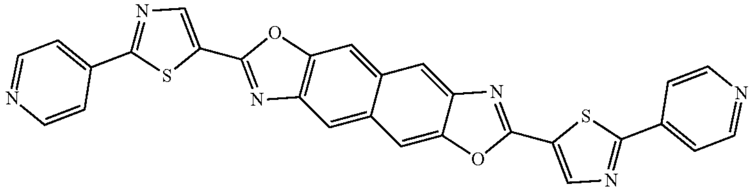
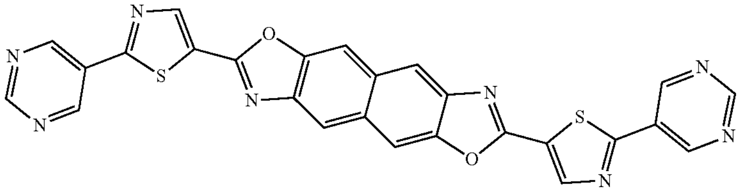
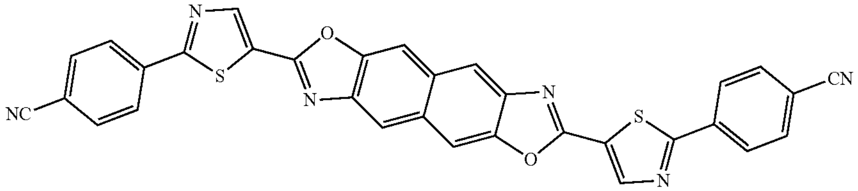
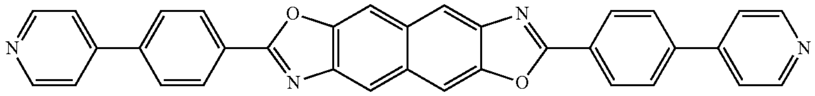
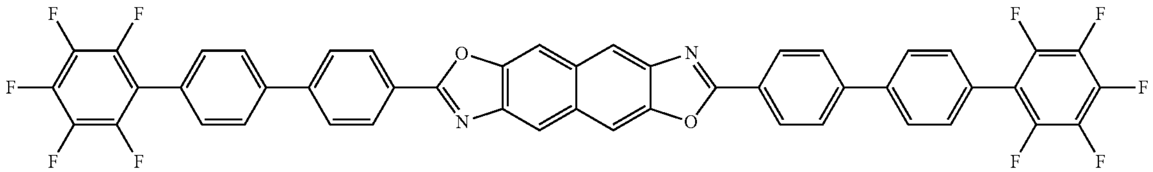
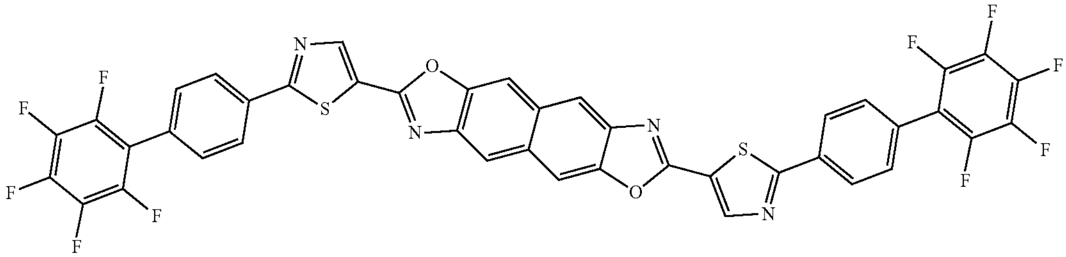
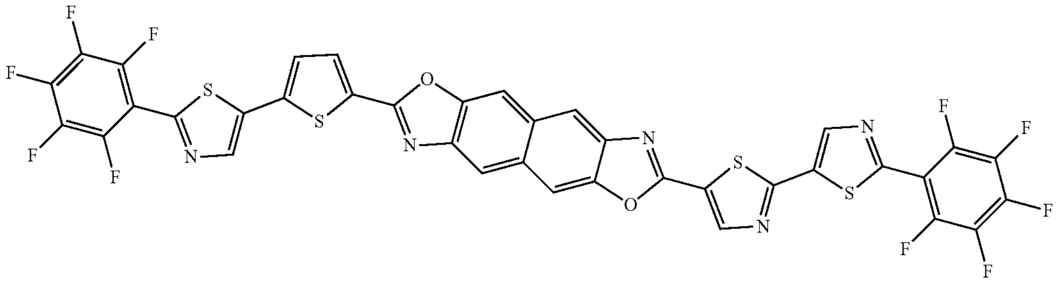

-continued
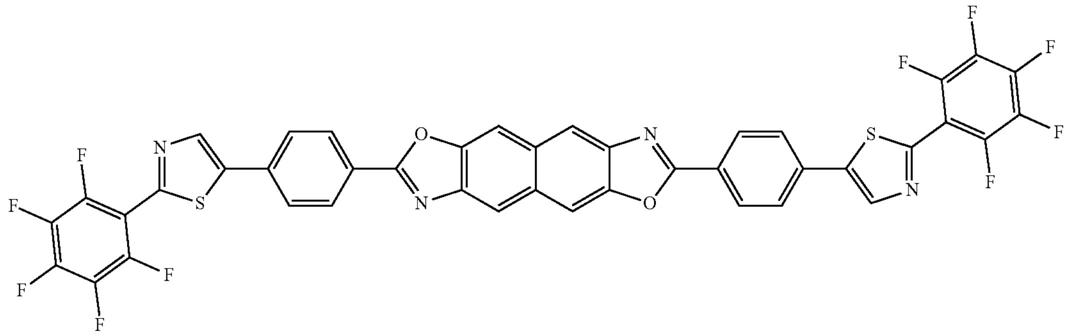
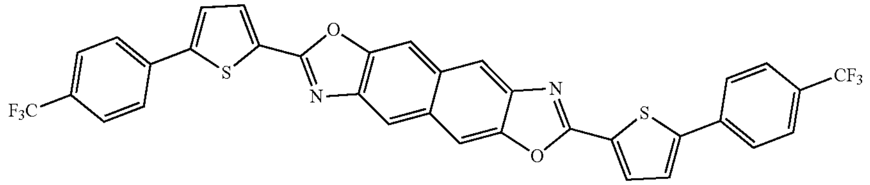
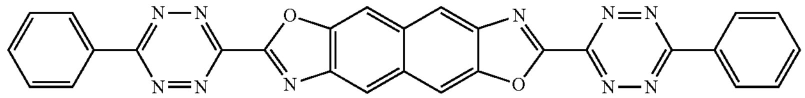
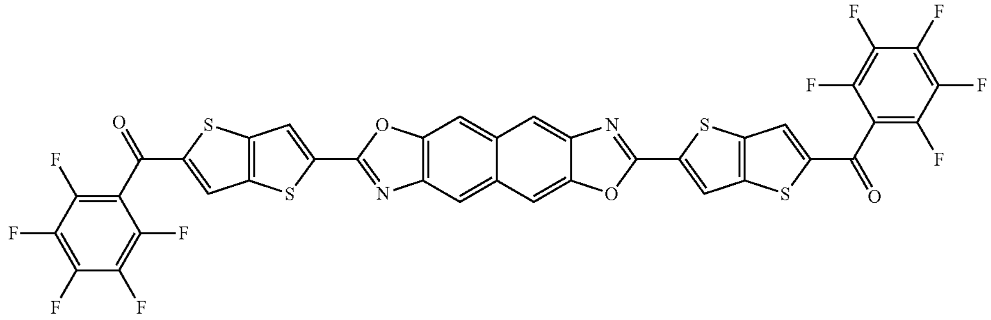
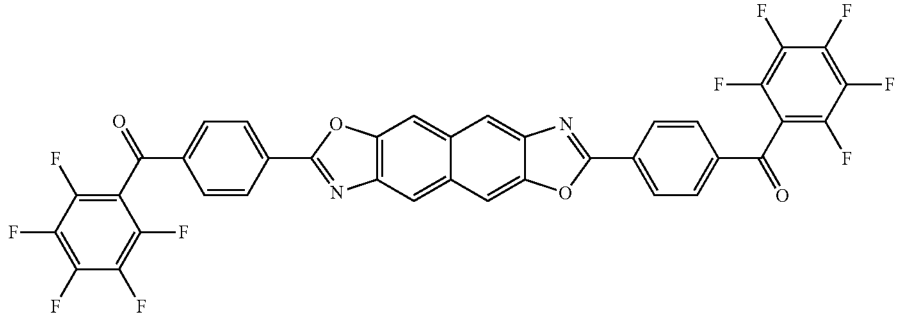
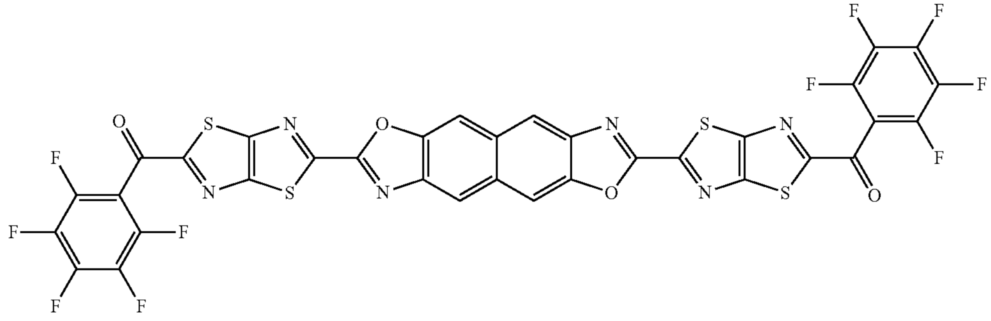

-continued
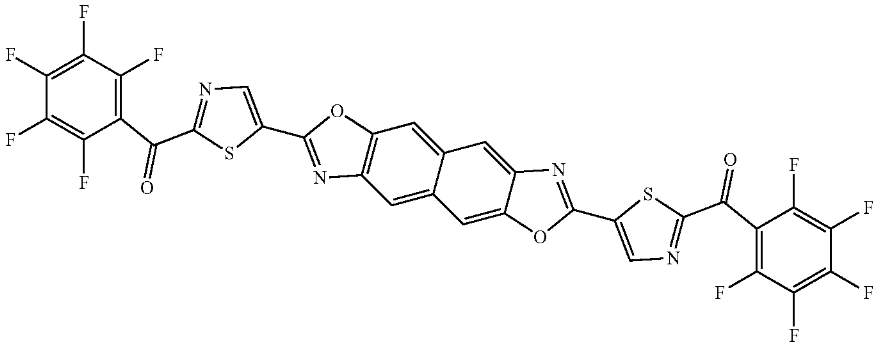
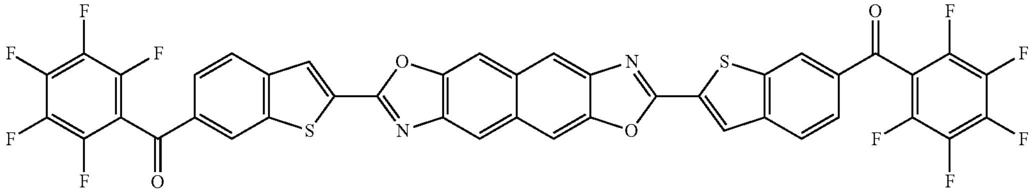
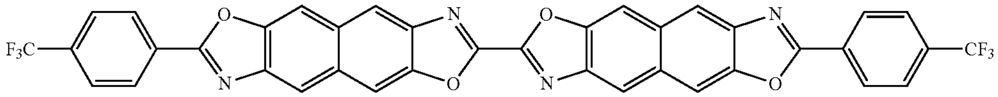
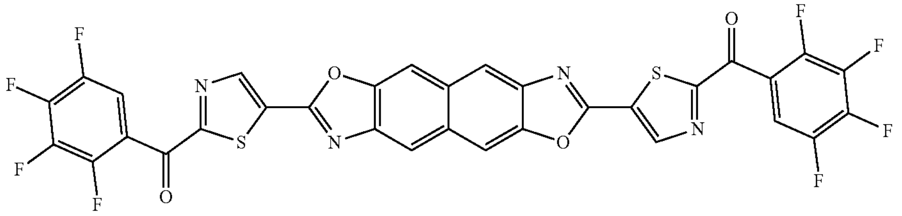
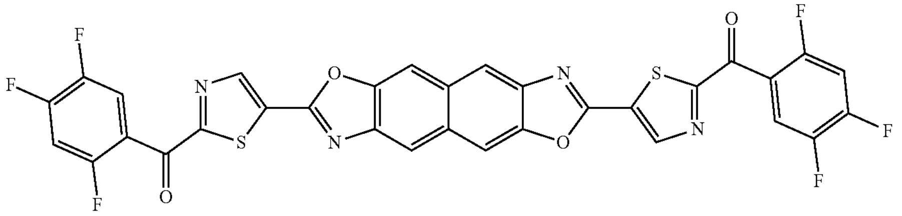
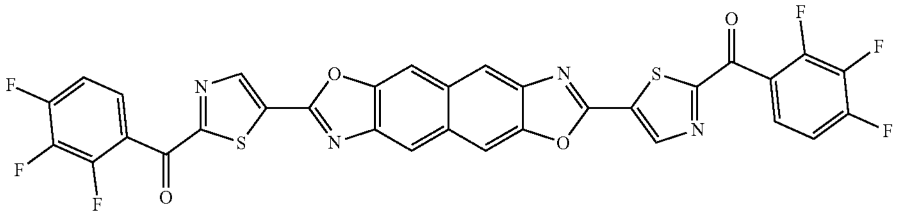
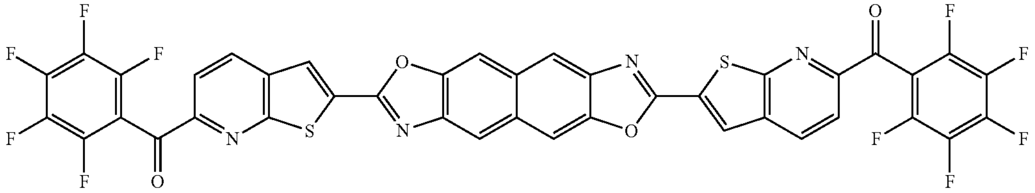

-continued
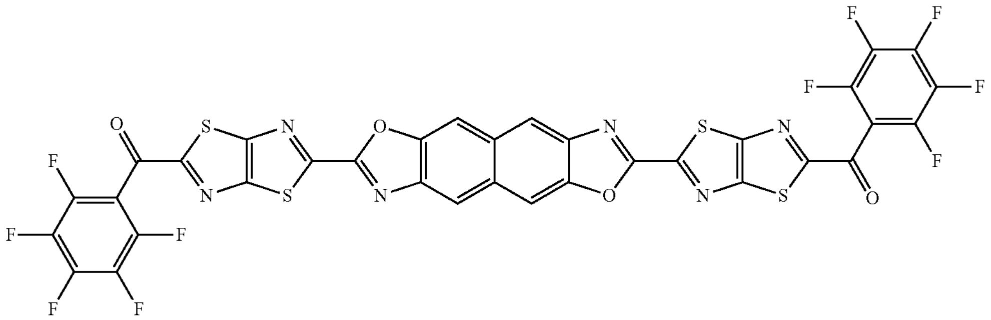
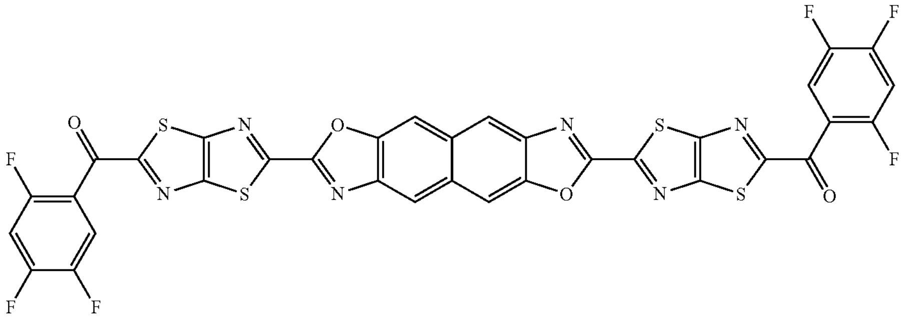
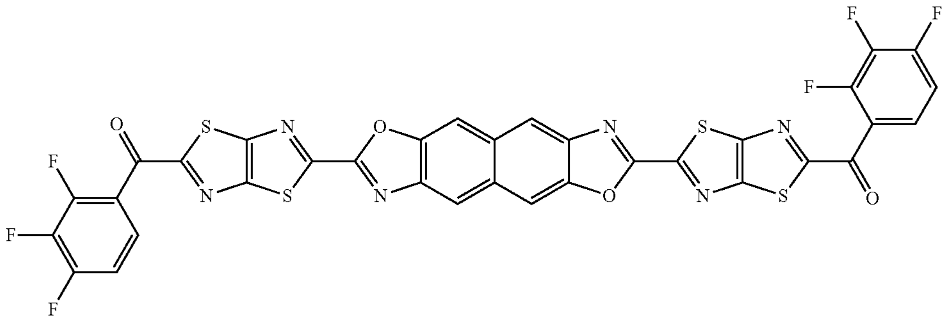
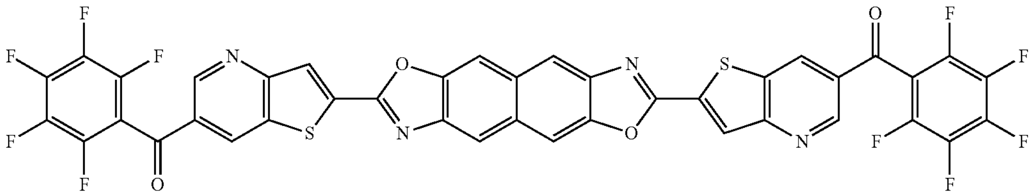
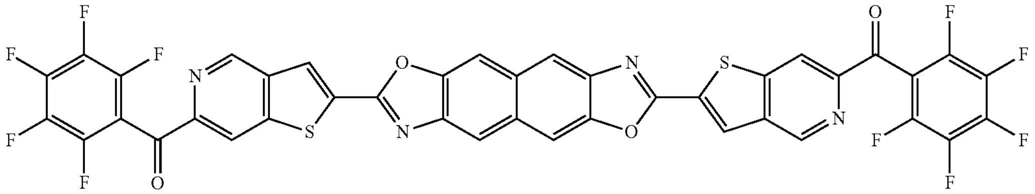
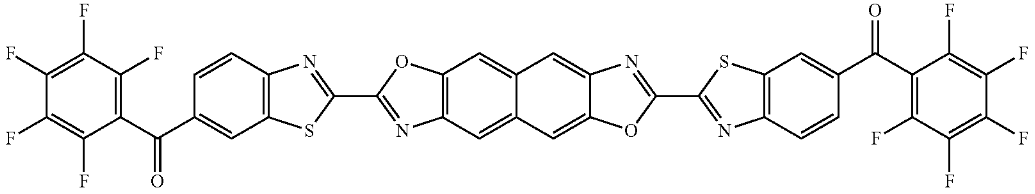

-continued
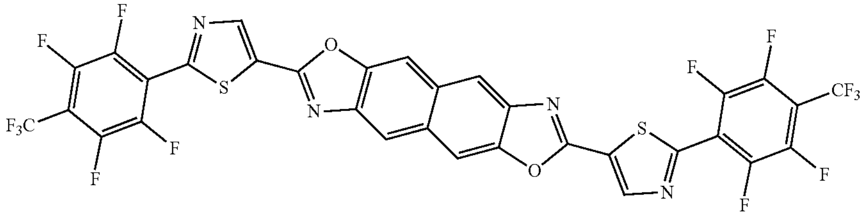
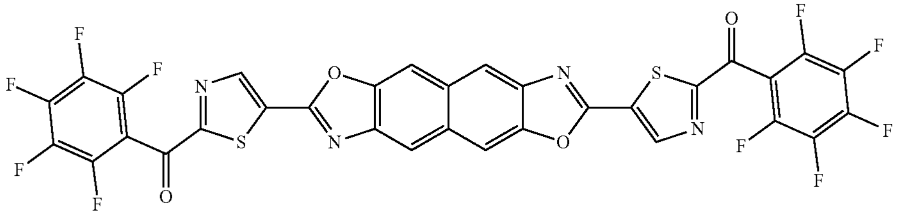
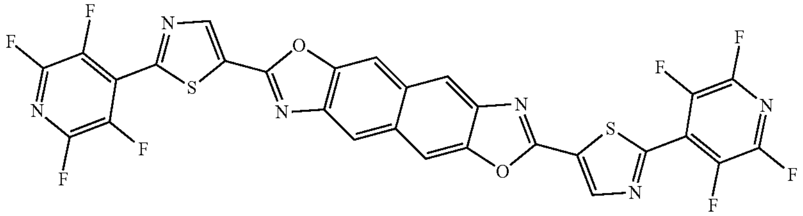
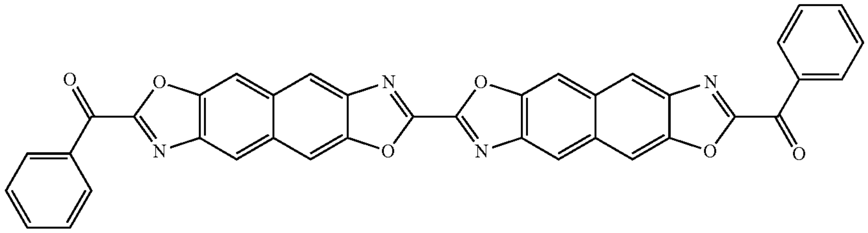
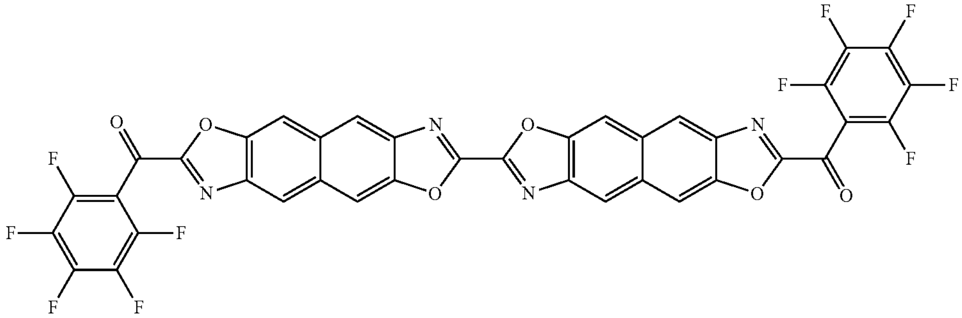
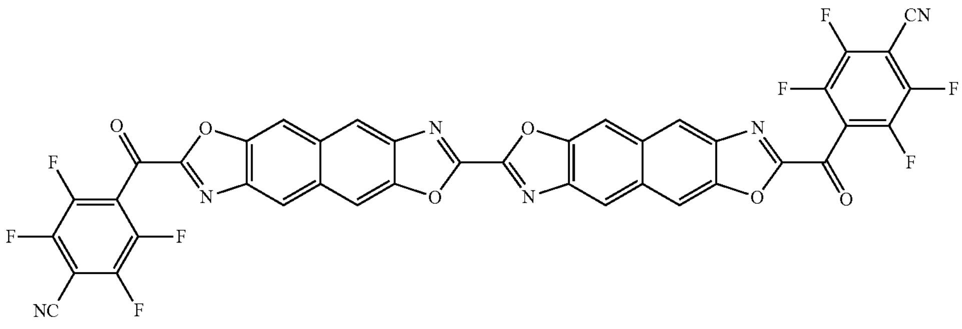

-continued
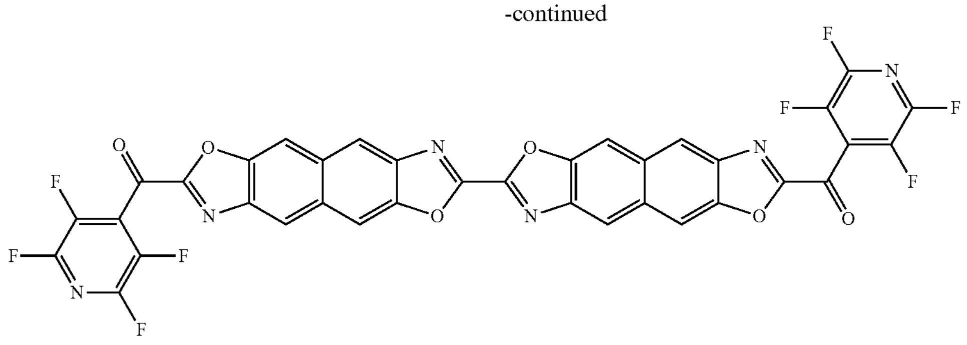
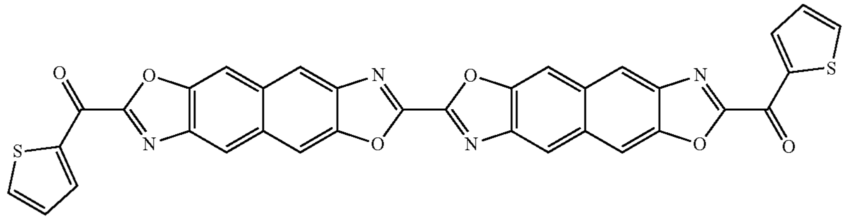
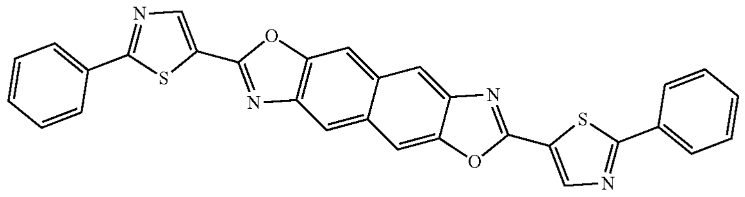
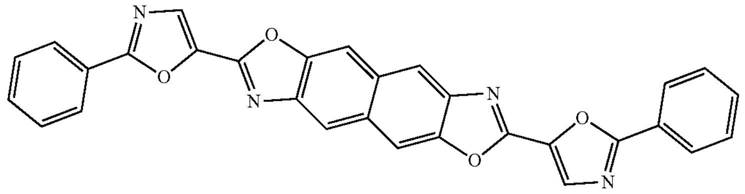
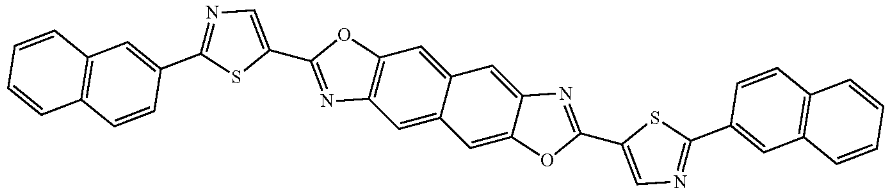
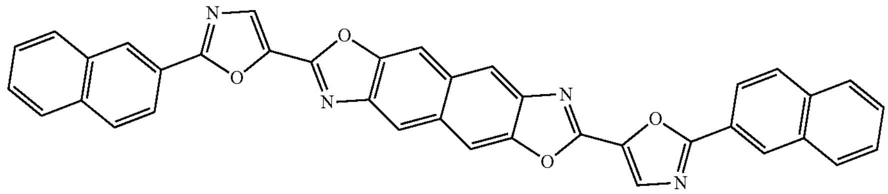
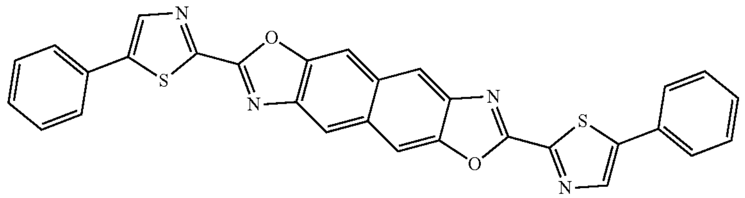
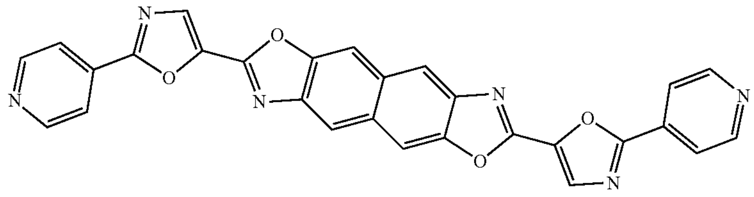

-continued
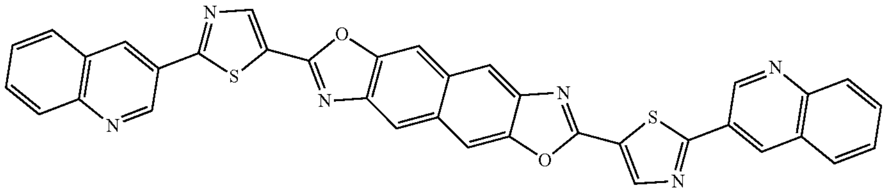
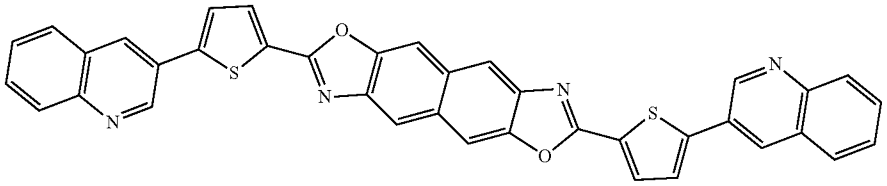
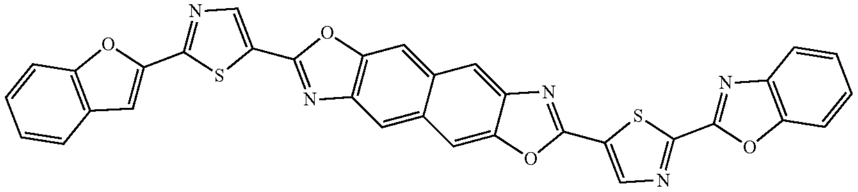
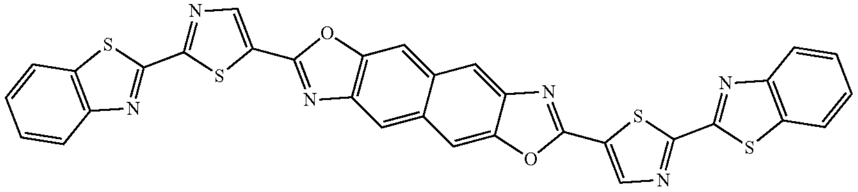
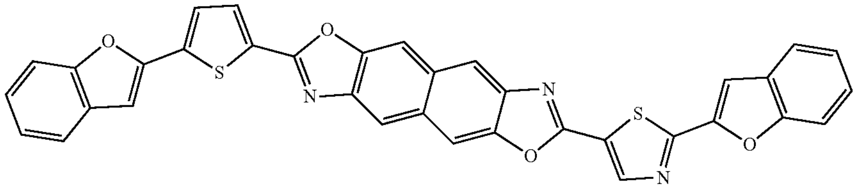
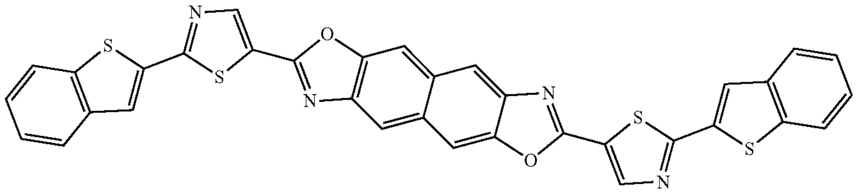
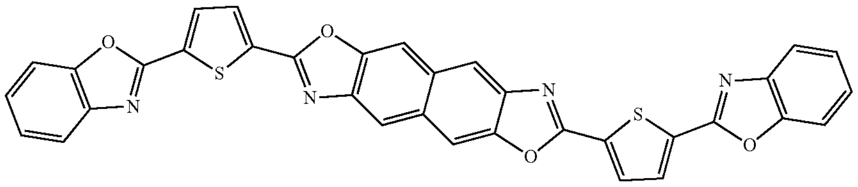
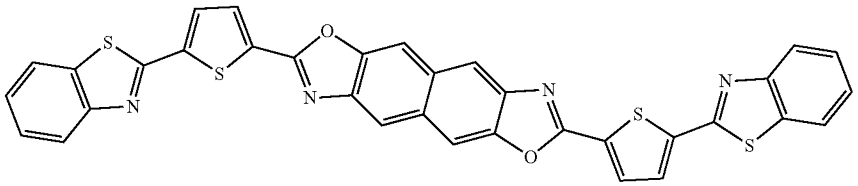
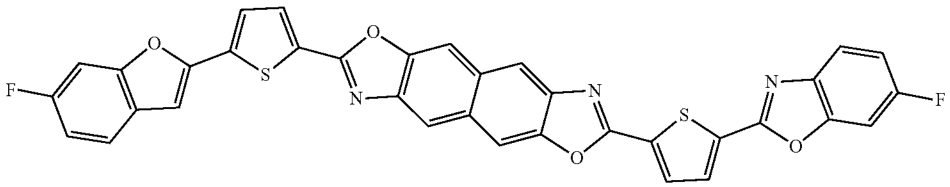

-continued
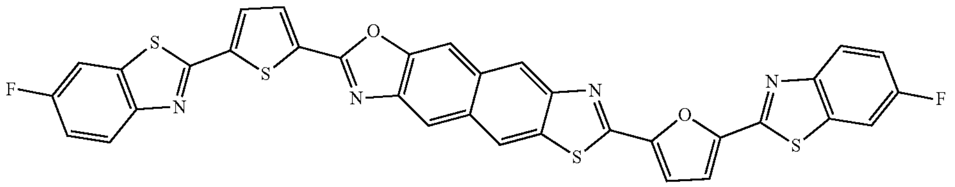
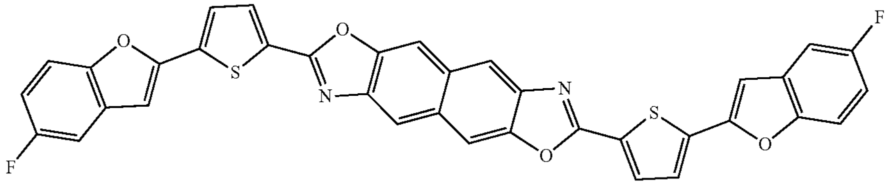
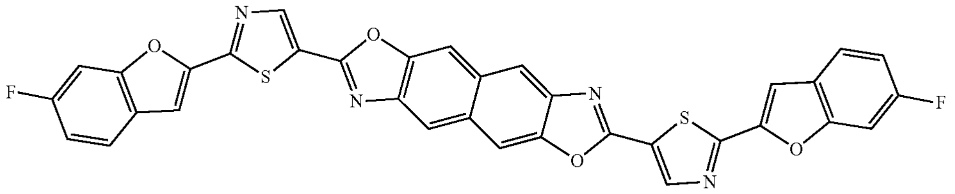
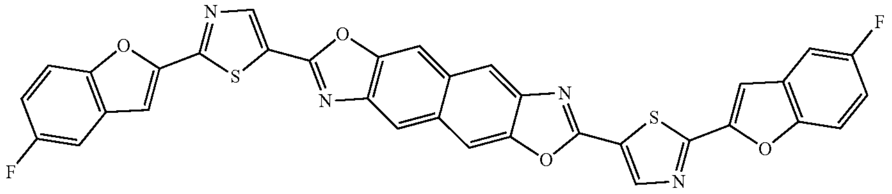
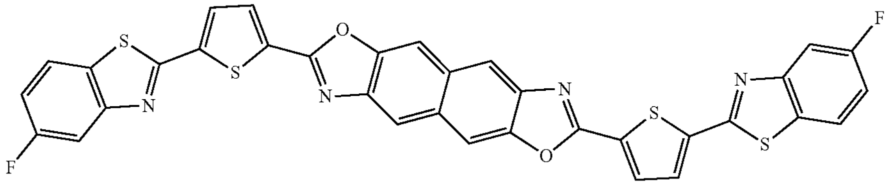
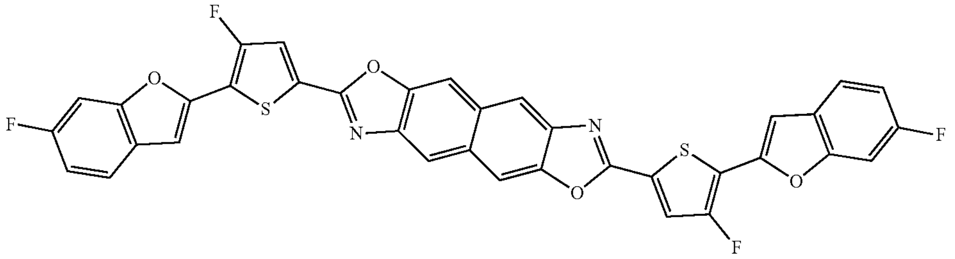
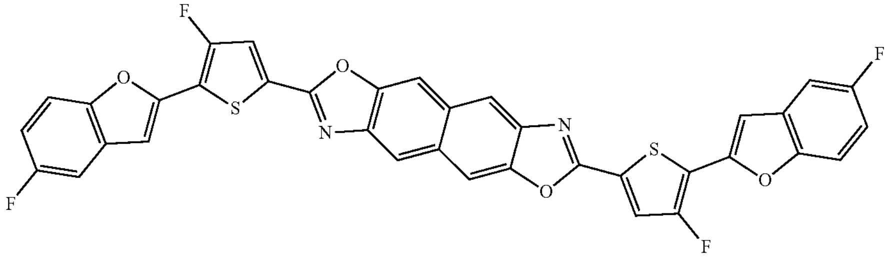
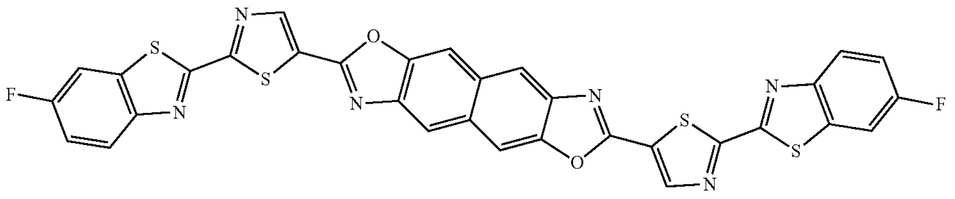

-continued
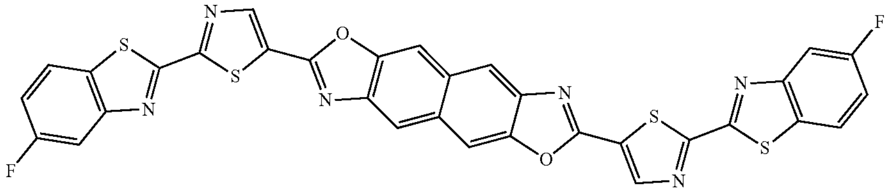
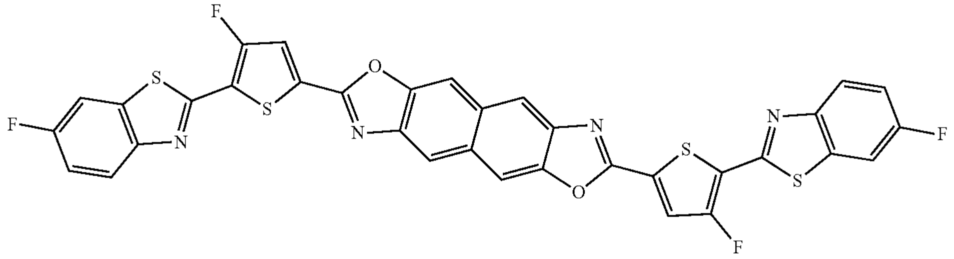
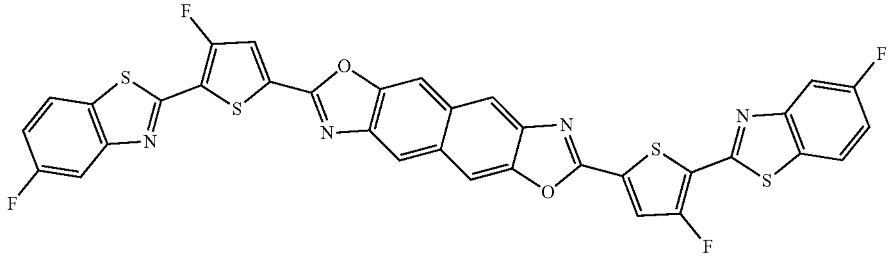
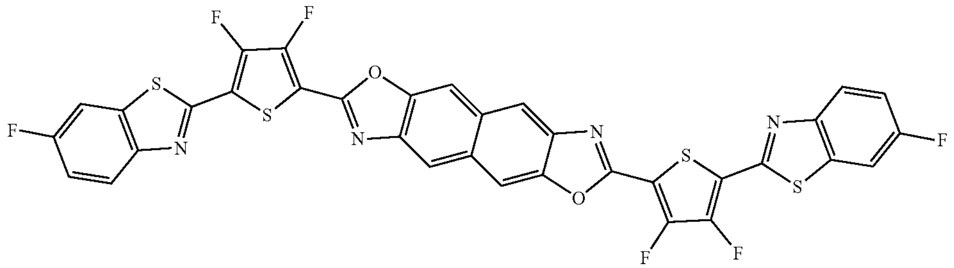
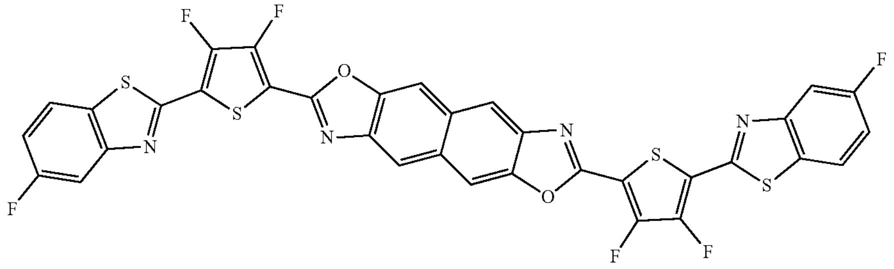
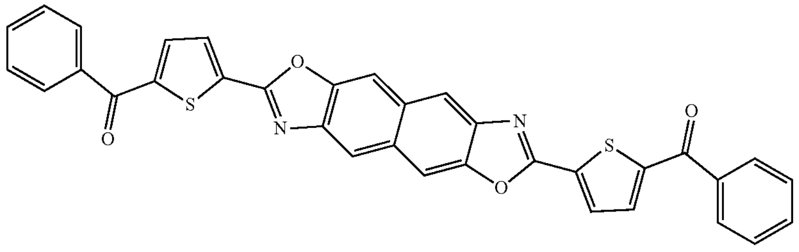

-continued
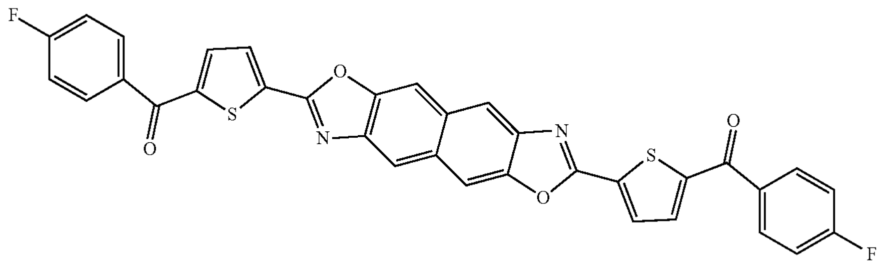
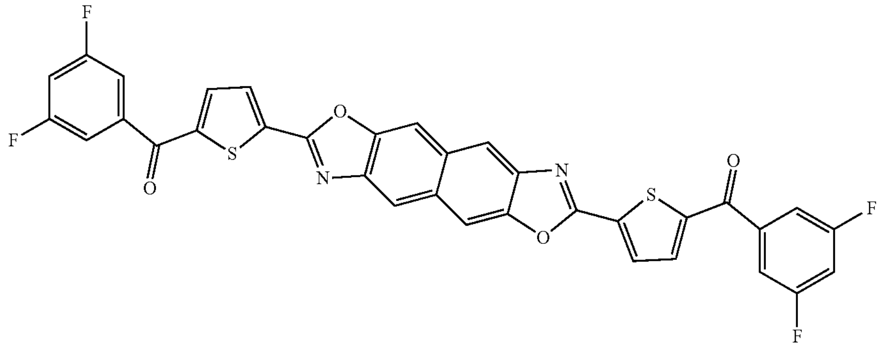
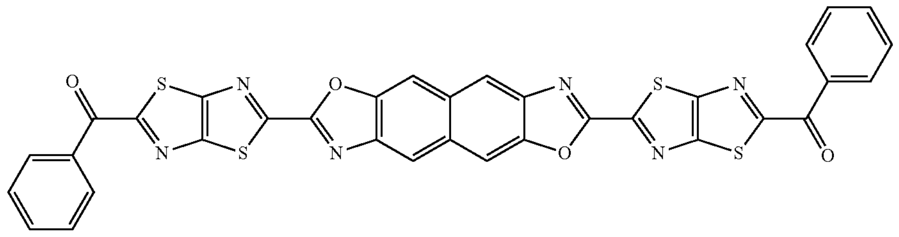
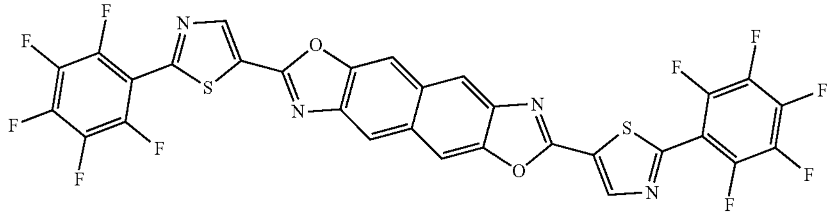
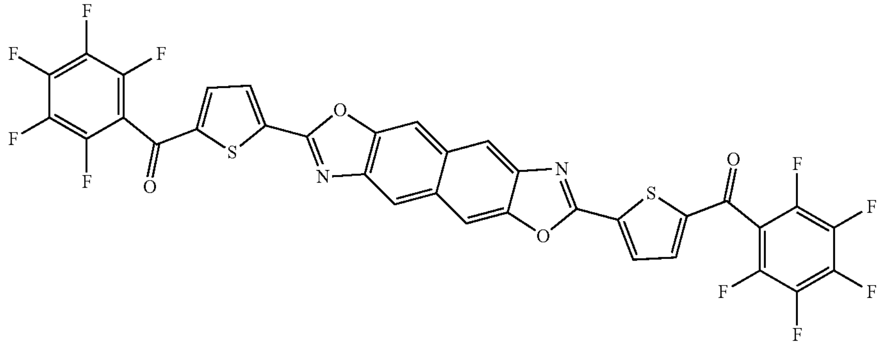
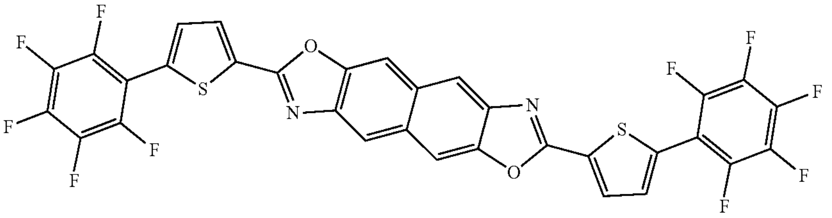

-continued
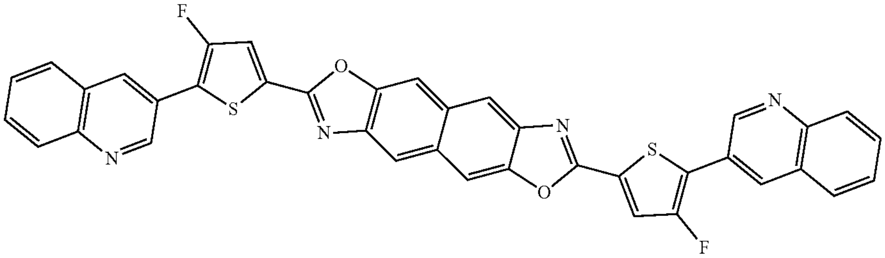
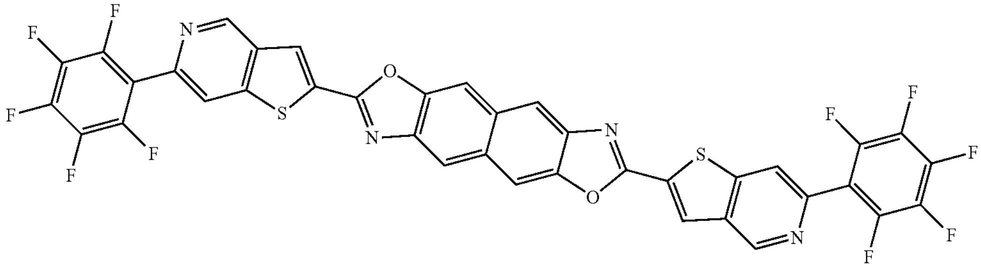
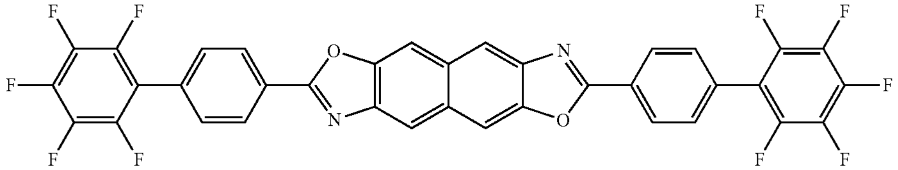
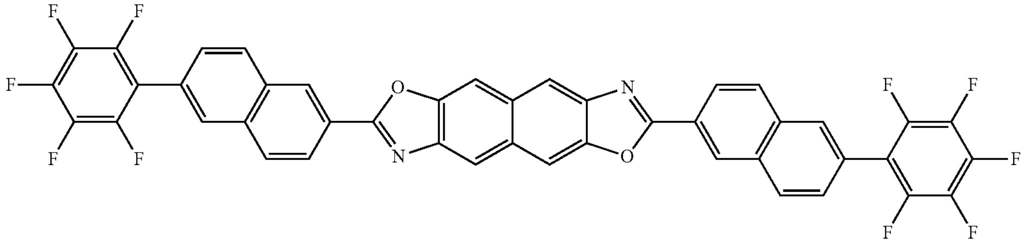
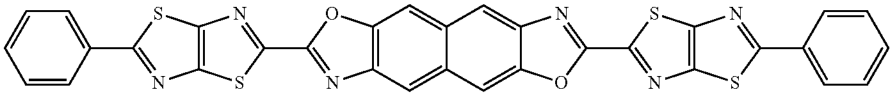
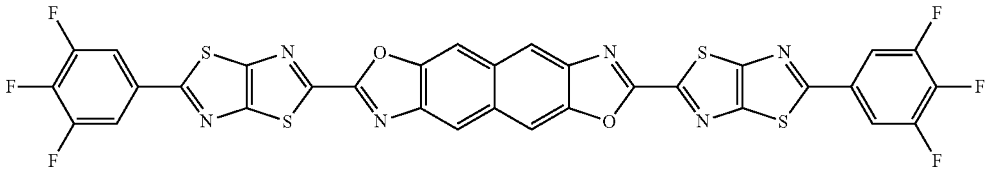
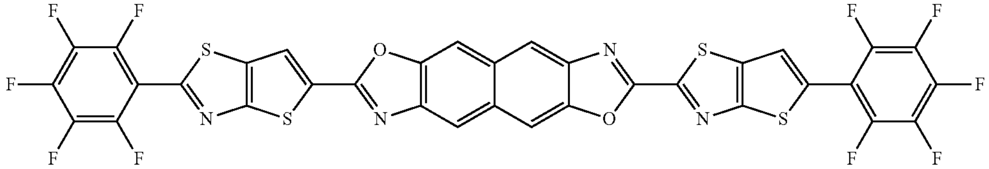
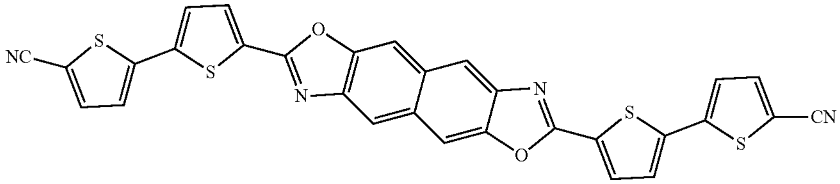

-continued
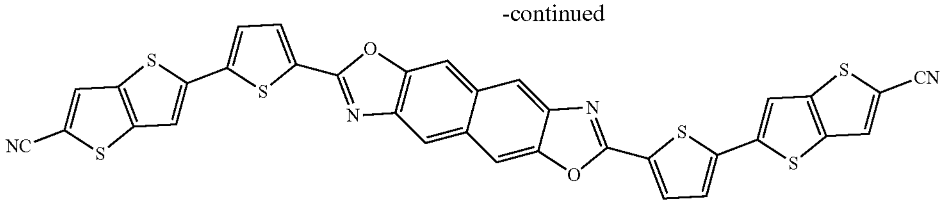
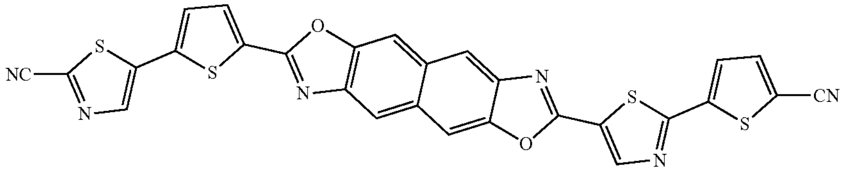
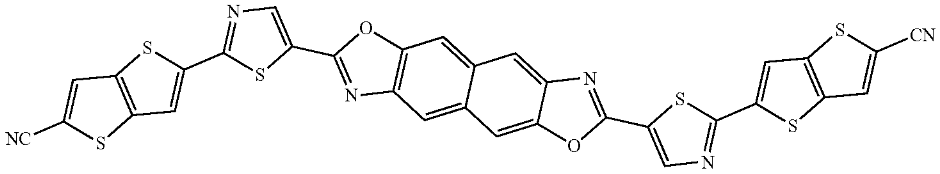
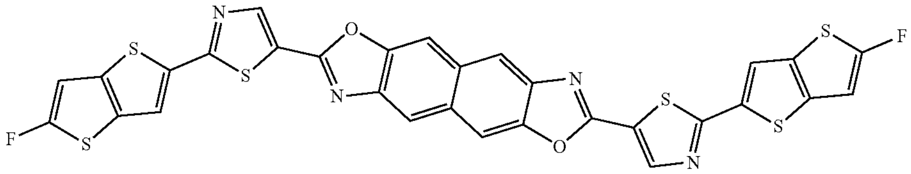
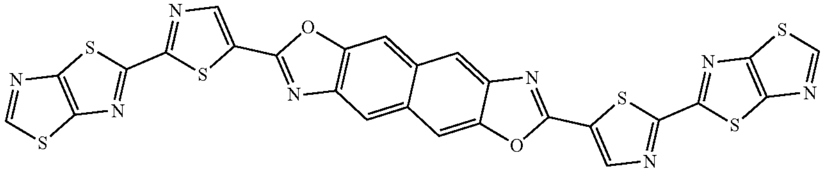
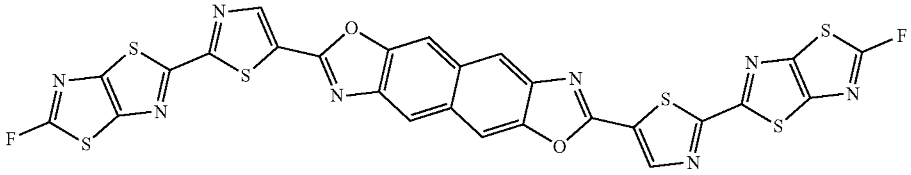
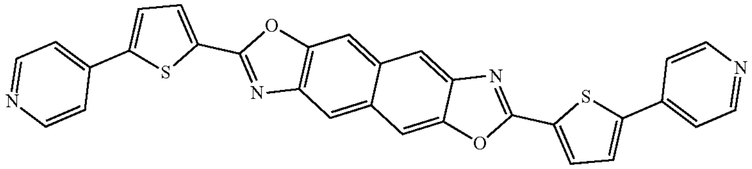
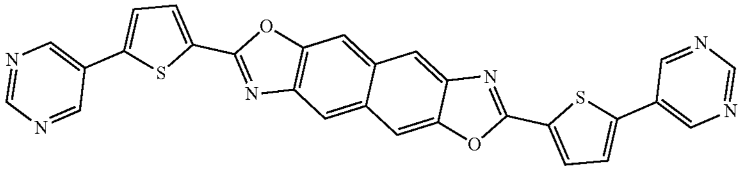
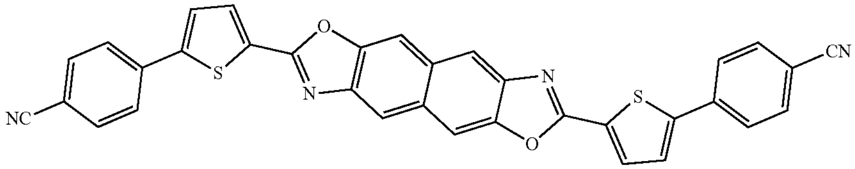

-continued
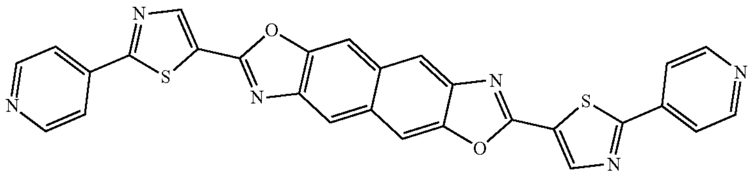
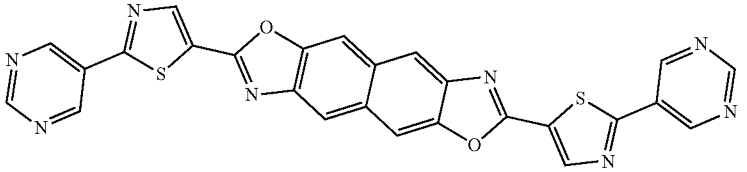
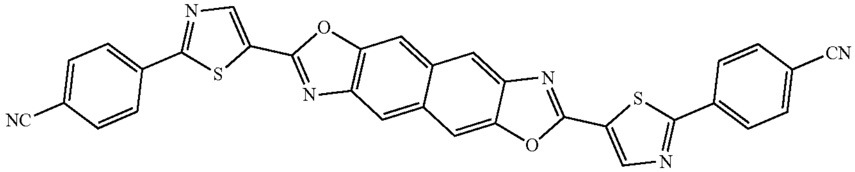
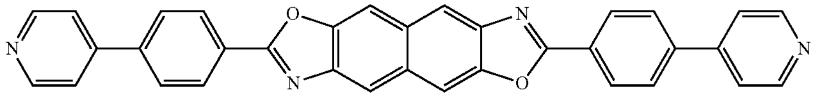
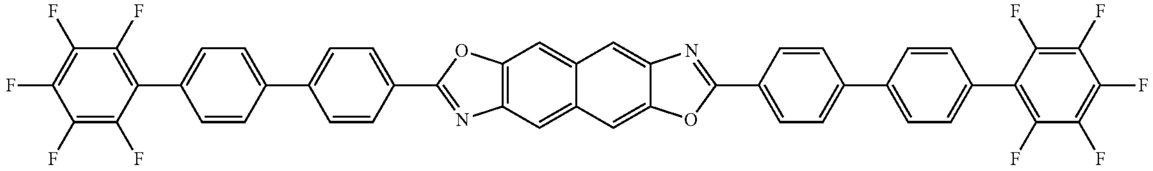
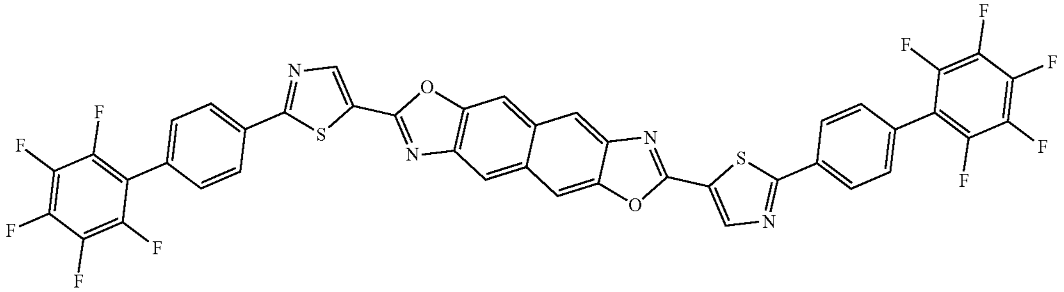
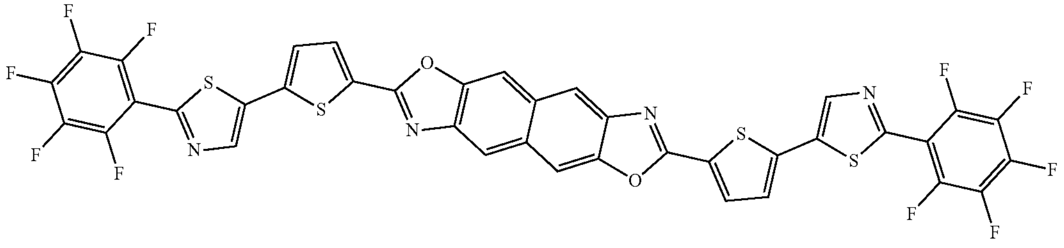
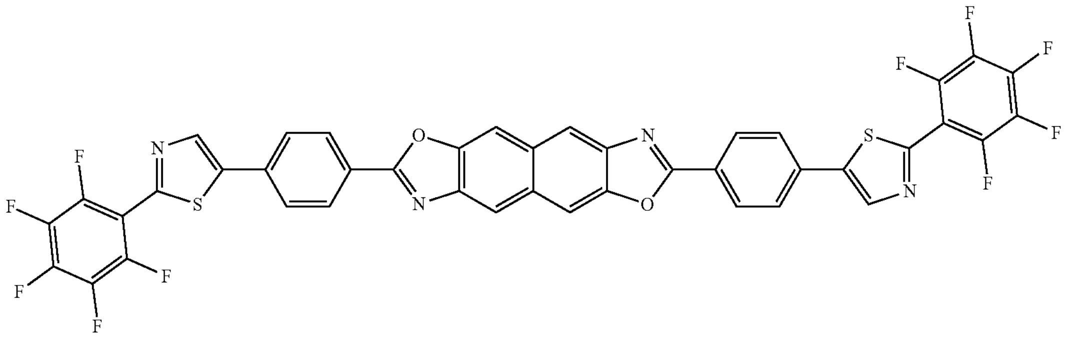

-continued
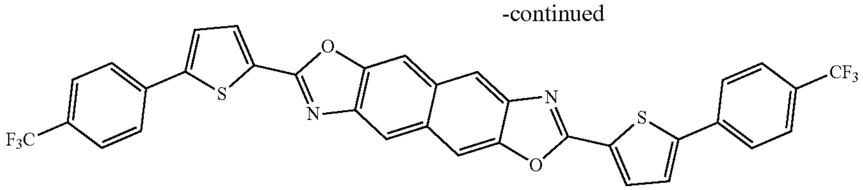
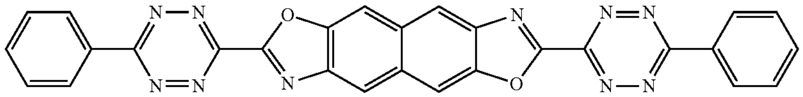
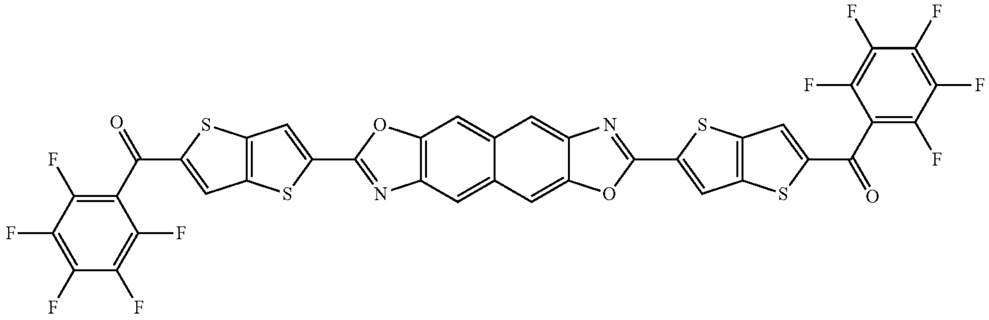
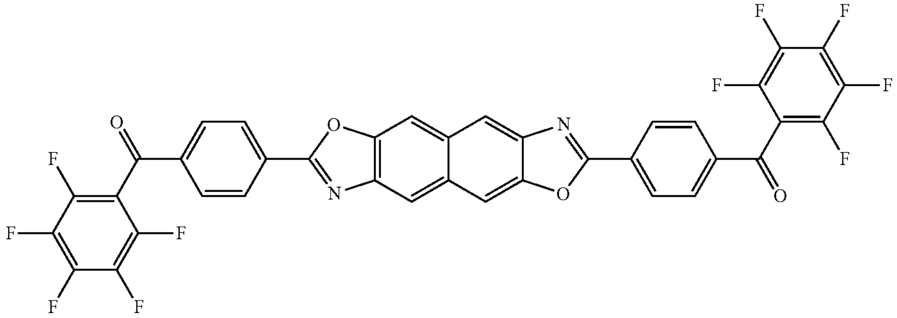
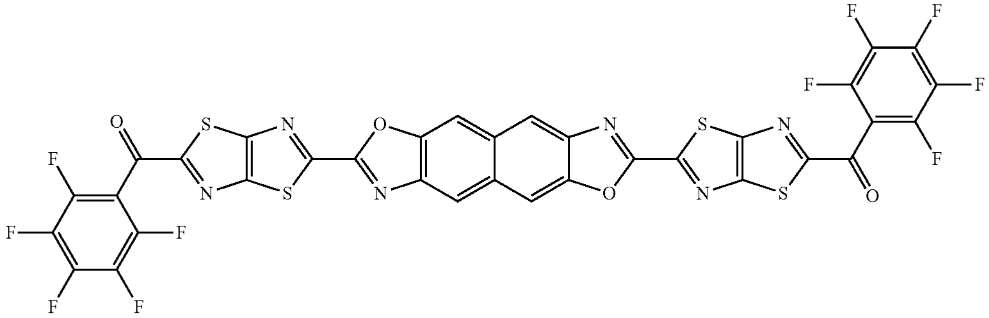
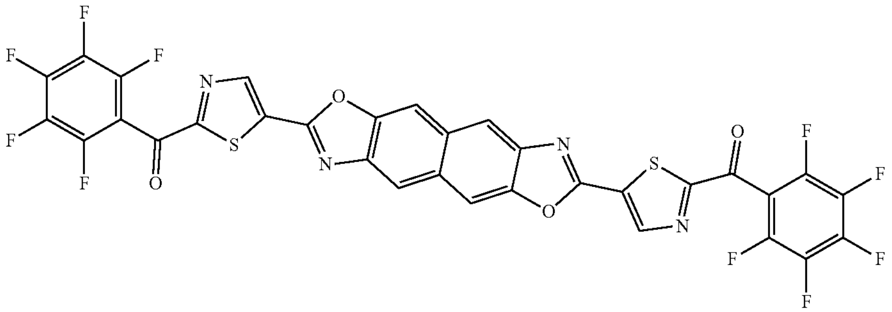
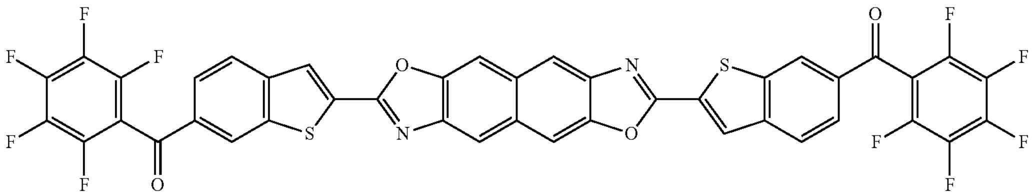

-continued
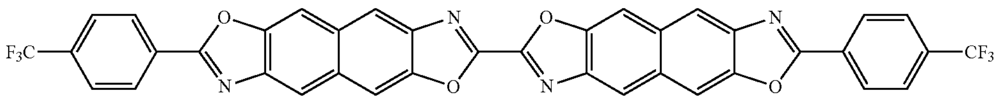
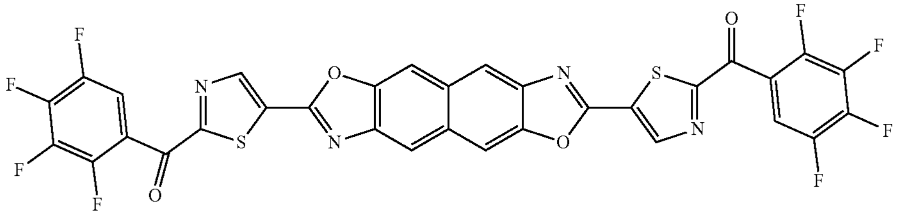
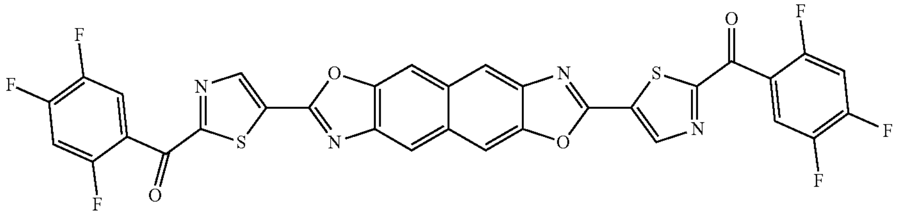
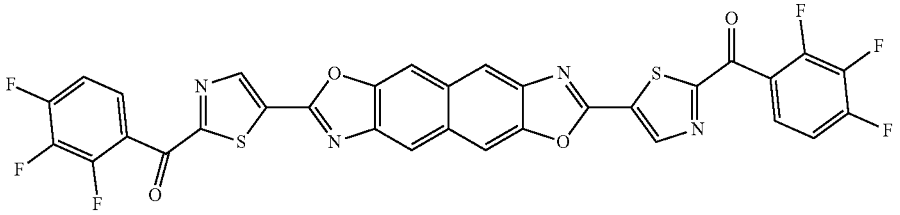
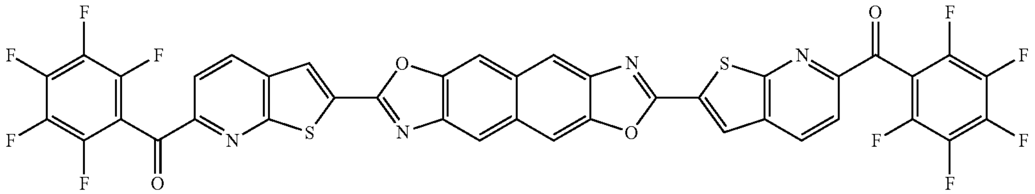
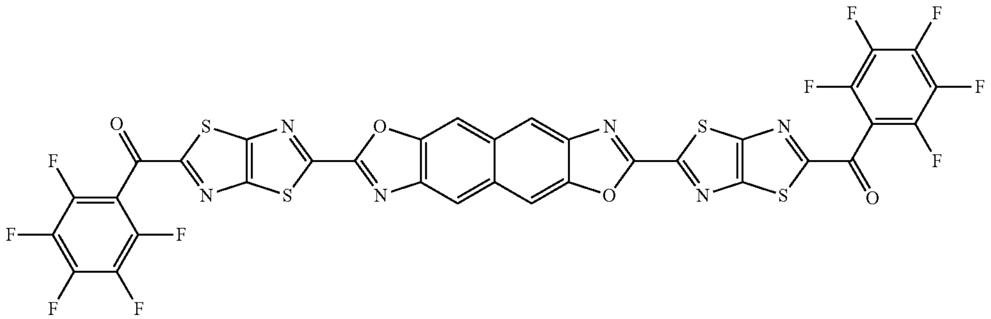
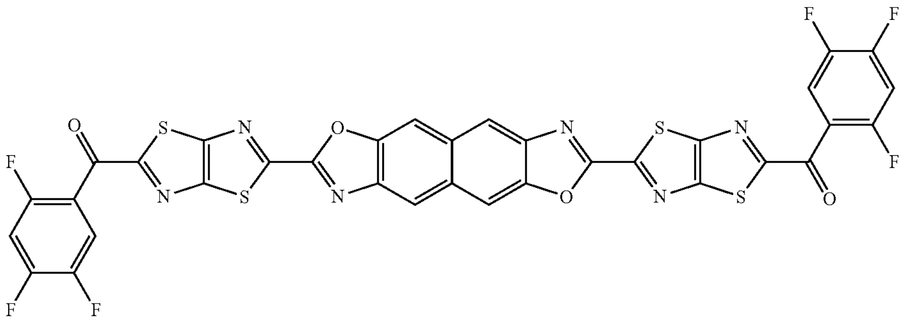

-continued
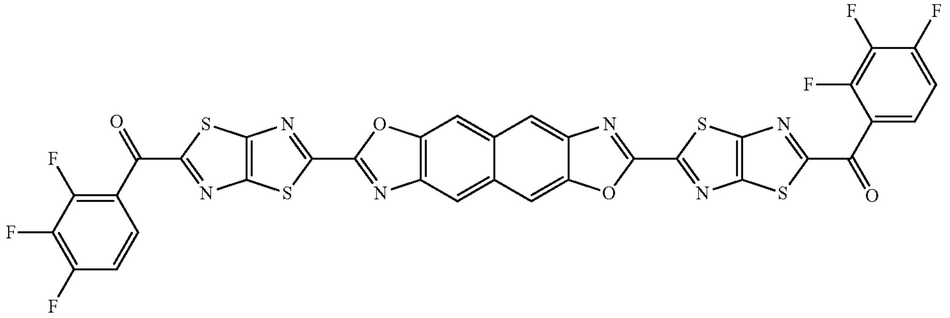
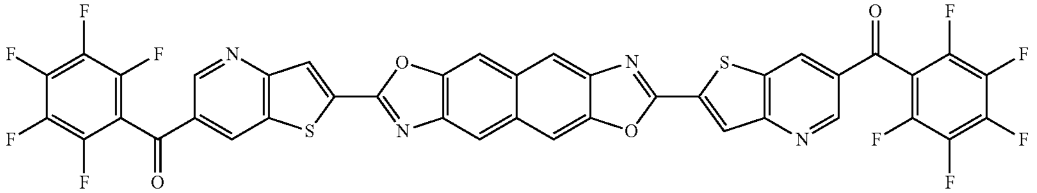
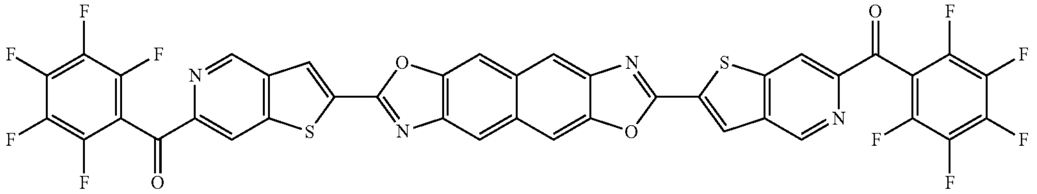
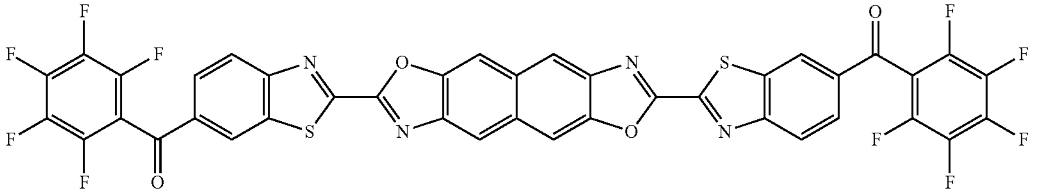
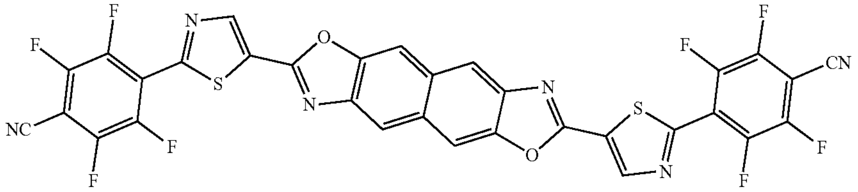
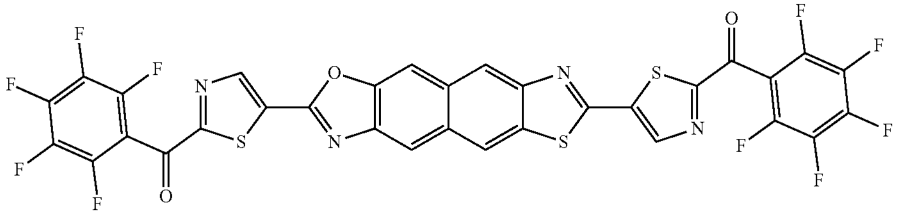
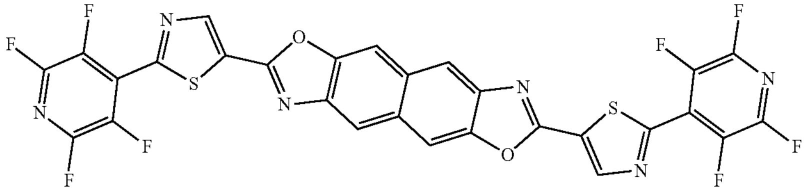
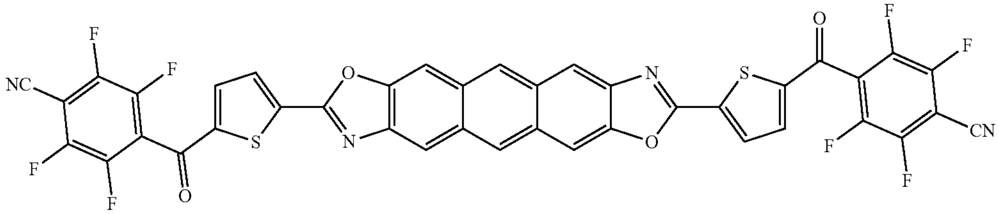

-continued
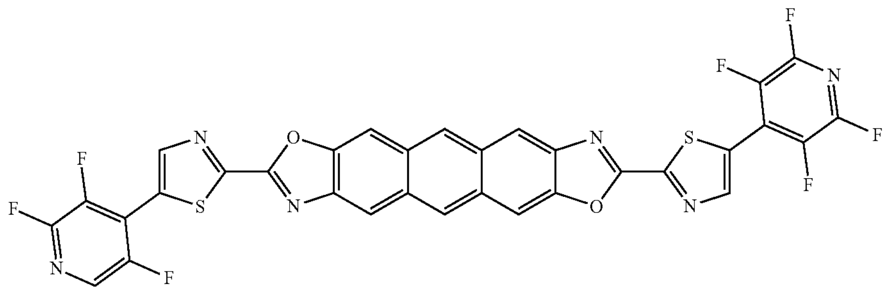
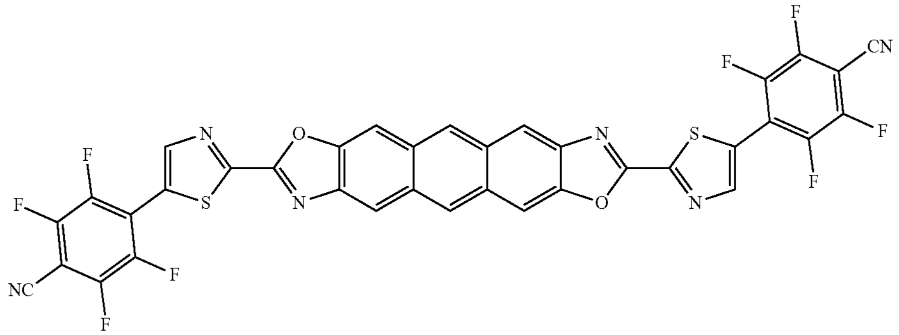
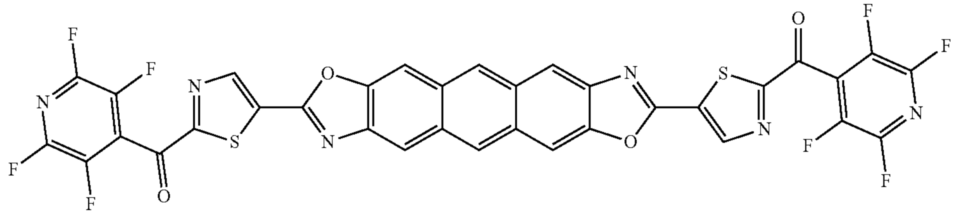
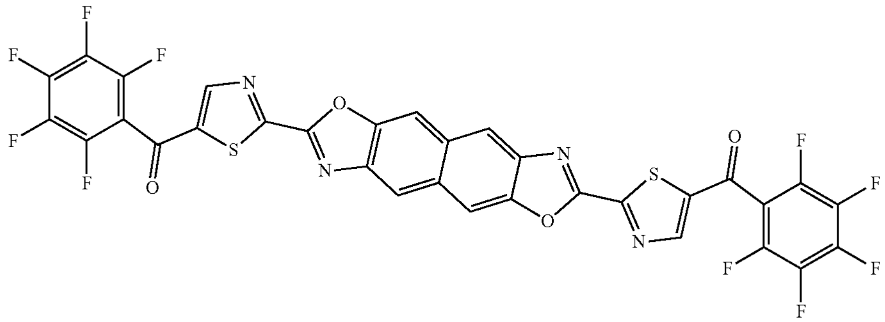
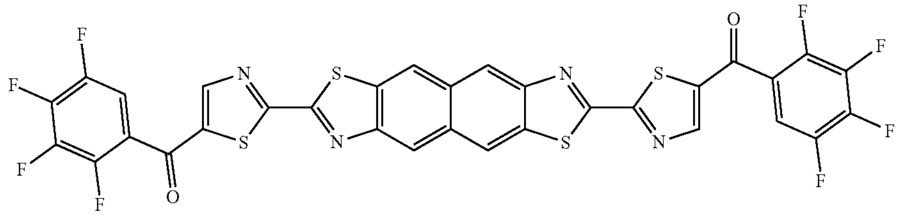
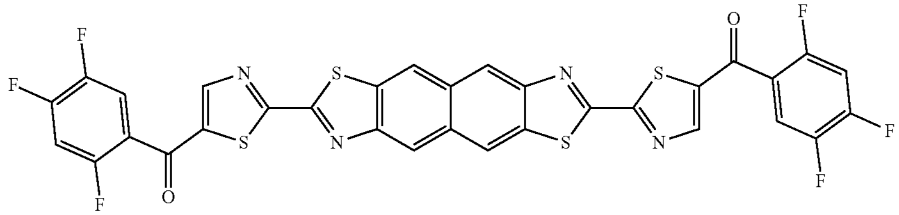

-continued
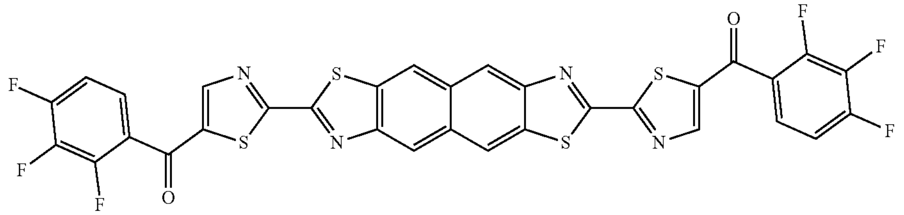
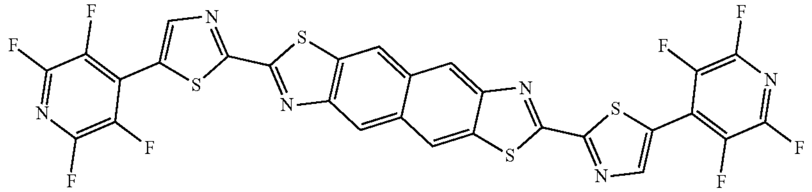
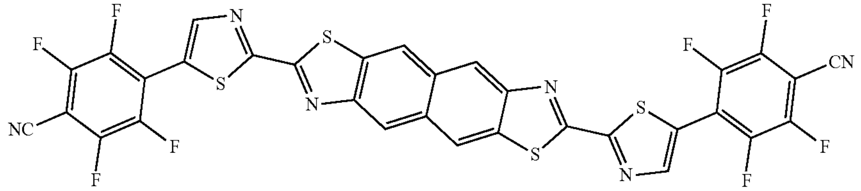
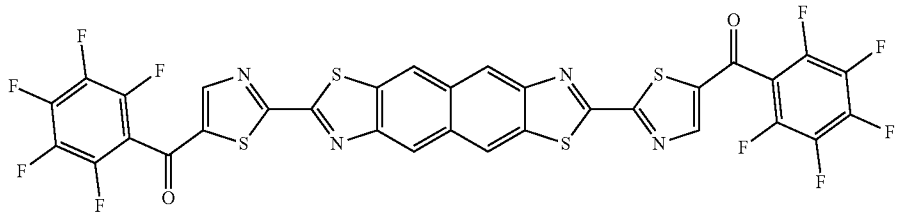
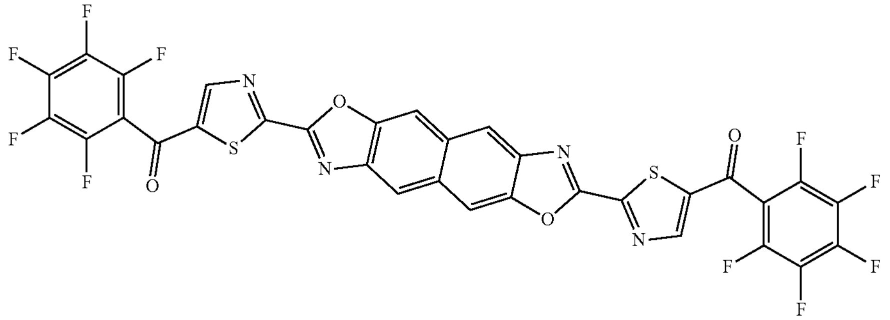
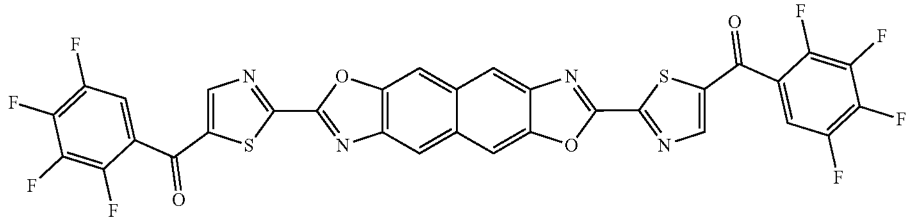
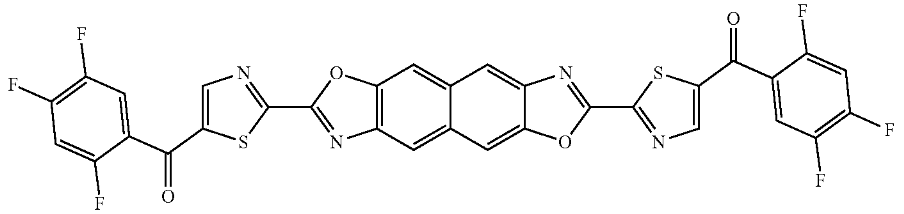

-continued
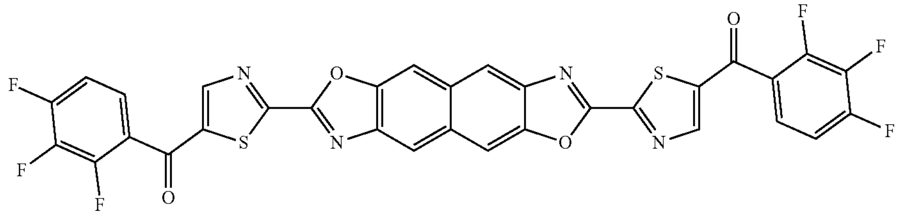
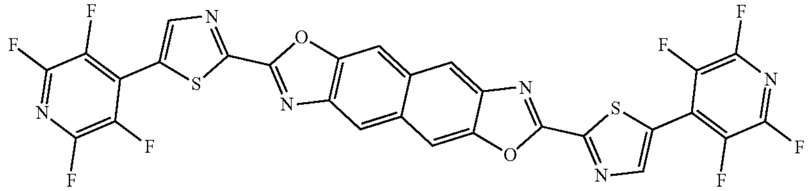
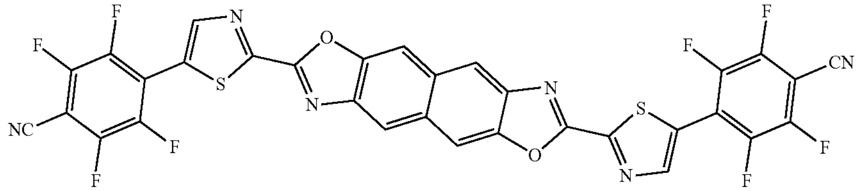
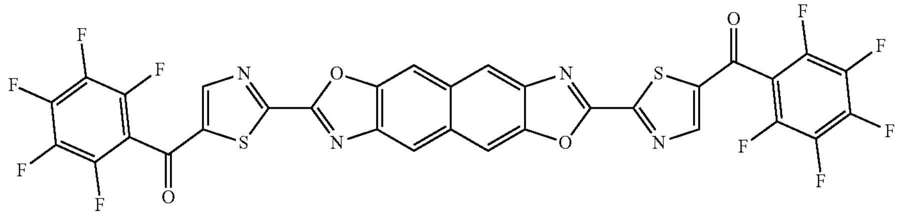
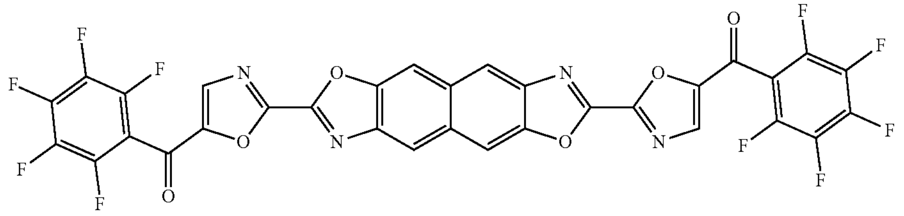
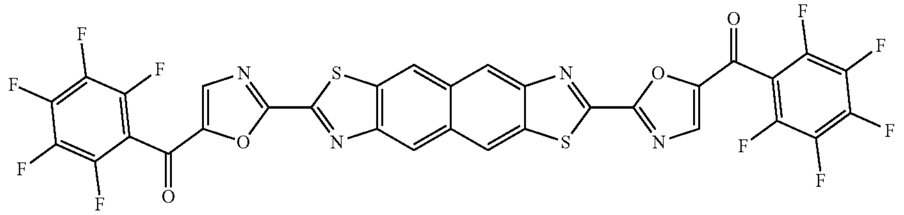
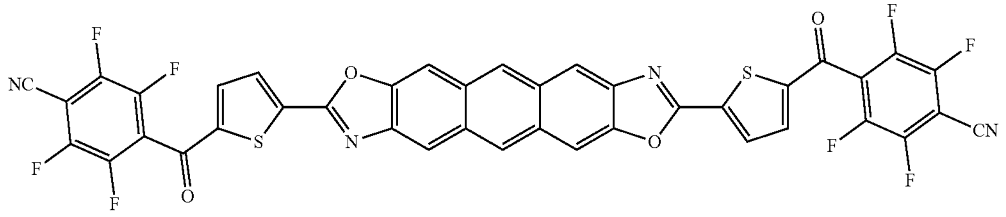

-continued
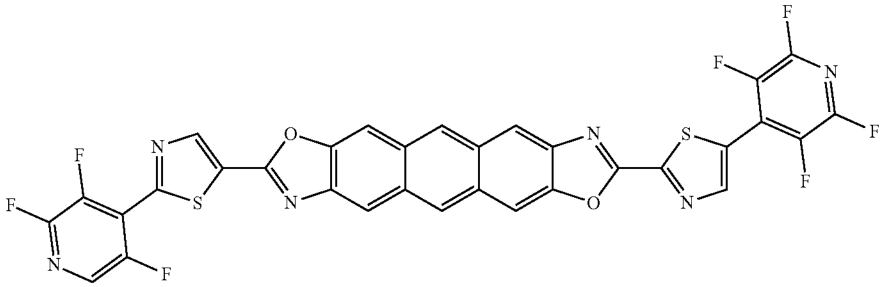
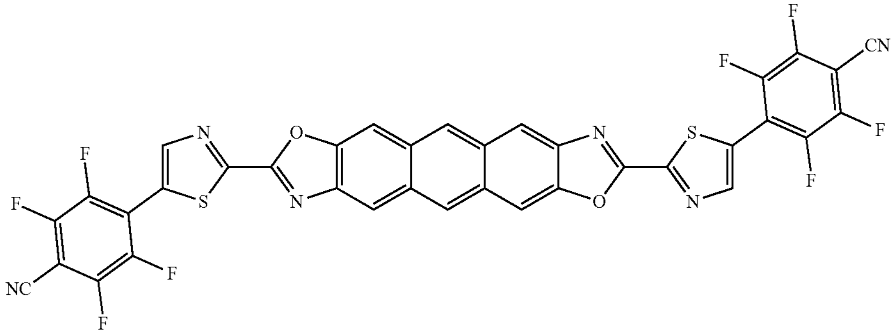
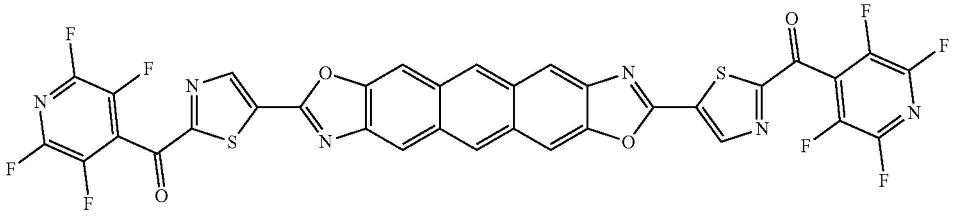
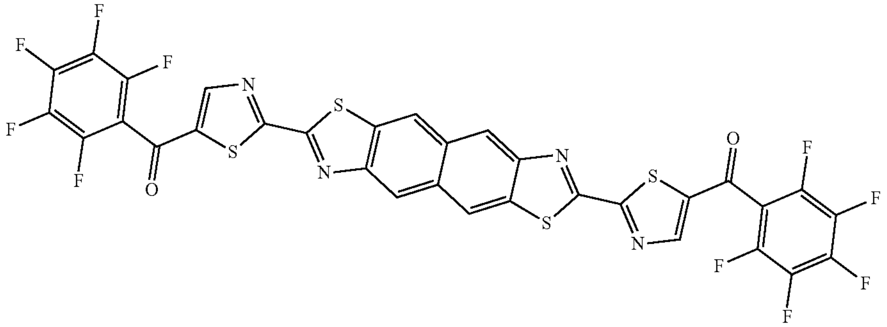
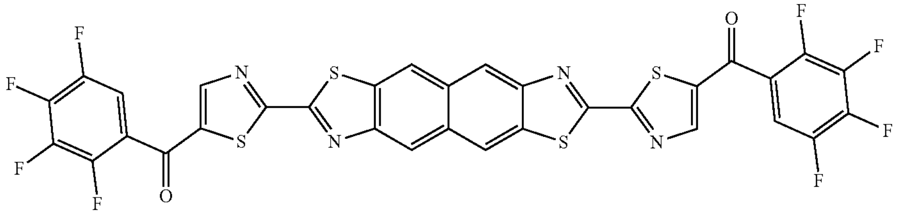
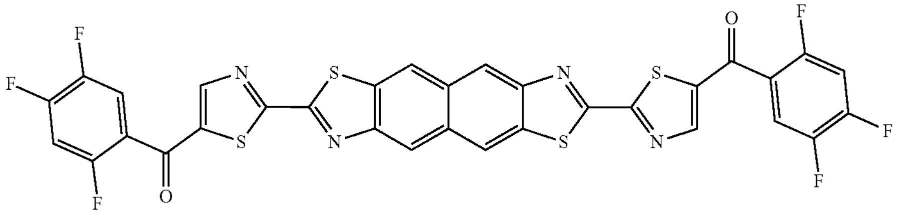

-continued
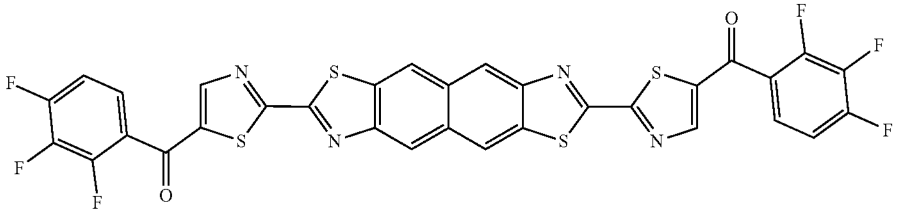
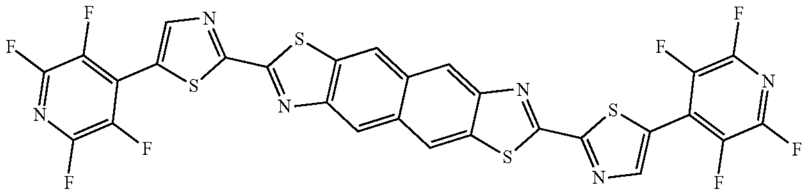
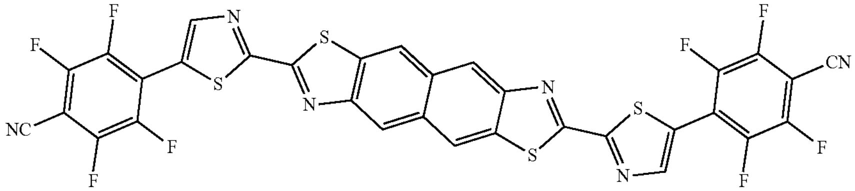
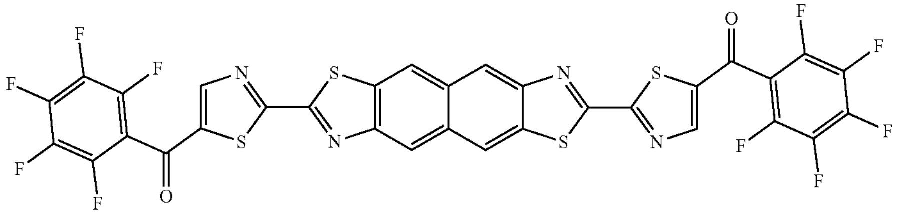
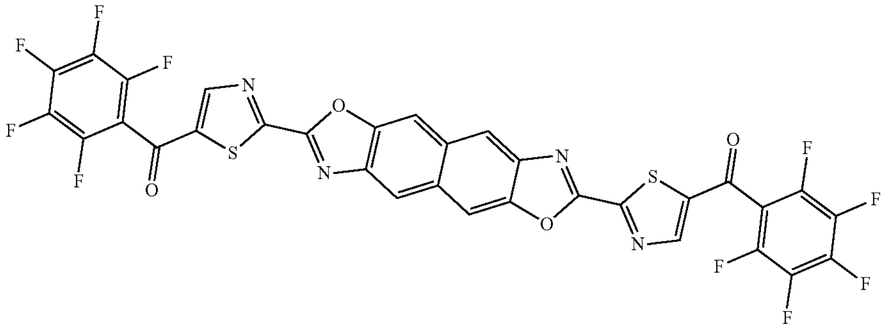
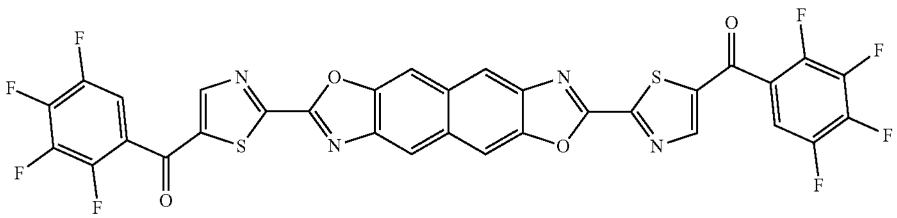
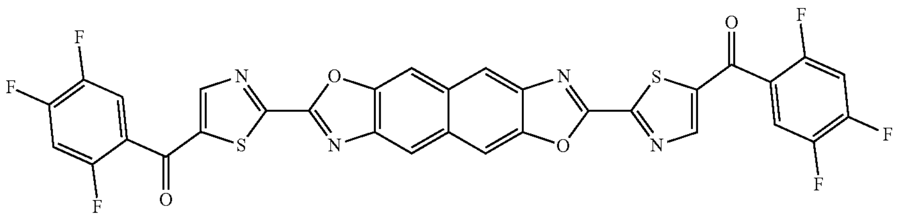

-continued

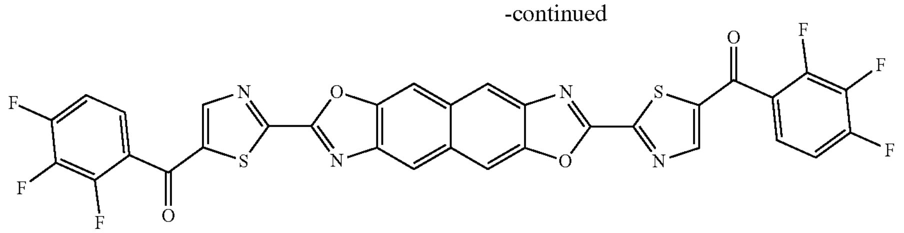

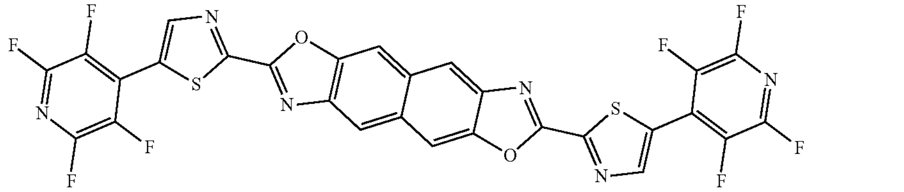

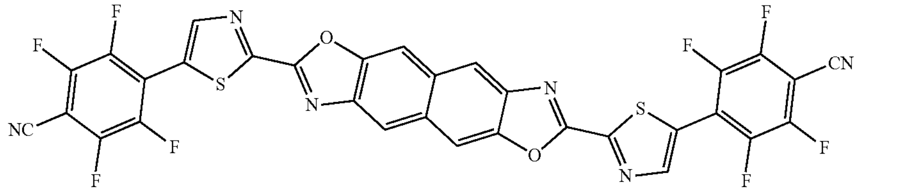

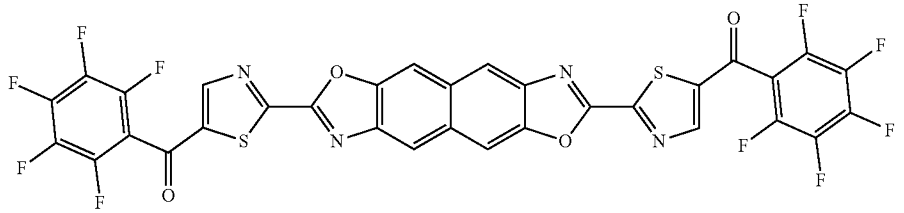

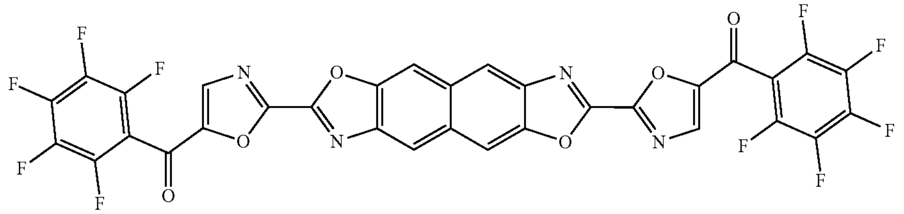

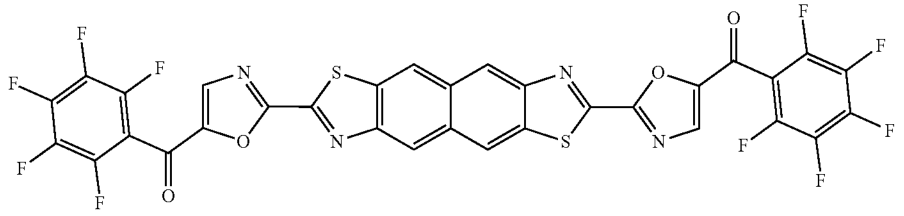

A molecular weight of the specific compound is not particularly limited, but is preferably 550 or more, and more preferably 600 or more. The molecular weight of the specific compound is preferably 1200 or less, and more preferably 1000 or less.

In a case where the molecular weight is 1200 or less, a vapor deposition temperature is not increased, and the compound is not easily decomposed. In a case where the molecular weight is 550 or more, a glass transition point of a vapor deposition film is not lowered, and the heat resistance of the photoelectric conversion element is improved.

The specific compound is particularly useful as a material of the photoelectric conversion film used for the imaging element, the optical sensor, or a photoelectric cell. The specific compound can also be used as a coloring material, a liquid crystal material, an organic semiconductor material, a charge transport material, a pharmaceutical material, and a fluorescent diagnostic material.

The maximum absorption wavelength of the specific compound is not particularly limited and is, for example, preferably within a range of 300 to 550 nm and more preferably within a range of 400 to 550 nm.

The maximum absorption wavelength is a value measured in a solution state (solvent: chloroform) by an absorption spectrum of the specific compound being adjusted to a concentration having an absorbance of about 0.5 to 1. However, in a case where the specific compound is not soluble in chloroform, a value measured by using the specific compound in which the specific compound is vapor-deposited and formed into a film state is defined as a maximum absorption wavelength of the specific compound.

The maximum absorption wavelength of the photoelectric conversion film is not particularly limited and is, for example, preferably within a range of 300 to 700 nm and more preferably within a range of 400 to 700 nm.

In addition, the specific compound can also be used as a p-type material (material having excellent hole transport properties), and a n-type material (material having excellent electron transport properties).

In a case where the specific compound is used as the n-type material, it is preferable that the specific compound satisfies one or more of the following requirements.

Requirement 1: The specific compound contains three or more (for example, 4 to 16) fluorine atoms (preferably fluorine atoms present as substituents of aromatic ring groups represented by $Ar^{11}$ to $Ar^{16}$ in Formula (1)) in the molecule.

Requirement 2: One or more (preferably 2 to 4) of $Ar^{11}$ to $Ar^{14}$ is a nitrogen-containing aromatic ring group containing a nitrogen atom as a ring member atom, and has a total of one or more (for example, 2 to 16) fluorine atoms or cyano groups (preferably, fluorine atoms present as substituents of aromatic ring groups represented by $Ar^{11}$ to $Ar^{16}$ in Formula (1)) in the molecule.

In a case where the specific compound is used as the p-type material, the specific compound is preferably a compound that does not satisfy any of the above requirements.

In a case where the specific compound is used as the p-type material, the ionization potential of the specific compound is preferably 5.0 to 6.0 eV.

In addition, in a case where the specific compound is used as the n-type material, the electron affinity of the specific compound is preferably 3.0 to 4.5 eV.

In the present specification, a value (value multiplied by −1) of a reciprocal number of the LUMO value obtained by the calculation of B3LYP/6-31G (d) using Gaussian '09 (software manufactured by Gaussian, Inc.) as a value of the electron affinity.

The specific compound contained in the photoelectric conversion film may be substantially only the specific compound used as the p-type material, may be substantially only the specific compound used as the n-type material, and may be both the specific compound used as the p-type material and the specific compound used as the n-type material.

The fact that the specific compound contained in the photoelectric conversion film is substantially only the specific compound used as the p-type material means that a content of the specific compound used as the p-type material (=a total film thickness of a film thickness of the specific compound used as the p-type material in terms of a single layer/a film thickness of all of the specific compound in terms of a single layer×100) is more than 90% by volume and 100% by volume or less (preferably, 95% to 100% by volume, and more preferably 99% to 100% by volume) with respect to all of the specific compound contained in the photoelectric conversion film.

The fact that the specific compound contained in the photoelectric conversion film is substantially only the specific compound used as the n-type material means that a content of the specific compound used as the n-type material (=a total film thickness of a film thickness of the specific compound used as the n-type material in terms of a single layer/a film thickness of all of the specific compound in terms of a single layer×100) is more than 90% by volume and 100% by volume or less (preferably, 95% to 100% by volume, and more preferably 99% to 100% by volume) with respect to all of the specific compound contained in the photoelectric conversion film.

In a case where the specific compound contained in the photoelectric conversion film is both the specific compound used as the p-type material and the specific compound used as the n-type material, a ratio of contents of the specific compound used as the p-type material and the specific compound used as the n-type material in the photoelectric conversion film (=a film thickness of the specific compound used as the p-type material in terms of a single layer/a film thickness of the specific compound used as the n-type material in terms of a single layer) is preferably 10/90 to 90/10, more preferably 40/60 to 60/40, and still more preferably 47/53 to 53/47.

The photoelectric conversion film may contain only one specific compound, two specific compounds, or three or more specific compounds.

The fact that the "photoelectric conversion film contains only one specific compound" means that the specific compound contained in the photoelectric conversion film may be substantially only one specific compound.

The fact that the "specific compound contained in the photoelectric conversion film is substantially only one specific compound" means that a content of the most common specific compound (=a total film thickness of a film thickness of the most common specific compound in terms of a single layer/a film thickness of all of the specific compound in terms of a single layer×100) is more than 90% by volume and 100% by volume or less (preferably, 95% to 100% by volume, and more preferably 99% to 100% by volume) with respect to all of the specific compound contained in the photoelectric conversion film.

In a case where only one specific compound is contained, the one specific compound may be the specific compound used as the p-type material or the specific compound used as the n-type material.

The fact that the "photoelectric conversion film contains two specific compounds" means that the specific compound contained in the photoelectric conversion film may be substantially two specific compounds.

The fact that the "specific compound contained in the photoelectric conversion film is substantially two specific compounds" means that a content of the most common two specific compounds (=a total film thickness of a film thickness of each of the most common two specific compounds in terms of a single layer/a total film thickness of all of the specific compound in terms of a single layer×100) is more than 90% by volume and 100% by volume or less (preferably, 95% to 100% by volume, and more preferably 99% to 100% by volume) with respect to all of the specific compound contained in the photoelectric conversion film.

In a case where the two specific compounds contained most are a specific compound A and a specific compound B, respectively, a ratio of contents of the specific compound A and the specific compound B in the photoelectric conversion film (=a film thickness of the specific compound A in terms of a single layer/a film thickness of the specific compound B in terms of a single layer) is preferably 10/90 to 90/10, more preferably 40/60 to 60/40, and still more preferably 47/53 to 53/47.

In a case where only two specific compounds are contained, both of the two specific compounds may be the specific compounds used as the p-type material, both of the two specific compounds may be the specific compounds used as the n-type material, or one specific compound is preferably a specific compound used as the p-type material and the other specific compound is preferably a specific compound used as the n-type material.

From the viewpoint of the responsiveness of the photoelectric conversion element, a content of the specific compound in the photoelectric conversion film (=film thickness of specific compound in terms of single layer/film thickness of photoelectric conversion film×100) is preferably 15% to 85% by volume.

Among these, in a case where the photoelectric conversion element contains only one specific compound, a content of the specific compound in the photoelectric conversion film is more preferably 20% to 60% by volume and still more preferably 25% to 40% by volume.

In a case where the photoelectric conversion element contains two specific compounds, a content of the specific compounds in the photoelectric conversion film is more preferably 40% to 80% by volume and still more preferably 60% to 75% by volume.

<Coloring Agent>

The photoelectric conversion film preferably contains a coloring agent as another component in addition to the specific compound described above.

The coloring agent is preferably an organic coloring agent.

Examples of the coloring agent include a cyanine coloring agent, a styryl coloring agent, a hemicyanine coloring agent, a merocyanine coloring agent (including zeromethine merocyanine (simple merocyanine)), a rhodacyanine coloring agent, an allopolar coloring agent, an oxonol coloring agent, a hemioxonol coloring agent, a squarylium coloring agent, a croconium coloring agent, an azamethine coloring agent, a coumarin coloring agent, an arylidene coloring agent, an anthraquinone coloring agent, a triphenylmethane coloring agent, an azo coloring agent, an azomethine coloring agent, a metallocene coloring agent, a fluorenone coloring agent, a flugide coloring agent, a perylene coloring agent, a phenazine coloring agent, a phenothiazine coloring agent, a quinone coloring agent, a diphenylmethane coloring agent, a polyene coloring agent, an acridine coloring agent, a quinoxaline coloring agent, an acridinone coloring agent, a diphenylamine coloring agent, a quinophthalone coloring agent, a phenoxazine coloring agent, a phthaloperylene coloring agent, a dioxane coloring agent, a porphyrin coloring agent, a chlorophyll coloring agent, a phthalocyanine coloring agent, a subphthalocyanine coloring agent, a metal complex coloring agent, compounds disclosed in paragraphs [0083] to [0089] of JP2014-82483A, compounds disclosed in paragraphs [0029] to [0033] of JP2009-167348A, compounds disclosed in paragraphs [0197] to [0227] of JP2012-077064A, compounds disclosed in paragraphs [0035] to [0038] of WO2018-105269A, compounds disclosed in paragraphs [0041] to [0043] of WO2018-186389A, compounds disclosed in paragraphs [0059] to [0062] of WO2018-186397A, compounds disclosed in paragraphs [0078] to [0083] of WO2019-009249A, compounds disclosed in paragraphs [0054] to [0056] of WO2019-049946A, compounds disclosed in paragraphs [0059] to [0063] of WO2019-054327A, compounds disclosed in paragraphs [0086] to [0087] of WO2019-098161A, and compounds disclosed in paragraphs [0085] to [0114] of WO2020-013246.

A content of the coloring agent in the photoelectric conversion film (=film thickness of coloring agent in terms of single layer/film thickness of photoelectric conversion film×100) is preferably 15% to 85% by volume, more preferably 20% to 60% by volume, and still more preferably 25% to 40% by volume.

A content of the coloring agent with respect to the total content of the specific compound and the coloring agent in the photoelectric conversion film (=(film thickness of coloring agent in terms of single layer/(film thickness of specific compound in terms of single layer+film thickness of coloring agent in terms of single layer)×100)) is preferably 15% to 75% by volume, more preferably 20% to 65% by volume, and still more preferably 25% to 60% by volume.

The coloring agent may be used alone, or two or more thereof may be used in combination.

<n-type Semiconductor Material>

The photoelectric conversion film preferably contains the n-type semiconductor material as another component in addition to the specific compound and coloring agent described above.

Among these, in a case where the photoelectric conversion film contains the specific compound used as the p-type material, it is preferable to contain the n-type semiconductor material, and in a case where the specific compound contained in the photoelectric conversion film is only the specific compound used as the p-type material, the photoelectric conversion film more preferably contains the n-type semiconductor material, and in a case where the photoelectric conversion film contains only one specific compound and the one specific compound is the specific compound used as the p-type material, the photoelectric conversion film still more preferably contains the n-type semiconductor material.

The n-type semiconductor material is an acceptor-property organic semiconductor material (a compound), and refers to an organic compound having a property of easily accepting an electron.

More specifically, the n-type semiconductor material is preferably an organic compound having a higher electron affinity than that of the specific compound in a case where the n-type semiconductor material is used by being brought in contact with the above-described specific compound.

In addition, the n-type semiconductor material is preferably an organic compound having a higher electron affinity than the coloring agent in a case where the n-type semiconductor material is used by being brought in contact with the above-described coloring agent.

The electron affinity of the n-type semiconductor material is preferably 3.0 to 5.0 eV.

Examples of the n-type semiconductor material include fullerenes selected from the group consisting of a fullerene and derivatives thereof, fused aromatic carbocyclic compounds (for example, a naphthalene derivative, an anthracene derivative, a phenanthrene derivative, a tetracene derivative, a pyrene derivative, a perylene derivative, and a fluoranthene derivative); a heterocyclic compound having a 5- to 7-membered ring having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); polyarylene compounds; fluorene compounds; cyclopentadiene compounds; silyl compounds; 1,4,5,8-naphthalenetetracarboxylic acid anhydride; 1,4,5,8-naphthalenetetracarboxylic acid anhydride imide derivative; oxadiazole derivative; anthraquinodimethane derivatives; diphenylquinone derivatives; bathocuproine, bathophenanthroline, and derivatives thereof; triazole compounds; a distyrylarylene derivative; a metal complex having a nitrogen-containing heterocyclic compound as a ligand; a silole compound; and compounds disclosed in paragraphs [0056] to [0057] of JP2006-100767A.

Among these, it is preferable that examples of the n-type semiconductor material include fullerenes selected from the group consisting of a fullerene and derivatives thereof.

Examples of the fullerenes include a fullerene $C_{60}$, a fullerene $C_{70}$, a fullerene $C_{76}$, a fullerene $C_{78}$, a fullerene $C_{80}$, a fullerene $C_{82}$, a fullerene $C_{84}$, a fullerene $C_{90}$, a fullerene $C_{96}$, a fullerene $C_{240}$, a fullerene $C_{540}$, and a mixed fullerene.

Examples of the fullerene derivatives include compounds in which a substituent is added to the above fullerenes. The substituent is preferably an alkyl group, an aryl group, or a heterocyclic group. The fullerene derivative is preferably compounds described in JP2007-123707A.

In a case where the photoelectric conversion film contains the n-type semiconductor material, a content of the n-type semiconductor material in the photoelectric conversion film (=film thickness of n-type semiconductor material in terms of single layer/film thickness of photoelectric conversion film×100) is preferably 15% to 75% by volume, more preferably 20% to 60% by volume, and still more preferably 25% to 50% by volume.

The n-type semiconductor material may be used alone, or two or more thereof may be used in combination.

In addition, in a case where the n-type semiconductor material includes fullerenes, a content of the fullerenes to a total content of the n-type semiconductor material (=(film thickness of fullerenes in terms of single layer/total film thickness of n-type semiconductor materials in terms of single layer)×100) is preferably 50% to 100% by volume, and more preferably 80% to 100% by volume.

The fullerenes may be used alone, or two or more thereof may be used in combination.

The molecular weight of the n-type semiconductor material is preferably 200 to 1200, and more preferably 200 to 1000.

The photoelectric conversion film is also substantially preferably composed of the specific compound, the coloring agent, and the n-type semiconductor material. "The photoelectric conversion film is substantially composed of only the specific compound, the coloring agent, and the n-type semiconductor material" means "the total content of the specific compound, the coloring agent, and the n-type semiconductor material with respect to the total mass of the photoelectric conversion film is 95% to 100% by mass".

<p-Type Semiconductor Material>

The photoelectric conversion film preferably further contains the p-type semiconductor material as another component in addition to the specific compound and coloring agent described above.

Among these, in a case where the photoelectric conversion film contains the specific compound used as the n-type material, it is preferable to contain the p-type semiconductor material, and in a case where the specific compound contained in the photoelectric conversion film is only the specific compound used as the n-type material, the photoelectric conversion film more preferably contains the p-type semiconductor material, and in a case where the photoelectric conversion film contains only one specific compound and the one specific compound is the specific compound used as the n-type material, the photoelectric conversion film still more preferably contains the p-type semiconductor material.

The p-type semiconductor material is a donor organic semiconductor material (a compound), and refers to an organic compound having a property of easily donating an electron.

More specifically, the p-type semiconductor material is preferably an organic compound having more excellent hole transport properties than a specific compound in the photoelectric conversion film, and is more preferably an organic compound having more excellent hole transport properties than any one of the specific compound or a coloring agent.

In the present specification, the hole transport properties (hole carrier mobility) of a compound can be evaluated by, for example, a time-of-flight method (a TOF method) or by using a field effect transistor element.

The hole carrier mobility of the p-type semiconductor material is preferably $10^{-4}$ $cm^2/V{\cdot}s$ or more, more preferably $10^{-3}$ $cm^2/V{\cdot}s$ or more, and still more preferably $10^{-2}$ $cm^2/V{\cdot}s$ or more. The upper limit of the hole carrier mobility described above is not particularly limited, but is preferably 10 $cm^2/V{\cdot}s$ or less, for example, from the viewpoint of suppressing the flow of a small amount of current without light irradiation.

In addition, the p-type semiconductor material preferably has a smaller ionization potential than the specific compound in the photoelectric conversion film, and more preferably has a smaller ionization potential than any one of the specific compound or a coloring agent.

Examples of the p-type semiconductor material include triarylamine compounds (for example, N,N'-bis(3-methylphenyl)-(1,1'-biphenyl)-4,4'-diamine (TPD), 4,4'-bis[N-(naphthyl)-N-Phenyl-amino] biphenyl (α-NPD), compounds disclosed in paragraphs [0128] to [0148] of JP2011-228614A, compounds disclosed in paragraphs [0052] to [0063] of JP2011-176259A, compounds disclosed in paragraphs [0119] to [0158] of JP2011-225544A, compounds disclosed in paragraphs [0044] to [0051] of JP2015-153910A, and compounds disclosed in paragraphs [0086] to [0090] of JP2012-094660A, pyrazoline compounds, styrylamine compounds, hydrazone compounds, polysilane compounds, thiophene compounds (for example, a thienothiophene derivative, a dibenzothiophene derivative, a benzodithiophene derivative, a dithienothiophene derivative, a [1] benzothieno [3,2-b] thiophene (BTBT) derivative, a thieno [3,2-f: 4,5-f'] bis [1] benzothiophene (TBBT) derivative, compounds disclosed in paragraphs [0031] to [0036] of JP2018-014474A, compounds disclosed in paragraphs [0043] to [0045] of WO2016-194630A, compounds disclosed in paragraphs [0025] to [0037], and [0099] to [0109] of WO2017-159684A, compounds disclosed in paragraphs [0029] to [0034] of JP2017-076766A, compounds disclosed in paragraphs [0015] to [0025] of WO2018-207722A, compounds disclosed in paragraphs [0045] to [0053] of JP2019-054228A, compounds disclosed in paragraphs [0045] to [0055] of WO2019-058995A, compounds disclosed in paragraphs [0063] to [0089] of WO2019-081416A, compounds disclosed in paragraphs [0033] to [0036] of JP2019-080052A, compounds disclosed in paragraphs [0044] to [0054] of WO2019-054125A, compounds disclosed in paragraphs [0041] to [0046] of WO2019-093188A, and the like), a cyanine compound, an oxonol compound, a polyamine compound, an indole compound, a pyrrole compound, a pyrazole compound, a polyarylene compound, a fused aromatic carbocyclic compound (for example, a naphthalene derivative, an anthracene derivative, a phenanthrene derivative, a tetracene derivative, a pentacene derivative, a pyrene derivative, a perylene derivative, and a fluoranthene derivative), a porphyrin compound, a phthalocyanine compound, a triazole compound, an oxadiazole compound, an imidazole compound, a polyarylalkane compound, a pyrazolone compound, an amino-substituted chalcone compound, an oxazole compound, a fluorenone compound, a silazane compound, and a metal complex having nitrogen-containing heterocyclic compounds as ligands.

The p-type semiconductor material is preferably a compound represented by Formula (p1), a compound represented by Formula (p2), a compound represented by Formula (p3), and a compound represented by Formula (p4), or is also preferably a compound represented by Formula (p5).

(p1)

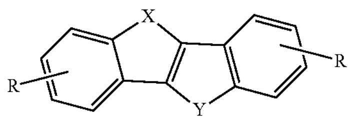

(p2)

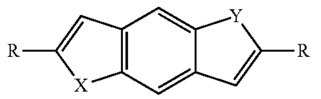

(p3)

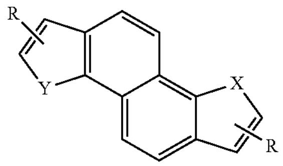

(p4)

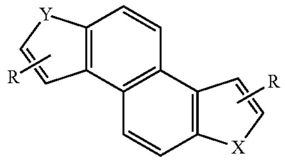

(p5)

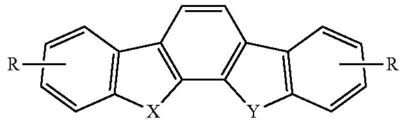

(p6)

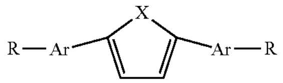

In Formulae (p1) to (p6), two R's are each independently a hydrogen atom, or a substituent (an alkyl group, an alkoxy group, a halogen atom, an alkylthio group, a (hetero)arylthio group, an alkylamino group, a (hetero)arylamino group, and a (hetero)aryl group. These groups each may further have a substituent as much as possible. For example, the (hetero) aryl group may be an arylaryl group, which may further have a substituent (that is, a biaryl group, and at least one of the aryl groups constituting this group may be a heteroaryl group)).

As R, a group represented by R in Formula (IX) of WO2019-081416A is also preferable.

X and Y each independently represent $—CR^2{}_2—$, a sulfur atom (—S—), an oxygen atom (—O—), $—NR^2—$, or $—SiR^2{}_2—$.

$R^2$ represents a hydrogen atom, an alkyl group (preferably a methyl group or a trifluoromethyl group), an aryl group, or a heteroaryl group, which may have a substituent. Two or more $R^2$'s may be the same or different from each other.

Ar represents an aromatic ring group (preferably a benzene ring group).

Among these, the p-type semiconductor material is preferably the compound represented by Formula (p1).

In a case where the photoelectric conversion film contains the p-type semiconductor material, a content of the p-type semiconductor material in the photoelectric conversion film (=film thickness of p-type semiconductor material in terms of single layer/film thickness of photoelectric conversion film×100) is preferably 15% to 75% by volume, more preferably 20% to 60% by volume, and still more preferably 25% to 50% by volume.

The n-type semiconductor material may be used alone, or two or more thereof may be used in combination.

The photoelectric conversion film is also substantially preferably composed of the specific compound, the coloring agent, and the p-type semiconductor material. "The photoelectric conversion film is substantially composed of only the specific compound, the coloring agent, and the p-type semiconductor material" means "the total content of the specific compound, the coloring agent, and the p-type semiconductor material with respect to the total mass of the photoelectric conversion film is 95% to 100% by mass".

The photoelectric conversion film is also substantially preferably composed of only the specific compound, the coloring agent, the n-type semiconductor material, and the p-type semiconductor material. "The photoelectric conversion film is substantially composed of only the specific compound, the coloring agent, the n-type semiconductor material, and the p-type semiconductor material" means "the total content of the specific compound, the coloring agent, the n-type semiconductor material, and the p-type semiconductor material with respect to the total mass of the photoelectric conversion film is 95% to 100% by mass".

In a case where the photoelectric conversion film contains a coloring agent, the photoelectric conversion film is preferably a mixture layer formed in a state where the specific compound and the coloring agent are mixed.

In addition, in a case where the photoelectric conversion film contains the n-type semiconductor material and/or the p-type semiconductor material, the photoelectric conversion film is preferably a mixture layer formed in a state where the specific compound, the n-type semiconductor material, and/or the p-type semiconductor material are mixed.

In addition, in a case where the photoelectric conversion film contains the coloring agent, the n-type semiconductor material, and/or the p-type semiconductor material, the photoelectric conversion film is preferably a mixture layer formed in a state where the specific compound, the coloring agent, the n-type semiconductor material, and/or the p-type semiconductor material are mixed.

The mixture layer is a layer in which two or more materials are mixed in a single layer.

The photoelectric conversion film containing the specific compound is a non-light emitting film, and has a feature different from organic light emitting diodes (OLEDs). The non-light emitting film is intended for a film having a light emission quantum efficiency of 1% or less, and the light emission quantum efficiency is preferably 0.5% or less, and more preferably 0.1% or less.

<Film Formation Method>

The photoelectric conversion film can be formed mostly by a dry film formation method. Examples of the dry film formation method include a physical vapor deposition method such as a vapor deposition method (in particular, a vacuum vapor deposition method), a sputtering method, and an ion plating method, a molecular beam epitaxy (MBE) method, and a chemical vapor deposition (CVD) method such as plasma polymerization. Among these, the vacuum vapor deposition method is preferable. In a case where the photoelectric conversion film is formed by the vacuum vapor deposition method, manufacturing conditions such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 400 nm.

[Electrode (Conductive Film)]

Electrodes (the upper electrode (the transparent conductive film) 15 and the lower electrode (the conductive film) 11) are formed of conductive materials. Examples of the conductive material include metals, alloys, metal oxides, electrically conductive compounds, and mixtures thereof.

Since light is incident through the upper electrode 15, the upper electrode 15 is preferably transparent to light to be detected. Examples of the materials constituting the upper electrode 15 include conductive metal oxides such as tin oxide (antimony tin oxide (ATO), fluorine doped tin oxide (FTO)) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; organic conductive materials such as polyaniline, polythiophene, and polypyrrole; carbon materials such as graphene and carbon nanotubes. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is, for example, 100 to 10000 Ω/□, and a degree of freedom of a range of the film thickness that can be thinned is large. In addition, as the thickness of the upper electrode (the transparent conductive film) 15 is thinner, the amount of light that the upper electrode absorbs is smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode 11 does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, and conductive compounds (for example, titanium nitride (TiN)) such as oxides or nitrides of these metals; mixtures or laminates of these metals and conductive metal oxides; organic conductive materials such as polyaniline, polythiophene, and polypyrrole; carbon materials such as graphene and carbon nanotubes.

The method of forming electrodes is not particularly limited, and can be appropriately selected in accordance with the electrode material. Specific examples thereof include a wet method such as a printing method and a coating method; a physical method such as a vacuum vapor deposition method, a sputtering method, and an ion plating method; and a chemical method such as a CVD method and a plasma CVD method.

In a case where the material of the electrode is ITO, examples thereof include an electron beam method, a sputtering method, a resistance heating vapor deposition method, a chemical reaction method (such as a sol-gel method), and a coating method with a dispersion of indium tin oxide.

<Charge Blocking Film: Electron Blocking Film and Hole Blocking Film>

It is also preferable that the photoelectric conversion element according to the embodiment of the present invention has one or more interlayers between the conductive film and the transparent conductive film, in addition to the photoelectric conversion film. An example of the interlayer includes a charge blocking film. In a case where the photoelectric conversion element has this film, the characteristics (such as photoelectric conversion efficiency and responsiveness) of the obtained photoelectric conversion element are more excellent. Examples of the charge blocking film include an electron blocking film and a hole blocking film. Hereinafter, each of the films will be described in detail.

<Electron Blocking Film>

The electron blocking film is a donor organic semiconductor material (compound), and a p-type organic semiconductor described above can be used, for example. The p-type organic semiconductor may be used alone, or two or more thereof may be used in combination.

Examples of the p-type organic semiconductor used in the electron blocking film include compounds having a smaller ionization potential than that of the n-type semiconductor material, and in a case where this condition is satisfied, the above-described coloring agents may be used.

A polymer material can also be used as the electron blocking film.

Examples of the polymer material include a polymer such as phenylenevinylene, fluorene, carbazole, indole, pyrene, pyrrole, picoline, thiophene, acetylene, and diacetylene, and a derivative thereof.

The electron blocking film may be formed of a plurality of films.

The electron blocking film may be formed of an inorganic material. In general, since an inorganic material has a dielectric constant larger than that of an organic material, in a case where the inorganic material is used in the electron blocking film, a large voltage is applied to the photoelectric conversion film. Therefore, the photoelectric conversion efficiency increases. Examples of the inorganic material that can be used for the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

<Hole Blocking Film>

A hole blocking film is an acceptor-property organic semiconductor material (compound), and the n-type semiconductor material described above and the like can be used.

The method of manufacturing the charge blocking film is not particularly limited, and examples thereof include a dry film formation method and a wet film formation method. Examples of the dry film formation method include a vapor deposition method and a sputtering method. The vapor deposition method may be any of a physical vapor deposition (PVD) method and a chemical vapor deposition (CVD) method, and the physical vapor deposition method such as a vacuum vapor deposition method is preferable. Examples of the wet film formation method include an ink jet method, a spray method, a nozzle printing method, a spin coating method, a dip coating method, a casting method, a die coating method, a roll coating method, a bar coating method, and a gravure coating method, and an ink jet method is preferable from the viewpoint of high accuracy patterning.

Each thickness of the charge blocking films (the electron blocking film and the hole blocking film) is preferably 3 to 200 nm, more preferably 5 to 100 nm, and still more preferably 5 to 30 nm.

[Substrate]

The photoelectric conversion element may further include a substrate. Types of the substrate to be used are not particularly limited, and examples of the substrate include a semiconductor substrate, a glass substrate, and a plastic substrate.

A position of the substrate is not particularly limited, and in general, the conductive film, the photoelectric conversion film, and the transparent conductive film are laminated on the substrate in this order.

[Sealing Layer]

The photoelectric conversion element may further include a sealing layer. The performance of a photoelectric conversion material may deteriorate noticeably due to the presence of deterioration factors such as water molecules. The deterioration can be prevented by coating and sealing the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be manufactured according to the description in paragraphs [0210] to [0215] of JP2011-082508A.

[Imaging Element and Optical Sensor]

An example of the application of the photoelectric conversion element includes an imaging element. The imaging element is an element that converts optical information of an image into an electric signal. In general, a plurality of the photoelectric conversion elements are arranged in a matrix on the same plane, and an optical signal is converted into an electric signal in each photoelectric conversion element (pixel) to sequentially output the electric signal to the outside of the imaging element for each pixel. Therefore, each pixel is formed of one or more photoelectric conversion elements and one or more transistors.

The imaging element is mounted on an imaging element such as a digital camera and a digital video camera, an electronic endoscope, and imaging modules such as a cellular phone.

The photoelectric conversion element according to the embodiment of the present invention is also preferably used for an optical sensor including the photoelectric conversion element according to the embodiment of the present invention. The photoelectric conversion element may be used alone as the optical sensor, and the photoelectric conversion element may be used as a line sensor in which the photoelectric conversion elements are linearly arranged or as a two-dimensional sensor in which the photoelectric conversion elements are arranged in a plane shape.

[Compound]

The present invention also relates to a compound.

The compound according to the embodiment of the present invention is the same compound as the above-described specific compound (compound represented by Formula (1)), and preferred conditions are also the same.

EXAMPLES

The present invention will be described in more detail based on Examples below. Materials, used amounts, ratios, treatment contents, treatment procedures, and the like described in the following Examples can be appropriately changed within the range that does not depart from the gist of the present invention. Therefore, the range of the present invention should not be limitatively interpreted by the following Examples.

[Compound (Evaluation Compound)]

<Synthesis of Compound (1-7)>

A compound (1-7) serving as a specific compound was synthesized according to the following scheme.

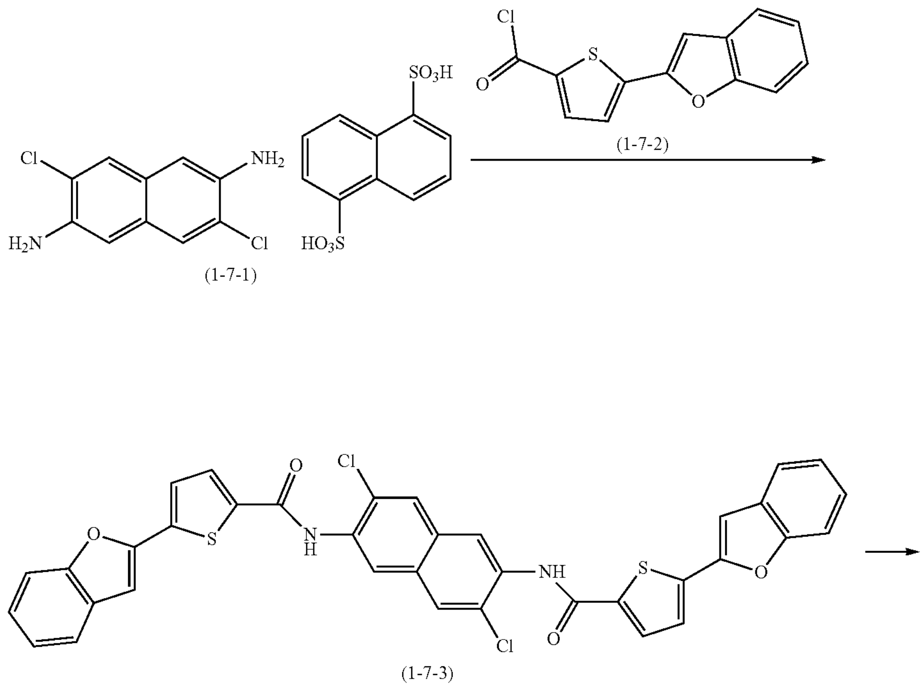

(1-7-1) (1-7-2)

(1-7-3)

-continued

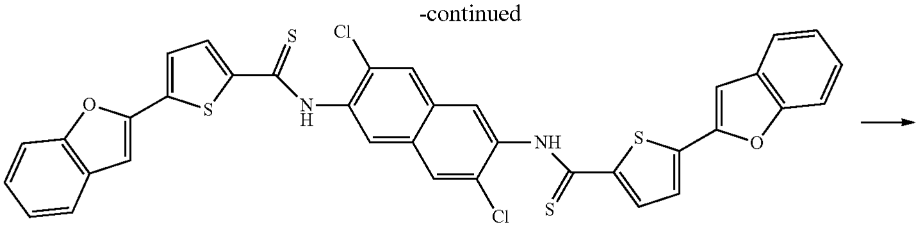

(1-7-4)

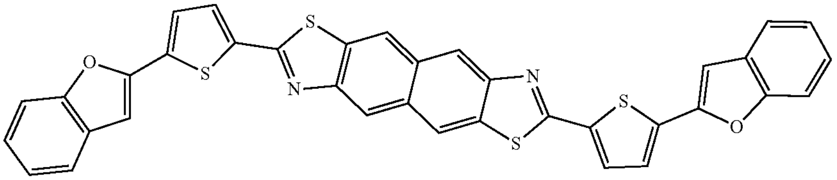

(1-7)

(Synthesis of Compound (1-7-3))

Compound (1-7-1) (1.0 mmol), compound (1-7-2) (4.0 mmol), triethylamine (20 mmol), and tetrahydrofuran of 20 mL were added to a glass reaction container to obtain a mixed solution. After the inside of the reaction container was replaced with nitrogen, the mixed solution was reacted for 5 hours under heating and reflux. The mixed solution was left to cool to room temperature (25° C.), 40 mL of methanol was then added to the mixed solution, and the precipitated precipitate was collected by filtration. The obtained solid (filter product) was suspended in 20 mL of tetrahydrofuran, heated under heating and reflux for 1 hour, and then collected by filtration. The obtained solid (filter product) was dried under reduced pressure to obtain 0.79 mmol of a compound (1-7-3).

The result of analysis of the compound (1-7-3) by 1H NMR (nuclear magnetic resonance method) is shown below.

Compound (1-7-3): 1H NMR (DMSO-$d_6$) δ (ppm) 7.31 (2H, t, J=7.4 Hz), 7.39 (2H, t, J=8.9 Hz), 7.48 (2H, s), 7.67 (2H, d, J=8.4 Hz), 7.71 (2H, d, J=8.4 Hz), 7.78 (2H, d, J)=4.0 Hz), 8.12 (2H, d, J=4.0 Hz), 8.22 (2H, s) 8.32 (2H, s), 10.5 (2H, s).

(Synthesis of Compound (1-7-4))

The compound (1-7-3) (0.75 mmol), a Lawson reagent (3.75 mmol), and 20 mL of o-dichlorobenzene were added to a glass reaction container to obtain a mixed solution. After the inside of the reaction container was replaced with nitrogen, the mixed solution was reacted at 150° C. for 5 hours. The mixed solution was left to cool to room temperature (25° C.), and precipitates precipitated were then collected by filtration. The obtained solid (filter product) was suspended in 20 mL of tetrahydrofuran, heated under heating and reflux for 1 hour, and then collected by filtration. The obtained solid (filter product) was dried under reduced pressure to obtain 0.60 mmol of a compound (1-7-4).

The result of analysis of the compound (1-7-4) by 1H NMR is shown below.

Compound (1-7-4): $^{1}$H NMR (DMSO-$d_6$) δ (ppm) 7.31 (2H, t, J=8.0 Hz), 7.37 (2H, t, J=8.0 Hz), 7.50 (2H, s), 7.66 (2H, d, J=8.3 Hz), 7.71 (2H, d, J=8.3 Hz), 7.79 (2H, d, J)=4.1 Hz), 8.03 (2H, d, J=4.1 Hz), 8.18 (2H, s) 8.37 (2H, s), 11.9 (2H, s).

(Synthesis of Compound (1-7))

The compound (1-7-4) (0.60 mmol), cesium carbonate (2.4 mmol), and 17 mL of N,N-dimethylacetamide were added to a glass reaction container to obtain a mixed solution. After the inside of the reaction container was replaced with nitrogen, the mixed solution was reacted at 150° C. for 5 hours. The mixed solution was left to cool to room temperature (25° C.), and precipitates precipitated in the mixed solution were then collected by filtration. The obtained solid (filter product) was suspended in water and then collected by filtration. A solid (filter product) thus obtained was dried under reduced pressure and then sublimated and purified to obtain 0.45 mmol of the compound (1-7).

Since the compound (1-7) was poorly soluble, its structure was identified by LDI-MS (soft laser desorption ionization mass spectrometry). The results of the identification are shown below.

Compound (1-7): LDI-MS: 638.1 (Mt).

Other specific compounds were also synthesized with reference to the above-described synthesis method.

The specific compound and comparative compound used in a test are shown below.

Hereinbelow, compounds (1-1) to (1-36) and compounds (2-1) to (2-17) are specific compounds.

Hereinafter, the specific compound and the Comparative compound are collectively referred to as an evaluation compound.

(1-1)
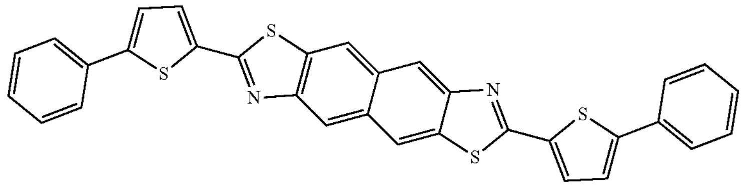
(1-2)
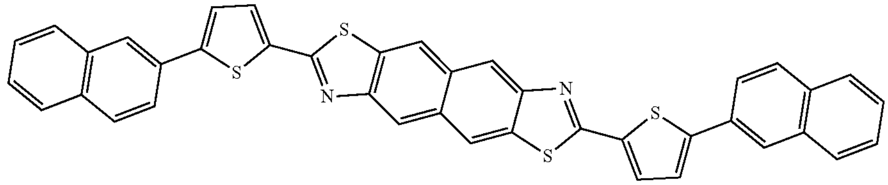
(1-3)
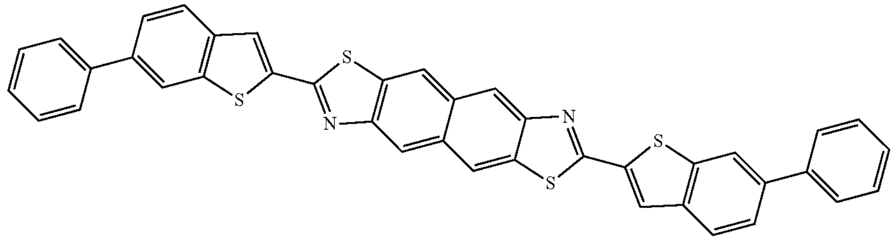
(1-4)
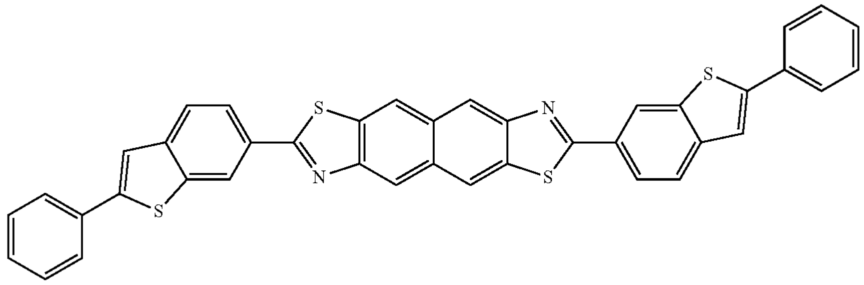
(1-5)
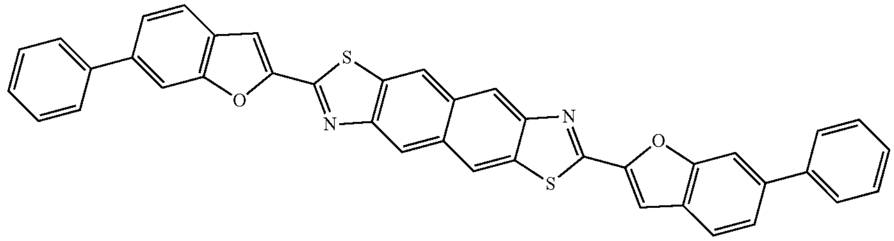
(1-6)
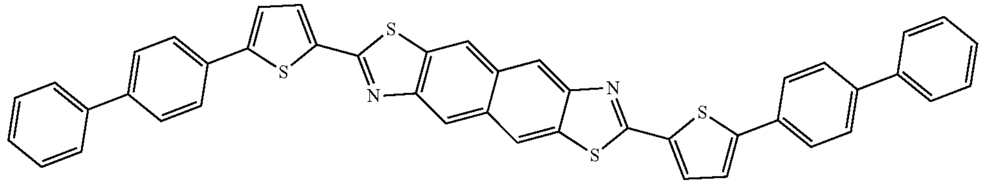
(1-7)
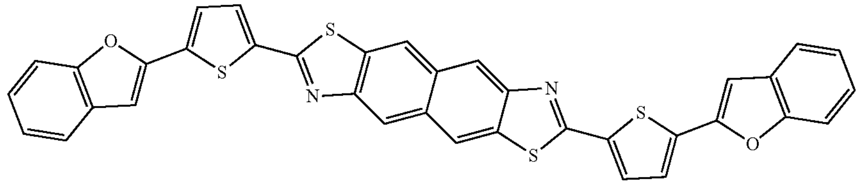

-continued
(1-8)
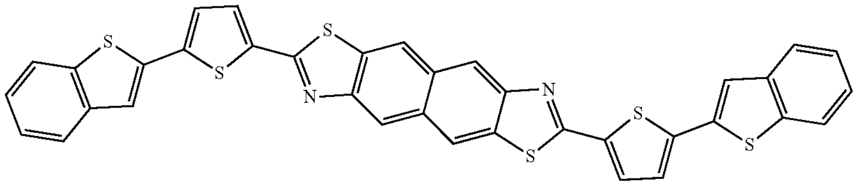
(1-9)
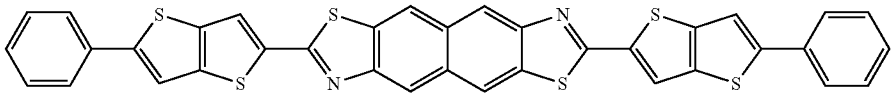
(1-10)
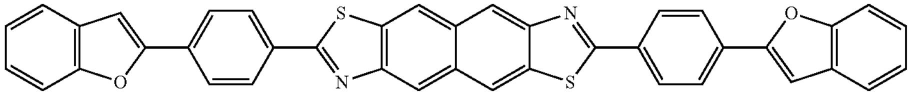
(1-11)
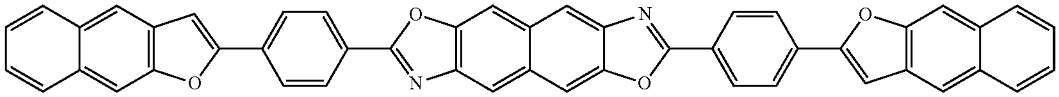
(1-12)
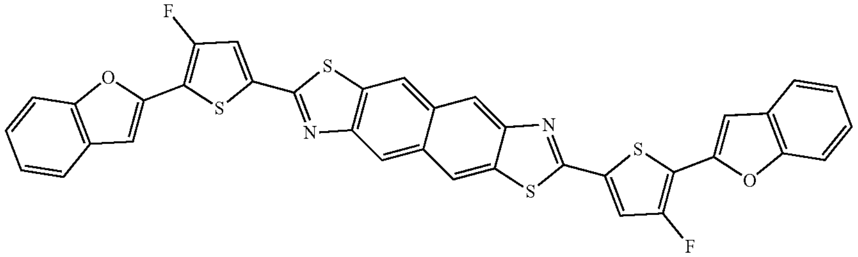
(1-13)
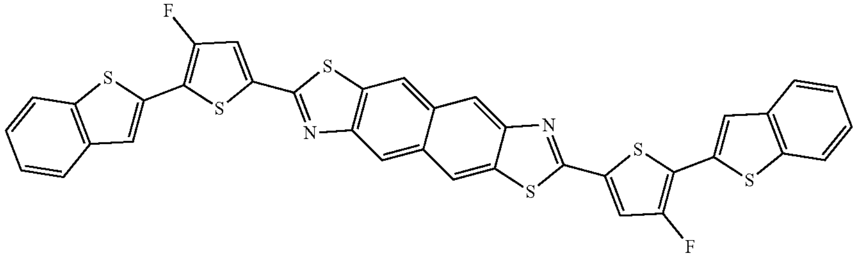
(1-14)
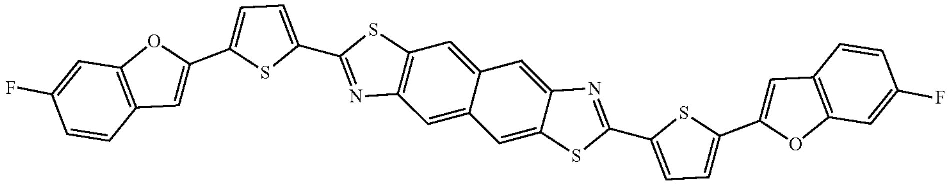
(1-15)
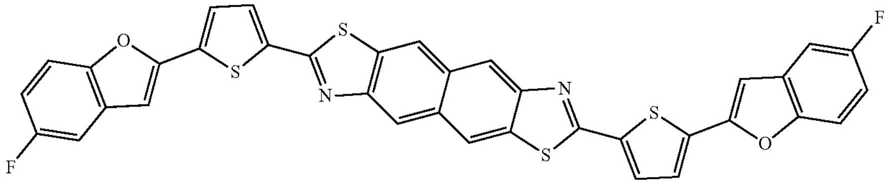

-continued
(1-16)
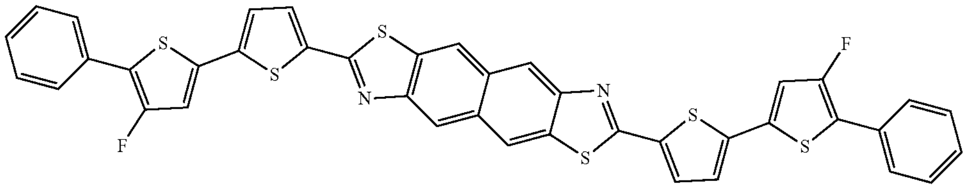
(1-17)
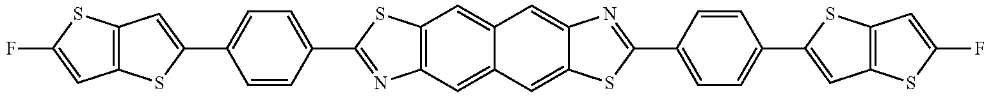
(1-18)
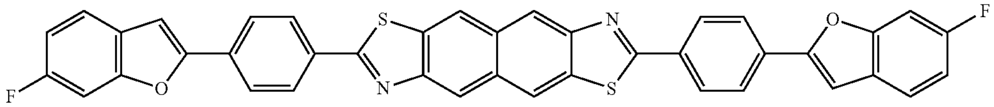
(1-19)
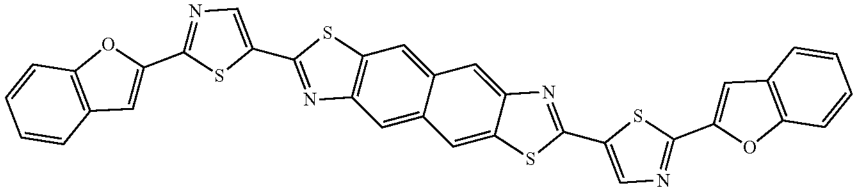
(1-20)
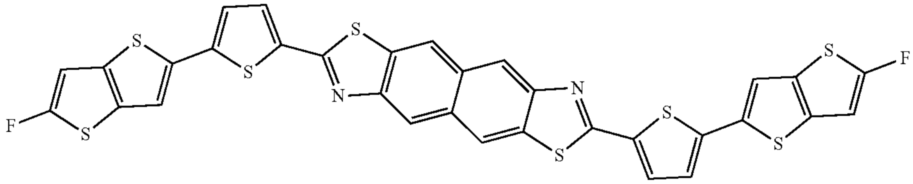
(1-21)
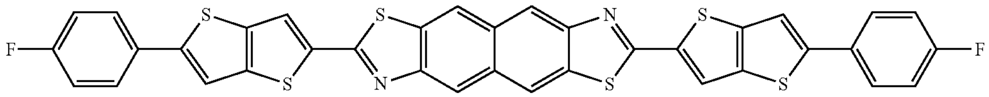
(1-22)
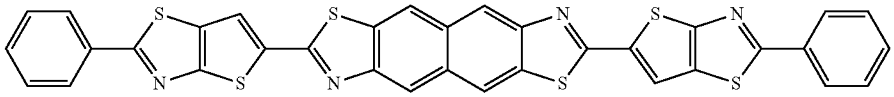
(1-23)
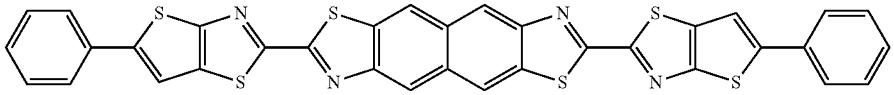
(1-24)
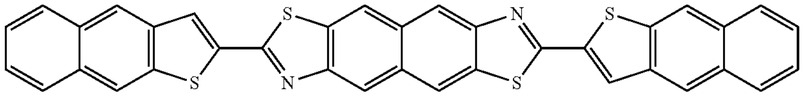
(1-25)
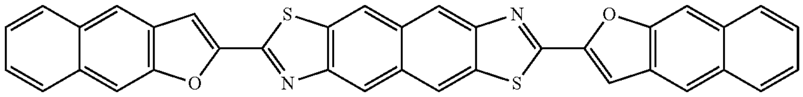
(1-26)
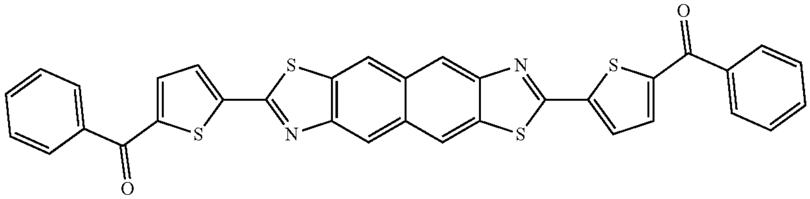

-continued
(1-27)
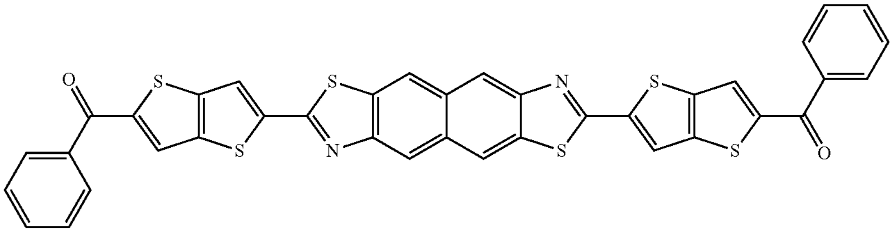
(1-28)
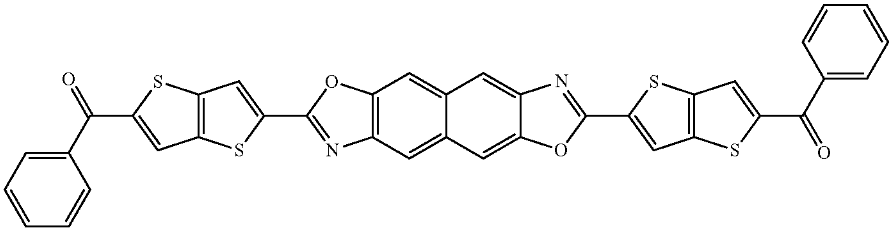
(1-29)
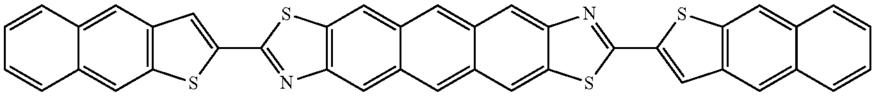
(1-30)
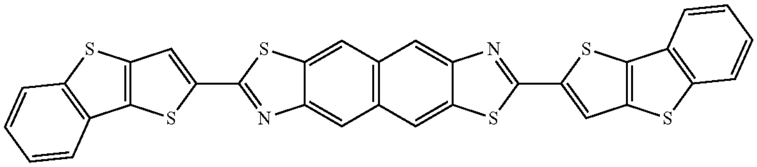
(1-31)
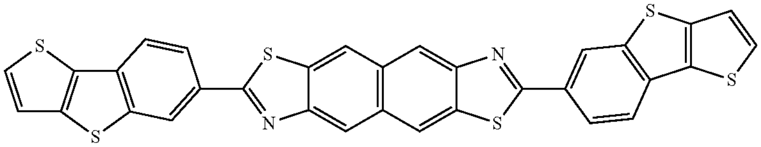
(1-32)
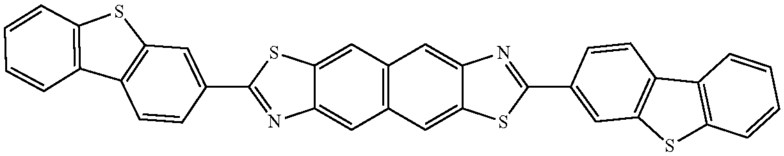
(1-33)
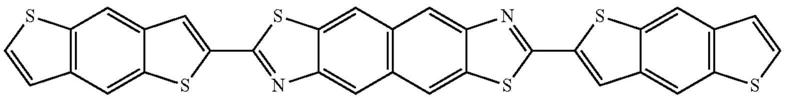
(1-34)
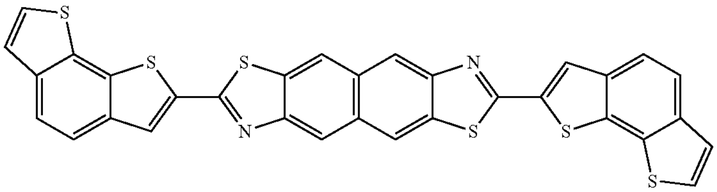

-continued
(1-35)
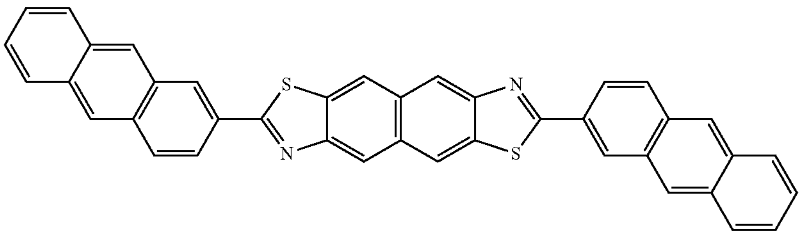
(1-36)
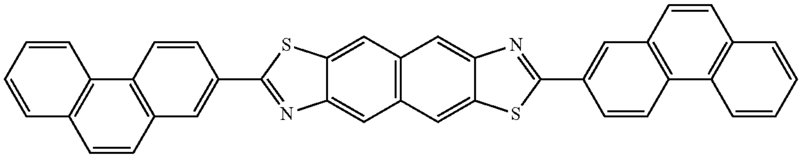
(2-1)
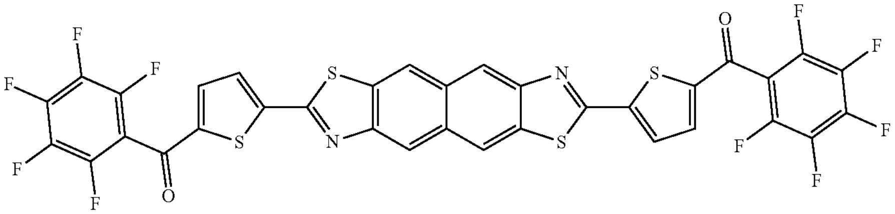
(2-2)
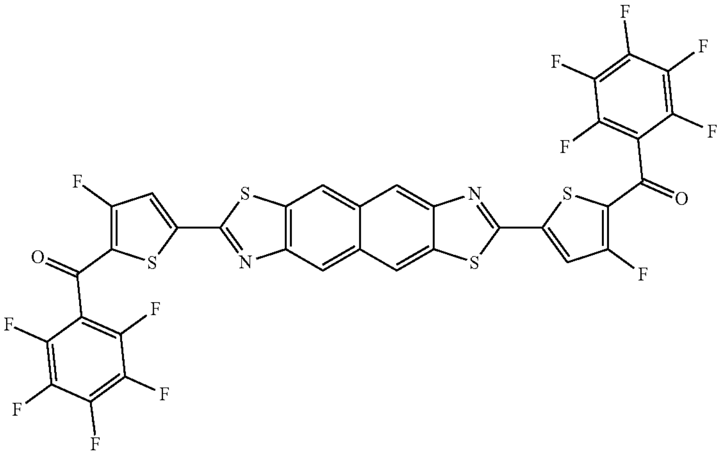
(2-3)
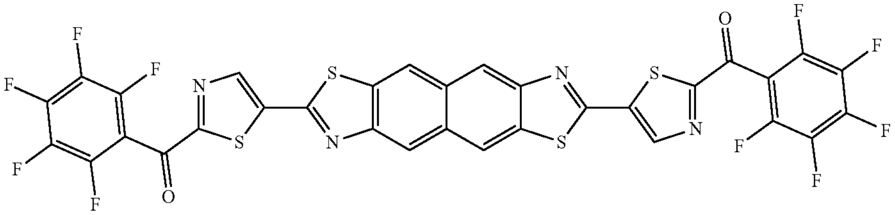
(2-4)
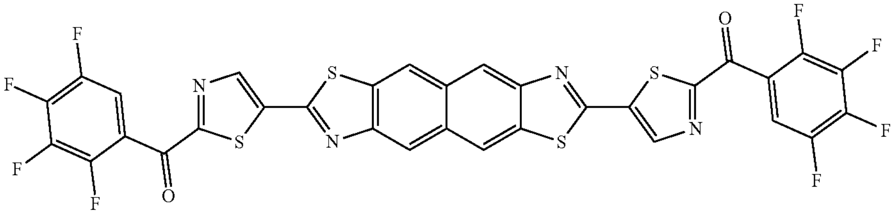

-continued
(2-5)
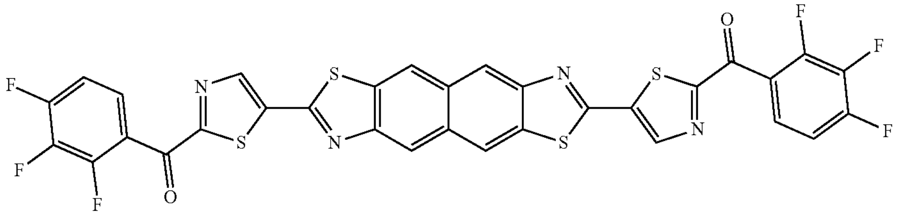
(2-6)
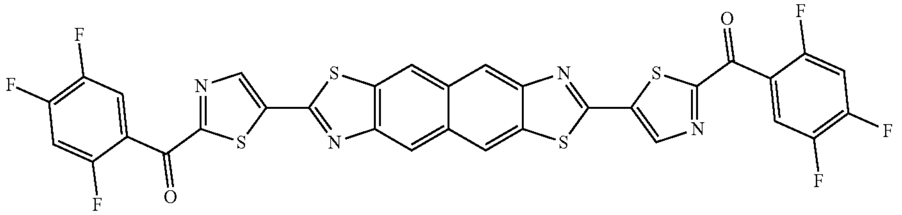
(2-7)
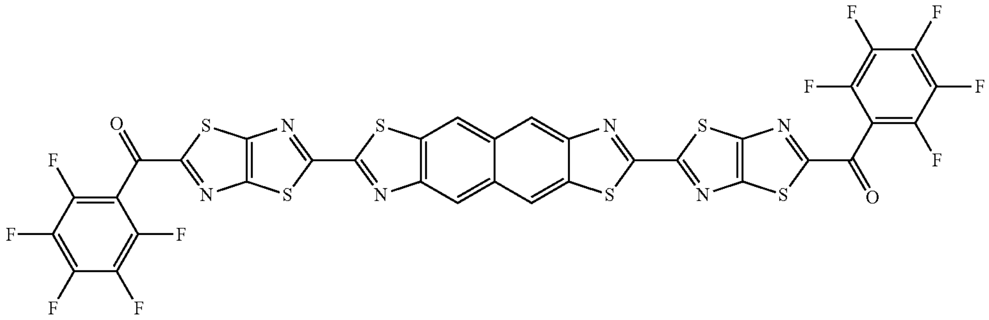
(2-8)
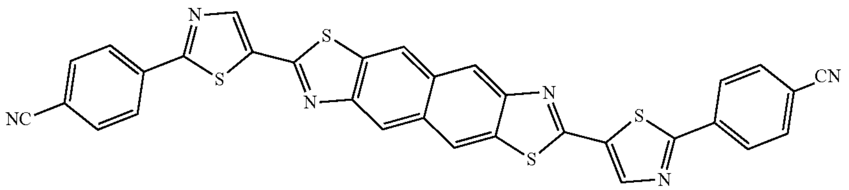
(2-9)
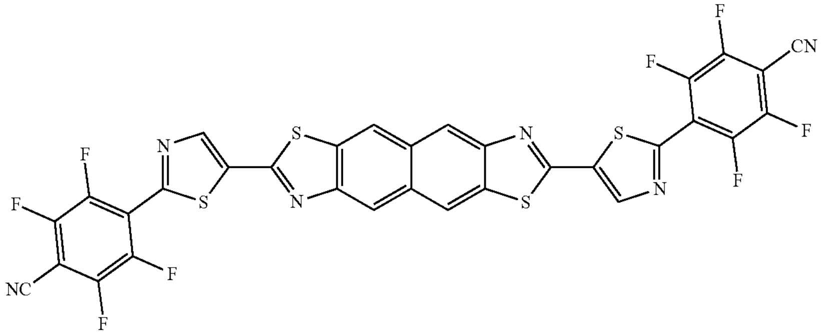
(2-10)
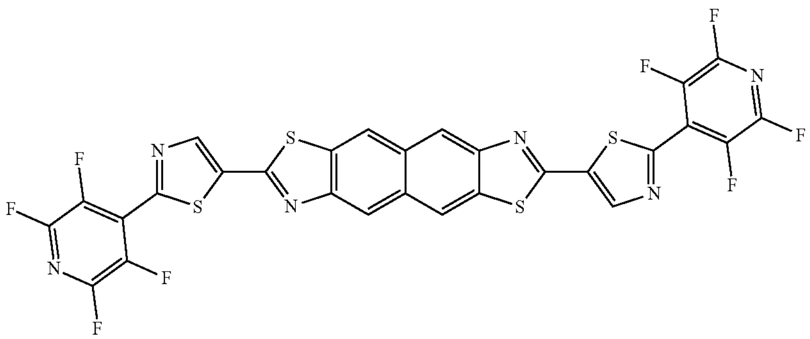

-continued
(2-11)
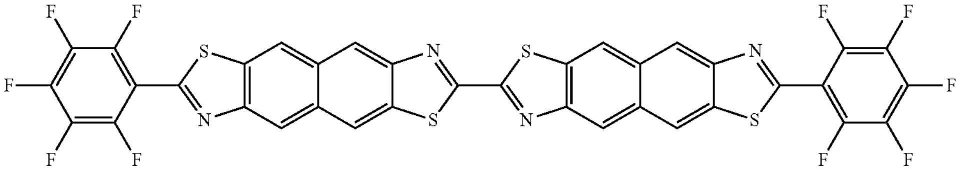
(2-12)
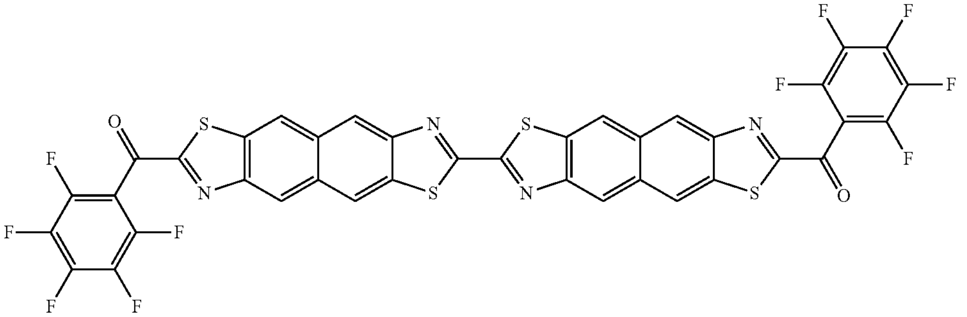
(2-13)
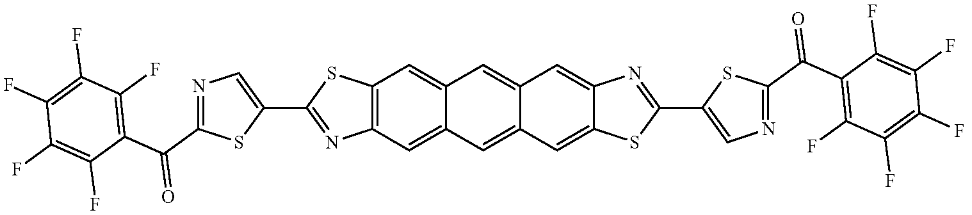
(2-14)
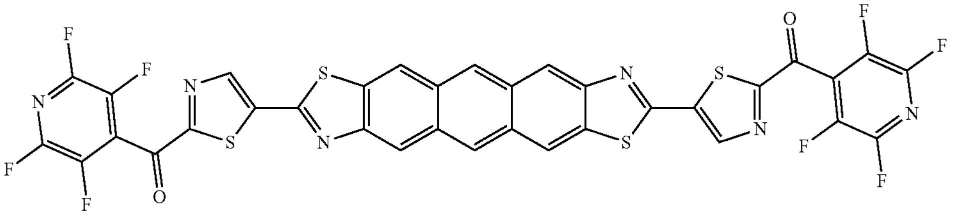
(2-15)
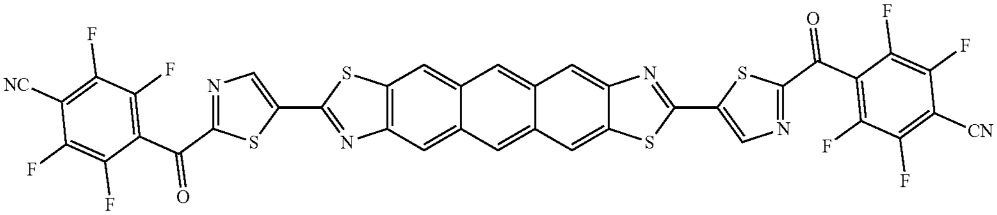
(2-16)
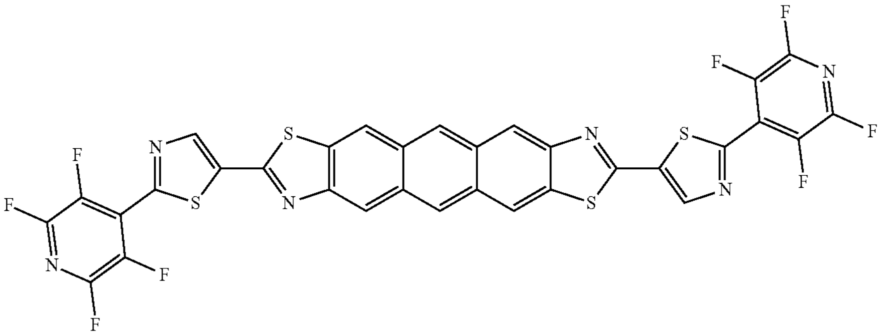

-continued
(2-17)
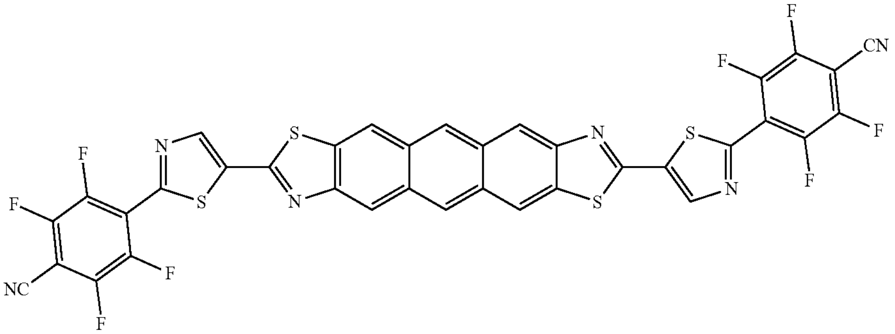
(C1-1)
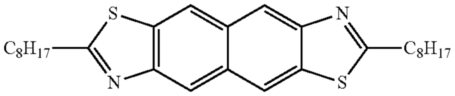
(C1-2)
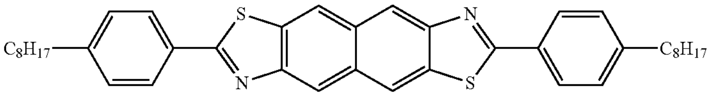
(C1-3)
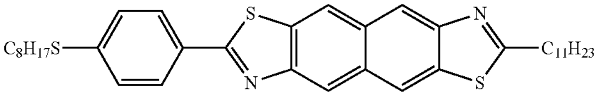
(C1-4)
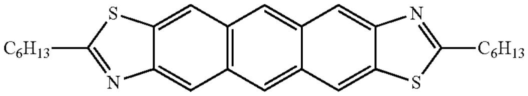
(C1-5)
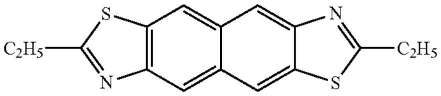
(C1-6)
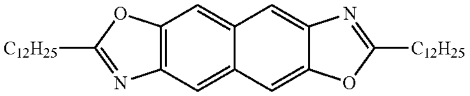
(C1-7)
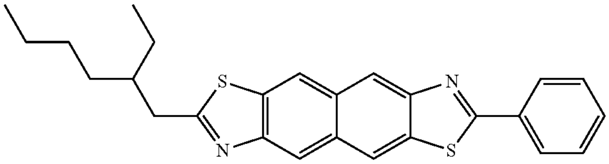
(C1-8)
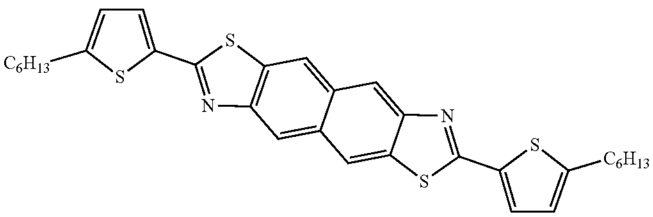

-continued
(C1-9)
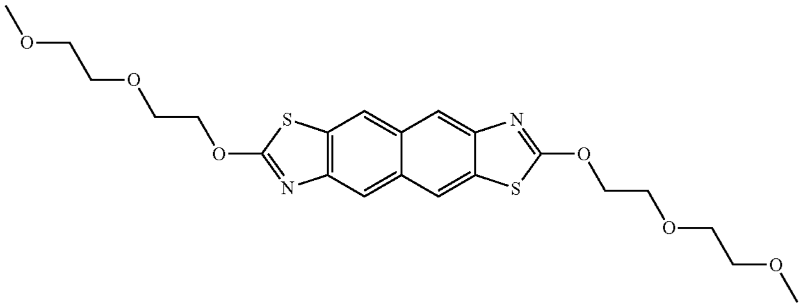
(C1-10)
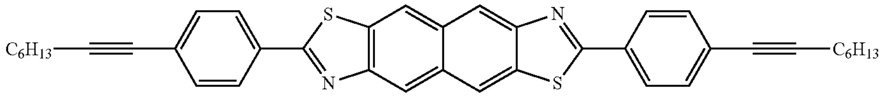
(C1-11)
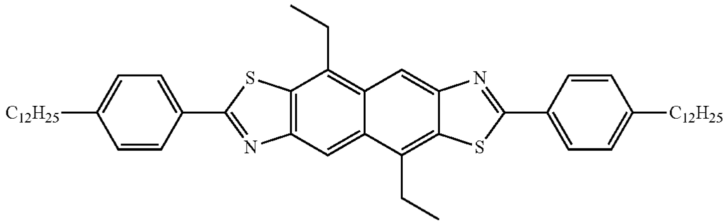
(C1-12)
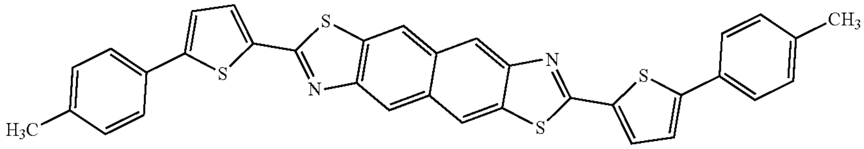
(C1-13)
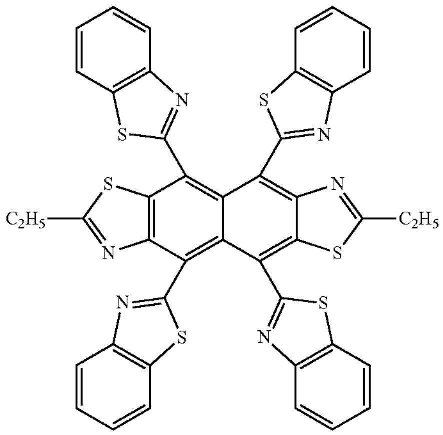
(C1-14)
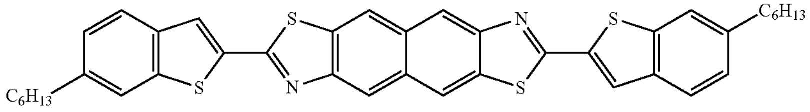

-continued
(C1-15)
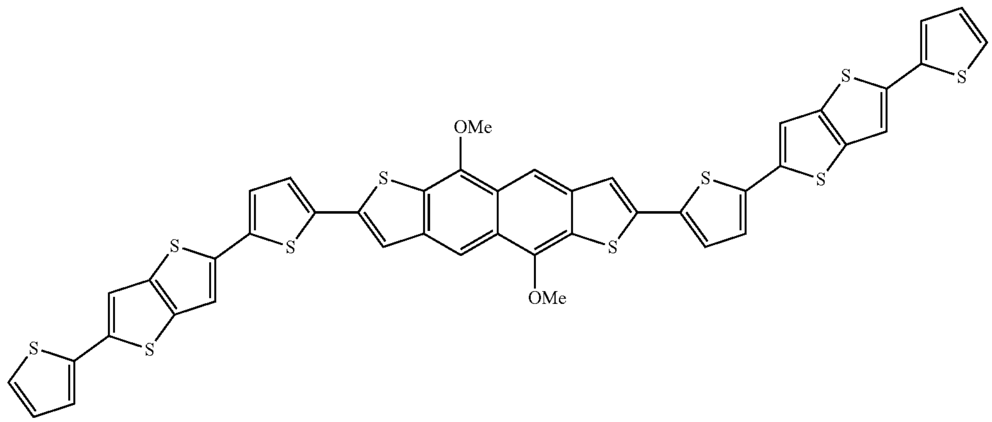
(C1-16)
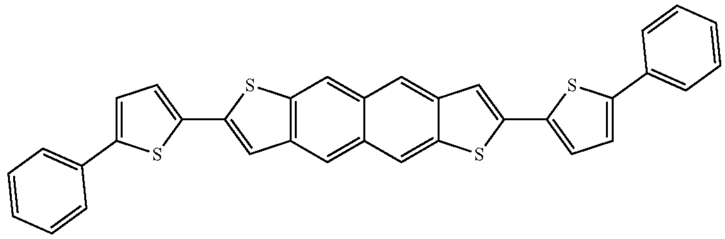
(C1-17)
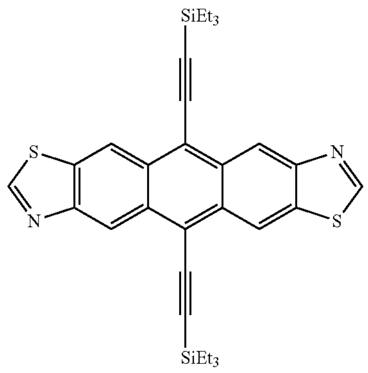
(C1-18)
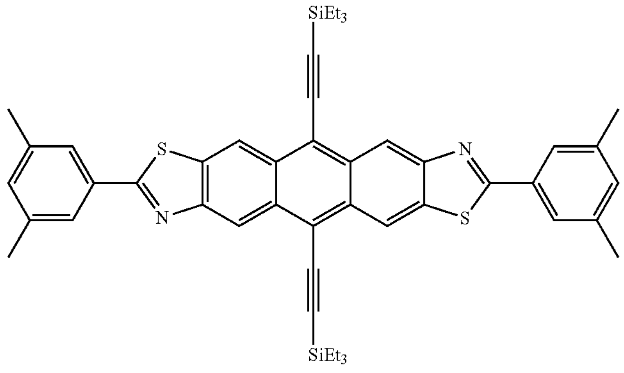

-continued
(C1-19)
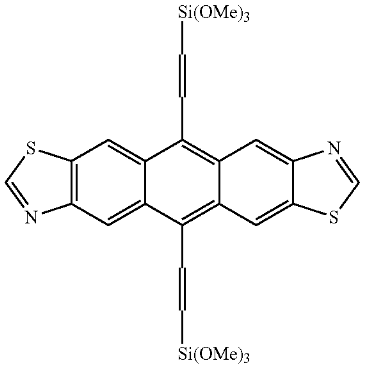
(C1-20)
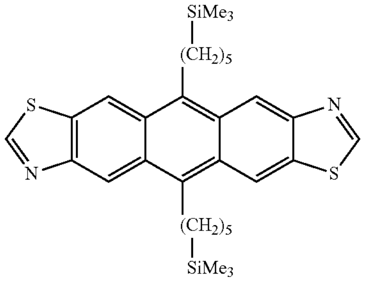
(C1-21)
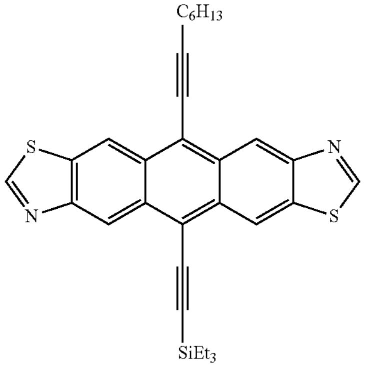
(C1-22)
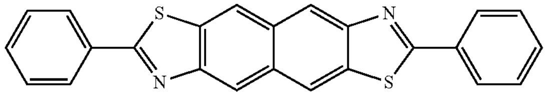
(C1-23)
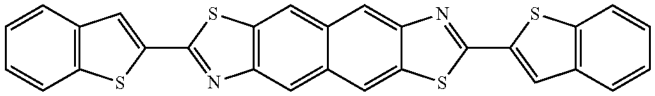

[Coloring Agent (Coloring Agent for Evaluation)]
The coloring agents illustrated below were coloring agents used in the evaluation, and were used in the production of photoelectric conversion elements described later.
B-1
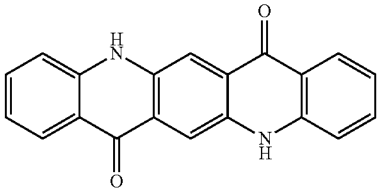
B-2
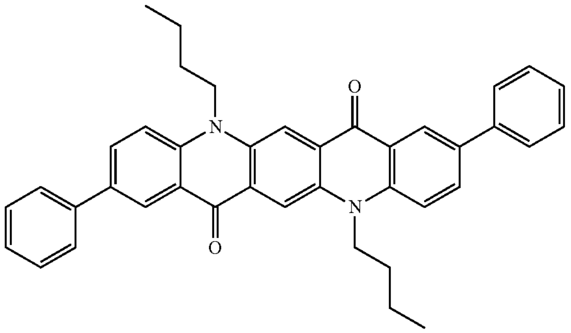
B-3
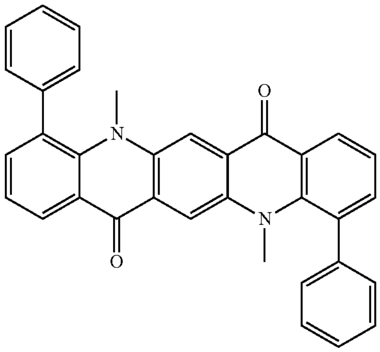
B-4
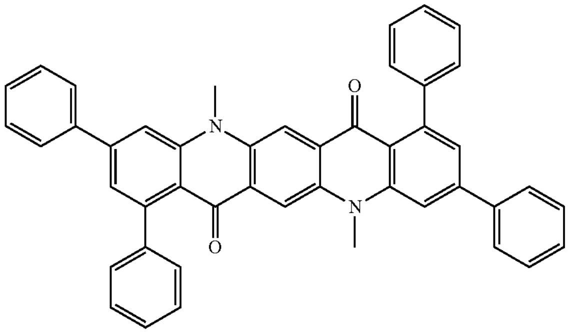
-continued
B-5
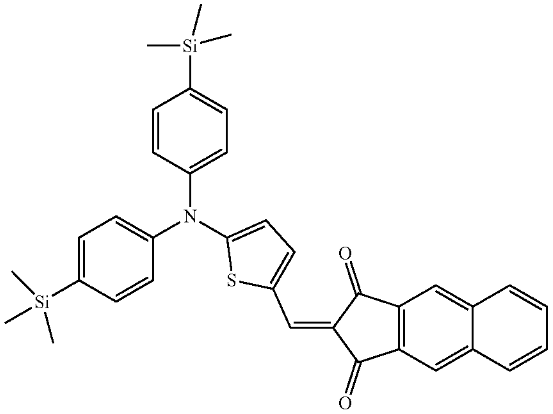
B-6
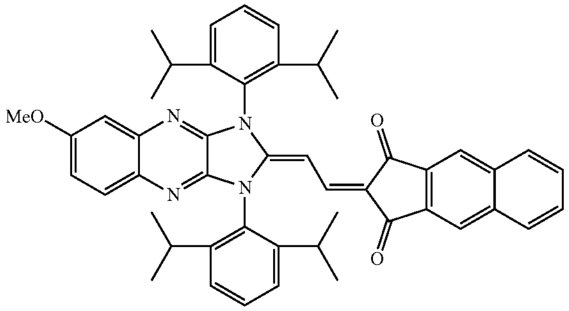
B-7
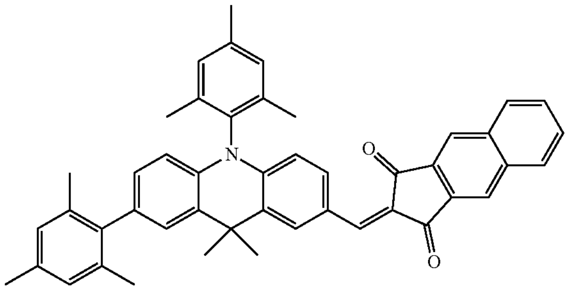
B-8
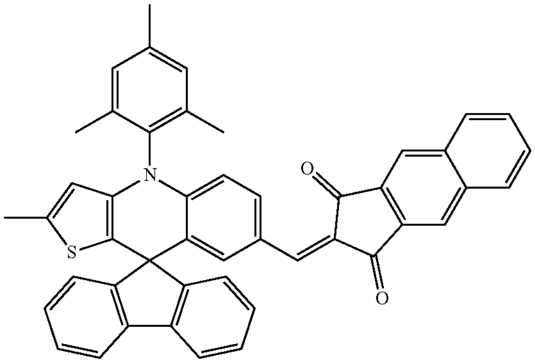

-continued
B-9
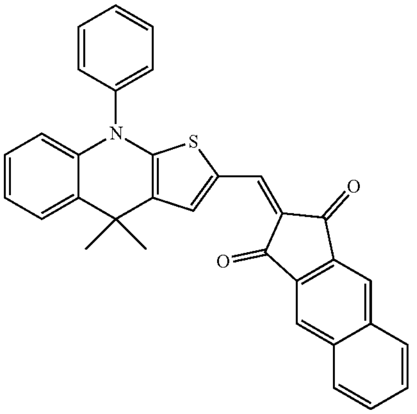
B-10
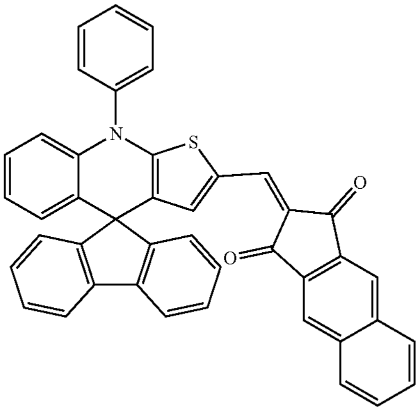
B-11
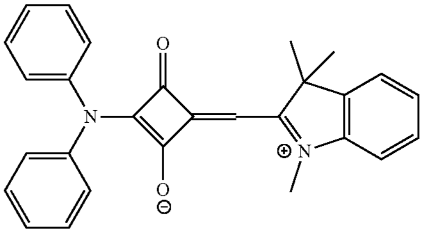
B-12
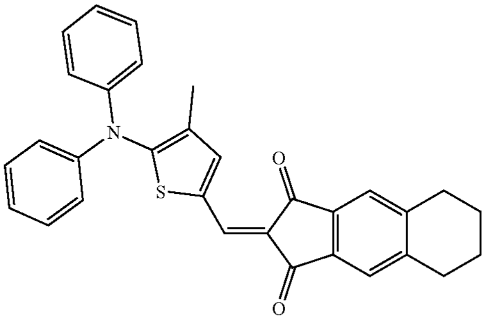
-continued
B-13
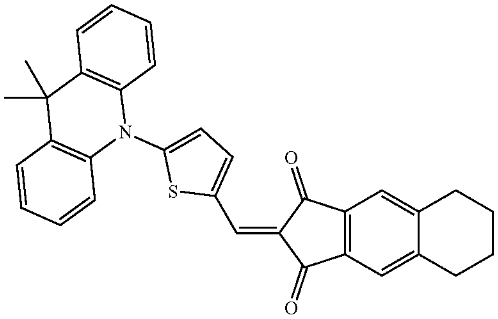
B-14
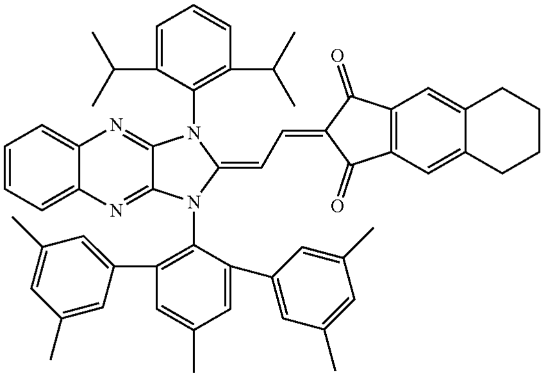
B-15
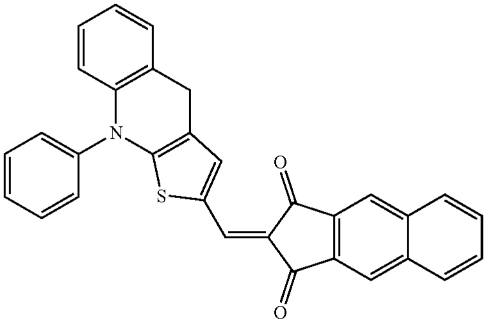
B-16
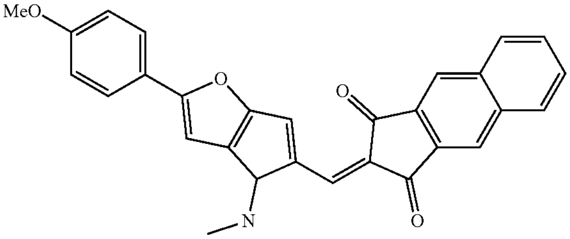

-continued

B-17

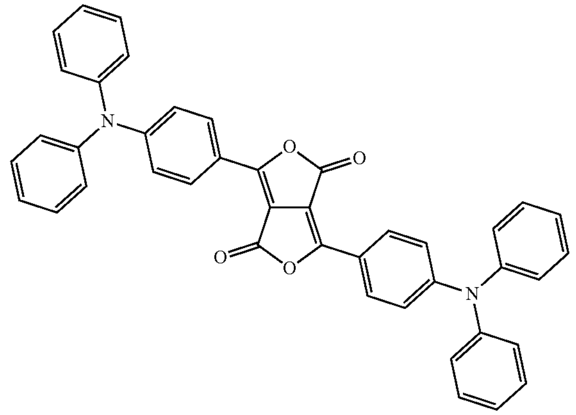

B-18

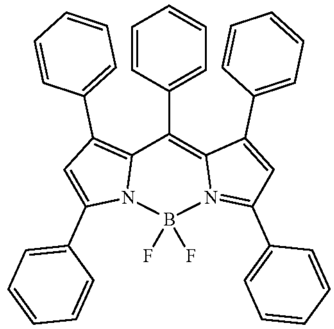

B-19

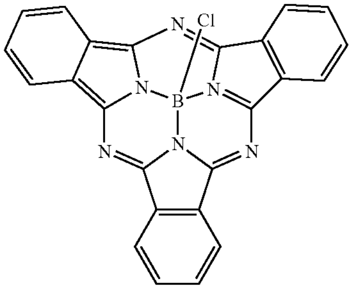

B-20

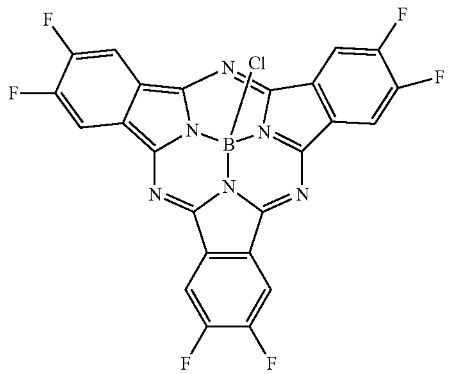

-continued

B-21

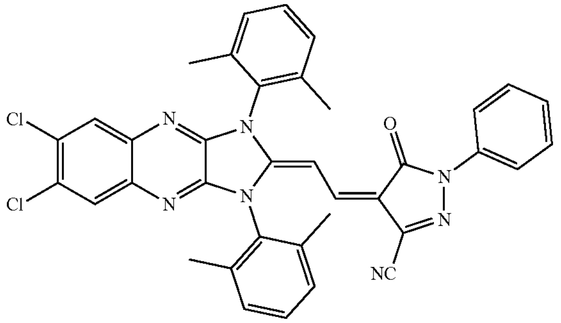

B-22

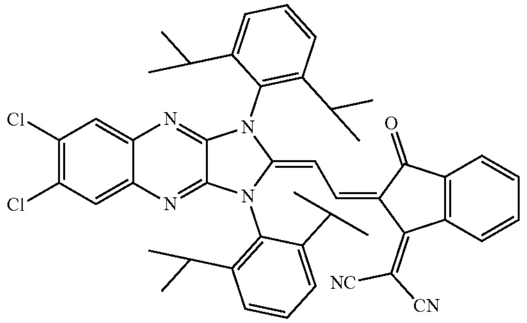

B-23

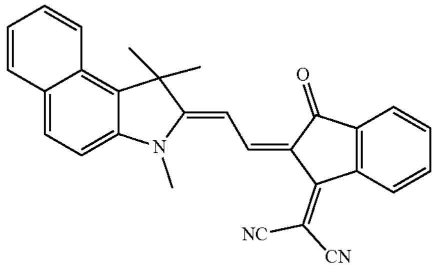

[n-Type Semiconductor Material]

Fullerene $C_{60}$ was used for the production of photoelectric conversion elements described later, as a n-type semiconductor material used for evaluations.

[p-Type Semiconductor Material]

The p-type semiconductor material described below was used for producing the photoelectric conversion elements described later, as the p-type semiconductor material used for evaluations.

D-1

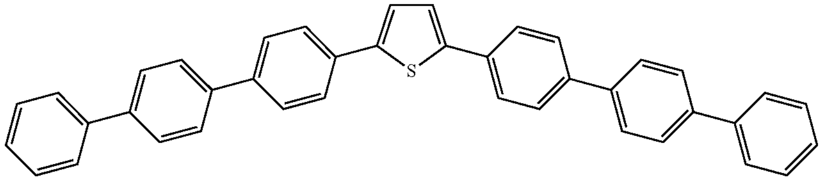

D-2

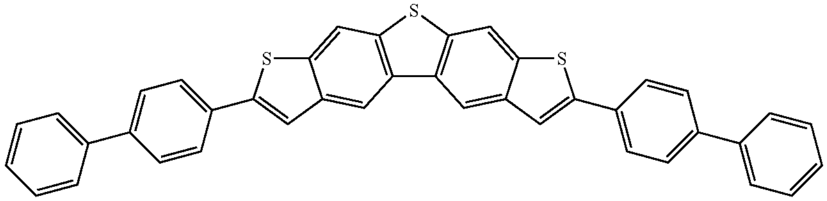

D-3

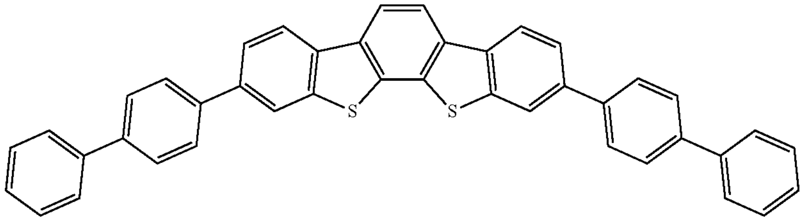

D-5

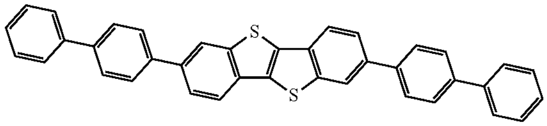

D-4

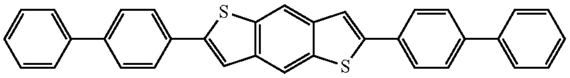

D-6

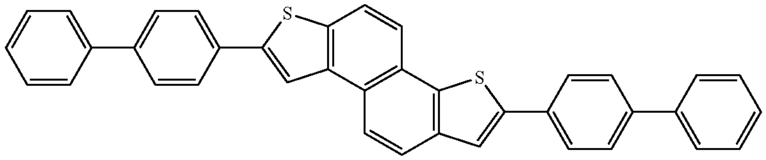

[Test]

The following Test X, Test Y, and Test Z were carried out using each of the materials shown in the above part.

In Test X, a photoelectric conversion film was produced and evaluated using a specific compound, a n-type semiconductor material, and a coloring agent, and in Test Y, a photoelectric conversion film was produced and evaluated using two specific compounds and a coloring agent, in Test Z, a photoelectric conversion film was produced and evaluated using a specific compound, a p-type semiconductor material, and a coloring agent.

[Test X]

Examples and Comparative Examples: Production of Photoelectric Conversion Element The photoelectric conversion element of the form illustrated in FIG. 2 was produced using the obtained compounds. Here, the photoelectric conversion element includes a lower electrode 11, an electron blocking film 16A, a photoelectric conversion film 12, a hole blocking film 16B, and an upper electrode 15.

Specifically, an amorphous ITO was formed into a film on a glass substrate by a sputtering method to form the lower electrode 11 (thickness: 30 nm). Furthermore, a compound (C-1) described below was formed into a film on the lower electrode 11 by a vacuum thermal vapor deposition method to form the electron blocking film 16A (thickness: 30 nm). Furthermore, each component shown in each of Examples or Comparative Examples shown in Table described in the below part was co-deposited on the electron blocking film 16A to form the photoelectric conversion film 12 as a mixture layer. A ratio of a vapor deposition rate of each component was adjusted so that a film thickness of each component in the photoelectric conversion film in terms of a single layer was a ratio shown in the "Component ratio" column in Table.

Furthermore, a compound (C-2) described below was vapor-deposited on the photoelectric conversion film 12 to form the hole blocking film 16B (thickness: 10 nm). Amorphous ITO was formed into a film on the hole blocking film 16B by a sputtering method to form the upper electrode 15 (the transparent conductive film) (thickness: 10 nm). A SiO film was formed as a sealing layer on the upper electrode 15 by a vacuum vapor deposition method, and thereafter, an aluminum oxide ($Al_2O_3$) layer was formed thereon by an atomic layer chemical vapor deposition (ALCVD) method to produce a photoelectric conversion element obtained in each of Examples or Comparative Examples.

C-1

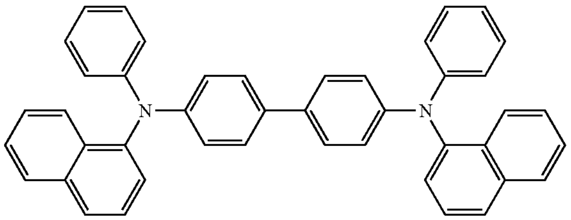

C-2

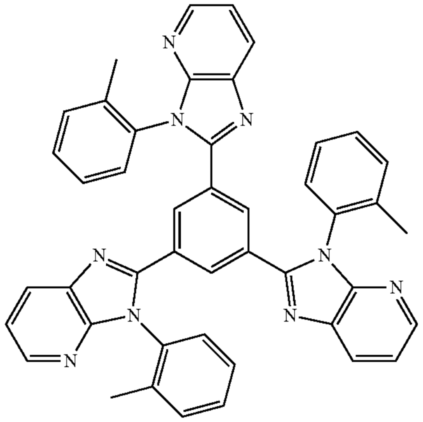

In the photoelectric conversion film of Examples in Test X, the compounds (1-1) to (1-36) exhibit properties as the p-type semiconductor.

<Evaluation of Dark Current>

The dark current of each of the obtained photoelectric conversion elements was measured by the following method.

A voltage was applied to the lower electrode and the upper electrode of each of the photoelectric conversion elements to have an electric field strength of $2.5\times10^5$ V/cm and current values (dark current) in a dark place were measured. Next, similarly, a voltage was applied to have an electric field strength of $7.5\times10^4$ V/cm, a current value (dark current) in a dark place was measured, a relative ratio was calculated from the following Expression, and the result was evaluated according to the following standard.

Relative ratio of dark current=(dark current of $2.5\times10^5$ V/cm)/(dark current of $7.5\times10^4$ V/cm)

A: Relative ratio of dark current is less than 2.0

B: Relative ratio of dark current is 2.0 or more and less than 2.5

C: Relative ratio of dark current is 2.5 or more and less than 3.0

D: Relative ratio of dark current is 3.0 or more and less than 3.5

E: Relative ratio of dark current is 3.5 or more

<Evaluation of Photoelectric Conversion Efficiency (Quantum Efficiency)>

The drive of each photoelectric conversion element thus obtained was confirmed by a method below.

A voltage was applied to each photoelectric conversion element to have an electric field strength of $7.5\times10^4$ V/cm. Thereafter, light was emitted from the upper electrode (transparent conductive film) side to evaluate the photoelectric conversion efficiency (external quantum efficiency) within the visible light range (400 to 700 nm).

An integral value of the photoelectric conversion efficiency in light at 400 to 700 nm was used to calculate a relative ratio of the integral value of the photoelectric conversion efficiency by Expression (S), and the evaluation according to the following standard was carried out.

Relative ratio=(Integral value of the photoelectric conversion efficiency of the photoelectric conversion element to be evaluated at 400 to 700 nm)/(Integral value of the photoelectric conversion efficiency of the photoelectric conversion element of Example 1-1 at 400 to 700 nm) Expression (S):

A: The relative ratio of the integral values of the photoelectric conversion efficiency is 1.4 or more.

B: The relative ratio of the integral values of the photoelectric conversion efficiency is 1.2 or more and less than 1.4.

C: The relative ratio of the integral values of the photoelectric conversion efficiency is 1.0 or more and less than 1.2.

D: The relative ratio of the integral values of the photoelectric conversion efficiency is 0.8 or more and less than 1.0.

E: The relative ratio of the integral values of the photoelectric conversion efficiency is less than 0.8.

<Evaluation of Electric Field Strength Dependence of Photoelectric Conversion Efficiency>

The electric field strength dependence of the quantum efficiency in each of the obtained photoelectric conversion elements was confirmed by the following method.

A voltage was applied to each photoelectric conversion element to have an electric field strength of $7.5\times10^4$ V/cm. Thereafter, light was emitted from the upper electrode (transparent conductive film) side to evaluate the photoelectric conversion efficiency (external quantum efficiency) within the visible light range (400 to 700 nm).

Furthermore, a voltage was applied to each photoelectric conversion element to have an electric field strength of $2.5\times10^5$ V/cm. Thereafter, light was emitted from the upper electrode (transparent conductive film) side to evaluate the photoelectric conversion efficiency (external quantum efficiency) within the visible light range (400 to 700 nm).

The integral value of the photoelectric conversion efficiency measured at each electric field strength at 400 to 700 nm was used to calculate the photoelectric conversion efficiency ratio by the following Expression and evaluate the electric field strength dependence of the photoelectric conversion efficiency according to the following standard.

Photoelectric conversion efficiency ratio=(Integral value of the photoelectric conversion efficiency at 400 to 700 nm under a condition in which a voltage is applied so that the electric field strength is $7.5\times10^4$ V/cm)/(Integral value of the photoelectric conversion efficiency at 400 to 700 nm under a condition in which a voltage is applied to the photoelectric conversion element to be evaluated so that the electric field strength is $2.5\times10^5$ V/cm)

A: The photoelectric conversion efficiency ratio is 0.9 or more.

B: The photoelectric conversion efficiency ratio is 0.8 or more and less than 0.9.

C: The photoelectric conversion efficiency ratio is 0.7 or more and less than 0.8.

D: The photoelectric conversion efficiency ratio is 0.6 or more and less than 0.7.

E: The photoelectric conversion efficiency ratio is less than 0.6.

<Result of Test X>

The features of the photoelectric conversion element of each of Examples and Comparative Examples in the present test (Test X) and the results of tests conducted using the photoelectric conversion element of each Examples and Comparative Examples are shown in Table 1 below.

In addition, in Table, the "Formula" column indicates which of the above-described Formulae the evaluation compound corresponds to. For example, the evaluation compound 1-1 used in Example 1-1 corresponds to the compound represented by Formula (16).

TABLE 1

| | Each component used to form photoelectric conversion film | | | | | | | Evaluation result | | |
|---|---|---|---|---|---|---|---|---|---|---|
| | Type | | | | Component ratio | | | | | |
| Table 1 (part 1) | Evaluation compound | Formula | n-Type semiconductor material | Coloring agent | Evaluation compound | n-Type semiconductor material | Coloring agent | Dark current | Photoelectric conversion efficiency | Electric field strength dependence of photoelectric conversion efficiency |
| Example 1-1 | 1-1 | 16 | Fullerene 60 | B-1 | 1.0 | 1.0 | 1.0 | B | B | A |
| Example 1-2 | 1-1 | 16 | Fullerene 60 | B-2 | 1.0 | 1.0 | 1.0 | B | B | A |
| Example 1-3 | 1-1 | 16 | Fullerene 60 | B-3 | 1.0 | 1.0 | 1.0 | B | B | A |
| Example 1-4 | 1-1 | 16 | Fullerene 60 | B-4 | 1.0 | 1.0 | 1.0 | B | B | A |
| Example 1-5 | 1-1 | 16 | Fullerene 60 | B-5 | 1.0 | 1.0 | 1.0 | B | B | A |
| Example 1-6 | 1-1 | 16 | Fullerene 60 | B-6 | 1.0 | 0.9 | 1.0 | B | B | A |
| Example 1-7 | 1-1 | 16 | Fullerene 60 | B-7 | 1.0 | 1.0 | 1.0 | B | B | A |
| Example 1-8 | 1-1 | 16 | Fullerene 60 | B-8 | 1.0 | 1.0 | 1.0 | B | B | A |
| Example 1-9 | 1-1 | 16 | Fullerene 60 | B-9 | 1.0 | 1.0 | 1.0 | B | B | A |
| Example 1-10 | 1-1 | 16 | Fullerene 60 | B-10 | 1.0 | 1.0 | 1.0 | B | B | A |
| Example 1-11 | 1-1 | 16 | Fullerene 60 | B-11 | 1.0 | 1.0 | 1.0 | B | B | A |
| Example 1-12 | 1-1 | 16 | Fullerene 60 | B-12 | 0.9 | 1.0 | 1.0 | B | B | A |
| Example 1-13 | 1-1 | 16 | Fullerene 60 | B-13 | 1.0 | 1.0 | 1.0 | B | B | A |
| Example 1-14 | 1-1 | 16 | Fullerene 60 | B-14 | 1.0 | 1.0 | 1.0 | B | B | A |
| Example 1-15 | 1-1 | 16 | Fullerene 60 | B-15 | 1.0 | 1.0 | 1.0 | B | B | A |
| Example 1-16 | 1-1 | 16 | Fullerene 60 | B-16 | 1.0 | 1.0 | 1.0 | B | B | A |
| Example 1-17 | 1-1 | 16 | Fullerene 60 | B-17 | 1.0 | 1.0 | 1.0 | B | B | A |
| Example 1-18 | 1-1 | 16 | Fullerene 60 | B-18 | 1.0 | 1.0 | 0.9 | B | B | A |
| Example 1-19 | 1-1 | 16 | Fullerene 60 | B-19 | 1.0 | 1.0 | 1.0 | B | B | A |
| Example 1-20 | 1-1 | 16 | Fullerene 60 | B-20 | 1.0 | 1.0 | 1.0 | B | B | A |
| Example 1-21 | 1-1 | 16 | Fullerene 60 | B-21 | 1.0 | 1.0 | 1.0 | B | B | A |
| Example 1-22 | 1-1 | 16 | Fullerene 60 | B-22 | 1.0 | 0.9 | 1.0 | B | B | A |
| Example 1-23 | 1-1 | 16 | Fullerene 60 | B-23 | 1.0 | 1.0 | 1.0 | B | B | A |
| Example 1-24 | 1-2 | 44 | Fullerene 60 | B-23 | 1.0 | 1.0 | 1.0 | B | A | A |
| Example 1-25 | 1-3 | 27 | Fullerene 60 | B-23 | 1.0 | 1.0 | 1.0 | B | A | A |
| Example 1-26 | 1-4 | 45 | Fullerene 60 | B-23 | 1.0 | 1.0 | 1.0 | B | A | A |
| Example 1-27 | 1-5 | 27 | Fullerene 60 | B-23 | 1.0 | 1.0 | 1.0 | B | A | A |
| Example 1-28 | 1-6 | 46 | Fullerene 60 | B-23 | 1.0 | 1.0 | 1.0 | B | A | A |
| Example 1-29 | 1-7 | 17 | Fullerene 60 | B-23 | 1.0 | 1.0 | 1.0 | B | A | A |
| Example 1-30 | 1-8 | 17 | Fullerene 60 | B-23 | 1.0 | 0.9 | 1.0 | B | A | A |
| Example 1-31 | 1-9 | 24 | Fullerene 60 | B-23 | 1.0 | 1.0 | 1.0 | B | A | A |
| Example 1-32 | 1-10 | 21 | Fullerene 60 | B-23 | 1.0 | 1.0 | 1.0 | B | A | A |
| Example 1-33 | 1-11 | 22 | Fullerene 60 | B-23 | 1.0 | 1.0 | 1.0 | B | A | A |
| Example 1-34 | 1-12 | 17 | Fullerene 60 | B-23 | 1.0 | 1.0 | 1.0 | A | C | B |
| Example 1-35 | 1-13 | 17 | Fullerene 60 | B-23 | 1.0 | 1.0 | 1.0 | A | C | B |
| Example 1-36 | 1-14 | 17 | Fullerene 60 | B-23 | 1.0 | 1.0 | 1.0 | A | C | B |
| Example 1-37 | 1-15 | 17 | Fullerene 60 | B-23 | 1.0 | 1.0 | 1.0 | A | C | B |
| Example 1-38 | 1-16 | 29 | Fullerene 60 | B-23 | 1.0 | 1.0 | 1.0 | A | C | B |
| Example 1-39 | 1-17 | 23 | Fullerene 60 | B-23 | 1.0 | 1.0 | 1.0 | A | C | B |
| Example 1-40 | 1-18 | 21 | Fullerene 60 | B-23 | 1.0 | 1.0 | 1.0 | A | C | B |
| Example 1-41 | 1-19 | 17 | Fullerene 60 | B-23 | 1.0 | 1.0 | 1.0 | A | C | B |
| Example 1-42 | 1-20 | 18 | Fullerene 60 | B-23 | 1.0 | 0.7 | 1.0 | A | C | B |
| Example 1-43 | 1-21 | 24 | Fullerene 60 | B-23 | 1.0 | 1.0 | 1.0 | A | C | B |
| Example 1-44 | 1-22 | 24 | Fullerene 60 | B-23 | 1.0 | 1.0 | 1.0 | A | C | B |
| Example 1-45 | 1-23 | 24 | Fullerene 60 | B-23 | 1.0 | 1.0 | 1.0 | A | C | B |

TABLE 2

| Table 1 (part 2) | Each component used to form photoelectric conversion film: Type: Evaluation compound | Type: Formula | Type: n-Type semiconductor material | Type: Coloring agent | Component ratio: Evaluation compound | Component ratio: n-Type semiconductor material | Component ratio: Coloring agent | Evaluation result: Dark current | Evaluation result: Photoelectric conversion efficiency | Evaluation result: Electric field strength dependence of photoelectric conversion efficiency |
|---|---|---|---|---|---|---|---|---|---|---|
| Example 1-46 | 1-24 | 28 | Fullerene 60 | B-23 | 1.0 | 1.0 | 1.0 | B | A | A |
| Example 1-47 | 1-25 | 28 | Fullerene 60 | B-23 | 1.0 | 1.0 | 1.0 | B | A | A |
| Example 1-48 | 1-26 | 31 | Fullerene 60 | B-23 | 1.0 | 0.6 | 1.0 | A | C | B |
| Example 1-49 | 1-27 | 32 | Fullerene 60 | B-23 | 1.0 | 1.0 | 1.0 | A | C | B |
| Example 1-50 | 1-28 | 32 | Fullerene 60 | B-23 | 1.0 | 1.0 | 1.0 | A | C | B |
| Example 1-51 | 1-29 | 41 | Fullerene 60 | B-23 | 1.0 | 1.0 | 1.0 | C | B | B |
| Example 1-52 | 1-30 | 54 | Fullerene 60 | B-23 | 1.0 | 1.0 | 1.0 | B | A | A |
| Example 1-53 | 1-31 | 55 | Fullerene 60 | B-23 | 1.0 | 1.0 | 1.0 | B | A | A |
| Example 1-54 | 1-32 | 56 | Fullerene 60 | B-23 | 1.0 | 1.0 | 1.0 | B | A | A |
| Example 1-55 | 1-33 | 57 | Fullerene 60 | B-23 | 1.0 | 1.0 | 1.0 | B | A | A |
| Example 1-56 | 1-34 | 58 | Fullerene 60 | B-23 | 1.0 | 1.0 | 1.0 | B | A | A |
| Example 1-57 | 1-35 | 59 | Fullerene 60 | B-23 | 1.0 | 1.0 | 1.0 | B | A | A |
| Example 1-58 | 1-36 | 60 | Fullerene 60 | B-23 | 1.0 | 1.0 | 1.0 | B | A | A |
| Comparative Example 1-1 | C1-1 | — | Fullerene 60 | B-23 | 1.0 | 1.0 | 1.0 | E | E | E |
| Comparative Example 1-2 | C1-2 | — | Fullerene 60 | B-23 | 1.0 | 1.0 | 1.0 | E | E | E |
| Comparative Example 1-3 | C1-3 | — | Fullerene 60 | B-23 | 1.0 | 1.0 | 1.0 | E | E | E |
| Comparative Example 1-4 | C1-4 | — | Fullerene 60 | B-23 | 1.0 | 1.0 | 1.0 | E | E | E |
| Comparative Example 1-5 | C1-5 | — | Fullerene 60 | B-23 | 1.0 | 1.0 | 1.0 | E | E | E |
| Comparative Example 1-6 | C1-6 | — | Fullerene 60 | B-23 | 1.0 | 1.0 | 1.0 | E | E | E |
| Comparative Example 1-7 | C1-7 | — | Fullerene 60 | B-23 | 1.0 | 1.0 | 1.0 | E | E | E |
| Comparative Example 1-8 | C1-8 | — | Fullerene 60 | B-23 | 1.0 | 1.0 | 1.0 | E | E | E |
| Comparative Example 1-9 | C1-9 | — | Fullerene 60 | B-23 | 1.0 | 1.0 | 1.0 | E | E | E |
| Comparative Example 1-10 | C1-10 | — | Fullerene 60 | B-23 | 1.0 | 1.0 | 1.0 | E | E | E |
| Comparative Example 1-11 | C1-11 | — | Fullerene 60 | B-23 | 1.0 | 1.0 | 1.0 | E | E | E |
| Comparative Example 1-12 | C1-12 | — | Fullerene 60 | B-23 | 1.0 | 1.0 | 1.0 | D | D | D |
| Comparative Example 1-13 | C1-13 | — | Fullerene 60 | B-23 | 1.0 | 1.0 | 1.0 | E | E | E |
| Comparative Example 1-14 | C1-14 | — | Fullerene 60 | B-23 | 1.0 | 1.0 | 1.0 | E | E | E |
| Comparative Example 1-15 | C1-15 | — | Fullerene 60 | B-23 | 1.0 | 1.0 | 1.0 | E | E | E |
| Comparative Example 1-16 | C1-16 | — | Fullerene 60 | B-23 | 1.0 | 1.0 | 1.0 | E | C | D |
| Comparative Example 1-17 | C1-17 | — | Fullerene 60 | B-23 | 1.0 | 1.0 | 1.0 | E | E | E |
| Comparative Example 1-18 | C1-18 | — | Fullerene 60 | B-23 | 1.0 | 1.0 | 1.0 | E | E | E |
| Comparative Example 1-19 | C1-19 | — | Fullerene 60 | B-23 | 1.0 | 1.0 | 1.0 | E | E | E |
| Comparative Example 1-20 | C1-20 | — | Fullerene 60 | B-23 | 1.0 | 1.0 | 1.0 | E | E | E |

TABLE 2-continued

| Table 1 (part 2) | Each component used to form photoelectric conversion film: Type: Evaluation compound | Type: Formula | Type: n-Type semiconductor material | Type: Coloring agent | Component ratio: Evaluation compound | Component ratio: n-Type semiconductor material | Component ratio: Coloring agent | Evaluation result: Dark current | Evaluation result: Photoelectric conversion efficiency | Evaluation result: Electric field strength dependence of photoelectric conversion efficiency |
|---|---|---|---|---|---|---|---|---|---|---|
| Comparative Example 1-21 | C1-21 | — | Fullerene 60 | B-23 | 1.0 | 1.0 | 1.0 | E | E | E |
| Comparative Example 1-22 | C1-22 | — | Fullerene 60 | B-23 | 1.0 | 1.0 | 1.0 | D | E | E |
| Comparative Example 1-23 | C1-23 | — | Fullerene 60 | B-23 | 1.0 | 1.0 | 1.0 | D | D | D |

From the result illustrated in Table 1, it was confirmed that the photoelectric conversion element according to the embodiment of the present invention, which is formed of the photoelectric conversion film containing the specific compound was excellent to exhibit the effect of the present invention.

Among these, in the case where the specific compound was the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y''$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom (Examples 1-1 to 1-33, Examples 1-46 and 1-47, and Examples 1-52 to 1-58), the effect was more excellent.

[Test Y]

Examples and Comparative Examples: Production of Photoelectric Conversion Element A photoelectric conversion element in each of Examples or Comparative Examples was manufactured in the same manner as in Test X.

In the photoelectric conversion film of Examples in Test Y, the compound (1-7) exhibited properties as the p-type semiconductor, and the compounds (2-1) to (2-17) exhibited properties as the n-type semiconductor.

<Evaluation of Dark Current>

The dark current of each of the obtained photoelectric conversion elements was measured by the following method.

A voltage was applied to the lower electrode and the upper electrode of each of the photoelectric conversion elements to have an electric field strength of $2.5\times10^5$ V/cm and current values (dark current) in a dark place were measured. As a result, it was confirmed that all of the photoelectric conversion elements had a dark current of 50 $nA/cm^2$ or less, which indicates that all of the photoelectric conversion elements had a sufficiently low dark current.

<Evaluation of Photoelectric Conversion Efficiency (Quantum Efficiency)>

In the same manner as in Test X, the photoelectric conversion efficiency (quantum efficiency) of each of the obtained photoelectric conversion elements was evaluated.

Note that, in the present test (Test Y), the following formula was adopted as Formula (S).

Relative ratio=(Integral value of the photoelectric conversion efficiency of the photoelectric conversion element to be evaluated at 400 to 700 nm)/(Integral value of the photoelectric conversion efficiency of the photoelectric conversion element of Example 2-1 at 400 to 700 nm)   Expression (S):

<Evaluation of Electric Field Strength Dependence of Photoelectric Conversion Efficiency>

In the same manner as in Test X, the electric field strength dependence of the photoelectric conversion efficiency of each of the obtained photoelectric conversion elements was evaluated. Note that, the applied voltages were $2.0\times10^5$ V/cm and $2.5\times10^5$ V/cm, and the photoelectric conversion efficiency ratio was calculated by the following Equation.

Photoelectric conversion efficiency ratio=(Integral value of the photoelectric conversion efficiency at 400 to 700 nm under a condition in which a voltage is applied so that the electric field strength is $2.0\times10^5$ V/cm)/(Integral value of the photoelectric conversion efficiency at 400 to 700 nm under a condition in which a voltage is applied to the photoelectric conversion element to be evaluated so that the electric field strength is $2.5\times10^5$ V/cm)

<Result of Test Y>

The features of the photoelectric conversion element of each of Examples and Comparative Examples in the present test (Test Y) and the results of tests conducted using the photoelectric conversion element of each Examples and Comparative Examples are shown in Table 2 below.

The "Formula" column in Table 2 indicates which formula the compound of 1 described in the evaluation compound corresponds to.

In the photoelectric conversion film of Examples in Test Z, the compounds (2-1) to (2-17) exhibit properties as the n-type semiconductor material.

<Evaluation of Dark Current>

In the same manner as in Test Y, the dark current was evaluated for each of the obtained photoelectric conversion elements.

As a result, it was confirmed that all of the photoelectric conversion elements had a dark current of 50 nA/cm$^2$ or less, which indicates that all of the photoelectric conversion elements had a sufficiently low dark current.

<Evaluation of Photoelectric Conversion Efficiency (Quantum Efficiency)>

TABLE 3

| | Each component used to form photoelectric conversion film | | | | | | | Evaluation result | |
|---|---|---|---|---|---|---|---|---|---|
| | Type | | | | Component ratio | | | | Electric field |
| Table 2 | Part 1 of evaluation compound | Formula | Part 2 of evaluation compound | Coloring agent | Part 1 of evaluation compound | Part 2 of evaluation compound | Coloring agent | Photoelectric conversion efficiency | strength dependence of photoelectric conversion efficiency |
| Example 2-1 | 2-1 | 31 | 1-7 | B-5 | 1.0 | 1.0 | 1.0 | C | A |
| Example 2-2 | 2-2 | 31 | 1-7 | B-5 | 1.0 | 1.0 | 0.8 | B | A |
| Example 2-3 | 2-3 | 31 | 1-7 | B-5 | 1.0 | 1.0 | 1.0 | A | A |
| Example 2-4 | 2-4 | 31 | 1-7 | B-5 | 1.0 | 1.0 | 1.0 | B | A |
| Example 2-5 | 2-5 | 31 | 1-7 | B-5 | 1.0 | 0.9 | 1.0 | B | A |
| Example 2-6 | 2-6 | 31 | 1-7 | B-5 | 1.0 | 1.0 | 1.0 | B | A |
| Example 2-7 | 2-7 | 32 | 1-7 | B-5 | 1.0 | 1.0 | 1.0 | A | A |
| Example 2-8 | 2-8 | 16 | 1-7 | B-5 | 0.9 | 1.0 | 1.0 | B | A |
| Example 2-9 | 2-9 | 16 | 1-7 | B-5 | 1.0 | 1.0 | 1.0 | A | A |
| Example 2-10 | 2-10 | 16 | 1-7 | B-5 | 1.0 | 1.0 | 0.9 | A | A |
| Example 2-11 | 2-11 | 35 | 1-7 | B-5 | 1.0 | 1.0 | 1.0 | B | A |
| Example 2-12 | 2-12 | 37 | 1-7 | B-5 | 1.0 | 1.0 | 1.0 | A | A |
| Example 2-13 | 2-13 | 42 | 1-7 | B-5 | 0.9 | 1.0 | 1.0 | A | A |
| Example 2-14 | 2-14 | 42 | 1-7 | B-5 | 1.0 | 1.0 | 1.0 | A | A |
| Example 2-15 | 2-15 | 42 | 1-7 | B-5 | 1.0 | 1.0 | 0.9 | A | A |
| Example 2-16 | 2-16 | 39 | 1-7 | B-5 | 1.0 | 1.0 | 1.0 | A | A |
| Example 2-17 | 2-17 | 39 | 1-7 | B-5 | 1.1 | 0.9 | 1.0 | A | A |

From the result illustrated in Table 2, it was confirmed that the photoelectric conversion element according to the embodiment of the present invention was excellent to exhibit the effect of the present invention in the case where the photoelectric conversion film containing the two specific compounds was used.

Among these, it was confirmed that the effect of the present invention is excellent (see the results of Examples 2-3, 2-7, 2-9, 2-10, 2-12 to 2-17, and the like) in a case where at least one of a requirement in which the specific compounds used as the n-type material (the compounds described in the "Evaluation compound 1" column) have an aromatic ring group containing a group serving as —N═ in the ring structure as $Ar^{11}$ and $Ar^{12}$, or a requirement in which n15 and n16 are each 1 is satisfied, and $Ar^{15}$ and $Ar^{16}$ are groups represented by Formula (8) in which $Y^{81}$ to $Y^{85}$ are each —CF═, —C(CN)—, or —N═.

[Test Z]

Examples and Comparative Examples: Production of Photoelectric Conversion Element A photoelectric conversion element of each of Examples or Comparative Examples was manufactured in the same manner as in Test X.

In the same manner as in Test X, the photoelectric conversion efficiency (quantum efficiency) of each of the obtained photoelectric conversion elements was evaluated.

Note that, in the present test (Test Z), the following formula was adopted as Formula (S).

Relative ratio=(Integral value of the photoelectric conversion efficiency of the photoelectric conversion element to be evaluated at 400 to 700 nm)/(Integral value of the photoelectric conversion efficiency of the photoelectric conversion element of Example 3-1 at 400 to 700 nm) Expression (S):

<Evaluation of Electric Field Strength Dependence of Photoelectric Conversion Efficiency>

In the same manner as in Test Y, the electric field strength dependence of the photoelectric conversion efficiency of each of the obtained photoelectric conversion elements was evaluated.

<Result of Test Z>

The features of the photoelectric conversion element of each of Examples and Comparative Examples in the present test (Test Z) and the results of tests conducted using the photoelectric conversion element of each Examples and Comparative Examples are shown in Table 3 below.

TABLE 4

| Table 3 | Each component used to form photoelectric conversion film: Type: Evaluation compound | Type: p-Type semiconductor material | Type: Coloring agent | Component ratio: Evaluation compound | Component ratio: p-Type semiconductor material | Component ratio: Coloring agent | Evaluation result: Photoelectric conversion efficiency | Evaluation result: Electric field strength dependence of photoelectric conversion efficiency |
|---|---|---|---|---|---|---|---|---|
| Example 3-1 | 2-1 | D-1 | B-6 | 1.0 | 1.0 | 1.0 | C | A |
| Example 3-2 | 2-1 | D-2 | B-6 | 1.0 | 1.0 | 1.0 | C | A |
| Example 3-3 | 2-1 | D-3 | B-6 | 1.0 | 1.0 | 1.0 | C | A |
| Example 3-4 | 2-1 | D-4 | B-6 | 1.0 | 1.0 | 1.0 | B | A |
| Example 3-5 | 2-1 | D-5 | B-6 | 1.0 | 1.0 | 1.0 | C | A |
| Example 3-6 | 2-1 | D-6 | B-6 | 1.0 | 1.0 | 1.0 | C | A |
| Example 3-7 | 2-2 | D-4 | B-6 | 1.0 | 1.0 | 1.0 | B | A |
| Example 3-8 | 2-3 | D-4 | B-6 | 1.0 | 1.0 | 1.0 | A | A |
| Example 3-9 | 2-4 | D-4 | B-6 | 1.0 | 1.0 | 1.0 | B | A |
| Example 3-10 | 2-5 | D-4 | B-6 | 1.0 | 1.0 | 1.0 | B | A |
| Example 3-11 | 2-6 | D-4 | B-6 | 1.0 | 1.0 | 1.0 | B | A |
| Example 3-12 | 2-7 | D-4 | B-6 | 1.0 | 1.0 | 1.0 | A | A |
| Example 3-13 | 2-8 | D-4 | B-6 | 1.0 | 1.0 | 1.0 | B | A |
| Example 3-14 | 2-9 | D-4 | B-6 | 1.0 | 1.0 | 1.0 | A | A |
| Example 3-15 | 2-10 | D-4 | B-6 | 1.0 | 1.0 | 1.0 | A | A |
| Example 3-16 | 2-11 | D-4 | B-6 | 1.0 | 1.0 | 1.0 | B | A |
| Example 3-17 | 2-12 | D-4 | B-6 | 1.0 | 1.0 | 1.0 | A | A |
| Example 3-18 | 2-13 | D-4 | B-6 | 1.0 | 1.0 | 1.0 | A | A |
| Example 3-19 | 2-14 | D-4 | B-6 | 1.0 | 1.0 | 1.0 | A | A |
| Example 3-20 | 2-15 | D-4 | B-6 | 1.0 | 1.0 | 1.0 | A | A |
| Example 3-21 | 2-16 | D-4 | B-6 | 1.0 | 1.0 | 1.0 | A | A |
| Example 3-22 | 2-17 | D-4 | B-6 | 1.0 | 1.0 | 1.0 | A | A |
| Comparative Example 1 | C1-1 | D-4 | B-6 | 1.0 | 1.0 | 1.0 | E | E |
| Comparative Example 2 | C1-2 | D-4 | B-6 | 1.0 | 1.0 | 1.0 | E | E |
| Comparative Example 3 | C1-3 | D-4 | B-6 | 1.0 | 1.0 | 1.0 | E | E |
| Comparative Example 4 | C1-4 | D-4 | B-6 | 1.0 | 1.0 | 1.0 | E | E |
| Comparative Example 5 | C1-5 | D-4 | B-6 | 1.0 | 1.0 | 1.0 | E | E |
| Comparative Example 6 | C1-6 | D-4 | B-6 | 1.0 | 1.0 | 1.0 | E | E |
| Comparative Example 7 | C1-7 | D-4 | B-6 | 1.0 | 1.0 | 1.0 | E | E |
| Comparative Example 8 | C1-8 | D-4 | B-6 | 1.0 | 1.0 | 1.0 | E | E |
| Comparative Example 9 | C1-9 | D-4 | B-6 | 1.0 | 1.0 | 1.0 | E | E |
| Comparative Example 10 | C1-10 | D-4 | B-6 | 1.0 | 1.0 | 1.0 | E | E |
| Comparative Example 11 | C1-11 | D-4 | B-6 | 1.0 | 1.0 | 1.0 | E | E |
| Comparative Example 12 | C1-12 | D-4 | B-6 | 1.0 | 1.0 | 1.0 | E | E |
| Comparative Example 13 | C1-13 | D-4 | B-6 | 1.0 | 1.0 | 1.0 | E | E |
| Comparative Example 14 | C1-14 | D-4 | B-6 | 1.0 | 1.0 | 1.0 | E | E |
| Comparative Example 15 | C1-15 | D-4 | B-6 | 1.0 | 1.0 | 1.0 | E | E |
| Comparative Example 16 | C1-16 | D-4 | B-6 | 1.0 | 1.0 | 1.0 | E | E |
| Comparative Example 17 | C1-17 | D-4 | B-6 | 1.0 | 1.0 | 1.0 | E | E |
| Comparative Example 18 | C1-18 | D-4 | B-6 | 1.0 | 1.0 | 1.0 | E | E |
| Comparative Example 19 | C1-19 | D-4 | B-6 | 1.0 | 1.0 | 1.0 | E | E |
| Comparative Example 20 | C1-20 | D-4 | B-6 | 1.0 | 1.0 | 1.0 | E | E |
| Comparative Example 21 | C1-21 | D-4 | B-6 | 1.0 | 1.0 | 1.0 | E | E |
| Comparative Example 22 | C1-22 | D-4 | B-6 | 1.0 | 1.0 | 1.0 | E | E |
| Comparative Example 23 | C1-23 | D-4 | B-6 | 1.0 | 1.0 | 1.0 | F | F |

From the result illustrated in Table 3, it was confirmed that the photoelectric conversion element according to the embodiment of the present invention was excellent to exhibit the effect of the present invention in the case where the photoelectric conversion film containing the specific compound and the p-type semiconductor material was used.

Among these, it was confirmed that the effect of the present invention is excellent (see the results of Examples 3-8, 3-12, 3-14, 3-15, 3-17 to 3-22, and the like) in a case where at least one of a requirement in which the specific compounds used as the n-type material have an aromatic ring group containing a group serving as —N═ in the ring structure as $Ar^{11}$ and $Ar^{12}$, or a requirement in which n15 and n16 are each 1 is satisfied, and $Ar^{15}$ and $Ar^{16}$ are groups represented by Formula (8) in which $Y^{81}$ to $Y^{85}$ are each —CF═, —C(CN)—, or —N═.

EXPLANATION OF REFERENCES

10a, 10b: Photoelectric conversion element
11: Conductive film (lower electrode)
12: Photoelectric conversion film
15: Transparent conductive film (upper electrode)
16A: Electron blocking film
16B: Hole blocking film

What is claimed is:

1. A photoelectric conversion element comprising, in the following order:

a conductive film;
a photoelectric conversion film; and
a transparent conductive film,
wherein the photoelectric conversion film contains a compound represented by Formula (1), (1)

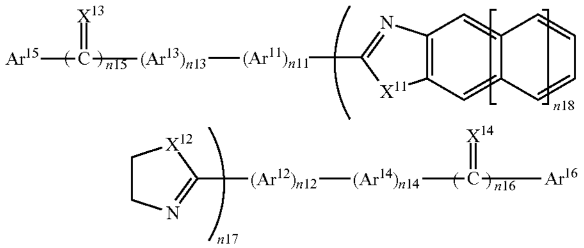

in Formula (1), $X^{11}$ and $X^{12}$ each independently represent a sulfur atom or an oxygen atom,
$Ar^{11}$ to $Ar^{16}$ each independently represent a monocyclic, bicyclic, or tricyclic aromatic ring group,
the aromatic ring group may have one or more groups selected from the group consisting of a halogen atom, a cyano group, and a trifluoromethyl group as a substituent,
$X^{13}$ and $X^{14}$ each independently represent an oxygen atom or a sulfur atom,
n11 to n16 each independently represent 0 or 1,
where, in a case where all of n11 to n16 are 0 and n17 is 1, $Ar^{15}$ and $Ar^{16}$ are the tricyclic aromatic ring groups,
n17 represents 1 or 2, and
n18 represents 1 or 2.

2. The photoelectric conversion element according to claim 1, wherein $Ar^{11}$ to $Ar^{14}$ are each independently a group represented by any of Formula (2) to Formula (7), (2)

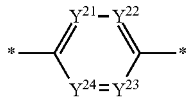

(3)

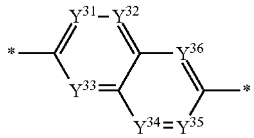

(4)

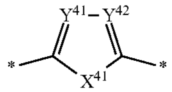

(5)

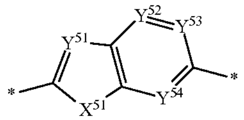

(6)

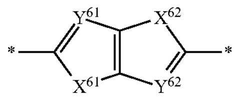

(7)

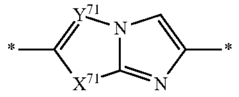

in Formula (2) to Formula (7), * represents a bonding position,
$Y^{21}$ to $Y^{24}$, $Y^{31}$ to $Y^{36}$, $Y^{41}$ and $Y^{42}$, $Y^{51}$ to $Y^{54}$, $Y^{61}$ and $Y^{62}$, and $Y^{71}$ each independently represent —CR═ or a nitrogen atom,
R represents a hydrogen atom, a halogen atom, a cyano group, or a trifluoromethyl group, and
$X^{41}$, $X^{51}$, $X^{61}$ and $X^{62}$, and $X^{71}$ each independently represent a sulfur atom, an oxygen atom, or a selenium atom.

3. The photoelectric conversion element according to claim 1, wherein $Ar^{15}$ and $Ar^{16}$ are each independently a group represented by any of Formula (8) to Formula (15) and Formula (47) to Formula (53), (8)

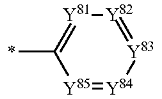

(9)

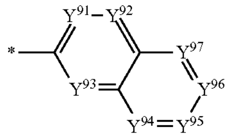

(10)

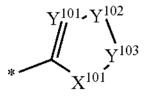

-continued (11)

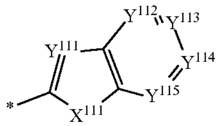

(12)

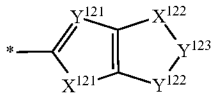

(13)

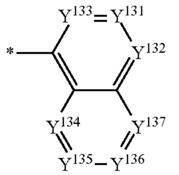

(14)

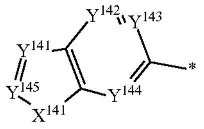

(15)

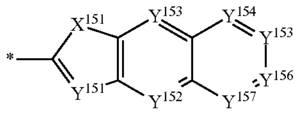

(47)

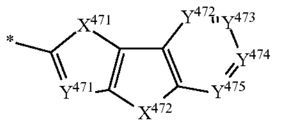

(48)

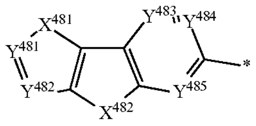

(49)

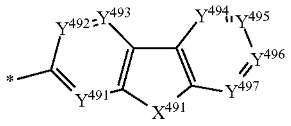

(50)

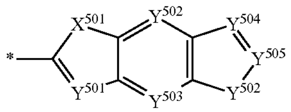

(51)

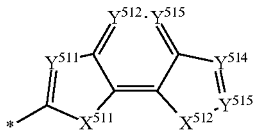

-continued (52)

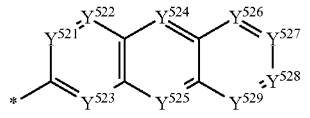

(53)

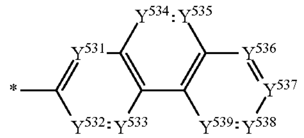

in Formula (8) to Formula (15) and Formula (47) to Formula (53), * represents a bonding position, $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{529}$ and $Y^{531}$ to $Y^{539}$ each independently represent —CR═ or a nitrogen atom, R represents a hydrogen atom, a halogen atom, a cyano group, or a trifluoromethyl group, and $X^{101}$, $X^{111}$, $X^{121}$ and $X^{122}$, $X^{141}$, $X^{151}$, $X^{471}$ to $X^{472}$, $X^{481}$ and $X^{482}$, $X^{491}$, $X^{501}$ and $X^{502}$, and $X^{511}$ and $X^{512}$ each independently represent a sulfur atom, an oxygen atom, or a selenium atom.

4. The photoelectric conversion element according to claim 1, wherein n11 and n12 each represent 1, n13 to n16 each represent 0, n17 represents 1, and n18 represents 1 or 2.

5. The photoelectric conversion element according to claim 1, wherein n11 to n14 each represent 1, n15 and n16 each represent 0, n17 represents 1, and n18 represents 1 or 2.

6. The photoelectric conversion element according to claim 1, wherein n11 to n16 each represent 0, n17 represents 1, and n18 represents 1 or 2.

7. The photoelectric conversion element according to claim 1, wherein n11 and n12 each represent 1, n13 and n14 each represent 0, n15 and n16 each represent 1, n17 represents 1, and n18 represents 1 or 2.

8. The photoelectric conversion element according to claim 1, wherein n11 to n14 each represent 0, n15 and n16 each independently represent 0 or 1, n17 represents 2, and n18 represents 1.

9. The photoelectric conversion element according to claim 1, wherein the compound represented by Formula (1) is a compound represented by any of Formula (16) to Formula (46) and Formula (54) to Formula (60),

(16)
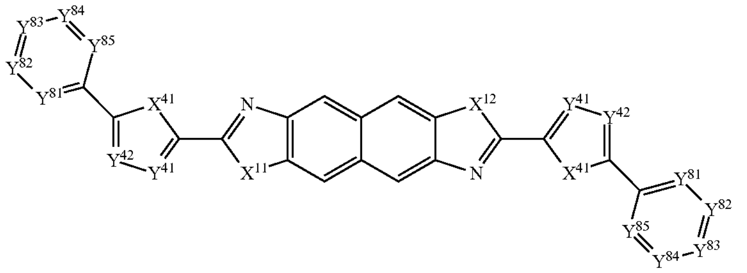
(17)
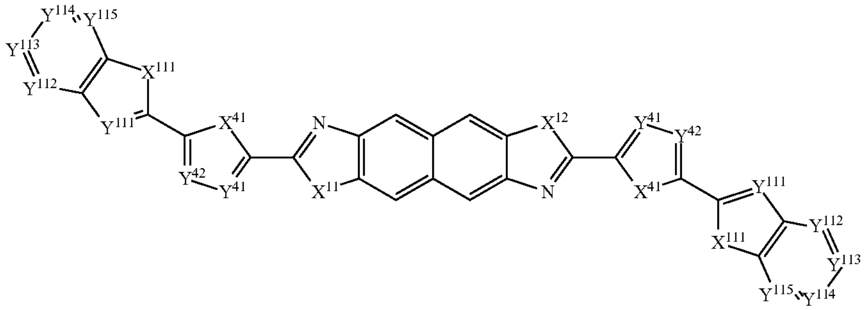
(18)
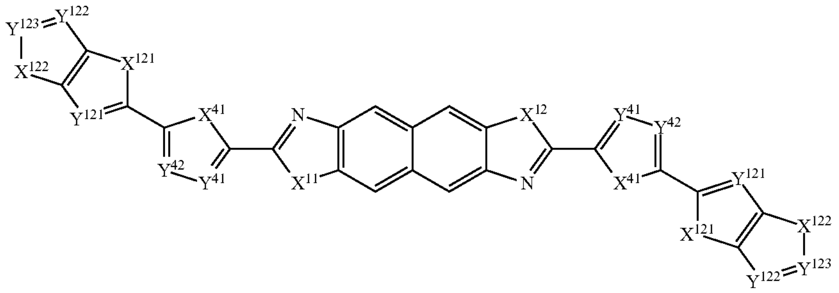
(19)
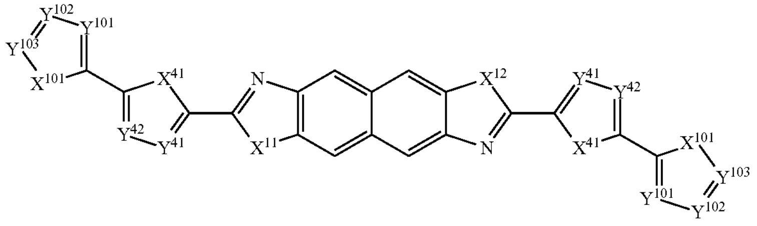
(20)
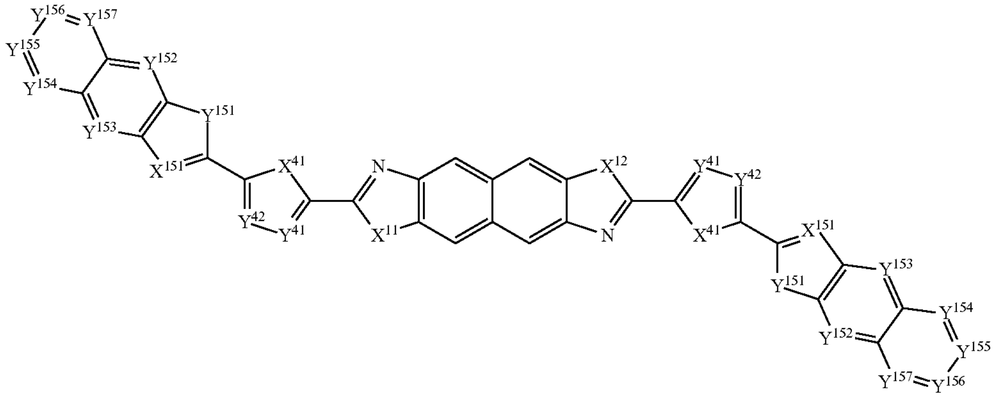

-continued
(21)
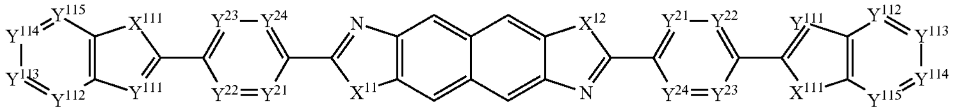
(22)
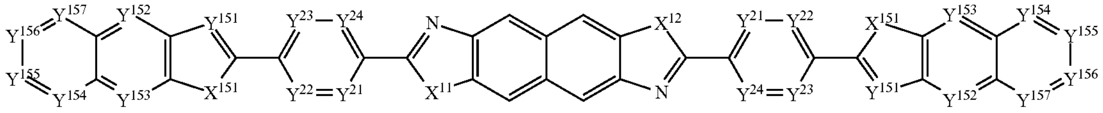
(23)
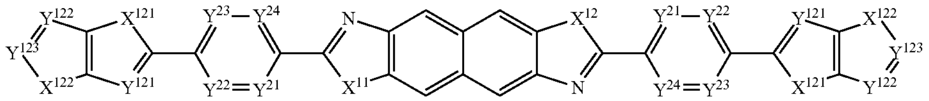
(24)
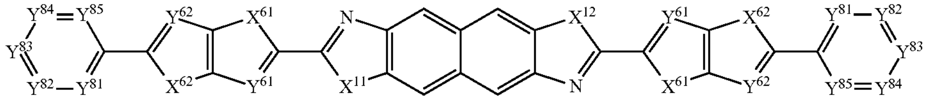
(25)
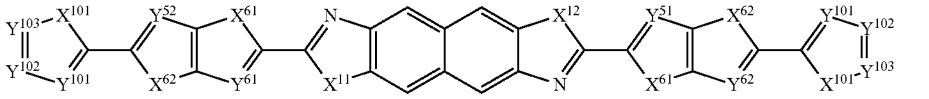
(26)
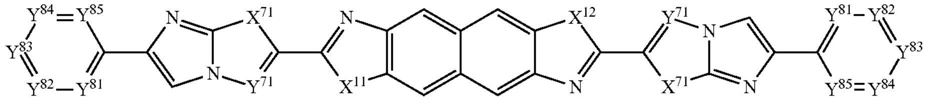
(27)
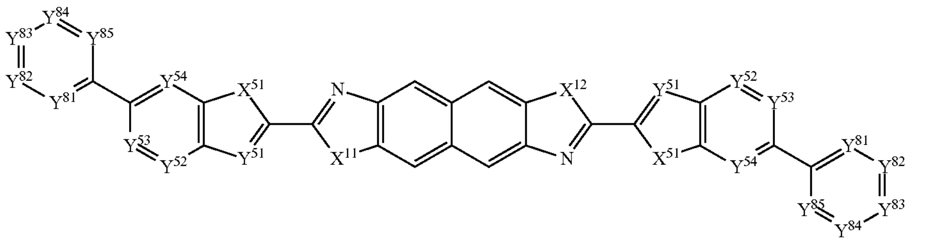
(28)
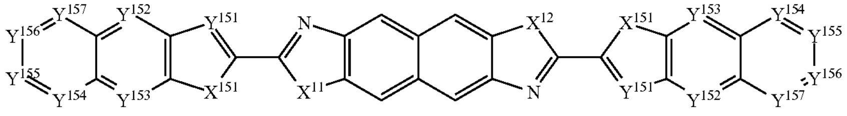
(29)
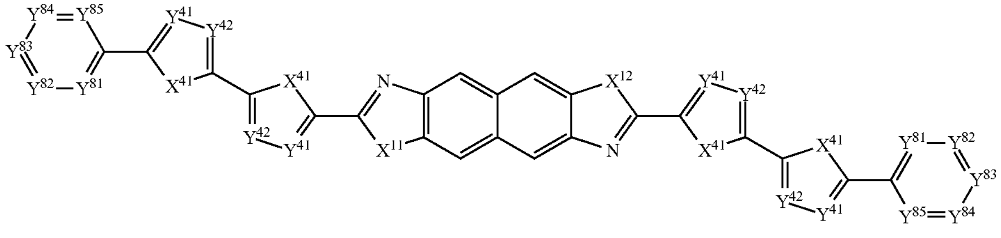
(30)
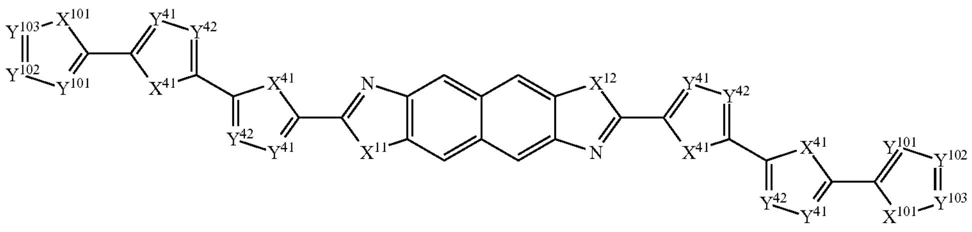

-continued
(31)
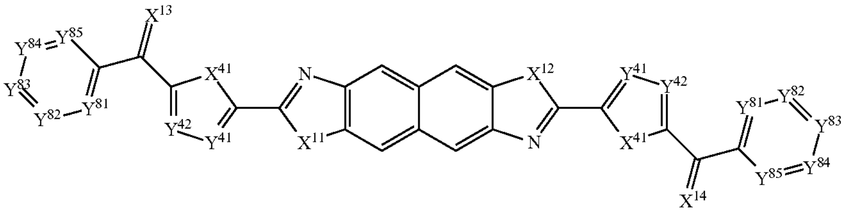
(32)
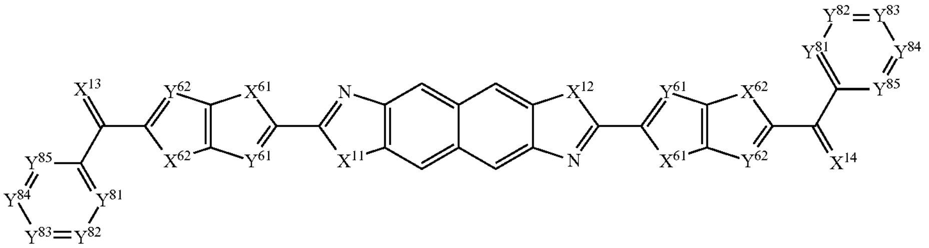
(33)
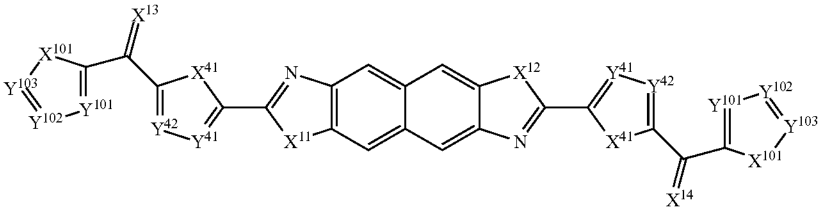
(34)
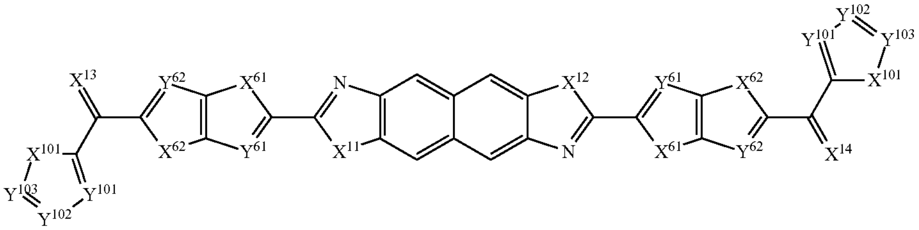
(35)
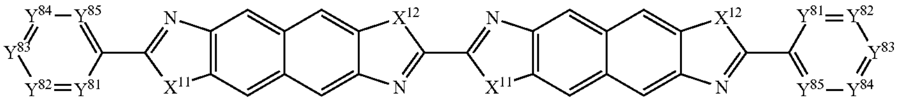
(36)
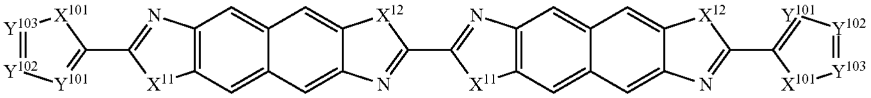
(37)
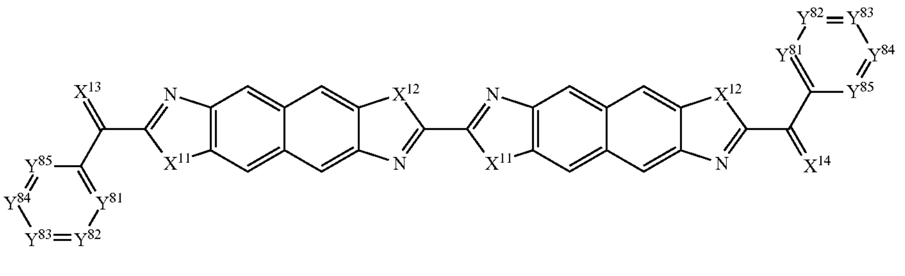

-continued
(38)
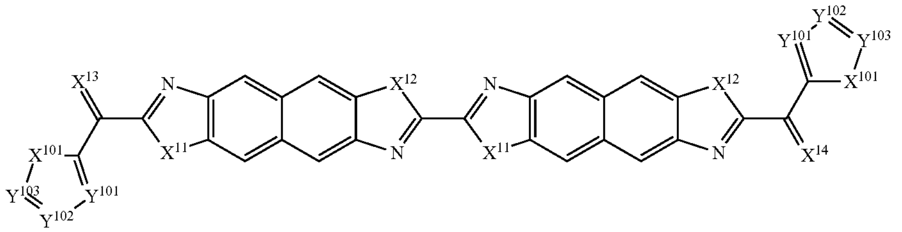
(39)
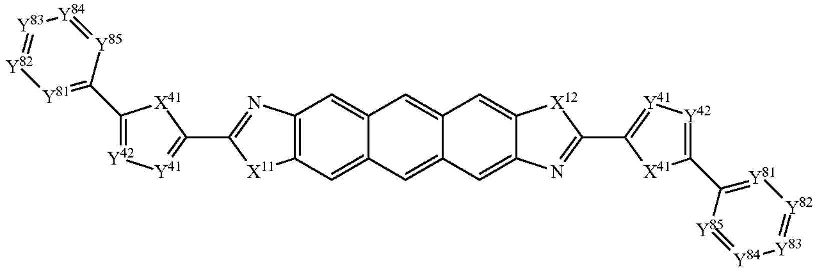
(40)
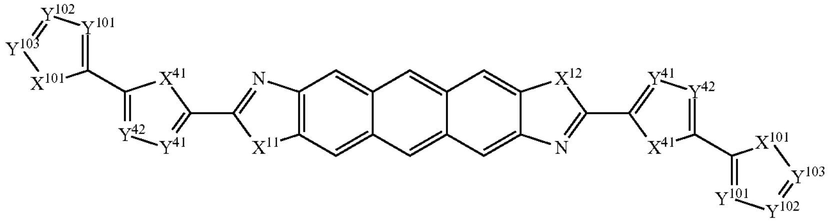
(41)
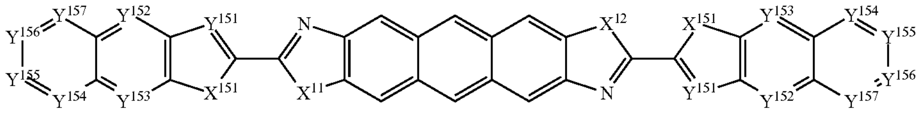
(42)
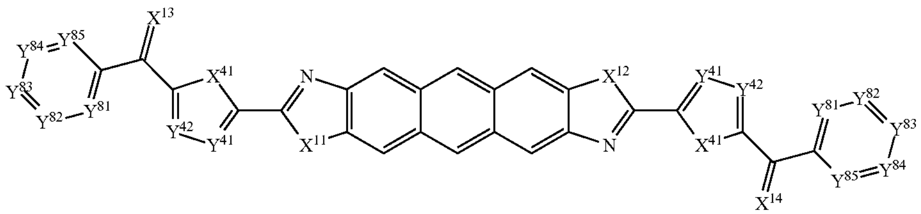
(43)
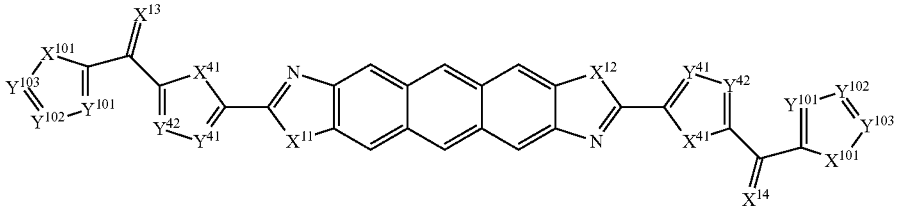
(44)
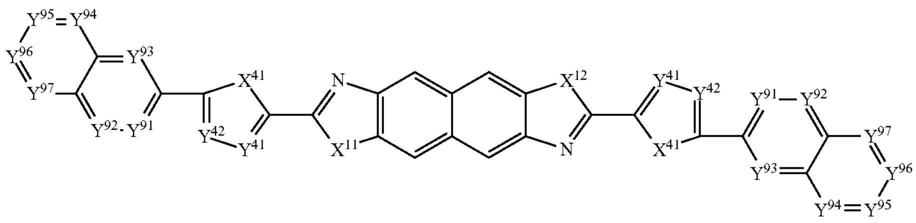

-continued
(45)
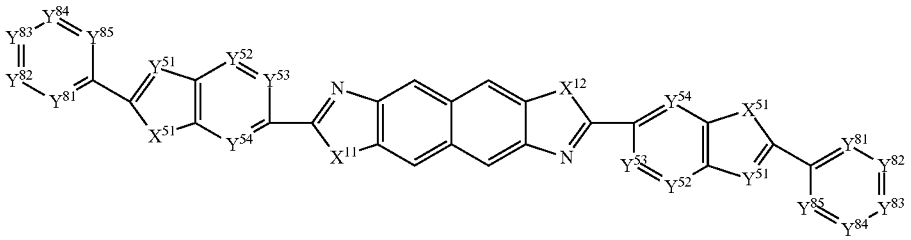
(46)
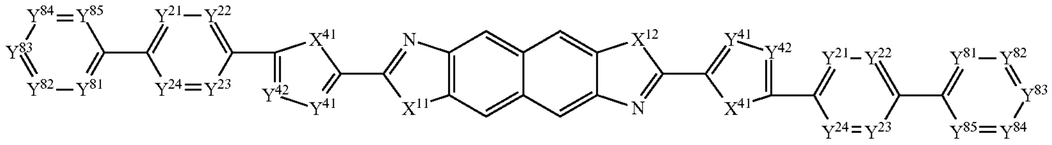
(54)
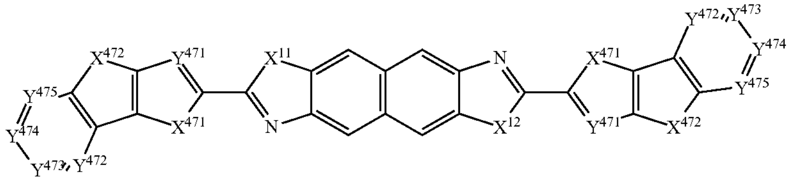
(55)
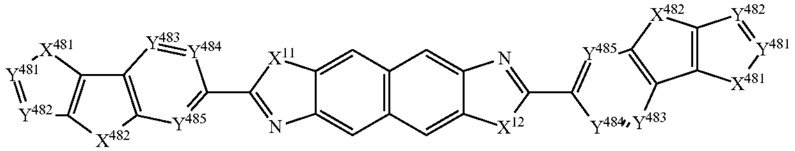
(56)
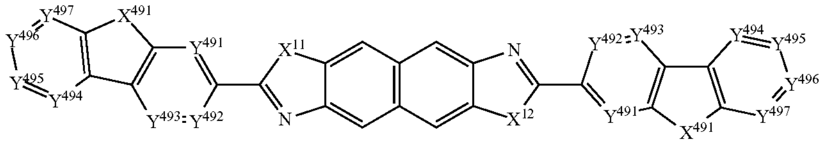
(57)
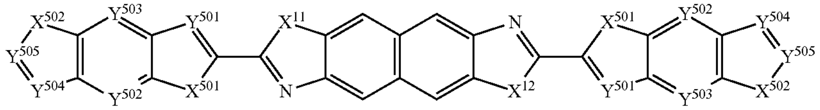
(58)
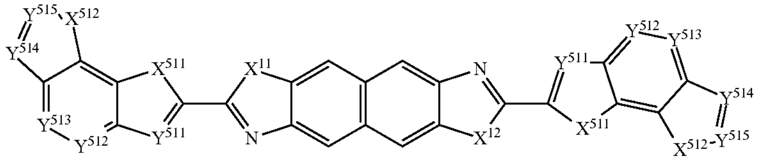
(59)
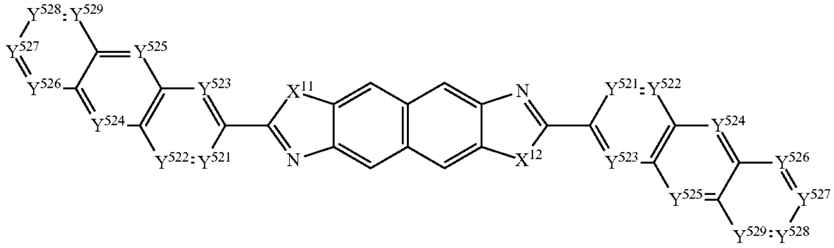

-continued (60)

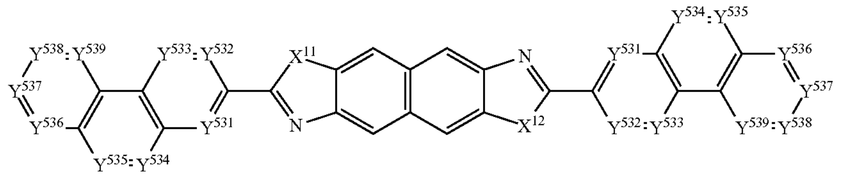

in Formula (16) to Formula (46) and Formula (54) to Formula (60), $Y^{21}$ to $Y^{24}$, $Y^{41}$ and $Y^{42}$, $Y^{51}$ to $Y^{54}$, $Y^{61}$ and $Y^{62}$, $Y^{71}$, $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{528}$, and $Y^{531}$ to $Y^{539}$ each independently represent —CR═ or a nitrogen atom, R represents a hydrogen atom, a halogen atom, a cyano group, or a trifluoromethyl group, $X^{11}$ to $X^{14}$ each independently represent a sulfur atom or an oxygen atom, and $X^{41}$, $X^{51}$, $X^{61}$ and $X^{62}$, $X^{71}$, $X^{101}$, $X^{111}$, $X^{121}$ and $X^{122}$, $X^{151}$, $X^{471}$, $X^{481}$ and $X^{482}$, $X^{491}$, $X^{501}$ and $X^{502}$, and $X^{511}$ and $X^{512}$ each independently represent a sulfur atom, an oxygen atom, or a selenium atom.

10. The photoelectric conversion element according to claim 9, wherein the compound represented by Formula (1) is the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y^{111}$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (29) in which $Y^{41}$ and $Y^{42}$ and $Y^{81}$ to $Y^{85}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom.

11. The photoelectric conversion element according to claim 9, wherein the compound represented by Formula (1) is the compound represented by any one of Formula (16), Formula (31), Formula (32), Formula (35), Formula (37), Formula (39), or Formula (42).

12. The photoelectric conversion element according to claim 1, wherein $X^{11}$ and $X^{12}$ each represent a sulfur atom.

13. The photoelectric conversion element according to claim 1, wherein the photoelectric conversion film further contains a n-type semiconductor material.

14. The photoelectric conversion element according to claim 13, wherein the n-type semiconductor material includes fullerenes selected from the group consisting of a fullerene and a derivative thereof.

15. The photoelectric conversion element according to claim 1, wherein the photoelectric conversion film further contains a p-type semiconductor material.

16. The photoelectric conversion element according to claim 1, wherein the photoelectric conversion film contains two compounds represented by Formula (1).

17. The photoelectric conversion element according to claim 1, wherein the photoelectric conversion film further contains a coloring agent.

18. The photoelectric conversion element according to claim 1, further comprising one or more interlayers between the conductive film and the transparent conductive film, in addition to the photoelectric conversion film.

19. An imaging element comprising the photoelectric conversion element according to claim 1.

20. An optical sensor comprising the photoelectric conversion element according to claim 1.

21. A compound represented by Formula (1), (1)

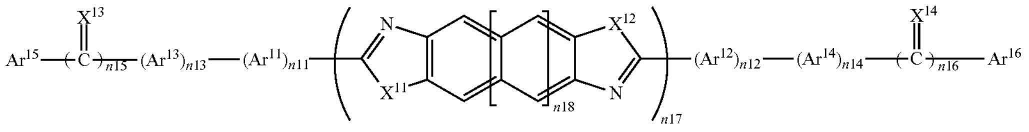

in Formula (1), $X^{11}$ and $X^{12}$ each independently represent a sulfur atom or an oxygen atom, $Ar^{11}$ to $Ar^{16}$ each independently represent a monocyclic, bicyclic, or tricyclic aromatic ring group, the aromatic ring group may have one or more groups selected from the group consisting of a halogen atom, a cyano group, and a trifluoromethyl group as a substituent, $X^{13}$ and $X^{14}$ each independently represent an oxygen atom or a sulfur atom, n11 to n16 each independently represent 0 or 1, where, in a case where all of n11 to n16 are 0 and n17 is 1, $Ar^{15}$ and $Ar^{16}$ are the tricyclic aromatic ring groups, n17 represents 1 or 2, and n18 represents 1 or 2.

22. The compound according to claim 21, wherein $Ar^{11}$ to $Ar^{14}$ are each independently a group represented by any of Formula (2) to Formula (7), (2)

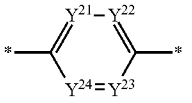

(3)

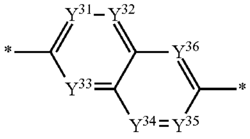

(4)

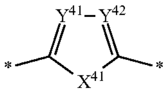

(5)

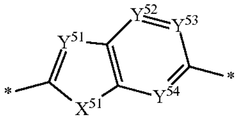

(6)

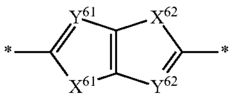

(7)

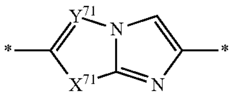

in Formula (2) to Formula (7), * represents a bonding position, $Y^{21}$ to $Y^{24}$, $Y^{31}$ to $Y^{36}$, $Y^{41}$ and $Y^{42}$, $Y^{51}$ to $Y^{54}$, $Y^{61}$ and $Y^{62}$, and $Y^{71}$ each independently represent —CR═ or a nitrogen atom, R represents a hydrogen atom, a halogen atom, a cyano group, or a trifluoromethyl group, and $X^{41}$, $X^{51}$, $X^{61}$ and $X^{62}$, and $X^{71}$ each independently represent a sulfur atom, an oxygen atom, or a selenium atom.

23. The compound according to claim 21, wherein $Ar^{15}$ and $Ar^{16}$ are each independently a group represented by any of Formula (8) to Formula (15) and Formula (47) to Formula (53), (8)

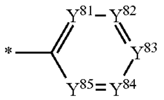

(9)

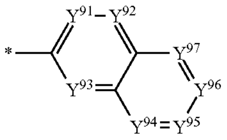

(10)

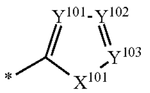

(11)

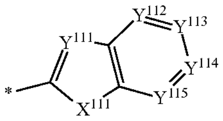

(12)

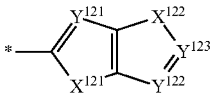

(13)

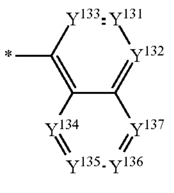

(14)

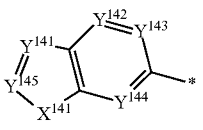

(15)

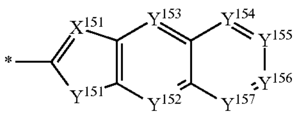

-continued (47)

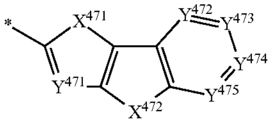

(48)

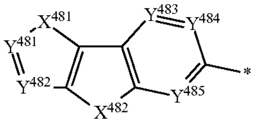

(49)

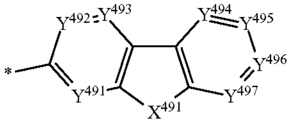

(50)

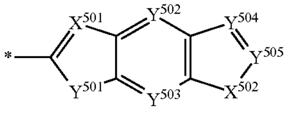

(51)

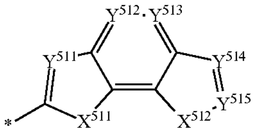

(52)

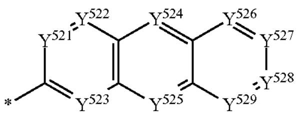

(53)

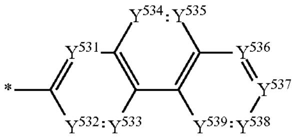

in Formula (8) to Formula (15) and Formula (47) to Formula (53), * represents a bonding position, $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{131}$ to $Y^{137}$, $Y^{141}$ to $Y^{145}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{528}$, and $Y^{531}$ to $Y^{539}$ each independently represent —CR═ or a nitrogen atom, R represents a hydrogen atom, a halogen atom, a cyano group, or a trifluoromethyl group, and $X^{101}$, $X^{111}$, $X^{121}$ and $X^{122}$, $X^{141}$, $X^{151}$, $X^{471}$, $X^{481}$ and $X^{482}$, $X^{491}$, $X^{501}$ and $X^{502}$, and $X^{511}$ and $X^{512}$ each independently represent a sulfur atom, an oxygen atom, or a selenium atom.

24. The compound according to claim 21, wherein n11 and n12 each represent 1, n13 to n16 each represent 0, n17 represents 1, and n18 represents 1 or 2.

25. The compound according to claim 21, wherein n11 to n14 each represent 1, n15 and n16 each represent 0, n17 represents 1, and n18 represents 1 or 2.

26. The compound according to claim 21, wherein n11 to n16 each represent 0, n17 represents 1, and n18 represents 1 or 2.

27. The compound according to claim 21, wherein n11 and n12 each represent 1, n13 and n14 each represent 0, n15 and n16 each represent 1, n17 represents 1, and n18 represents 1 or 2.

28. The compound according to claim 21, wherein n11 to n14 each represent 0, n15 and n16 each independently represent 0 or 1, n17 represents 2, and n18 represents 1.

29. The compound according to claim 21, wherein the compound represented by Formula (1) is a compound represented by any of Formula (16) to Formula (46) and Formula (54) to Formula (60), (16)

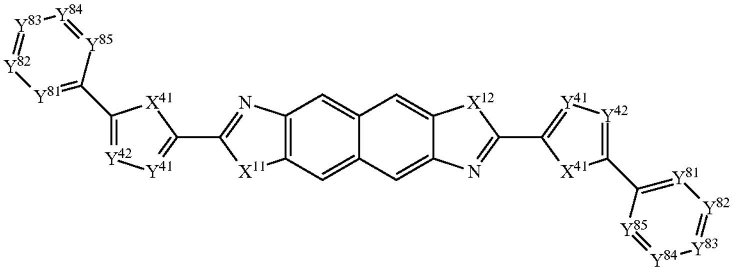

(17)

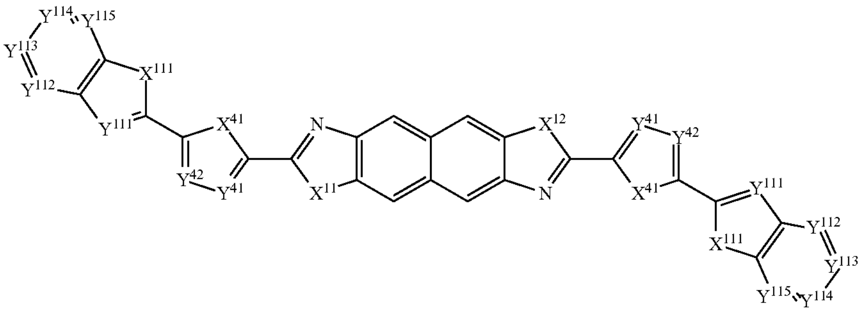

-continued
(18)
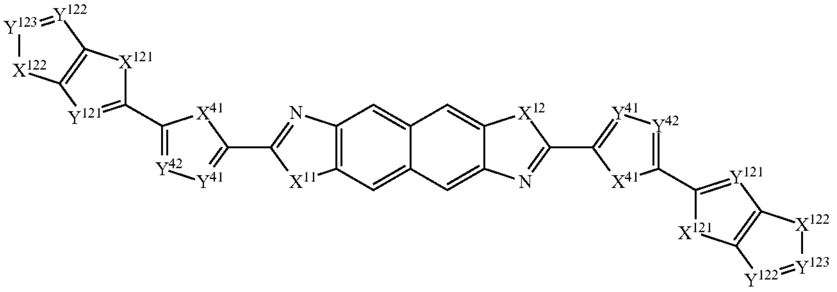
(19)
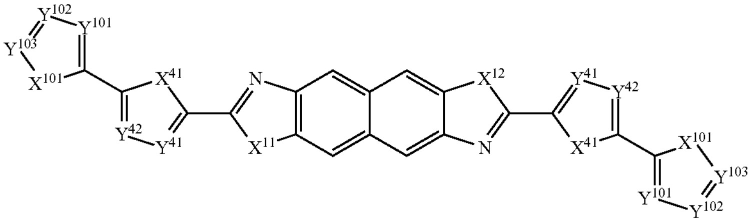
(20)
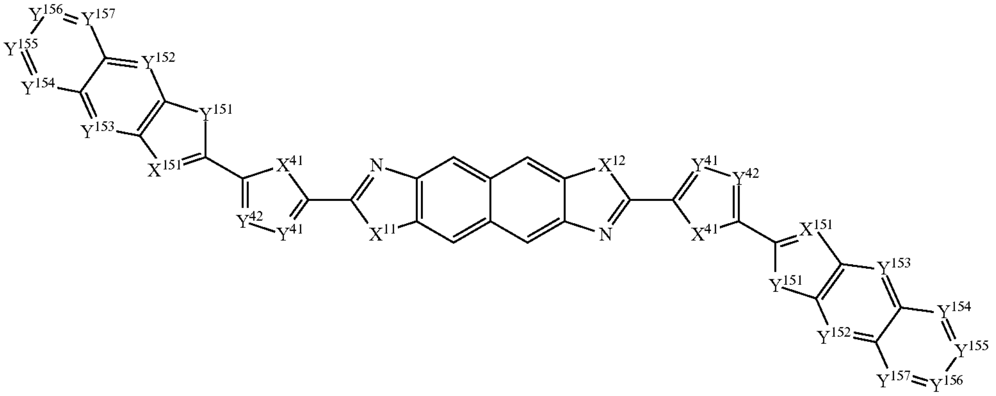
(21)
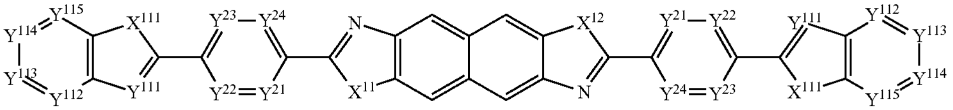
(22)
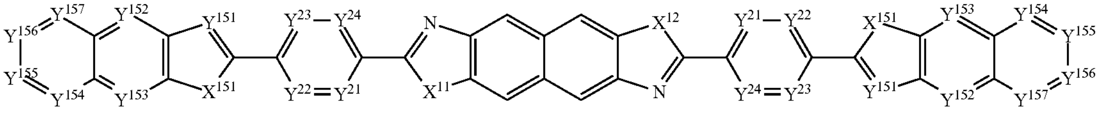
(23)
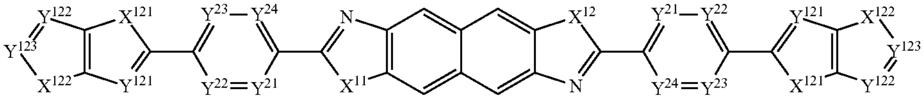
(24)
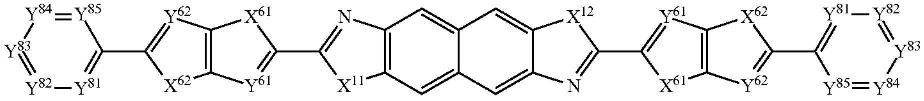
(25)
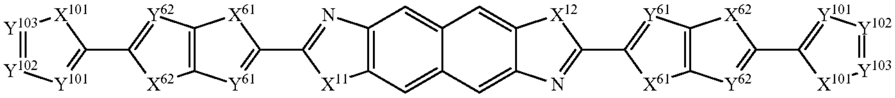
(26)
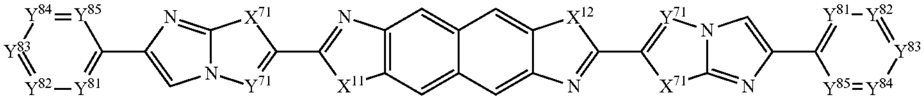

-continued
(27)
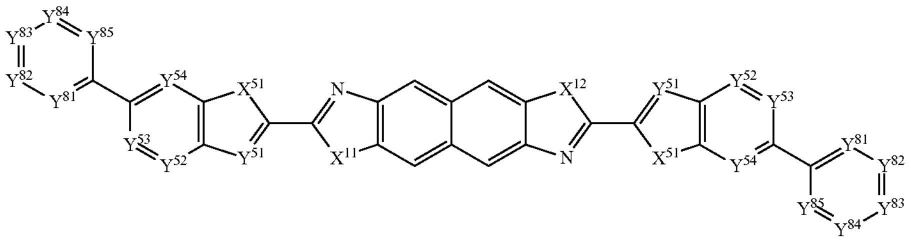
(28)
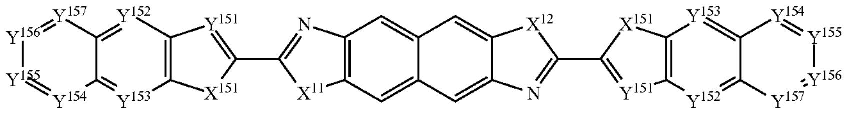
(29)
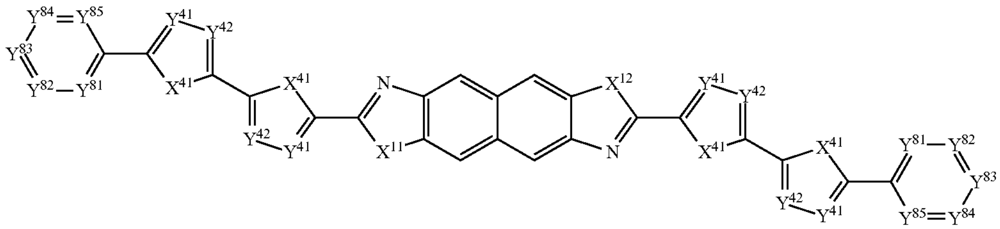
(30)
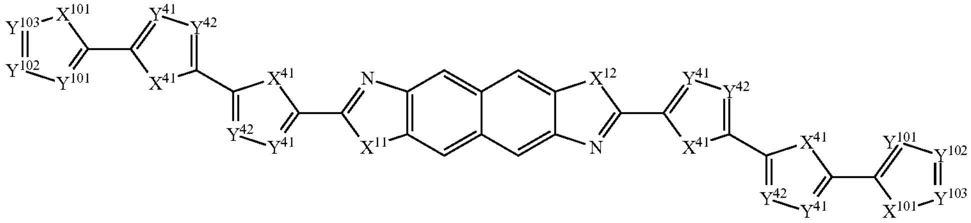
(31)
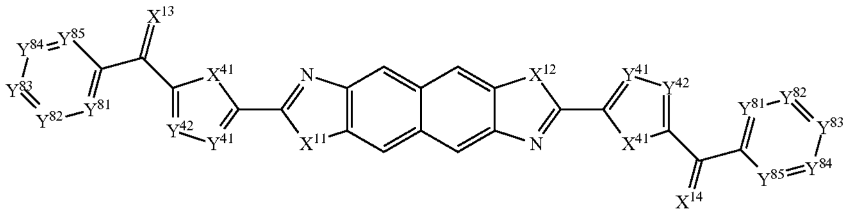
(32)
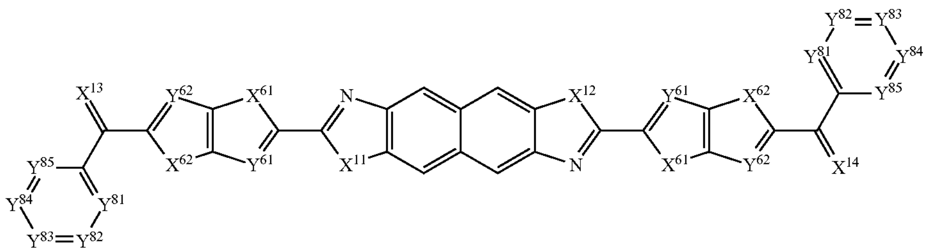
(33)
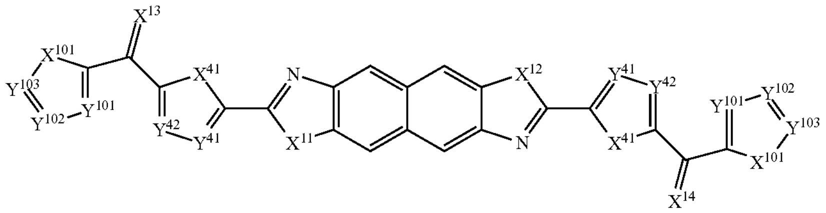

-continued
(34)
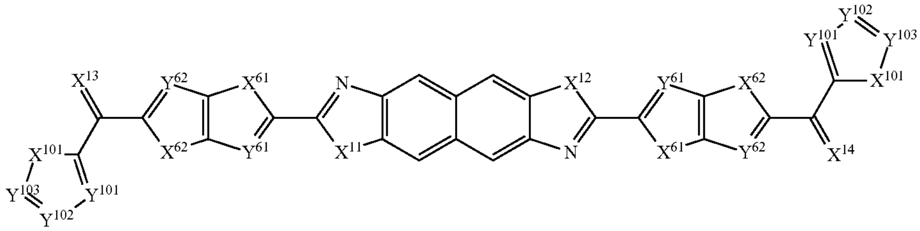
(35)
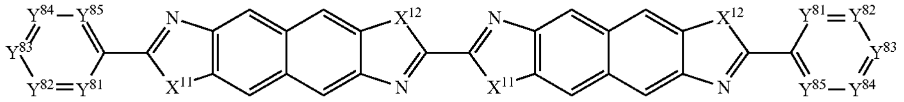
(36)
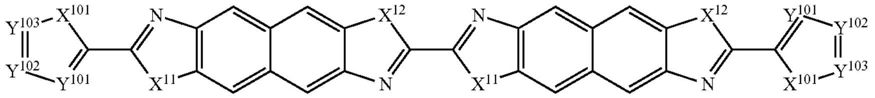
(37)
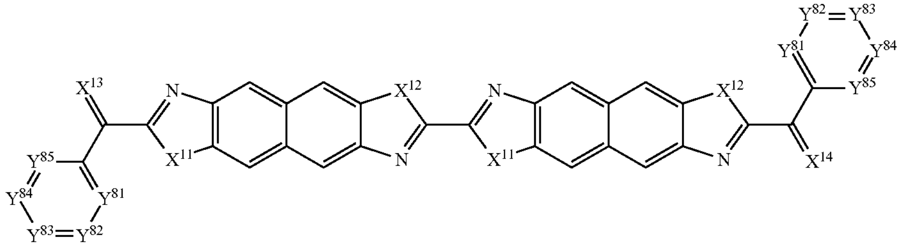
(38)
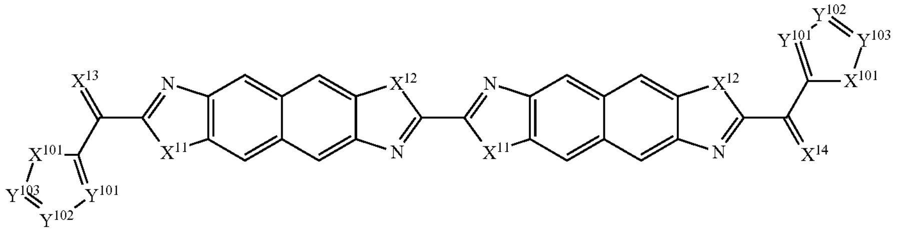
(39)
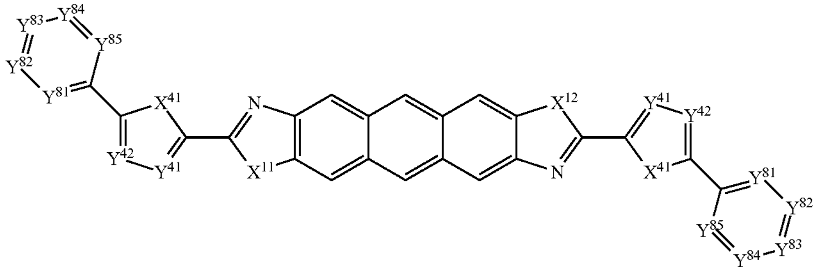
(40)
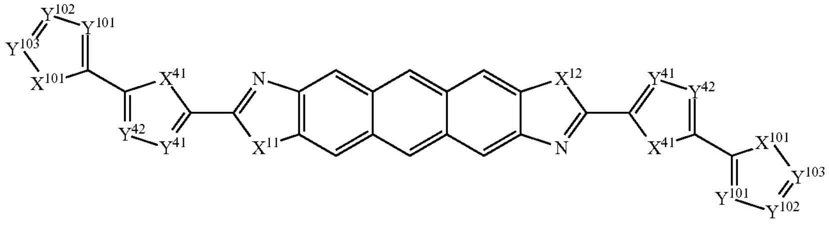
(41)
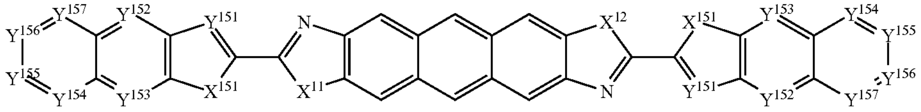

-continued
(42)
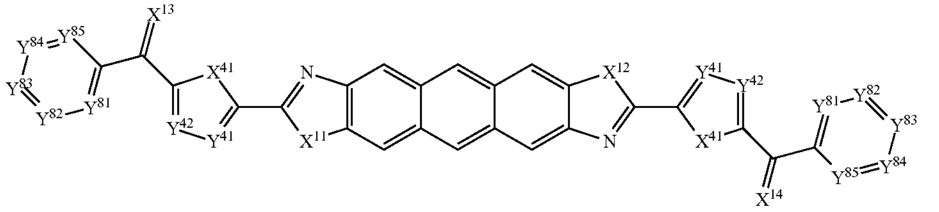
(43)
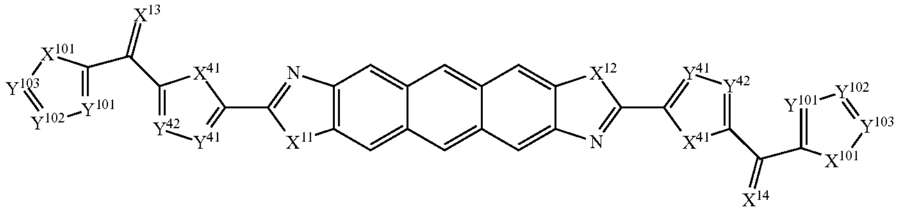
(44)
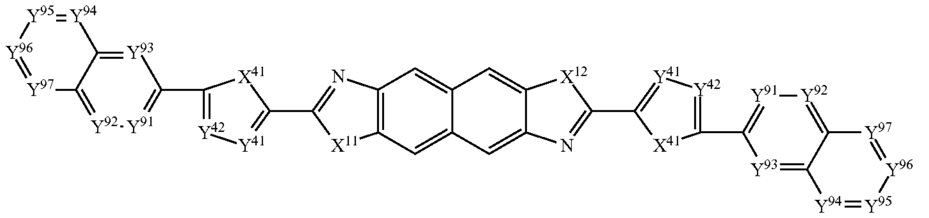
(45)
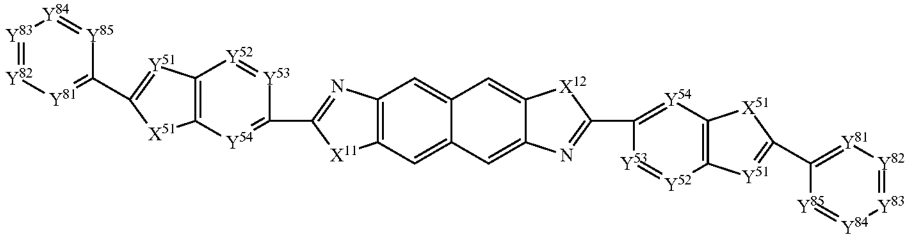
(46)
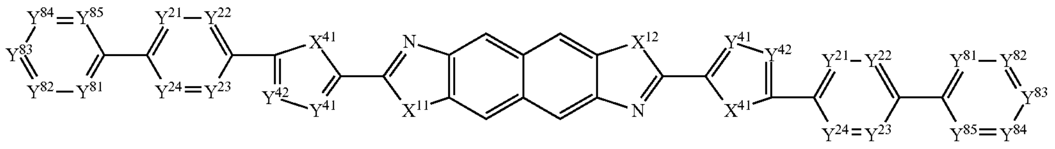
(54)
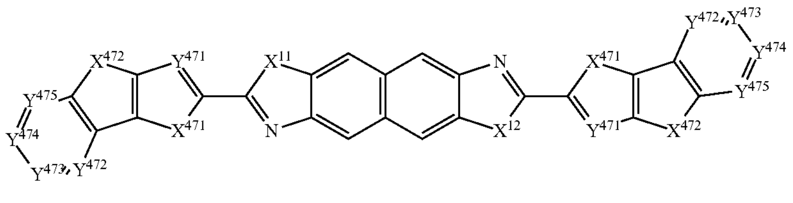
(55)
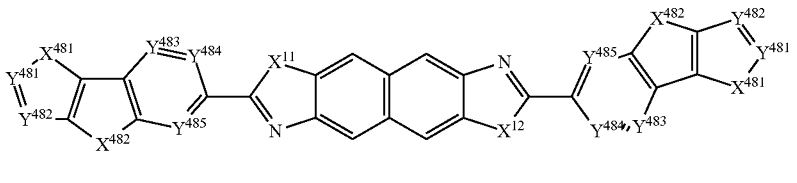
(56)
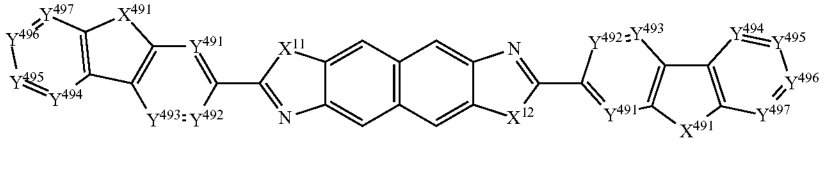

-continued (57)

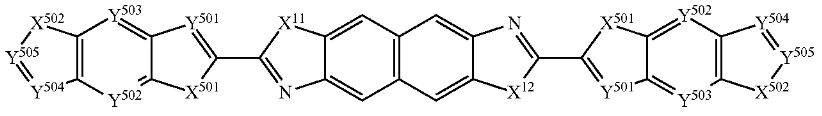

(58)

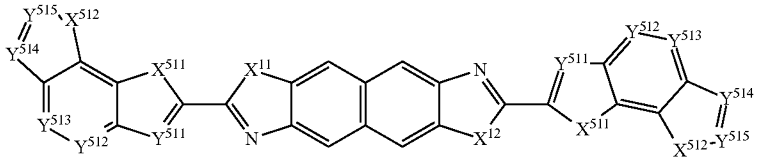

(59)

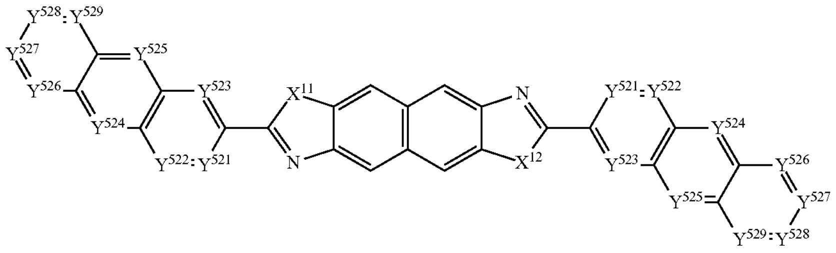

(60)

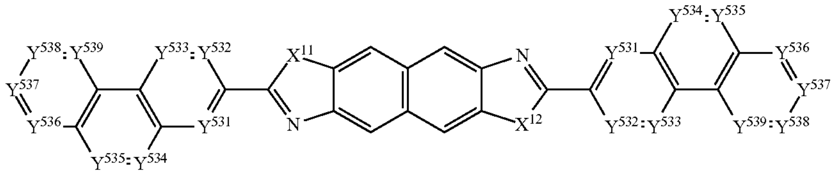

in Formula (16) to Formula (46) and Formula (54) to Formula (60), $Y^{21}$ to $Y^{24}$, $Y^{41}$ and $Y^{42}$, $Y^{51}$ to $Y^{54}$, $Y^{61}$ and $Y^{62}$, $Y^{71}$, $Y^{81}$ to $Y^{85}$, $Y^{91}$ to $Y^{97}$, $Y^{101}$ to $Y^{103}$, $Y^{111}$ to $Y^{115}$, $Y^{121}$ to $Y^{123}$, $Y^{151}$ to $Y^{157}$, $Y^{471}$ to $Y^{475}$, $Y^{481}$ to $Y^{485}$, $Y^{491}$ to $Y^{497}$, $Y^{501}$ to $Y^{505}$, $Y^{511}$ to $Y^{515}$, $Y^{521}$ to $Y^{528}$, and $Y^{531}$ to $Y^{539}$ each independently represent —CR═ or a nitrogen atom, R represents a hydrogen atom, a halogen atom, a cyano group, or a trifluoromethyl group, $X^{11}$ to $X^{14}$ each independently represent a sulfur atom or an oxygen atom, and $X^{41}$, $X^{51}$, $X^{61}$ and $X^{62}$, $X^{71}$, $X^{101}$, $X^{111}$, $X^{121}$ and $X^{122}$, $X^{151}$, $X^{471}$, $X^{481}$ and $X^{482}$, $X^{491}$, $X^{501}$ and $X^{502}$, and $X^{511}$ and $X^{512}$ each independently represent a sulfur atom, an oxygen atom, or a selenium atom.

30. The compound according to claim 29, wherein the compound represented by Formula (1) is the compound represented by Formula (16) in which $Y^{41}$ and $Y^{42}$ and $Y^{81}$ to $Y^{85}$ are each —CR═, and R is a hydrogen atom, the compound represented by Formula (17) in which $Y^{41}$ and $Y^{42}$ and $Y^{111}$ to $Y^{115}$ are each —CR═, and R is a hydrogen atom, the compound represented by Formula (21) in which $Y^{21}$ to $Y^{24}$ and $Y^{111}$ to $Y^{115}$ are each —CR═, and R is a hydrogen atom, the compound represented by Formula (22) in which $Y^{21}$ to $Y^{24}$ and $Y^{151}$ to $Y^{157}$ are each —CR═, and R is a hydrogen atom, the compound represented by Formula (24) in which $Y^{61}$ and $Y^{62}$ and $Y^{81}$ to $Y^{85}$ are each —CR═, and R is a hydrogen atom, the compound represented by Formula (27) in which $Y^{51}$ to $Y^{54}$ and $Y^{81}$ to $Y^{85}$ are each —CR═, and R is a hydrogen atom, the compound represented by Formula (28) in which $Y^{151}$ to $Y^{157}$ are each —CR═, and R is a hydrogen atom, the compound represented by Formula (29) in which $Y^{41}$ and $Y^{42}$ and $Y^{81}$ to $Y^{85}$ are each —CR═, and R is a hydrogen atom, the compound represented by Formula (44) in which $Y^{41}$ and $Y^{42}$ and $Y^{91}$ to $Y^{97}$ are each —CR═, and R is a hydrogen atom, the compound represented by Formula (45) in which $Y^{51}$ to $Y^{54}$ and $Y^{81}$ to $Y^{85}$ are each —CR═, and R is a hydrogen atom, the compound represented by Formula (46) in which $Y^{21}$ to $Y^{24}$, $Y^{41}$ and $Y^{42}$, and $Y^{81}$ to $Y^{85}$ are each —CR═, and R is a hydrogen atom, the compound represented by Formula (54) in which $Y^{471}$ to $Y^{475}$ are each —CR═, and R is a hydrogen atom, the compound represented by Formula (55) in which $Y^{481}$ to $Y^{485}$ are each —CR═, and R is a hydrogen atom, the compound represented by Formula (56) in which $Y^{491}$ to $Y^{497}$ are each —CR═, and R is a hydrogen atom, the compound represented by Formula (57) in which $Y^{501}$ to $Y^{505}$ are each —CR═, and R is a hydrogen atom, the compound represented by Formula (58) in which $Y^{511}$ to $Y^{515}$ are each —CR═, and R is a hydrogen atom, the compound represented by Formula (59) in which $Y^{521}$ to $Y^{528}$ are each —CR═, and R is a hydrogen atom, or the compound represented by Formula (59) in which $Y^{531}$ to $Y^{539}$ are each —CR═, and R is a hydrogen atom.

31. The compound according to claim 29, wherein the compound represented by Formula (1) is the compound represented by any one of Formula (16), Formula (31), Formula (32), Formula (35), Formula (37), Formula (39), or Formula (42).

32. The compound according to claim 21, wherein $X^{11}$ and $X^{12}$ each represent a sulfur atom.

* * * * *